(12) United States Patent  
Nakano et al.

(10) Patent No.: US 8,008,506 B2
(45) Date of Patent: Aug. 30, 2011

(54) INDAZOLE COMPOUNDS

(75) Inventors: Seiji Nakano, Tokyo (JP); Taisuke Iwanami, Tokyo (JP); Kei Yamanishi, Tokyo (JP); Yasuhiro Wada, Tokyo (JP); Akifumi Morimoto, Tokyo (JP)

(73) Assignee: Asahi Kasei Pharma Corporation, Tokyo (JP)

( * ) Notice: Subject to any disclaimer, the term of this patent is extended or adjusted under 35 U.S.C. 154(b) by 0 days.

(21) Appl. No.: 12/569,295

(22) Filed: Sep. 29, 2009

(65) Prior Publication Data

US 2010/0160256 A1 Jun. 24, 2010

Related U.S. Application Data

(60) Provisional application No. 61/104,036, filed on Oct. 9, 2008.

(51) Int. Cl.
C07D 231/56 (2006.01)
A61K 31/416 (2006.01)

(52) U.S. Cl. ............... 548/361.1; 548/361.5; 548/362.5; 514/406; 514/407

(58) Field of Classification Search .................. None
See application file for complete search history.

(56) References Cited

U.S. PATENT DOCUMENTS

| | | | |
|---|---|---|---|
| 2,787,515 A | 4/1957 | Frederic et al. | |
| 4,378,361 A | 3/1983 | Schromm et al. | |
| 5,767,133 A | 6/1998 | Dow et al. | |
| 5,859,044 A | 1/1999 | Dow et al. | |
| 6,037,362 A | 3/2000 | Miyoshi et al. | |
| 6,172,099 B1 | 1/2001 | Miyoshi et al. | |
| 6,187,809 B1 | 2/2001 | Miyoshi et al. | |
| 6,353,025 B1 | 3/2002 | Tamai et al. | |
| 6,495,701 B1 | 12/2002 | Matsubara et al. | |
| 6,545,053 B1 | 4/2003 | Miyoshi et al. | |
| 6,861,444 B2 | 3/2005 | Ikuta et al. | |
| 7,049,445 B2 | 5/2006 | Ikuta et al. | |
| 7,199,147 B2 | 4/2007 | Imazaki et al. | |
| 7,217,724 B2 | 5/2007 | Ueno et al. | |
| 7,271,190 B2 * | 9/2007 | Miyoshi et al. | 514/403 |
| 7,511,069 B2 * | 3/2009 | Miyoshi et al. | 514/403 |
| 7,598,284 B2 | 10/2009 | Miyoshi et al. | |
| 2002/0120148 A1 | 8/2002 | Taniguchi et al. | |
| 2003/0040538 A1 | 2/2003 | Miyoshi et al. | |
| 2003/0139475 A1 | 7/2003 | Miyoshi et al. | |
| 2003/0191174 A1 | 10/2003 | Ikuta et al. | |
| 2004/0053967 A1 | 3/2004 | Hara et al. | |
| 2004/0102437 A1 | 5/2004 | Takami et al. | |
| 2004/0127546 A1 | 7/2004 | Ikuta et al. | |
| 2004/0138286 A1 | 7/2004 | Imazaki et al. | |
| 2005/0020602 A1 | 1/2005 | Miyoshi et al. | |
| 2006/0063762 A1 | 3/2006 | Ueno et al. | |
| 2008/0015242 A1 | 1/2008 | Miyoshi et al. | |
| 2008/0076815 A1 | 3/2008 | Miyoshi et al. | |
| 2008/0306160 A1 | 12/2008 | Kobayashi et al. | |
| 2009/0170826 A1 | 7/2009 | Hagihara et al. | |

(Continued)

FOREIGN PATENT DOCUMENTS

DE 24 29 253 6/1974

(Continued)

OTHER PUBLICATIONS

U.S. Appl. No. 12/569,324 to Seiji Nakano et al., which was filed Sep. 29, 2009.

(Continued)

*Primary Examiner* — Kamal Saeed
*Assistant Examiner* — Nyeemah A Grazier
(74) *Attorney, Agent, or Firm* — Greenblum & Bernstein, PLC

(57) ABSTRACT

Provided are compounds represented by the following formula (A-1) and formula (1), or salts thereof. The compounds of formula (A-1) and formula (1) or salts thereof have β3 adrenergic receptor agonist activity, and thus are useful as therapeutic and prophylactic agent for diabetes mellitus, obesity, hyperlipidemia, depression, diseases caused by gallstones or hypermotility of the biliary tract, diseases caused by hyperactivity of the digestive tract, interstitial cystitis, overactive bladder or urinary incontinence, or as therapeutic and prophylactic agents for diseases concomitant with decreased tears.

General formula

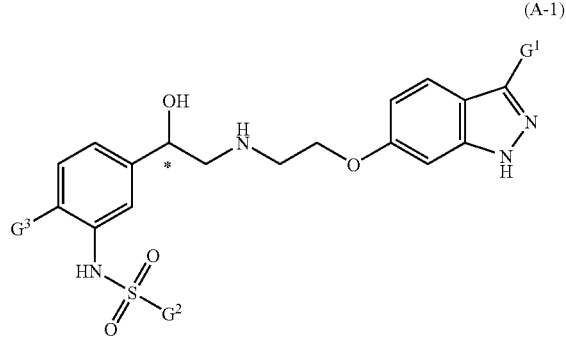

(A-1)

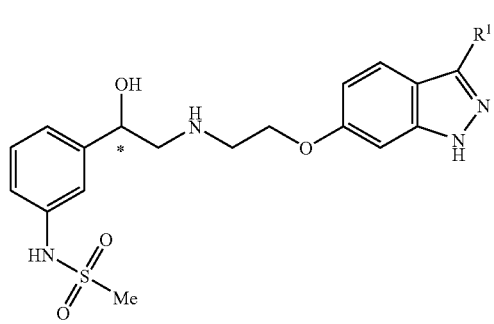

(1)

15 Claims, No Drawings

U.S. PATENT DOCUMENTS

2010/0152265 A1* 6/2010 Nakano et al. .................. 514/406

FOREIGN PATENT DOCUMENTS

| | | |
|---|---|---|
| DE | 26 51 572 | 6/1977 |
| EP | 0 008 653 | 3/1980 |
| EP | 0 023 385 | 2/1981 |
| EP | 0 171 702 | 2/1986 |
| EP | 0 238 973 | 3/1987 |
| EP | 0 455 006 | 4/1991 |
| EP | 659 737 | 6/1995 |
| EP | 1 174 425 | 3/2000 |
| EP | 1 043 308 | 10/2000 |
| EP | 1 142 883 | 10/2001 |
| GB | 1 565 080 | 11/1976 |
| JP | 55-53262 | 4/1980 |
| JP | 58-41860 | 3/1983 |
| JP | 8-165276 | 6/1996 |
| WO | 94/29290 | 12/1994 |
| WO | 95/29159 | 11/1995 |
| WO | 96/35670 | 11/1996 |
| WO | 97/25311 | 7/1997 |
| WO | 99/01431 | 1/1999 |
| WO | 99/31045 | 6/1999 |
| WO | 99/51564 | 10/1999 |
| WO | 00/35890 | 6/2000 |
| WO | 00/59287 | 10/2000 |
| WO | 00/59885 | 10/2000 |
| WO | 01/56988 | 8/2001 |
| WO | 01/83451 | 11/2001 |
| WO | 01/83452 | 11/2001 |
| WO | 01/83453 | 11/2001 |
| WO | 02/060873 | 8/2002 |
| WO | 02/074306 | 9/2002 |
| WO | 02/100833 | 12/2002 |
| WO | 03/035620 | 5/2003 |
| WO | 03/106418 | 12/2003 |
| WO | 2007/026630 | 3/2007 |
| WO | 2007/063821 | 6/2007 |

OTHER PUBLICATIONS

U.S. Appl. No. 12/608,483 to Seiji Nakano et al., which was filed Oct. 29, 2009.

Zhong et al., "$\alpha_1$-Adrenoceptor subtypes," Eur. J. Phamacol., vol. 375, pp. 261-276, 1999.

Arch et al., "Atypical $\beta$-adrenoceptor on brown adipocytes as target for anti-obesity drugs," Nature, vol. 309, pp. 163-165, May 1984.

Arch et al., "Prospects for $\beta_3$-adrenoceptor agonists in the treatment of obesity and diabetes", International Journal of Obesity, vol. 20, pp. 191-199, 1996.

Largis et al., "Antidiabetic and Antiobesity Effects of a Highly Selective $\beta_3$-Adrenoceptor Agonist (CL 316,243)", Drug Development Research, vol. 32, pp. 69-76, 1994.

Fisher et al., "A Selective Human $\beta_3$-Adrenergic Receptor Agonist Increases Metabolic Rate in Rhesus Monkeys", J. Clin. Invest., vol. 101, pp. 2387-2393, 1998.

Berkowitz et al., "Distribution of $\beta_3$-Adrenoceptor mRNA in human tissues," Eur. J. Phamacol., vol. 289, pp. 223-228, 1995.

Howe, "$\beta_3$-Adrenergic Agonists," Drugs of the Future, vol. 18, No. 6, pp. 529-549, 1993.

De Ponti et al., "Functional evidence for the presence of $\beta_3$-adrenoceptors in the guinea pig common bile duct and colon," Pharmacology, vol. 51, pp. 288-297, 1995.

Rodriguez et al., "Evidence for the presence of $\beta_3$-adrenergic receptor mRNA in the human brain," Brain Res. Mol. Brain Res., vol. 29, No. 2, pp. 369-375, 1995.

Fujimura et al., "Expression and Possible Functional Role of the $\beta_3$-Adrenoceptor in Human and Rat Detrusor Muscle", The Journal of Urology, vol. 161, pp. 680-685, 1999.

Takeda et al., "Evidence for $\beta_3$-Adrenoceptor Subtypes in Relaxation of the Human Urinary Bladder Detrusor: Analysis by Molecular Biological and Pharmacological Methods," The Journal of Pharmacology and Experimental Therapeutics, vol. 288, pp. 1367-1373, 1999.

Bishop, "Recent advances in the discovery of $\alpha_1$-adrenoceptor agonists," Current Topics in Medicinal Chemistry, vol. 7, pp. 135-145, 2007.

Michel et al., "$\alpha_1$-, $\alpha_2$- $\beta_3$-adrenoceptors in the urinary bladder, urethra and prostate," Br. J. Pharmacol., vol. 147, pp. S88-S119, 2006.

Patani et al., "Bioisosterism: A Rational Approach in Drug Design," Chem Rev, vol. 96 (8), pp. 3147-3176, 1996.

Hoey et al., "Characteristics of cyanopindolol analogues active at the $\beta_3$-adrenoceptor in rate ileum" Br. J. Pharm., vol. 119, pp. 564-568, 1996.

Cantello et al., "BRL 35135," Drugs of the Future, vol. 16(9), pp. 797-800, 1991.

Humber et al., "Disodium (R,R)-5-[2-[[2-(3-Chlorophenyl-2-hydroxyethyl)-amino]propyl]1,3-benzodioxole-2,2-dicarboxylate (CL 316,243). A Potent $\beta$-Adreneric Agonist Virtually Specific for $\beta_3$ Receptors. A Promising Antidiabetic and Antiobesity Agent", J. Med. Chem., 1992, vol. 35, pp. 3081-3084.

* cited by examiner

INDAZOLE COMPOUNDS

CROSS REFERENCE TO RELATED APPLICATIONS

This application claims the benefit of U.S. Provisional Application No. 61/104,036, filed Oct. 9, 2008.

TECHNICAL FIELD

The present invention relates to indazole compounds having a β3 adrenergic receptor agonist activity, a pharmaceutical composition containing the same, and uses of the compounds and the composition.

BACKGROUND ART

Noradrenaline and adrenaline are known to exhibit a variety of actions against the nerves or smooth muscles and the like in the living body, as neurotransmitters and hormones. Therefore, adrenergic receptor binding and responding to these neurotransmitters/hormones are considered as important target molecules for drugs in various treatments.

Adrenergic receptor belongs to the G protein-coupled receptor family, and is classified to three subfamilies, namely, $\alpha_1$, $\alpha_2$ and β adrenergic receptor. That is, the adrenergic receptor subfamilies are all activated by binding with noradrenaline and adrenaline, but once activated, the receptor are known to utilize different intracellular signal transduction paths. It is suggested that $\alpha_1$ adrenergic receptor primarily induce increase in calcium ions, $\alpha_2$ adrenergic receptor induce inhibition of adenylyl cyclase, while β adrenergic receptor induce stimulation of adenylyl cyclase (see, for example, Non-Patent Document 1).

Accordingly, the physiological actions associated with activation of the subfamilies also vary. For example, the β adrenergic receptor subfamily is further classified into three subtypes β1, β2 and β3, but among them, the β1 adrenergic receptor agonist activity causes an increase in the heart rate, and the β2 adrenergic receptor agonist activity causes relaxation of smooth muscle tissues. Particularly, it is known that when the β2 adrenergic receptor agonist activity effects relaxation of vascular smooth muscles, it causes a decrease in the blood pressure.

β3 adrenergic receptor is reported to be present in adipocytes as well as the brain, gallbladder, prostate gland, intestinal tract and the like. Therefore, the β3 adrenergic receptor agonist activity is thought to be useful for the prevention and treatment of diabetes mellitus, obesity, hyperlipidemia, depression, diseases caused by gallstones or hypermotility of the biliary tract or diseases caused by hyperactivity of the digestive tract, diseases concomitant with decreased tears, or the like (see, for example, Non-Patent Documents 2 to 9; Patent Documents 1 and 2).

Furthermore, β3 adrenergic receptor is also expressed in urinary bladder smooth muscles, and it has been revealed that β3 adrenergic receptor stimulation induces relaxation of urinary bladder smooth muscles (see, for example, Non-Patent Documents 10 and 11). Thus, β3 adrenergic receptor agonists are expected to be useful as prophylactic and therapeutic agents for frequent urination or urinary incontinence in overactive bladder.

On the other hand, in regard to the α1 adrenergic receptor, which belong to another adrenergic receptor subfamily, it is reported that this receptor is expressed in the vas deferens, submaxillary gland, kidney, spleen, liver and aorta as well as in the prostate gland and urethra in rat, and selective antagonists having the relevant receptor are in use for the treatment of benign prostatic hyperplasia (see, for example, Non-Patent Documents 1 and 13).

On the contrary, the agonists of α1 adrenergic receptor, for example, phenylephrine, methoxamine, metaraminol and midodrine, are known to increase the blood pressure through vascular contraction in the peripheral tissues, and are used as hypertensors (see, for example, Non-Patent Document 12). Non-Patent Document 12 also describes the relationship between the subtype-selective activation of α1 adrenergic receptor and urinary incontinence. That is, it is described that α1 adrenergic receptor is further classified into subtypes such as α1A, α1B and α1D, and among them, selective agonists to the α1A subtype are expected to find a possible use in the treatment or prevention of stress incontinence through the contractile action of bladder neck or urethral smooth muscles.

As it is obvious from the above, in order to use an agonist or antagonist that binds to an adrenergic receptor for the treatment of specific diseases according to the purposes, it is usually preferable to also take into consideration the selectivity on the receptor subfamily of the relevant drug, and more particularly, on the subtype within such a subfamily. In particular, when it is intended to use an agonist of β adrenergic receptor in the treatment of diabetes mellitus, obesity, hyperlipidemia, depression, diseases caused by gallstones or hypermotility of the biliary tract or diseases caused by hyperactivity of the digestive tract, frequent urination or urinary incontinence in overactive bladder, or diseases accompanying decreased tears, it is conventional practice to select an agonist having high selectivity to the β3 adrenergic receptor subtype among others. That is, as described above, stimulation against the β1 and β2 adrenergic receptor subtypes may be considered as a fear for causing an undesired increase in the heart rate or decrease in the blood pressure, depending on the patient.

Likewise, it is also preferable to regard the stimulation against α1 adrenergic receptor, which belong to another subfamily, as a factor causing originally unintended secondary physiological actions in the blood vessels of peripheral tissues, depending on the patient.

Patent Document 3 describes a compound having a β3 adrenergic receptor agonist activity [formula (4) shown below].

Formula (4) described in Patent Document 3:

[Chemical Formula 1]

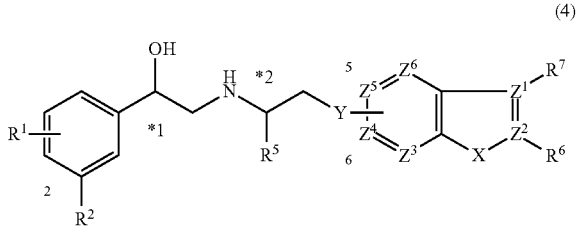

(4)

However, Patent Document 3 does not suggest any advantages of a drug that is capable of stimulating a β3 adrenergic receptor in preference to an α1 adrenergic receptor, and the document is not intended to teach that a compound having a specific structure is capable of stimulating a β3 adrenergic receptor even in preference to an α1 adrenergic receptor.

Patents Documents 4 and 5 also describe compounds having a β3 adrenergic receptor agonist activity [formula (5) and (6) shown below], but there is no disclosure on the selective stimulation of β3 adrenergic receptor in comparison with the stimulation of α1 adrenergic receptor.

Formula (5) described in Patent Document 4:

[Chemical Formula 2]

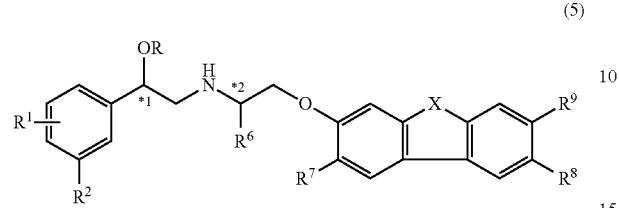

(5)

Formula (6) described in Patent Document 5:

[Chemical Formula 3]

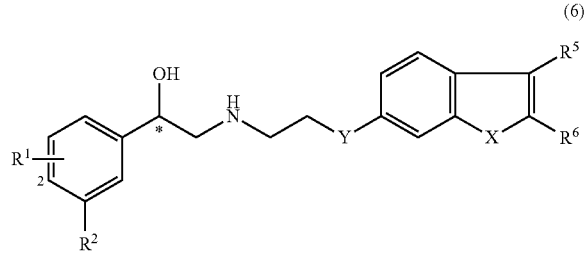

(6)

LIST OF THE PRIOR ART DOCUMENTS

[Patent Document]

[Patent Document 1] International Publication No. WO99/31045 pamphlet

[Patent Document 2] International Publication No. WO2007/026630 pamphlet

[Patent Document 3] International Publication No. WO03/035620 pamphlet

[Patent Document 4] International Publication No. WO97/25311 pamphlet

[Patent Document 5] International Publication No. WO01/83451 pamphlet

[Non-Patent Document]

[Non-Patent Document 1] Eur. J. Pharmacol., Vol. 375, pp. 261-276, 1999

[Non-Patent Document 2] Nature, Vol. 309, pp. 163-165, 1984

[Non-Patent Document 3] Int. J. Obes. Relat. Metab. Disord., Vol. 20, pp. 191-199, 1996

[Non-Patent Document 4] Drug Development Research, Vol. 32, pp. 69-76, 1994

[Non-Patent Document 5] J. Clin. Invest., Vol. 101, pp. 2387-2393, 1998

[Non-Patent Document 6] Eur. J. Pharmacol., Vol. 289, pp. 223-228, 1995

[Non-Patent Document 7] Drugs of the Future, Vol. 18, No. 6, pp. 529-549, 1993

[Non-Patent Document 8] Pharmacology, Vol. 51, pp. 288-297, 1995

[Non-Patent Document 9] Brain Res. Mol. Brain Res., Vol. 29, No. 2, pp. 369-375, 1995

[Non-Patent Document 10] J. Urology, Vol. 161, pp. 680-685, 1999

[Non-Patent Document 11] J. Pharmacol. Exp. Ther., Vol. 288, pp. 1367-1373, 1999

[Non-Patent Document 12] Current Topics in Medicinal Chemistry, Vol. 7, pp. 135-145, 2007

[Non-Patent Document 13] Br. J. Pharmacol., Vol. 147, pp. S88-S119, 2006

SUMMARY OF THE INVENTION

Problems to be Solved by the Invention

It is an object of the present invention to provide a drug that selectively stimulates a β3 adrenergic receptor, and more particularly, a drug capable of stimulating a β3 adrenergic receptor in preference to an α1 adrenergic receptor (in the present specification, also referred to as "β3/α1 adrenergic receptor selective agonist"). This drug may be used in the treatment and prevention of diabetes mellitus, obesity, hyperlipidemia, depression, diseases caused by gallstones or hypermotility of the biliary tract, diseases caused by hyperactivity of the digestive tract, interstitial cystitis, overactive bladder or urinary incontinence, diseases accompanying decreased tears and the like, while minimizing the expression of undesirable physiological actions incidental on the α1 adrenergic receptor stimulation.

Means for Solving the Problems

It was found that a compound having a certain type of specific structure is capable of stimulating a β3 adrenergic receptor in preference to an α1 adrenergic receptor. Therefore, the subject compound can be utilized as the β3/α1 adrenergic receptor-selective agonist.

Specifically, the present invention relates to the following.

[1] A compound represented by the following formula (A-1):

[Chemical Formula 4]

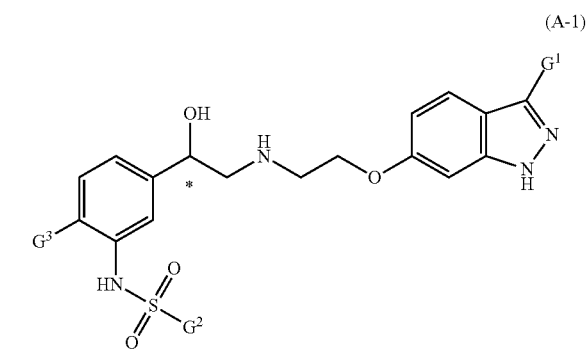

(A-1)

wherein $G^1$ represents a methyl group, an ethyl group, an n-propyl group, an isopropyl group, $-CF_3$, $-OMe$, $-CH_2OMe$ or $-CH_2CH_2CONMe_2$; $G^2$ represents a methyl group, an ethyl group, an n-propyl group, an isopropyl group or a phenyl group; $G^3$ represents a hydrogen atom, a fluorine atom or a chlorine atom; with the proviso that when $G^1$ is a methyl group or $-OMe$, compounds in which $G^2$ is a methyl group, an ethyl group or an n-propyl group, and $G^3$ is a hydrogen atom, a fluorine atom or a chlorine atom, are excluded; and a symbol * means an asymmetric carbon atom, or a salt thereof.

[2] A compound represented by the following formula (1):

[Chemical Formula 5]

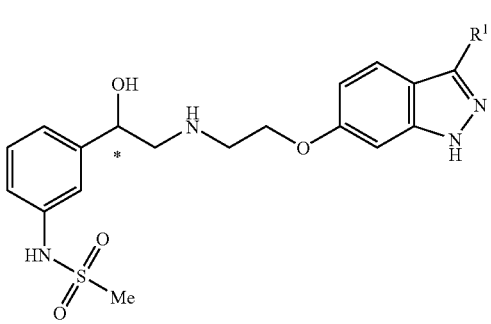

(1)

wherein R¹ represents an ethyl group, an n-propyl group, an isopropyl group, —CF₃, —CH₂OMe or —CH₂CH₂CONMe₂; and a symbol * means an asymmetric carbon atom,
or a salt thereof.
[3] The compound according to [1] above, or a salt thereof, wherein the asymmetric carbon atom represented by the symbol * has the (R)-configuration.
[4] The compound according to [2] above, or a salt thereof, wherein the asymmetric carbon atoms represented by the symbol * has the (R)-configuration.
[5] A compound selected from the group consisting of the following:
(R)-N-(3-(2-(2-(3-ethylindazol-6-yloxy)ethylamino)-1-hydroxyethyl)phenyl)methanesulfonamide;
(R)-N-(3-(2-(2-(3-n-propylindazol-6-yloxy)ethylamino)-1-hydroxyethyl)phenyl)methanesulfonamide;
(R)-N-(3-(2-(2-(3-isopropylindazol-6-yloxy)ethylamino)-1-hydroxyethyl)phenyl)methanesulfonamide;
(R)-N-(3-(2-(2-(3-trifluoromethylindazol-6-yloxy)ethylamino)-1-hydroxyethyl)phenyl)methanesulfonamide;
(R)-N-(3-(2-(2-(3-methoxymethylindazol-6-yloxy)ethylamino)-1-hydroxyethyl)phenyl)methanesulfonamide;
(R)-3-(6-(2-(2-hydroxy-2-(3-methylsulfonamido)phenyl)ethylamino)ethoxy)indazol-3-yl)-N,N-dimethylpropanamide;
(R)-N-(2-chloro-5-(1-hydroxy-2-(2-(3-isopropylindazol-6-yloxy)ethylamino)ethyl)phenyl)methanesulfonamide;
(R)-N-(5-(2-(2-(3-ethylindazol-6-yloxy)ethylamino)-1-hydroxyethyl)-2-fluorophenyl)methanesulfonamide;
(R)-N-(2-chloro-5-(2-(2-(3-ethylindazol-6-yloxy)ethylamino)-1-hydroxyethyl)phenyl)methanesulfonamide;
(R)-N-(2-fluoro-5-(1-hydroxy-2-(2-(3-(trifluoromethyl)indazol-6-yloxy)ethylamino)ethyl)phenyl)methanesulfonamide;
(R)-N-(2-chloro-5-(1-hydroxy-2-(2-(3-(trifluoromethyl)indazol-6-yloxy)ethylamino)ethyl)phenyl)methanesulfonamide;
(R)-N-(3-(1-hydroxy-2-(2-(3-methylindazol-6-yloxy)ethylamino)ethyl)phenyl)propane-2-sulfonamide;
(R)-N-(3-(2-(2-(3-ethylindazol-6-yloxy)ethylamino)-1-hydroxyethyl)phenyl)propane-2-sulfonamide;
(R)-N-(3-(1-hydroxy-2-(2-(3-methylindazol-6-yloxy)ethylamino)ethyl)phenyl)benzenesulfonamide;
(R)-N-(3-(2-(2-(3-ethylindazol-6-yloxy)ethylamino)-1-hydroxyethyl)phenyl)benzenesulfonamide;
(R)-N-(3-(1-hydroxy-2-(2-(3-methoxyindazol-6-yloxy)ethylamino)ethyl)phenyl)benzenesulfonamide; and
(R)-N-(3-(2-(2-(3-ethylindazol-6-yloxy)ethylamino)-1-hydroxyethyl)phenyl)ethanesulfonamide,
or a salt thereof.
[5-1]
(R)-N-(3-(2-(2-(3-ethylindazol-6-yloxy)ethylamino)-1-hydroxyethyl)phenyl)methanesulfonamide or a salt thereof.
[5-2]
(R)-N-(3-(2-(2-(3-n-propylindazol-6-yloxy)ethylamino)-1-hydroxyethyl)phenyl)methanesulfonamide or a salt thereof.
[5-3]
(R)-N-(3-(2-(2-(3-isopropylindazol-6-yloxy)ethylamino)-1-hydroxyethyl)phenyl)methanesulfonamide or a salt thereof.
[5-4]
(R)-N-(3-(2-(2-(3-trifluoromethylindazol-6-yloxy)ethylamino)-1-hydroxyethyl)phenyl)methanesulfonamide or a salt thereof.
[5-5]
(R)-N-(3-(2-(2-(3-methoxymethylindazol-6-yloxy)ethylamino)-1-hydroxyethyl)phenyl)methanesulfonamide or a salt thereof.
[5-6]
(R)-3-(6-(2-(2-hydroxy-2-(3-methylsulfonamido)phenyl)ethylamino)ethoxy)indazol-3-yl)-N,N-dimethylpropanamide or a salt thereof.
[5-7]
(R)-N-(2-chloro-5-(1-hydroxy-2-(2-(3-isopropylindazol-6-yloxy)ethylamino)ethyl)phenyl)methanesulfonamide or a salt thereof.
[5-8]
(R)-N-(5-(2-(2-(3-ethylindazol-6-yloxy)ethylamino)-1-hydroxyethyl)-2-fluorophenyl)methanesulfonamide or a salt thereof.
[5-9]
(R)-N-(2-chloro-5-(2-(2-(3-ethylindazol-6-yloxy)ethylamino)-1-hydroxyethyl)phenyl)methanesulfonamide or a salt thereof.
[5-10]
(R)-N-(2-fluoro-5-(1-hydroxy-2-(2-(3-(trifluoromethyl)indazol-6-yloxy)ethylamino)ethyl)phenyl)methanesulfonamide or a salt thereof.
[5-11]
(R)-N-(2-chloro-5-(1-hydroxy-2-(2-(3-(trifluoromethyl)indazol-6-yloxy)ethylamino)ethyl)phenyl)methanesulfonamide or a salt thereof.
[5-12]
(R)-N-(3-(1-hydroxy-2-(2-(3-methylindazol-6-yloxy)ethylamino)ethyl)phenyl)propane-2-sulfonamide or a salt thereof.
[5-13]
(R)-N-(3-(2-(2-(3-ethylindazol-6-yloxy)ethylamino)-1-hydroxyethyl)phenyl)propane-2-sulfonamide or a salt thereof.
[5-14]
(R)-N-(3-(1-hydroxy-2-(2-(3-methylindazol-6-yloxy)ethylamino)ethyl)phenyl)benzenesulfonamide or a salt thereof.
[5-15]
(R)-N-(3-(2-(2-(3-ethylindazol-6-yloxy)ethylamino)-1-hydroxyethyl)phenyl)benzenesulfonamide or a salt thereof.
[5-16]
(R)-N-(3-(1-hydroxy-2-(2-(3-methoxyindazol-6-yloxy)ethylamino)ethyl)phenyl)benzenesulfonamide or a salt thereof.
[5-17]
(R)-N-(3-(2-(2-(3-ethylindazol-6-yloxy)ethylamino)-1-hydroxyethyl)phenyl)ethanesulfonamide or a salt thereof.

[6] A compound selected from the group consisting of the following:

(R)-N-(3-(2-(2-(3-ethylindazol-6-yloxy)ethylamino)-1-hydroxyethyl)phenyl)methanesulfonamide;

(R)-N-(3-(2-(2-(3-n-propylindazol-6-yloxy)ethylamino)-1-hydroxyethyl)phenyl)methanesulfonamide;

(R)-N-(3-(2-(2-(3-isopropylindazol-6-yloxy)ethylamino)-1-hydroxyethyl)phenyl)methanesulfonamide;

(R)-N-(3-(2-(2-(3-trifluoromethylindazol-6-yloxy)ethylamino)-1-hydroxyethyl)phenyl)methanesulfonamide;

(R)-N-(3-(2-(2-(3-methoxymethylindazol-6-yloxy)ethylamino)-1-hydroxyethyl)phenyl)methanesulfonamide; and (R)-3-(6-(2-(2-hydroxy-2-(3-methylsulfonamido)phenyl)ethylamino)ethoxy)indazol-3-yl)-N,N-dimethylpropanamide, or a salt thereof.

[7] A β3 adrenergic receptor agonist containing the compound according to any one of [1] to [6] above or a salt thereof, as an active ingredient.

[8] A medicine containing the compound according to anyone of [1] to [6] above or a salt thereof, as an active ingredient.

[9] The medicine according to [8] above, being a prophylactic and/or therapeutic agent for overactive bladder and urinary incontinence.

[10] A method for activating a β3 adrenergic receptor in a body of a patient, the method including administering the compound according to any one of [1] to [6] above or a salt thereof, to a patent in need of a prevention and/or treatment of overactive bladder and urinary incontinence.

[10-1] The method according to [10] above, wherein the administration does not substantially activate an α1 adrenergic receptor in the body of the patient.

[10-2] The method according to [10] above, wherein the patient is a patient who should avoid substantial activation of α1 adrenergic receptor due to drug administration.

[11] A method for a prevention and/or treatment of overactive bladder and urinary incontinence, the method including administering an effective amount of the compound according to any one of [1] to [6] above or a salt thereof to a patient.

[11-1] The method according to [11] above, wherein the patient is a patient who should avoid substantial activation of α1 adrenergic receptor due to drug administration.

[12] A method for a prevention and/or treatment of urinary incontinence, the method including administering an effective amount of the compound according to any of [1] to [6] above or a salt thereof to a patient.

[12-1] The method according to [12] above, wherein the patient is a patient who should avoid substantial activation of α1 adrenergic receptor due to drug administration.

[13] A compound represented by the following formula (2):

[Chemical Formula 6]

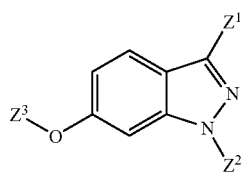

(2)

wherein $Z^1$ represents a methyl group, an ethyl group, an n-propyl group, an isopropyl group, —$CF_3$, —OMe, —$CH_2$OMe or —$CH_2CH_2CONMe_2$; $Z^2$ represents a hydrogen atom, a tert-butoxycarbonyl group, a benzyl group, a tetrahydropyranyl group, or an acetyl group; $Z^3$ represents a hydrogen atom, a benzyl group, a methyl group, a methanesulfonyl group, or a tert-butyldiphenylsilyl group; with the proviso that when $Z^1$ is a methyl group, the following combinations are excluded: $Z^2$ (hydrogen atom), $Z^3$ (hydrogen atom); $Z^2$ (hydrogen atom), $Z^3$ (methyl group); $Z^2$ (hydrogen atom), $Z^3$ (benzyl group); $Z^2$ (benzyl group), $Z^3$ (hydrogen atom); $Z^2$ (benzyl group), $Z^3$ (methyl group); $Z^2$ (tert-butoxycarbonyl group), $Z^3$ (hydrogen atom); $Z^2$ (tert-butoxycarbonyl group), $Z^3$ (methyl group); and $Z^2$ (tert-butoxycarbonyl group), $Z^3$ (benzyl group), and when $Z^1$ is —OMe, the following combinations are excluded: $Z^2$ (benzyl group), $Z^3$ (hydrogen atom); $Z^2$ (benzyl group), $Z^3$ (methyl group), or a salt thereof.

[14] A compound represented by the following formula (3):

[Chemical Formula 7]

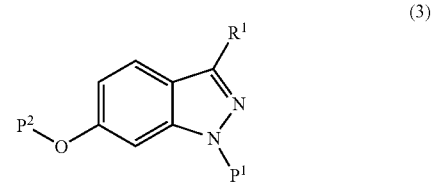

(3)

wherein $R^1$ represents an ethyl group, an n-propyl group, an isopropyl group, —$CF_3$, —$CH_2$OMe or —$CH_2CH_2CONMe_2$; $P^1$ represents a hydrogen atom, a tert-butoxycarbonyl group, a benzyl group, a tetrahydropyranyl group or an acetyl group; and $P^2$ represents a hydrogen atom, a benzyl group, a methyl group, a methanesulfonyl group or a tert-butyldiphenylsilyl group, or a salt thereof.

[15] A compound selected from the group consisting of the following:

1-benzyl-3-isopropylindazol-6-ol;
3-isopropylindazol-6-ol;
6-(tert-butyldiphenylsilyloxy)-3-isopropylindazole;
tert-butyl 6-(tert-butyldiphenylsilyloxy)-3-isopropylindazole-1-carboxylate;
tert-butyl 6-hydroxy-3-isopropylindazole-1-carboxylate;
1-benzyl-3-ethylindazol-6-ol;
3-ethylindazol-6-ol;
6-(tert-butyldiphenylsilyloxy)-3-ethylindazole;
tert-butyl 6-hydroxy-3-ethylindazole-1-carboxylate;
tert-butyl 6-(tent-butyldiphenylsilyloxy)-3-ethylindazole-1-carboxylate;
1-benzyl-3-n-propylindazol-6-ol;
1-(tetrahydro-2H-pyran-2-yl)-3-trifluoromethylindazol-6-ol;
3-trifluoromethylindazol-6-ol;
tert-butyl 6-hydroxy-3-trifluoromethylindazole-1-carboxylate;
3-(6-hydroxy-1-(tetrahydro-2H-pyran-2-yl)-indazole-N,N-dimethylpropanamide;
tert-butyl 3-(3-(dimethylamino)-3-oxopropyl)-6-hydroxyindazole-1-carboxylate;
3-(methoxymethyl)-1-(tetrahydro-2H-pyran-2-yl)-indazol-6-ol;
tert-butyl 6-(benzyloxy)-3-methoxyindazole-1-carboxylate; and
tert-butyl 6-hydroxy-3-methoxyindazole-1-carboxylate,
or a salt thereof.

[16] A compound selected from the group consisting of the following:
1-benzyl-3-isopropylindazol-6-ol;
3-isopropylindazol-6-ol;
6-(tert-butyldiphenylsilyloxy)-3-isopropylindazole;
tert-butyl 6-(tert-butyldiphenylsilyloxy)-3-isopropylindazole-1-carboxylate;
tert-butyl 6-hydroxy-3-isopropylindazole-1-carboxylate;
1-benzyl-1-ethylindazol-6-ol;
3-ethylindazol-6-ol;
6-(tert-butyldiphenylsilyloxy)-3-ethylindazole;
tert-butyl 6-hydroxy-3-ethylindazole-1-carboxylate;
tert-butyl 6-(tert-butyldiphenylsilyloxy)-3-ethylindazole-1-carboxylate;
1-benzyl-3-n-propylindazol-6-ol;
1-(tetrahydro-2H-pyran-2-yl)-3-trifluoromethylindazol-6-ol;
3-trifluoromethylindazol-6-ol;
tert-butyl 6-hydroxy-3-trifluoromethylindazole-1-carboxylate;
3-(6-hydroxy-1-(tetrahydro-2H-pyran-2-yl)-indazole-N,N-dimethylpropanamide; and
3-(methoxymethyl)-1-(tetrahydro-2H-pyran-2-yl)-indazol-6-ol,
or a salt thereof.

Effects of the Invention

The "compound represented by the formula (A-1) or a salt thereof" or the "compound represented by the formula (1) or a salt thereof" (hereinafter, may be simply referred to as a "compound of the present invention") has an excellent feature that when administered to a human or animal, the compound has an effect of relaxing the urinary bladder smooth muscles as a result of its potent β3 adrenergic receptor agonist activity, and has high β3/α1 adrenergic receptor selectivity, and thus an excellent pharmaceutical composition for the treatment of overactive bladder and urinary incontinence can be provided.

DESCRIPTION OF THE PREFERRED EMBODIMENTS

Hereinafter, the present invention will be described in detail.

According to the present specification, unless particularly stated otherwise, as it is obvious to those skilled in the art, the symbol:

[Chemical Formula 8]

represents bonding to the other side of the paper plane (that is, α-configuration), the symbol:

[Chemical Formula 9]

represents bonding to the front side of the paper plane (that is, β-configuration), and the symbol:

[Chemical Formula 10]

represents either the α-configuration or the β-configuration, or a mixture thereof.

The compound of the present invention will be explained in detail below.

The compound of the present invention is defined as follows.

Formula (A-1):

[Chemical Formula 11]

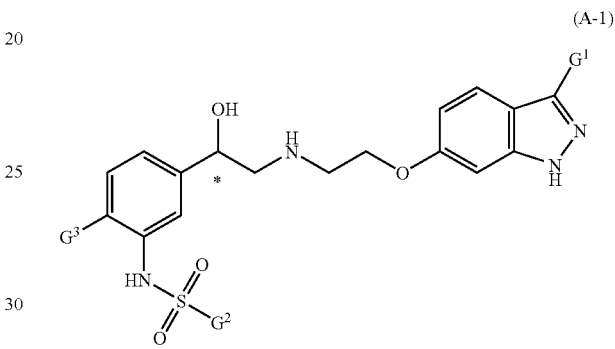

(A-1)

In the formula (A-1), $G^1$ represents a methyl group, an ethyl group, an n-propyl group, an isopropyl group, —$CF_3$, —OMe, —$CH_2$OMe or —$CH_2CH_2CONMe_2$; $G^2$ represents a methyl group, an ethyl group, an n-propyl group, an isopropyl group or a phenyl group; $G^3$ represents a hydrogen atom, a fluorine atom or a chlorine atom; with the proviso that when $G^1$ is a methyl group or —OMe, compounds in which $G^2$ is a methyl group, an ethyl group or an n-propyl group, and $G^3$ is a hydrogen atom, a fluorine atom or a chlorine atom, are excluded; and the symbol * means an asymmetric carbon atom.

$G^1$ is preferably an ethyl group, an n-propyl group, an isopropyl group, —$CF_3$, —$CH_2$OMe or —$CH_2CH_2CONMe_2$, more preferably an ethyl group, an isopropyl group or —$CF_3$, and particularly preferably an ethyl group. An ethyl group may be preferred in some embodiments, an isopropyl group may be preferred in other embodiment's, and —$CF_3$ may be preferred in still other embodiments.

$G^2$ is preferably a methyl group, an ethyl group, an n-propyl group, an isopropyl group or a phenyl group, more preferably a methyl group, an isopropyl group or a phenyl group, and particularly preferably a methyl group. An isopropyl group may be preferred in some embodiments, and a phenyl group may be preferred in other embodiments.

$G^3$ is preferably a hydrogen atom or a chlorine atom, and particularly preferably a hydrogen atom. A chlorine atom is preferred in some embodiments.

However, compounds of the formula in which when $G^1$ is a methyl group or —OMe, $G^2$ is a methyl group, an ethyl group or an n-propyl group, and $G^3$ is a hydrogen atom, a fluorine atom or a chlorine atom, are excluded.

The symbol * means an asymmetric carbon atom.

Formula (1):

[Chemical Formula 12]

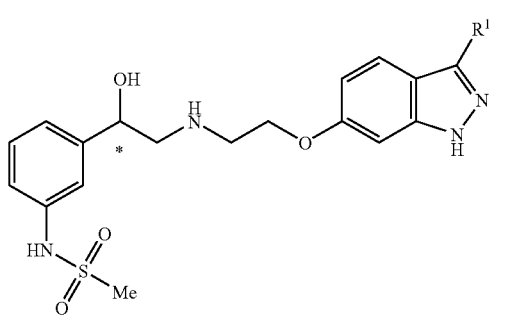

In the formula (1), R$^1$ represents an ethyl group, an n-propyl group, an isopropyl group, —CF$_3$, —CH$_2$OMe or —CH$_2$CH$_2$CONMe$_2$.

The symbol * means an asymmetric carbon atom.

R$^1$ is preferably an ethyl group, an n-propyl group, an isopropyl group, —CF$_3$, —CH$_2$OMe or —CH$_2$CH$_2$CONMe$_2$, more preferably an ethyl group, an isopropyl group or —CF$_3$, and particularly preferably an ethyl group. An isopropyl group or —CF$_3$ may be preferred in some embodiments.

In the structural formula of the compound of the present invention, the carbon atom represented by the symbol * is an asymmetric carbon atom. Examples of the configuration of this asymmetric carbon atom are the S-configuration and the R-configuration, and the R-configuration is preferred. The compound of the present invention includes all of any optical isomer that is based on the asymmetric carbon and is optically pure, any mixture of various optical isomers, or racemic form. For example, isomers based on the presence of an asymmetric carbon atom or the like (an R- or S-isomer, an isomer based on α- or β-configuration, an enantiomer, a diastereomer, or the like), optically active substances having optical activity (D- or L-form, or d- or l-form), isomers based on the difference in polarity on the basis of chiral chromatographic separation (more polar form or less polar form), equilibrium compounds, rotational isomers, tautomeric isomers, or mixtures thereof at arbitrary ratios, or racemic mixtures are all included in the compound of the present invention.

As used herein, the "compound represented by formula (A-1)" or the "compound represented by formula (1)" is generally understood as a free-form compound represented by the formula (A-1) or formula (1). Examples of the salt thereof include the following salts.

That is, in regard to the salt for the compound of the present invention, the type is not particularly limited and is acceptable as long as the salt is an acid addition salt. The salt may also be in the form of intramolecular counterion. Particularly when it is intended to use the salt as an active ingredient of medicine, it is particularly preferable that the salt be a pharmaceutically acceptable salt. When disclosure is made in the present specification in connection with the use as a medicine, a salt for the compound of the present invention is conventionally understood as a pharmaceutically acceptable salt. The types of acid forming pharmaceutically acceptable salts are well known to those skilled in the art, and for example, those described by Berge, et al. in J. Pharm. Sci., 1-19 (1977), may be mentioned. Examples of the acid addition salt include inorganic acid salts such as hydrochlorides, hydrobromides, hydroiodides, nitrates, sulfates, hydrogen sulfates, phosphates or hydrogen phosphates; and organic acid salts such as acetates, trifluoroacetates, gluconates, lactates, salicylates, citrates, tartrates, ascorbates, succinates, maleates, fumarates, formates, benzoates, methanesulfonates, ethanesulfonates or p-toluenesulfonates.

For example, when it is intended to obtain a salt with an inorganic acid, it is preferable to dissolve the compound represented by formula (A-1) or formula (1) in an aqueous solution containing at least one equivalent of a desired inorganic acid. In this reaction, a water-miscible inert organic solvent such as methanol, ethanol, acetone or dioxane may be mixed in. For example, a solution of hydrochloride may be obtained by using hydrochloric acid.

The compound of the present invention may be an anhydride. It is also preferable that the compound of the present invention is a hydrate.

The compound of the present invention is preferably a solvate, but the compound being a non-solvate may also be mentioned as a preferred example.

The compound of the present invention may be in the form of crystals, or may be in an amorphous form. The crystals may be single crystals, or may be a mixture of plural crystal forms. The compound may also be in the form of an arbitrary mixture of crystals and an amorphous material.

More specifically speaking, the compound of the present invention may be an anhydride and a non-solvate of the "compound represented by formula (A-1)" or the "compound represented by formula (1)," or may be a hydrate and/or a solvate thereof. Furthermore, instances in which the compound is also in the form of crystals of these different forms are shown as preferred embodiments.

Furthermore, the compound of the present invention may be an anhydride and a non-solvate of the "salt of the compound represented by formula (A-1)" or the "salt of the compound represented by formula (1)," or may be a hydrate and/or a solvate thereof. Furthermore, the compound may be an anhydride and a non-solvate of the salt, or a hydrate and/or a solvate of the salt.

Combinations of preferred substituents for the compound of the present invention represented by the formula (1) include the following combinations.

(1) A compound of the present invention in which the asymmetric carbon atom represented by the symbol * has the (R)-configuration;

(2) A compound of the present invention, in which R$^1$ is an ethyl group, an n-propyl group, an isopropyl group, —CF$_3$, —CH$_2$OMe or —CH$_2$CH$_2$CONMe$_2$;

(3) A compound of the present invention, in which R$^1$ is an ethyl group, an n-propyl group, an isopropyl group, —CF$_3$, —CH$_2$OMe or —CH$_2$CH$_2$CONMe$_2$, and the asymmetric carbon atom represented by the symbol * has the (R)-configuration;

(4) A compound of the present invention, in which R$^1$ is an ethyl group, and the asymmetric carbon atom represented by the symbol * has the (R)-configuration;

(5) A compound of the present invention, in which R$^1$ is an n-propyl group, and the asymmetric carbon atom represented by the symbol * has the (R)-configuration;

(6) A compound of the present invention, in which R$^1$ is an isopropyl group, and the asymmetric carbon atom represented by the symbol * has the (R)-configuration;

(7) A compound of the present invention, in which R$^1$ is —CF$_3$, and the asymmetric carbon atom represented by the symbol * has the (R)-configuration;

(8) A compound of the present invention, in which R$^1$ is —CH$_2$OMe, and the asymmetric carbon atom represented by the symbol * has the (R)-configuration; and (9) A compound of the present invention, in which $R^1$ is —$CH_2CH_2CONMe_2$, and the asymmetric carbon atom represented by the symbol * has the (R)-configuration.

Combinations of preferred substituents for the compound of the present invention represented by formula (A-1) include the following combinations.

(10) A compound of the present invention, in which $G^1$ is a methyl group, $G^2$ is an isopropyl group or a phenyl group, $G^3$ is a hydrogen atom, and the asymmetric carbon atom represented by the symbol * has the (R)-configuration;

(11) A compound of the present invention, in which $G^1$ is an ethyl group, $G^2$ is a methyl group, an ethyl group, an n-propyl group, an isopropyl group or a phenyl group, $G^3$ is a hydrogen atom, and the asymmetric carbon atom represented by the symbol * has the (R)-configuration;

(12) A compound of the present invention, in which $G^1$ is an n-propyl group, $G^2$ is a methyl group, an ethyl group, an n-propyl group, an isopropyl group or a phenyl group, $G^3$ is a hydrogen atom, and the asymmetric carbon atom represented by the symbol * has the (R)-configuration;

(13) A compound of the present invention, in which $G^1$ is a —$CF_3$ group, $G^2$ is a methyl group, an ethyl group, an n-propyl group, an isopropyl group or a phenyl group, $G^3$ is a hydrogen atom, and the asymmetric carbon atom represented by the symbol * has the (R)-configuration;

(14) A compound of the present invention, in which $G^1$ is a —OMe group, $G^2$ is an isopropyl group or a phenyl group, $G^3$ is a hydrogen atom, and the asymmetric carbon atom represented by the symbol * has the (R)-configuration;

(15) A compound of the present invention, in which $G^1$ is a —$CH_2OMe$ group, $G^2$ is a methyl group, an ethyl group, an n-propyl group, an isopropyl group or a phenyl group, $G^3$ is a hydrogen atom, and the asymmetric carbon atom represented by the symbol * has the (R)-configuration;

(16) A compound of the present invention, in which $G^1$ is a —$CH_2CH_2CONMe_2$ group, $G^2$ is a methyl group, an ethyl group, an n-propyl group, an isopropyl group or a phenyl group, $G^3$ is a hydrogen atom, and the asymmetric carbon atom represented by the symbol * has the (R)-configuration;

(17) A compound of the present invention, in which $G^1$ is an ethyl group, $G^2$ is a methyl group, $G^3$ is a fluorine atom or a chlorine atom, and the asymmetric carbon atom represented by the symbol * has the (R)-configuration;

(18) A compound of the present invention, in which $G^1$ is an isopropyl group, $G^2$ is a methyl group, $G^3$ is a chlorine atom, and the asymmetric carbon atom represented by the symbol * has the (R)-configuration;

(19) A compound of the present invention, in which $G^1$ is a —$CF_3$ group, $G^2$ is a methyl group, $G^3$ is a fluorine atom or a chlorine atom, and the asymmetric carbon atom represented by the symbol * has the (R)-configuration; and

(20) The compound of the present invention according to any one of (1) to (19) above, being a compound in free form. This is also exemplified as a preferred embodiment of the present invention. A salt thereof may also be exemplified as a preferred embodiment, and hydrochloride may be mentioned as a particularly preferred example of such a salt.

Specific examples of preferable compounds of the present invention include the following compounds:

(R)-N-(3-(2-(2-(3-ethylindazol-6-yloxy)ethylamino)-1-hydroxyethyl)phenyl)methanesulfonamide;
(R)-N-(3-(2-(2-(3-n-propylindazol-6-yloxy)ethylamino)-1-hydroxyethyl)phenyl)methanesulfonamide;
(R)-N-(3-(2-(2-(3-isopropylindazol-6-yloxy)ethylamino)-1-hydroxyethyl)phenyl)methanesulfonamide;
(R)-N-(3-(2-(2-(3-trifluoromethylindazol-6-yloxy)ethylamino)-1-hydroxyethyl)phenyl)methanesulfonamide;
(R)-N-(3-(2-(2-(3-methoxymethylindazol-6-yloxy)ethylamino)-1-hydroxyethyl)phenyl)methanesulfonamide;
(R)-3-(6-(2-(2-hydroxy-2-(3-methylsulfonamide)phenyl)ethylamino)ethoxy)indazol-3-yl)-N,N-dimethylpropanamide;
(R)-N-(2-chloro-5-(1-hydroxy-2-(2-(3-isopropylindazol-6-yloxy)ethylamino)ethyl)phenyl)methanesulfonamide;
(R)-N-(5-(2-(2-(3-ethylindazol-6-yloxy)ethylamino)-1-hydroxyethyl)-2fluorophenyl)methanesulfonamide;
(R)-N-(2-chloro-5-(2-(2-(3-ethylindazol-6-yloxy)ethylamino)-1-hydroxyethyl)phenyl)methanesulfonamide;
(R)-N-(2-fluoro-5-(1-hydroxy-2-(2-(3-(trifluoromethyl)indazol-6-yloxy)ethylamino)ethyl)phenyl)methanesulfonamide;
(R)-N-(2-chloro-5-(1-hydroxy-2-(2-(3-(trifluoromethyl)indazol-6-yloxy)ethylamino)ethyl)phenyl)methanesulfonamide;
(R)-N-(3-(1-hydroxy-2-(2-(3-methylindazol-6-yloxy)ethylamino)ethyl)phenyl)propane-2-sulfonamide;
(R)-N-(3-(2-(2-(3-ethylindazol-6-yloxy)ethylamino)-1-hydroxyethyl)phenyl)propane-2-sulfonamide;
(R)-N-(3-(1-hydroxy-2-(2-(3-methylindazol-6-yloxy)ethylamino)ethyl)phenyl)benzenesulfonamide;
(R)-N-(3-(2-(2-(3,-ethylindazol-6-yloxy)ethylamino)-1-hydroxyethyl)phenyl)benzenesulfonamide;
(R)-N-(3-(1-hydroxy-2-(2-(3-methoxyindazol-6-yloxy)ethylamino)ethyl)phenyl)benzenesulfonamide; and
(R)-N-(3-(2-(2-(3-ethylindazol-6-yloxy)ethylamino)-1-hydroxyethyl)phenyl)ethanesulfonamide.

Specific examples of more preferable compounds of the present invention include the following compounds:
(R)-N-(3-(2-(2-(3-ethylindazol-6-yloxy)ethylamino)-1-hydroxyethyl)phenyl)methanesulfonamide;
(R)-N-(3-(2-(2-(3-n-propylindazol-6-yloxy)ethylamino)-1-hydroxyethyl)phenyl)methanesulfonamide;
(R)-N-(3-(2-(2-(3-isopropylindazol-6-yloxy)ethylamino-1-hydroxyethyl)phenyl)methanesulfonamide;
(R)-N-(3-(2-(2-(3-trifluoromethylindazol-6-yloxy)ethylamino)-1-hydroxyethyl)phenyl)methanesulfonamide;
(R)-N-(3-(2-(2-(3-methoxymethylindazol-6-yloxy)ethylamino)-1-hydroxyethyl)phenyl)methanesulfonamide;
(R)-3-(6-(2-(2-hydroxy-2-(3-methylsulfonamide)phenyl)ethylamino)ethoxy)indazol-3-yl)-N,N-dimethylpropanamide;
(R)-N-(5-(2-(2-(3-ethylindazol-6-yloxy)ethylamino)-1-hydroxyethyl)-2-fluorophenyl)methanesulfonamide;
(R)-N-(2-chloro-5-(2-(2-(3-ethylindazol-6-yloxy)ethylamino)-1-hydroxyethyl)phenyl)methanesulfonamide;
(R)-N-(2-chloro-5-(1-hydroxy-2-(2-(3-(trifluoromethyl)indazol-6-yloxy)ethylamino)ethyl)phenyl)methanesulfonamide; and
(R)-N-(3-(1-hydroxy-2-(2-(3-methoxyindazol-6-yloxy)ethylamino)ethyl)phenyl)benzenesulfonamide.

The compound of the present invention can be produced by, for example, the reaction paths shown in Schemes 1 to 17 described below, but the production method is not particularly limited. For example, the compound of the present invention can be produced by modifying or converting the substituent of the compound that serves as a precursor of the subject compound by combining one or more reactions described in conventional chemistry literatures and the like. In addition, unless particularly stated otherwise, the methods described below are described using compounds in free form for convenience, but under certain situations, salts of the compounds in free form may be used for the production.

The reaction time for each of the reactions is not particularly limited, but since the state of reaction progress can be easily traced by means of the analysis means that will be mentioned below, it is preferable to terminate the reaction at a time point where the quantity of the target product reaches the maximum. In the following schemes 1 to 17, the expression "STEP" means a process, and for example, "STEP 1-1" means process 1-1.

Examples of the protective group used in the present invention include a protective group for indazole (—NH—), a protective group for a hydroxyl group (—OH), a protective group for a methanesulfonamide group (—NHSO$_2$Me), a protective group for an amino group (—NH—, or —NH$_2$), and the like.

Examples of the protective group for indazole (—NH—) include a trityl group, a benzyl group, a methylbenzyl group, a chlorobenzyl group, a dichlorobenzyl group, a fluorobenzyl group, a trifluoromethylbenzyl group, a nitrobenzyl group, a methoxyphenyl group, an N-methylaminobnezyl group, an N,N-dimethylaminobenzyl group, a phenacyl group, an acetyl group, a trifluoroacetyl group, a pivaloyl group, a benzoyl group, a methoxycarbonyl group, an ethoxycarbonyl group, an allyl oxycarbonyl (Alloc) group, a 2,2,2-trichloroethoxycarbonyl group, a benzyloxycarbonyl (Cbz) group, a tert-butoxycarbonyl (Boc) group, a 1-methyl-1-(4-biphenyl)ethoxycarbonyl (Bpoc) group, a 9-fluorenylmethoxycarbonyl group, an N,N-dimethylsulfonyl group, a methanesulfonyl group, a benzenesulfonyl group, a p-toluenesulfonyl group, a mesitylenesulfonyl group, a p-methoxyphenylsulfonyl group, a tetrahydropyranyl (THP) group, a tetrahydrofuryl group, an allyl group, a methoxymethyl (MOM) group, a methoxyethoxymethyl (MEM) group, a benzyloxymethyl (BOM) group, a 2-(trimethylsilyl)ethoxymethyl (SEM) group, and the like.

Examples of the protective group for a hydroxyl group (—OH) include an alkyl group having 1 to 4 carbon atoms, an alkenyl group having 2 to 4 carbon atoms, an alkyl group having 1 to 4 carbon atoms substituted with an alkoxy group having 1 to 4 carbon atoms, an alkyl group having 1 to 4 carbon atoms substituted with 1 to 3 halogen atoms, a silyl group substituted with three identical or different alkyl groups each having 1 to 4 carbon atoms or with a phenyl group, a tetrahydropyranyl group, a tetrahydrofuryl group, a propargyl group, a trimethylsilylethyl group, and the like. Specific examples include a methyl group, an ethyl group, a tert-butyl group, an allyl group, a methoxymethyl (MOM) group, a methoxyethoxymethyl (MEM) group, a trichloroethyl group, a phenyl group, a methylphenyl group, a chlorophenyl group, a benzyl group, a methylbenzyl group, a chlorobenzyl group, a dichlorobenzyl group, a fluorobenzyl group, a trifluoromethylbenzyl group, a nitrobenzyl group, a methoxyphenyl group, an N-methylaminobenzyl group, an N,N-dimethylaminobenzyl group, a phenacyl group, a trityl group, a 1-ethoxyethyl (EE) group, a tetrahydropyranyl (THP) group, a tetrahydrofuryl group, a propargyl group, a trimethylsilyl (TMS) group, a triethylsilyl (TES) group, a tert-butyldimethylsilyl (TBDMS) group, a tert-butyldiphenylsilyl (TBDPS) group, an acetyl (Ac) group, a pivaloyl group, a benzoyl group, an allyloxycarbonyl (Allot) group, a 2,2,2-trichloroethoxycarbonyl (Troc) group, and the like.

Examples of the protective group for a methanesulfonamide group (—NHSO$_3$Me) include a methoxycarbonyl group, an ethoxycarbonyl group, a tert-butoxycarbonyl (Boc) group, a benzyl group, a methylbenzyl group, a chlorobenzyl group, a dichlorobenzyl group, a fluorobenzyl group, a trifluoromethylbenzyl group, a nitrobenzyl group, a methoxyphenyl group, an N-methylaminobenzyl group, an N,N-dimethylaminobenzyl group, a tert-butyl group, a diphenylmethyl group, a methoxyphenyl group, and the like.

Examples of the protective group for an amino group (—NH— or —NH$_2$) include a benzyl group, a methylbenzyl group, a chlorobenzyl group, a dichlorobenzyl group, a fluorobenzyl group, a trifluoromethylbenzyl group, a nitrobenzyl group, a methoxyphenyl group, an N-methylaminobenzyl group, an N,N-dimethylaminobenzyl group, a phenacyl group, an acetyl group, a trifluoroacetyl group, a pivaloyl group, a benzoyl group, an allyloxycarbonyl group, a 2,2,2-trichloroethoxycarbonyl group, a benzyloxycarbonyl group, a tert-butoxycarbonyl (Boc) group, a 1-methyl-1-(4-biphenyl)ethoxycarbonyl (Bpoc) group, a 9-fluorenylmethoxycarbonyl group, a 2-nitrobenzenesulfonyl group, a 4-nitrobenzenesulfonyl group, a 2,4-dinitrobenzenesulfonyl group, a benzyloxymethyl (BOM) group, a 2-(trimethylsilyl)ethoxymethyl (SEM) group, and the like.

The compound with such a protective group can be converted to the target compound by detaching the protective group during the production process, or simultaneously with or subsequently to the production in the final step. The protection/deprotection reactions may be carried out according to a known method, for example, a method described in "Protective Groups in Organic Synthesis", published by John Wiley and Sons (printed in 2007), but the reaction may be carried out by, for example, the methods listed in the following (1) to (3).

(1) The deprotection reaction under acidic conditions can be carried out, for example, in an inert solvent and in the presence of an organic acid, a Lewis acid, an inorganic acid or a mixture of these, at a temperature of −10° C. to 100° C. The amount of use of the acid is preferably an equimolar amount to a large excess, and a method of adding ethanethiol, 1,2-ethanedithiol or the like as an additive may be adopted.

Examples of the inert solvent include dichloromethane, chloroform, 1,4-dioxane, ethyl acetate, methyl tert-butyl ether, tetrahydrofuran, anisole and the like. The organic acid may be acetic acid, trifluoroacetic acid, methanesulfonic acid, p-toluenesulfonic acid, or the like. The Lewis acid may be boron tribromide, boron trifluoride, aluminum bromide, aluminum chloride or the like. The inorganic acid may be hydrochloric acid, hydrogen chloride-1,4-dioxane, hydrogen chloride-ethyl acetate, hydrobromic acid, sulfuric acid or the like. Examples of the organic acid, Lewis acid or inorganic acid, or a mixture of these may be hydrogen bromide/acetic acid, and the like.

(2) The deprotection reaction based on hydrogenolysis can be carried out, for example, in an inert solvent added with 0.1. to 300% by weight of a catalyst, in the presence of a hydrogen source such as hydrogen gas at normal temperature or under pressure, ammonium formate or hydrazine hydrate, at a temperature of −10° C. to 70° C. Furthermore, the reaction solution can also be subjected to a reaction by further adding an inorganic acid in a 0.05-fold molar amount to a large excess.

Examples of the inert solvent include ethers such as tetrahydrofuran, dioxane, dimethoxyethane or diethyl ether; an alcohol such as methanol or ethanol; benzene analogs such as benzene or toluene; a ketone such as acetone or methyl ethyl ketone; a nitrile such as acetonitrile; an amide such as dimethylformamide; an ester such as ethyl acetate; water, acetic acid or the like, each used singly or as solvent mixtures thereof. The catalyst may be a palladium on carbon powder, platinum oxide (PtO$_2$), activated nickel, or the like. The inorganic acid may be hydrochloric acid, sulfuric acid or the like.

(3) The deprotection reaction of a silyl group can be carried out, for example, in an organic solvent that is miscible with water, at a temperature of −10 to 60° C. using fluoride ions or the like.

The organic solvent may be tetrahydrofuran, acetic acid, acetonitrile or the like. The fluoride ions may be generated using, for example, tetra-n-butylammonium fluoride, hydrofluoric acid, a hydrogen fluoride-pyridine complex, or a hydrogen fluoride-triethylamine complex.

Hereinafter, the method for producing the compound represented by formula (1) according to an embodiment of the present invention will be described in detail with scheme 1 to scheme 12.

Scheme 1
[Chemical Formula 13]
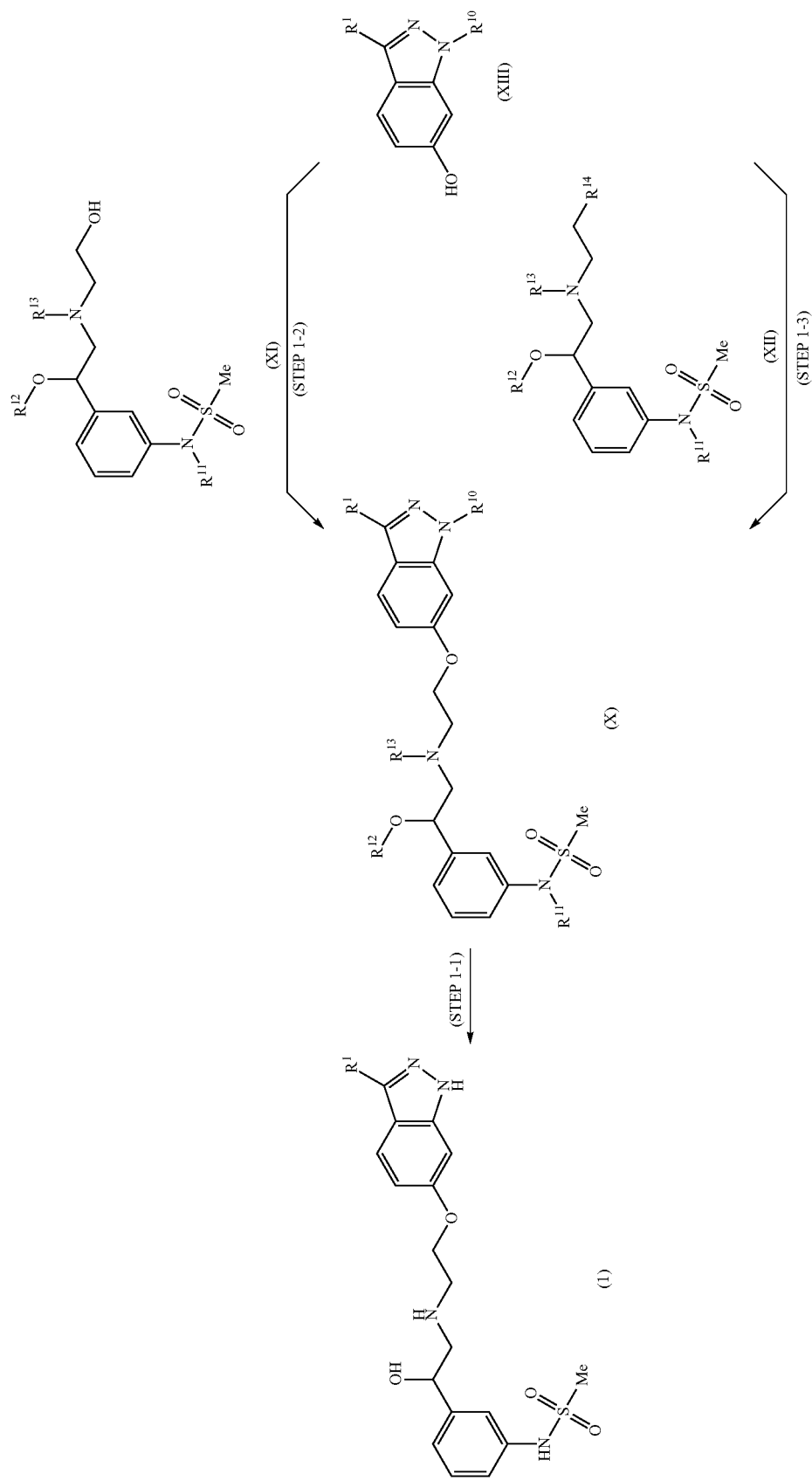

In each of the formulas in the scheme 1, $R^1$ has the same meaning as defined above; $R^{10}$ represents a hydrogen atom or the protective group for indazole mentioned above, and is preferably a benzyl group, a tert-butoxycarbonyl group or a tetrahydropyranyl group; $R^{11}$ represents a hydrogen atom or the protective group for methanesulfonamide mentioned above, and is preferably a benzyl group or a tert-butoxycarbonyl group; $R^{12}$ represents a hydrogen atom or a protective group for a hydroxyl group mentioned above, and is preferably a triethylsilyl group or a tert-butyldimethylsilyl group; $R^{13}$ represents a hydrogen atom or a protective group amino group mentioned above, and is preferably a benzyl group or a tert-butoxycarbonyl group; and $R^{14}$ represents a leaving group, and examples thereof include a chlorine atom, a bromine atom, an iodine atom, a p-toluenesulfonyloxy group, a methanesulfonyloxy group or the like, with a bromine atom being preferred. Preferred combinations of $R^{10}$, $R^{11}$, $R^{12}$ and $R^{13}$ include $R^{10}$ (benzyl group), $R^{11}$ (benzyl group), $R^{12}$ (triethylsilyl group), $R^{13}$ (benzyl group); $R^{10}$ (tert-butoxycarbonyl group), $R^{11}$ (tert-butoxycarbonyl group), $R^{12}$ (triethylsilyl group), $R^{13}$ (tert-butoxycarbonyl group); or $R^{10}$ (tetrahydropyranyl group), $R^{11}$ (tert-butoxycarbonyl group), $R^{12}$ (triethylsilyl group), $R^{13}$ (tert-butoxycarbonyl group).

Process 1-1 (STEP 1-1)

A compound represented by the formula (1) can be produced by subjecting a compound represented by the formula (X) to a deprotection reaction according to a known method, for example, a method described in "Protective Groups in Organic Synthesis", published by John Wiley and Sons (printed in 2007). As a suitable example, it is preferable to carry out the aforementioned deprotection reaction under acidic conditions, or to carry out the aforementioned deprotection reaction based on hydrogenolysis alone, or it is preferable to use these reactions in combination. At any rate, an appropriate deprotection reaction may be selected for the various protective groups present in the compound represented by the formula (X).

Process 1-2 (STEP 1-2)

The compound represented by the formula (X) is obtained by allowing a compound represented by the formula (XI) and a compound represented by the formula (XIII) to react in the presence of a phosphine and an azo compound in an inert solvent.

As the inert solvent, ethers such as diethyl ether, tetrahydrofuran or dimethoxyethane; a halogen-based solvent such as methylene chloride; benzene analogs such as benzene, toluene or xylene; or the like may be used singly, or a solvent mixture of these may be used, and toluene is preferred. The phosphine may be triphenylphosphine, tributylphosphine or the like, and triphenylphosphine is preferred. The azo compound may be diethyl azodicarboxylate, diisopropyl azodicarboxylate, N,N,N',N'-tetramethylazodicarboxamide, 1,1'-(azodicarbonyl)dipiperidine, N,N,N',N'-tetraisopropylcarboxamide, or the like, and N,N,N',N'-tetramethylazodicarboxamide is preferred.

The amount of use of the phosphine may be 1- to 10-fold the molar amount of the compound represented by the formula (XI) or the compound represented by the formula (XIII), and a 1.5- to 5-fold molar amount is preferred. The amount of use of the azo compound may be 1- to 10-fold the molar amount of the compound represented by the formula (XI) or the compound represented by the formula (XIII), and a 1.5- to 5-fold molar amount is preferred. The molar ratio of the compound represented by the formula (XI) and the compound represented by the formula (XIII) may be such that compound represented by formula (XI)/compound represented by formula (XIII)=0.25 to 4. The reaction temperature may be from −20° C. to the reflux temperature, and is preferably from 0° C. to 40° C. The reaction time maybe from 0.1 hour to 48 hours, and is preferably from 0.1 to 12 hours.

Process 1-3 (STEP 1-3)

The compound represented by the formula (X) is obtained by allowing a compound represented by the formula (XII) and a compound represented by the formula (XIII) to react in the presence of a base in an inert solvent.

As the inert solvent, water, an alcohol solvent such as methanol or ethanol, or N,N-dimethylformamide, tetrahydrofuran, 1,4-dioxane, acetone, 2-butanone, dimethyl sulfoxide, acetonitrile or the like may be used singly, or a solvent mixture of these may be used, but water, N,N-dimethylformamide or acetone is preferred. The base may be an alkali metal compound such as potassium carbonate, sodium carbonate, cesium carbonate, sodium hydrogen carbonate, potassium hydroxide, sodium hydroxide, sodium methoxide or potassium t-butoxide; or an organic tertiary amine such as pyridine, 4-dimethylaminopyridine, 1,8-diazabicyclo[5,4,0]undecene, trimethylamine, diisopropylethylamine or triethylamine. Sodium hydroxide may be mentioned as a preferred example.

The amount of use of the base may be 1- to 10-fold the molar amount, and preferably 1- to 5-fold the molar amount, of the compound represented by the formula (XII). The molar ratio of the compound represented by the formula (XII) and the compound represented by the formula (XIII) may be such that compound represented by formula (XII)/compound represented by formula (XIII)=0.2 to 5. The reaction temperature may be from −10° C. to the reflux temperature, and is preferably from 0 to 80° C. The reaction time may be from 0.1 to 48 hours, and is preferably from 0.1 to 12 hours.

If the reaction progress is slow, a catalyst such as potassium iodide or sodium iodide may be added as necessary, in an amount of 0.1- to 1.5-fold the molar amount of the compound represented by the formula (XII).

Scheme 2

[Chemical Formula 14]

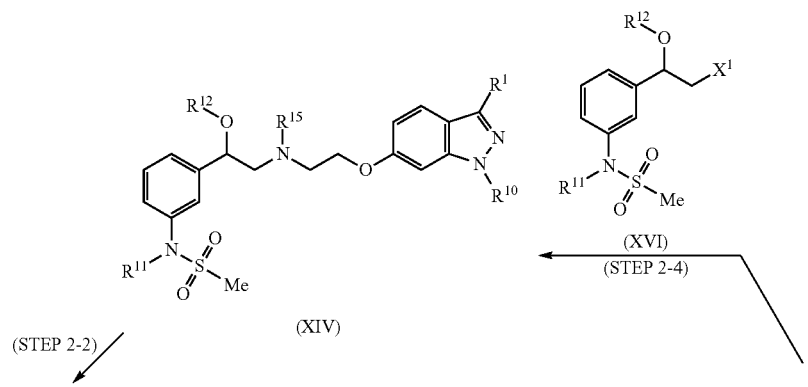

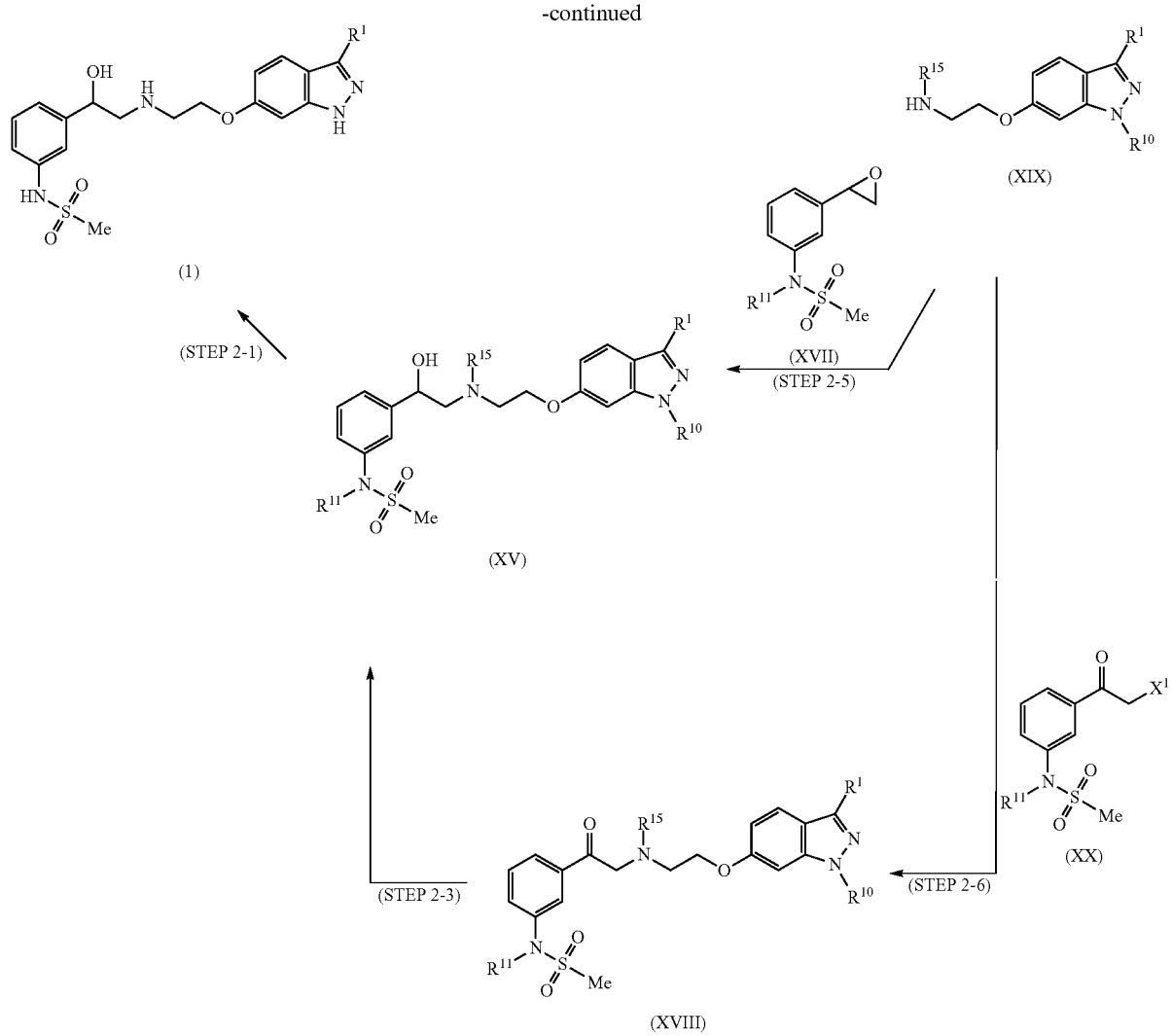

In each of the formulas in the scheme 2, $R^1$ has the same meaning as defined above; $R^{10}$ has the same meaning as defined as above, and is preferably a benzyl group, a tert-butoxycarbonyl group or a tetrahydropyranyl group, and more preferably a benzyl group; $R^{11}$ has the same meaning as defined above, and is preferably a benzyl group; $R^{12}$ has the same meaning as defined above, and is preferably a triethylsilyl group or a tert-butyldimethylsilyl group; $R^{15}$ represents a hydrogen atom or the protective group for an amino group mentioned above, and is preferably a benzyl group; and $X^1$ is a leaving group, and may be, for example, a chlorine atom, a bromine atom, an iodine atom, a p-toluenesulfonyloxy group, a methanesulfonyloxy group or the like, with a chlorine atom, a bromine atom or an iodine atom being preferred. Preferred combinations of $R^{10}$, $R^{11}$, $R^{12}$ and $R^{15}$ in the compound represented by the formula (XIV) include $R^{10}$ (benzyl group), $R^{11}$ (benzyl group) $R^{12}$ (triethylsilyl group), $R^{15}$ (benzyl group); $R^{10}$ (tert-butoxycarbonyl group), $R^{11}$ (benzyl group), $R^{12}$ (triethylsilyl group), $R^{15}$ (benzyl group); and $R^{10}$ (tetrahydropyranyl group), $R^{11}$ (benzyl group), $R^{12}$ (triethylsilyl group), $R^{15}$ (benzyl group); and a more preferred combination is $R^{10}$ (benzyl group), $R^{11}$ (benzyl group), $R^{12}$ (triethylsilyl group), $R^{15}$ (benzyl group). Preferred combinations of $R^{10}$, $R^{11}$ and $R^{15}$ in the compound represented by the formula (XV) include $R^{10}$ (benzyl group), $R^{11}$ (benzyl group), $R^{15}$ (benzyl group); $R^{10}$ (tert-butoxycarbonyl group), $R^{11}$ (benzyl group), $R^{15}$ (benzyl group); and a more preferred combination is $R^{10}$ (benzyl group), $R^{11}$ (benzyl group), $R^{15}$ (benzyl group). Preferred combinations of $R^{10}$ and $R^{15}$ in the compound represented by the formula (XIX) include $R^{10}$ (benzyl group), $R^{15}$ (benzyl group); $R^{10}$ (tert-butoxycarbonyl group), $R^{15}$ (benzyl group) and (tetrahydropyranyl group), $R^{15}$ (benzyl group), and a more preferred combination is $R^{10}$ (benzyl group), $R^{15}$ (benzyl group).

Process 2-1 (STEP 2-1)

A compound represented by the formula (1) can be produced by subjecting a compound represented by the formula (XV) to a deprotection reaction according to a known method, for example, a method described in "Protective Groups in Organic Synthesis", published by John Wiley and Sons (printed in 2007). As a suitable example, it is preferable to carry out the aforementioned deprotection reaction under acidic conditions, or to carry out the aforementioned deprotection reaction based on hydrogenolysis alone, or it is preferable to use these reactions in combination. At any rate, an appropriate deprotection reaction may be selected for various protective groups present in the compound represented by the formula (XV) For example, in the case of a compound represented by the formula (XV) with the combination of $R^{10}$ (benzyl group), $R^{11}$ (benzyl group) and $R^{15}$ (benzyl group), the deprotection reaction based on hydrogenolysis is preferred. The deprotection reaction based on hydrogenolysis may be a reaction carried out in an inert solvent added with a catalyst and hydrochloric acid, and in the presence of hydrogen gas. A method of obtaining the compound represented by the formula (1) by subjecting a compound represented by the formula (XV) to a reaction in an inert solvent added with a catalyst, and in the presence of hydrogen gas, to detach the protective groups $R^{11}$ (benzyl group) and $R^{15}$ (benzyl group), subsequently adding hydrochloric acid to the reaction solution, and subjecting the reaction solution to a reaction in the presence of hydrogen gas to detach the protective group $R^{10}$ (benzyl group), may also be listed as a particularly preferred deprotection method.

As the inert solvent, an alcohol such as methanol or ethanol may be used alone, or a solvent mixture of these may be used, and ethanol is preferred. As the catalyst, a palladium on carbon powder is preferred.

The amount of use of the catalyst is preferably from 2 to 40% by weight based on the compound represented by the formula (XV). The amount of use of hydrochloric acid is preferably from 0.15- to 3-fold the molar amount of the compound represented by the formula (XV). The hydrogen gas used is preferably at normal pressure or under pressure. The reaction temperature may be from 20° C. to the reflux temperature, and is preferably from 30° C. to 60° C. The reaction time may be from 0.5 hours to 24 hours, and is preferably from 0.5 hours to 10 hours.

Process 2-2 (STEP 2-2)

A compound represented by the formula (1) can be produced by subjecting a compound represented by the formula (XIV) to a deprotection reaction according to a known method, for example, a method described in "Protective Groups in Organic Synthesis", published by John Wiley and Sons (printed in 2007). As a suitable example, a deprotection reaction under acidic conditions may be performed, the deprotection reaction based on hydrogenolysis described above may be performed alone, or these reactions are used in combination. At any rate, an appropriate deprotection reaction may be selected for various protective groups present in the compound represented by the formula (XIV). For example, the deprotection reaction based on hydrogenolysis may be carried out by the method previously mentioned in the process 2-1, or the like.

Process 2-3 (STEP 2-3)

The process can be carried out according to the method described in WO 03/035620 (the disclosure of which is incorporated herein). That is, the compound represented by the formula (XV) is obtained by reacting a compound represented by the formula (XVIII) with a reducing agent in an inert solvent.

Examples of the inert solvent include an alcohol such as methanol, ethanol or 2-propanol; or tetrahydrofuran, dimethylformamide, dimethyl sulfoxide and the like. The reducing agent may be sodium borohydride, sodium cyanoborohydride, borane, or the like.

Unless asymmetrical reduction is particularly carried out, the compound represented by the formula (XV) obtainable by the present reduction reaction is obtained as a racemic mixture.

An example of the technique to obtain an optically active form is a technique of separating an optically active form by converting a racemic mixture into an addition salt with an optically active acid such as camphorsulfonic acid or mandelic acid, and then subjecting the acid addition salt to fractionated crystallization. Another example is a technique of separating an optically active form using a commercially available column for optical resolution. Alternatively, a technique of performing asymmetrical reduction may also be mentioned. Examples of the asymmetrical reduction reaction include a method described in WO 00/58287 (the disclosure of which is incorporated herein), that is, a method of performing asymmetrical reduction together with a hydrogen-supplying compound in the presence of a catalyst for asymmetrical reduction, or the like.

Process 2-4 (STEP 2-4)

The compound represented by the formula (XIV) is obtained by allowing a compound represented by the formula (XVI) and a compound represented by the formula (XIX) to react in an inert solvent, and if necessary, in the presence of a base added thereto.

As the inert solvent, N,N-dimethylformamide, N,N-dimethylacetamide, dimethylsulfoxide, acetonitrile or the like may be used singly, or a solvent mixture of these may be used, and N,N-dimethylformamide is preferred. The base may be a tertiary amine such as triethylamine, diisopropylethylamine, or 1,8-diazabicyclo[5,4,0]undecene; or an alkali metal compound such as potassium carbonate, sodium carbonate, cesium carbonate or sodium hydrogen carbonate, and triethylamine or diisopropylethylamine is preferred.

The amount of use of the base may be, for example, 0 to 10-fold the molar amount of the compound represented by the formula (XVI), and is preferably a 0 to 5-fold molar amount. The molar ratio of the compound represented by the formula (XVI) and the compound represented by the formula (XIX) is preferably such that compound represented by formula (XVI)/compound represented by formula (XIX)=0.2 to 5, and particularly preferably 0.5 to 2. The reaction temperature may be from −10° C. to the reflux temperature, and is preferably from 0° C. to 80° C. The reaction time may be from 0.1 to 48 hours, and is preferably from 2 to 20 hours.

If the reaction progress is slow, a catalyst such as potassium iodide or sodium iodide may be added as necessary, in an amount of 0.1- to 1.5-fold the molar amount of the compound represented by the formula (XVI).

Process 2-5 (STEP 2-5)

The compound represented by the formula (XV) is obtained by allowing a compound represented by the formula (XVII) and a compound represented by the formula (XIX) to react in an inert solvent.

As the inert solvent, an alcohol such as methanol, ethanol, 1-butanol, 2-butanol or 2-propanol, or N,N-dimethylformamide, N,N-dimethylacetamide, dimethylsulfoxide, acetonitrile or the like may be used alone, or a solvent mixture of these may be used, but 2-propanol is preferred.

The molar ratio of the compound represented by the formula (XVII) and the compound represented by the formula (XIX) is preferably such that compound represented by formula (XVII)/compound represented by formula (XIX)=0.2 to 5, and more preferably 0.75 to 1.5. The reaction temperature may be from −10° C. to the reflux temperature, and is preferably from 60° C. to the reflux temperature. The reaction time maybe from 0.5 to 48 hours, and is preferably from 12 to 48 hours.

A Lewis acid catalyst may also be added, if necessary.

Process 2-6 (STEP 2-6)

The compound represented by the formula (XVIII) is obtained by allowing a compound represented by the formula (XIX) and a compound represented by the formula (XX) to react in an inert solvent, and if necessary, in the presence of abase added thereto. As the inert solvent, N,N-dimethylformamide, N,N-dimethylacetamide, dimethyl sulfoxide, acetonitrile or the like may be used alone, or a solvent mixture of these may be used, but N,N-dimethylformamide may be mentioned as a preferred example. Examples of the base include an organic tertiary amine such as triethylamine, diisopropylethylamine or 1,8-diazabiccylo[5,4,0]undecene; or an alkali metal compound such as potassium carbonate, sodium carbonate, cesium carbonate or sodium hydrogen carbonate, and triethylamine or diisopropylethylamine is preferred.

The amount of use of the base may be, for example, 0 to 10-fold the molar amount of the compound represented by the formula (XX), and is preferably 0 to 5-fold. The molar ratio of the compound represented by the formula (XIX) and the compound represented by the formula (XX) is preferably such that compound represented by formula (XIX)/compound represented by formula (XX)=0.2 to 5, and more preferably 0.5 to 2. The reaction temperature may be from −10° C. to the reflux temperature, and is preferably from 0 to 80° C. The reaction time may be from 0.5 to 48 hours, and is preferably 2 hours to 20 hours.

If the reaction progress is slow, a catalyst such as potassium iodide or sodium iodide may be added as necessary, in an amount of 0.1- to 1.5-fold the molar amount of the compound represented by the formula (XX).

The compound of the present invention thus obtainable, and various raw material compounds and intermediates can be isolated and purified according to conventional methods such as extraction, distillation, chromatography and crystallization.

Among the compounds used in the scheme 1 or 2, the compounds represented by formula (XI), (XII), (VI) (XVII), (XIX) and (XX) are can be obtained by the methods shown in scheme 3 to scheme 12. In the following scheme 3 to scheme 12, the expression "STEP" has the same meaning as defined above.

In each of the formulas in the scheme 3, $R^{11}$ has the same meaning as defined above, and is preferably a benzyl group; and $X^1$ has the same meaning as defined above, and is preferably a chlorine atom.

Process 3-1 (STEP 3-1)

A compound (XXIII) is obtained by, for example, allowing 3-aminoacetophenone (XXI) and methanesulfonyl chloride (XXII), which are commercially available from Wako Pure Chemical Industries, Ltd. and the like, to react in an inert solvent in the presence of a base added thereto.

Examples of the inert solvent include a hydrocarbon-based solvent such as toluene; a halogen-based hydrocarbon such as dichloromethane, chloroform or 1,2-dichloroethane; acetonitrile, and the like. The base may be an organic base such as triethylamine, N,N-diisopropylethylamine or pyridine; or an inorganic base such as potassium carbonate or sodium hydrogen carbonate.

The amount of use of the base may be 1- to 6-fold the molar amount of 3-aminoacetophenone (XXI), and is preferably a 1- to 3-fold molar amount. The amount of use of methanesulfonyl chloride (XXII) may be usually 1- to 6-fold the molar amount of 3-aminoacetophenone (XXI), and is preferably a 1- to 3-fold molar amount. The reaction temperature may be from −10° C. to 60° C., and is preferably from −10° C. to 30° C. The reaction time may be from 0.1 to 48 hours, and is preferably from 0.2 to 24 hours.

Process 3-2 (STEP: 3-2)

A compound represented by the formula (XXIV) is obtained by performing a protection reaction of a sulfonamide group in the compound (XXIII) according to a known method such as, for example, a method described in "Protective Groups in Organic Synthesis", published by John Wiley and Sons (printed in 2007). A suitable example may be a method of obtaining the compound represented by the for- Scheme 3

[Chemical Formula 15]

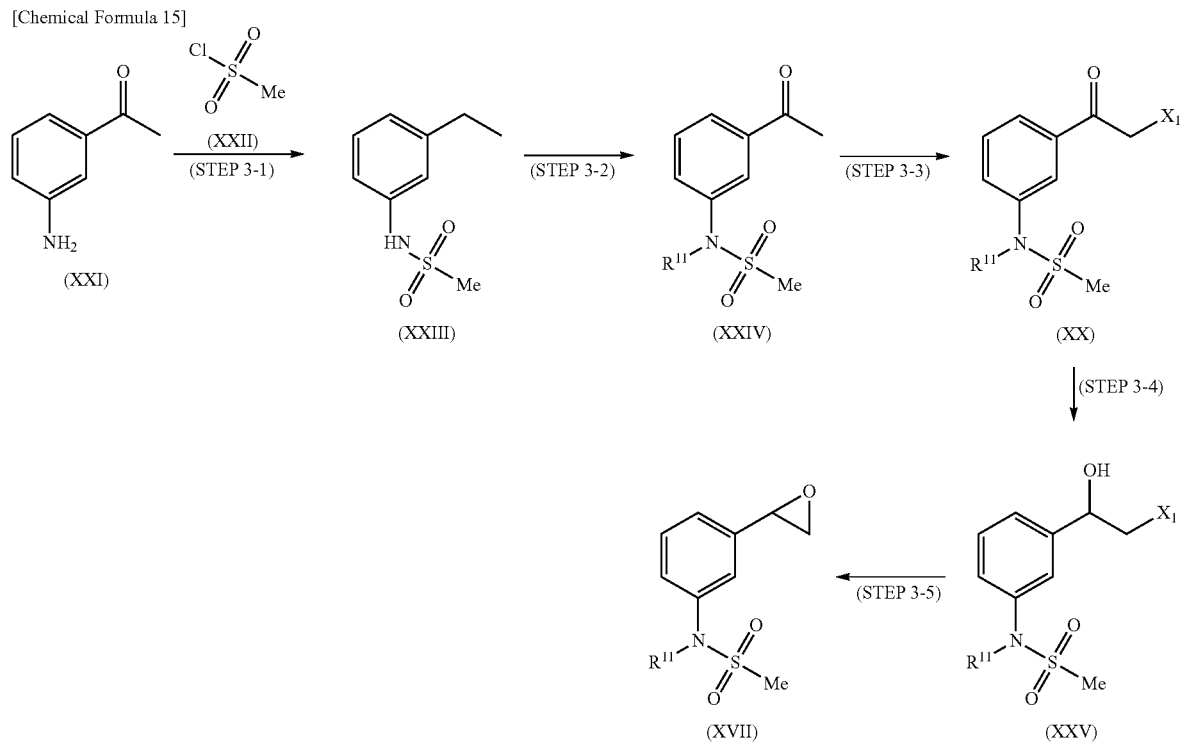

mula (XXIV) by allowing, when R[11] is a benzyl group, the compound (XXIII) and a benzylating agent to react in an inert solvent and in the presence of a base and a catalyst added thereto.

As the inert solvent, a ketone-based solvent such as acetone, an aprotic polar solvent such as N,N-dimethylformamide, or the like may be used alone, or a solvent mixture of these may be used. The benzylating agent may be benzyl iodide, benzyl bromide, benzyl chloride or the like, and is preferably benzyl chloride. The base may be an organic base such as triethylamine, N,N-diisopropylethylamine or pyridine; or an inorganic base such as potassium carbonate or sodium hydrogen carbonate, and the base is preferably potassium carbonate. The catalyst may be potassium iodide, sodium iodide or the like, and is preferably sodium iodide.

The amount of use of the base is preferably 1- to 5-fold the molar amount of the compound (XXIII). The amount of use of the catalyst is preferably 0.005- to 0.05-fold the molar amount of the compound (XXIII). The reaction temperature may be from 0° C. to the reflux temperature, and is preferably from 50° C. to 100° C. The reaction time is preferably from 1 to 24 hours.

Process 3-3 (STEP 3-3)

The compound represented by the formula (XX) is obtained by allowing a compound represented by the formula (XXIV) to react with a halogenating agent in an inert solvent, and if necessary, in the presence of methanol further added thereto.

The inert solvent may be a halogen-based hydrocarbon such as dichloromethane, 1, 2-dichloroethane or chloroform, and is preferably dichloromethane. The halogenating agent may be chlorine gas, bromine gas, sulfuryl chloride or the like, and is preferably sulfuryl chloride.

The amount of use of the halogenating agent is preferably 1- to 2-fold the molar amount of the compound represented by the formula (XXIV). The amount of use of methanol may be 0 to 5-fold the molar amount of the compound represented by the formula (XXIV), and is preferably a 0.1- to 2-fold molar amount. The reaction temperature is preferably from –10° C. to 50° C. The reaction time, including the time for dropwise addition of the halogenating agent and methanol, is preferably from 1 to 10 hours.

Process 3-4 (STEP 3-4)

A compound represented by the formula (XXV) is obtained by reacting the compound represented by the formula (XX) with a reducing agent in an organic solvent.

The organic solvent may be, for example, an alcohol solvent such as methanol or ethanol; or ethers solvent such as tetrahydrofuran. The reducing agent may be, for example, sodium borohydride.

Unless an asymmetrical reduction reaction is particularly carried out, the compound represented by the formula (XXV) obtainable through this reduction reaction is obtained as a racemic mixture.

The technique of obtaining an optically active form may be a technique of performing an asymmetrical reduction reaction. The asymmetrical reduction reaction can be performed according to the methods described in conventional literatures in chemistry, for example, a method described in "Lectures on Experimental Chemistry, 4th Edition" (edited by the Chemical Society of Japan, published by Maruzen Co., Ltd.), Vol. 26, pp. 23-68, or a method described in the reference documents cited therein. As a suitable example, there may be mentioned a method of obtaining the compound represented by the formula (XXV) by allowing the compound represented by the formula (XX) to react with a hydrogen source in an organic solvent, in the presence of a catalyst added thereto.

As the organic solvent, an alcohol solvent such as methanol, ethanol or 2-propanol; ethers solvent such as tetrahydrofuran; a halogen-based hydrocarbon solvent such as dichloromethane, 1,2-dichloroethane or chloroform; an ester solvent such as ethyl acetate; acetonitrile or the like may be used alone, or a solvent mixture of these may be used. The hydrogen source may be hydrogen gas, a formic acid-triethylamine complex or the like, and is preferably a formic acid-triethylamine complex. The catalyst may be an arene-chiral diamine-ruthenium (II) complex or the like, and a [(s,s)-N-(p-toluenesulfonyl)-1,2-diphenylethylenediamine]-p-cymene-ruthenium complex, a [(s,s)-N-(p-toluenesulfonyl)-1,2-diphenylethylenediamine]-mesitylene-ruthenium complex, or the like is preferred.

The amount of use of the formic acid-triethylamine complex is preferably 1- to 10-fold the molar amount of the compound represented by the formula (XX), in terms of the mole number of formic acid. The ratio of the formic acid-triethylamine complex is preferably such that the mole number of formic acid is 1- to 10-fold the mole number of triethylamine. The amount of use of the catalyst may be such that compound represented by formula (XXV)/amount of catalyst=S/C=10 to 10000 by mole, and S/C=100 to 1000 by mole is preferable. The reaction temperature may be from 0° C. to the reflux temperature, and is preferably from 20° C. to the reflux temperature. The reaction time, including the time for dropwise addition of the formic acid-triethylamine complex, may be from 0.1 hours to 24 hours, and is preferably from 0.5 hours to 12 hours.

Process 3-5 (STEP 3-5)

The compound represented by the formula (XVII) is obtained by allowing the compound represented by the formula (XXV) to react with a base added thereto, in an inert solvent.

As the inert solvent, water, an alcohol solvent such as methanol or ethanol; N,N-dimetylformamide, tetrahydrofuran, 1,4-dioxane, acetone, 2-butanone, dimethyl sulfoxide, acetonitrile or the like may be used alone, or a solvent mixture of these may be used, and methanol is preferred. Examples of the base include alkali metal compounds such as potassium carbonate, sodium carbonate, cesium carbonate, sodium hydrogen carbonate, potassium hydroxide, sodium hydroxide, sodium methoxide, a 28 sodium methoxide-methanol solution, and potassium t-butoxide; and organic tertiary amines such as pyridine, 4-dimethylaminopyridine, 1,8-diazabicyclo[5,4,0]undecene, trimethylamine and triethylamine.

The amount of use of the base is preferably 1- to 10-fold the molar amount of the compound represented by the formula (XXV). The reaction temperature may be from –40° C. to the reflux temperature, and is preferably from –10° C. to 50° C. The reaction time may be from 0.1 hour to 48 hours, and is preferably from 2 to 20 hours.

Scheme 4

[Chemical Formula 16]

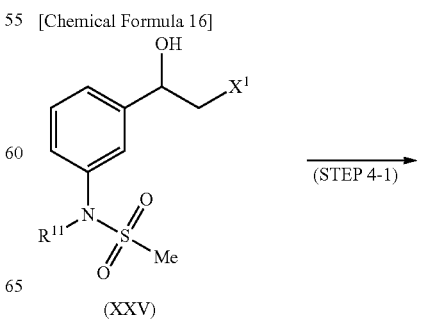

(XXV)

(STEP 4-1)

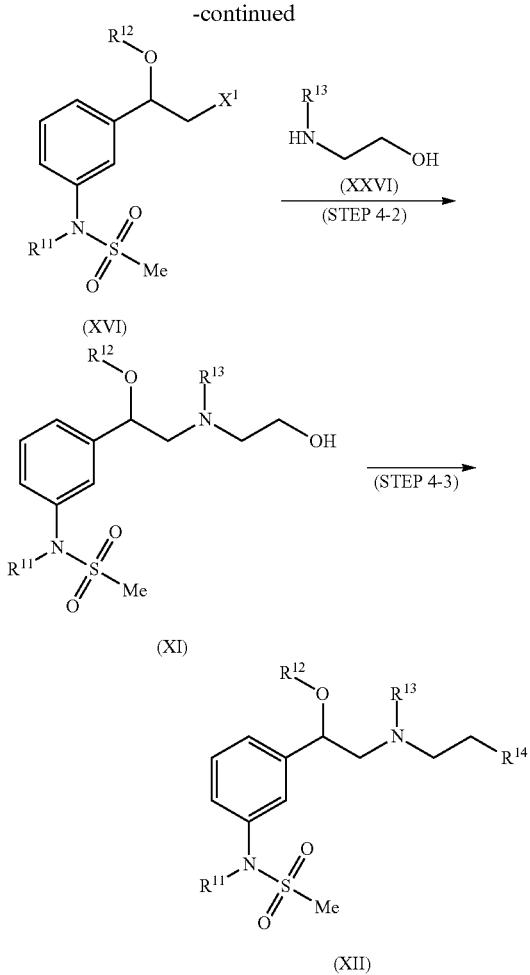

In each of the formulas in the scheme 4, $R^{11}$ has the same meaning as defined above, and is preferably a benzyl group or a tert-butoxycarbonyl group; $R^{12}$ has the same meaning as defined above, and is preferably a triethylsilyl group or a tert-butyldimethylsilyl group; $R^{13}$ has the same meaning as defined above, and is preferably a hydrogen atom, a benzyl group or a tert-butoxycarbonyl group; $R^{14}$ has the same meaning as defined above, and is preferably a p-toluenesulfonyloxy group, a methanesulfonyloxy group or a bromine atom; and $X^1$ has the same meaning as defined above, and may be a chlorine atom, a bromine atom or an iodine atom, with an iodine atom being preferred. A preferred combination of $R^{11}$, $R^{12}$ and $R^{13}$ in the compound represented by the formula (XI) is $R^{11}$ (benzyl, group) $R^{12}$ (triethylsilyl group), $R^{13}$ (benzyl group); or $R^{11}$ (tert-butoxycarbonyl group), $R^{12}$ (triethylsilyl group), $R^{13}$ (tert-butoxycarbonyl group).

Process 4-1 (STEP 4-1)

A compound represented by the formula (XVI) can be obtained by performing the protection reaction of a hydroxyl group of the compound represented by the formula (XXV), which can be obtained by the production method described in the scheme 3 or the like, according to a known method such as, for example, a method described in "Protective Groups in Organic Synthesis", published by John Wiley and Sons (printed in 2007). A suitable example may be a method of obtaining the compound represented by the formula (XVI) by reacting the compound represented by the formula (XXV) with a silylating agent in an inert solvent in the presence of a base added thereto. The inert solvent may be N,N-dimethylformamide or the like. The base maybe imidazole or the like. The silylating agent may be triethylchlorosilane, tert-butyldimethylchlorosilane or the like.

Process 4-2 (STEP 4-2)

The process can be carried out according to the method described in WO 03/035620. That is, a compound represented by the formula (XI) is obtained by allowing the compound represented by the formula (XVI) and a compound represented by the formula (XXVI) to react in a solventless state or in an inert solvent, and if necessary, in the presence of a base added thereto.

As the inert solvent, N,N-dimethylformamide, N,N-dimethylacetamide, dimethyl sulfoxide, acetonitrile or the like maybe used alone, or a solvent mixture of these may be used, but N,N-dimethylformamide is preferred. Examples of the base include tertiary amines such as triethylamine, diisopropylethylamine and 1,8-diazabicyclo[5,4,0]undecene; and alkali metal compounds such as potassium carbonate, sodium carbonate, cesium carbonate and sodium hydrogen carbonate, and triethylamine or diisopropylethylamine is preferred.

The amount of use of the base may be 0 to 10-fold the molar amount of the compound represented by the formula (XVI), and is preferably a 1- to 5-fold molar amount The amount of use of the compound represented by the formula (XXVI) may be 1- to 10-fold the molar amount of the compound represented by the formula (XVI), and is preferably a 1- to 5-fold molar amount. The reaction temperature may be from $-10°$ C. to the reflux temperature, and is preferably from $50°$ C. to the reflux temperature. The reaction time may be from 0.5 to 48 hours, and is preferably from 1 to 24 hours.

If the reaction progress is slow, a catalyst such as potassium iodide or sodium iodide may also be added, if necessary, in an amount of 0.1- to 1.5-fold the molar amount of the compound represented by the formula (XVI).

Furthermore, as exemplified in Reference Example 57 and Reference Example 58, modification with appropriate protective groups is also acceptable.

Process 4-3 (STEP 4-3)

A compound represented by the formula (XII) is obtained by subjecting the compound represented by the formula (XI) to a reaction according to a method described in conventional literatures in chemistry such as, for example, a method described in "Lectures on Experimental Chemistry, $4^{th}$ Edition" (edited by the Chemical Society of Japan, published by Maruzen Co., Ltd.), Vol. 19, pp. 438-446, or a method described in the reference documents cited therein. As a suitable example, there may be mentioned a method of obtaining the compound represented by the formula (XII) by allowing the compound represented by the formula (XI) to react in an organic solvent, with a halogenating reagent and a phosphine added thereto.

As the inert solvent, a halogenated hydrocarbon such as dichloromethane or chloroform; ethers such as tetrahydrofuran; a hydrocarbon-based solvent such as benzene or toluene; or the like may be used alone, or a solvent mixture of these may be used, but dichloromethane is preferred. Examples of the halogenating reagent include carbon tetrachloride, N-chlorosuccinimide, N-bromosuccinimide, carbon tetrachloride, N-iodosuccinimide, and the like, but N-bromosuccinimide is preferred. Examples of the phosphine include triphenylphosphine, n-butylphosphine, and the like, but triphenylphosphine is preferred.

The amount of use of the halogenating regent is preferably 1- to 10-fold the molar amount of the compound represented by the formula (XI). The amount of use of the phosphine is preferably 1- to 10-fold the molar amount of the compound represented by the formula (XI). The reaction temperature may be from −10° C. to the reflux temperature, and is preferably from −10° C. to 40° C. The reaction time may be from 0.1 hours to 24 hours, and is preferably from 0.5 to 12 hours.

Furthermore, a compound represented by the formula (XII) can also be obtained by reacting a compound represented by the formula (XI) with a halogenating reagent in an inert solvent; and if necessary, in the presence of a base added to.

As the inert solvent, a halogenated hydrocarbon such as dichloromethane or chloroform; ethers such as tetrahydrofuran; a hydrocarbon-based solvent such as benzene or toluene; or the like may be used alone, or a solvent mixture of these may be used. Examples of the halogenating reagent include thionyl chloride, thionyl bromide, and the like. Examples of the base include organic tertiary amines such as triethylamine, diisopropylethylamine, 1,8-diazabicyclo[5,4,0]undecene; and the like.

The amount of use of the halogenating reagent is preferably 1- to 10-fold the molar amount of the compound represented by the formula (XI). The amount of use of the base may be 0 to 10-fold the molar amount of the compound represented by the formula (XI), and is preferably a 1- to 10-fold molar amount. The reaction temperature may be from −10° C. to the reflux temperature, and is preferably from −10° C. to 40° C. The reaction time may be from 0.1 hours to 24 hours, and is preferably from 0.5 hours to 12 hours.

toxycarbonyl group or a tetrahydropyranyl group, and more preferably a benzyl group; $R^{15}$ has the same meaning as defined above, and is preferably a benzyl group; $R^{16}$ represents a hydrogen atom or a protective for an amino group, and when $R^{16}$ is a protective group for an amino group, it is preferably a group identical with $R^{15}$, or a group that can be detached selectively to $R^{15}$. In some embodiments, a preferred combination is such that $R^{15}$ is a group that can be detached selectively to $R^{16}$. $X^2$ represents a leaving group, and may be a chlorine atom, a bromine atom, an iodine atom, a p-toluenesulfonyloxy group, a methanesulfonyloxy group, or the like. A preferred combination of $R^{15}$ and $R^{16}$ for the compound represented by the formula (XXVII) is $R^{15}$ (benzyl group), $R^{16}$ (benzyl group). Preferred combinations of $R^{10}$, $R^{15}$ and $R^{16}$ for the compound represented by the formula (XXIX) include $R^{10}$ (benzyl group), $R^{15}$ (benzyl group), $R^{16}$ (benzyl group); $R^{10}$ (tert-butoxycarbonyl group), $R^{15}$ (benzyl group), $R^{16}$ (benzyl group); and $R^{10}$ (tetrahydropyranyl group), $R^{15}$ (benzyl group), $R^{16}$ (benzyl group), and a more preferred combination is $R^{10}$ (benzyl group), $R^{15}$ (benzyl group), $R^{16}$ (benzyl group). A preferred combination of $R^{10}$ and $R^{15}$ for the compound represented by the formula (XIX) is $R^{10}$ (benzyl group), $R^{15}$ (benzyl group).

For example, a compound represented by the formula (XXVII) with $R^{15}$ (benzyl group) and $R^{16}$ (benzyl group); a compound represented by the same formula with $R^{15}$ (benzyl group) and $R^{16}$ (hydrogen atom); a compound represented by the same formula with $R^{15}$ (hydrogen atom) and $R^{16}$ (hydrogen atom); and the like are available from Tokyo Chemical Industry Co., Ltd., or the like.

Process 5-1 (STEP 5-1)

A compound represented by the formula (XXVIII) is obtained by reacting a compound represented by the formula (XXVII) with a base and a sulfonylating reagent added thereto, in an inert solvent.

As the inert solvent, a halogenated hydrocarbon such as dichloromethane or chloroform; or ethers such as tetrahydrofuran may be used alone, or a solvent mixture of these may be used. Examples of the base include organic tertiary amines such as pyridine, triethylamine, diisopropylethylamine, and 1,8-diazabicyclo[5,4,0]undecene; and alkali metal compounds such as potassium carbonate, sodium carbonate, cesium carbonate and sodium hydrogen carbonate, and triethylamine is preferred. The sulfonylating reagent may be p-toluenesulfonyl chloride, methanesulfonyl chloride, or the like.

The amount of use of the sulfonylating reagent may be 1- to 10-fold the molar amount of the compound represented by the formula (XXVII), and is preferably a 1- to 2-fold molar amount. The amount of use of the base may be 1- to 10-fold the molar amount of the compound represented by the formula (XXVII), and is preferably a 1- to 2-fold molar amount. The reaction temperature may be from −20° C. to the reflux temperature, and is preferably from −10° C. to 50° C. The reaction time may be usually from 0.1 to 24 hours, and is preferably from 1 to 10 hours, including the time for dropwise addition of the reagent.

A compound represented by the formula (XXVIII) can be obtained by subjecting a compound represented by the formula (XXVII) to a reaction according to a method described in conventional literatures in chemistry such as, for example, a method described in "Lectures on Experimental Chemistry, 4$^{th}$ Edition" (edited by the Chemical Society of Japan, published by Maruzen Co., Ltd.), Vol. 19, pp. 438-446, or a method described in the reference documents cited therein. As a suitable example, there may be mentioned a method of obtaining the compound represented by the formula (XX-

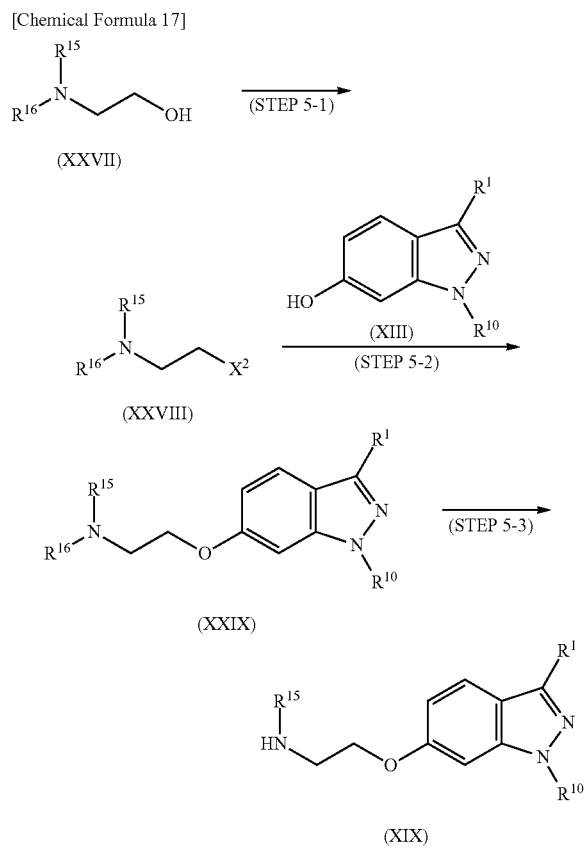

Scheme 5

[Chemical Formula 17]

(XXVII)

(XXVIII)

(XXIX)

(XIX)

In each of the formulas in the scheme 5, $R^1$ has the same meaning as defined above; $R^{10}$ has the same meaning as defined above, and is preferably a benzyl group, a tert-bu- VIII) by reacting the compound represented by the formula (XXVII) with a halogenating reagent and a phosphine added thereto, in an inert solvent.

As the inert solvent, a halogenated hydrocarbon such as dichloromethane or chloroform; ethers such as tetrahydrofuran; a hydrocarbon-based solvent such as benzene or toluene; or the like may be used alone, or a solvent mixture of these may be used. The halogenating reagent may be carbon tetrachloride, N-chlorosuccinimide, N-bromosuccinimide, carbon tetrabromide, N-iodosuccinimide, or the like. The phosphine may be triphenylphosphine, n-butylphosphine or the like, and is triphenylphosphine.

The amount of use of the halogenating reagent is preferably 1- to 10-fold the molar amount of the compound represented by the formula (XXVII). The amount of use of the phosphine is preferably 1- to 10-fold the molar amount of the compound represented by the formula (XXVII). The reaction temperature may be from −10° C. to the reflux temperature, and is preferably from −10° C. to 40° C. The reaction time may be from 0.1 hours to 24 hours, and is preferably from 0.5 to 12 hours.

Furthermore, in a separate method, the compound represented by the formula (XXVIII) can also be obtained by reacting the compound represented by the formula (XXVII) with a halogenating reagent in an inert solvent, and if necessary, in the presence of a base added thereto.

As the inert solvent, a halogenated hydrocarbon such as dichloromethane or chloroform; ethers such as tetrahydrofuran; a hydrocarbon-based solvent such as benzene or toluene; or the like may be used singly, or a solvent mixture of these may be used.

The halogenating reagent may be thionyl chloride, thionyl bromide, phosphorus tribromide, or the like. The base may be an organic tertiary amine such as pyridine, 4-dimethylaminopyridine, triethylamine, diisopropylethylamine, or 1,8-diazabicyclo[5,4,0]undecene; or the like.

The amount of use of the halogenating reagent is preferably 1- to 10-fold the molar amount of the compound represented by the formula (XXVII). The amount of use of the base may be 0 to 10-fold the molar amount of the compound represented by the formula (XXVII), and is preferably a 1- to 10-fold molar amount. The reaction temperature may be from −10° C. to the reflux temperature, and is preferably from −10° C. to 40° C. The reaction time maybe from 0.1 hours to 24 hours, and is preferably from 0.5 hours to 12 hours.

Process 5-2 (STEP 5-2)

A compound represented by the formula (XXIX) is obtained by allowing a compound represented by the formula (XIII) and a compound represented by the formula (XXVIII) to react in an inert solvent in the presence of a base added thereto.

As the inert solvent, tetrahydrofuran, N,N-dimethylformamide, N,N-dimethylacetamide, dimethyl sulfoxide, acetonitrile or the like may be used alone, or a solvent mixture of these may be used. Examples of the base include alkali metal compounds such as potassium carbonate, sodium carbonate, cesium carbonate, sodium hydrogen carbonate, potassium hydroxide, sodium hydroxide, sodium methoxide, a 28% sodium methoxide-methanol solution and potassium t-butoxide; and organic tertiary amines such as pyridine, 4-dimethylaminopyridine, 1,6-diazabicyclo[5,4,0]undecene, trimethylamine and triethylamine.

The amount of use of the base may be 1- to 10-fold the molar amount of the compound represented by the formula (XIII), and is preferably a 1- to 5-fold molar amount. The amount of use of the compound represented by the formula (XXVIII) maybe 1- to 10-fold the molar amount of the compound represented by the formula (XIII), and is preferably a 1- to 3-fold molar amount. The reaction temperature may be from −20° C. to the reflux temperature, and is preferably from 0° C. to 60° C. The reaction time may be from 0.1 hours to 48 hours, and is preferably 2 to 24 hours, including the time for dropwise addition of the reagent.

If the reaction progress is slow, a catalyst such as potassium iodide or sodium iodide may also be added, if necessary, in an amount of 0.1- to 1.5-fold the molar amount of the compound represented by the formula (XXVIII).

Process 5-3 (STEP 5-3)

When removal of the protective group of the compound represented by the formula (XXIX) is necessary, a deprotection reaction for $R^{16}$ may be carried out selectively to $R^{10}$ and $R^{15}$, according to a known method such as, for example, a method described in "Protective Groups in Organic Synthesis", published by John Wiley and Sons (printed in 2007). In other embodiments, a deprotection reaction for $R^{15}$ may be carried out selectively to $R^{10}$ and $R^{16}$. For example, there may be mentioned certain conditions in which, when $R^{15}$ and $R^{16}$ are all benzyl groups in the formula (XXIX), one of the benzyl groups of $R^{15}$ and $R^{16}$ is detached selectively to the other. As an example of such conditions, there may be mentioned a method of obtaining a compound represented by the formula (XIX) by carrying out the reaction in an inert solvent and in the presence of hydrogen gas at normal pressure or under pressure, while controlling the reaction by adding a catalyst or hydrochloric acid.

The inert solvent may be an alcohol-based solvent such as methanol or ethanol, and ethanol is preferred. The catalyst is preferably a palladium on carbon powder.

The amount of use of the catalyst may be 1 to 40% by weight, and preferably 5 to 40% by weight, based on the compound represented by the formula (XXIX). The amount of use of hydrochloric acid may be 0.05- to 3-fold the molar amount of the compound represented by the formula (XXIX), and is preferably a 0.1- to 1-fold molar amount. The reaction temperature may be from 0° C. to 60° C. and is preferably from 0° C. to 40° C. The reaction time may be from 0.1 hours to 24 hours, and is preferably from 0.1 to 12 hours.

The compound represented by the formula (XXIX) may also be obtained according to the method described in scheme 6.

Scheme 6

[Chemical Formula 18]

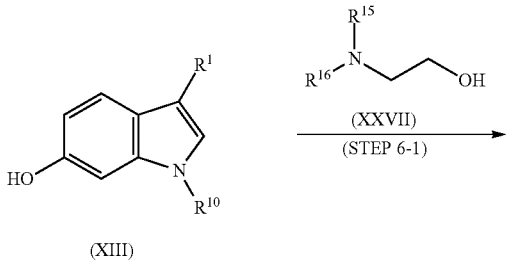

(XIII)

(XXVII)

(STEP 6-1)

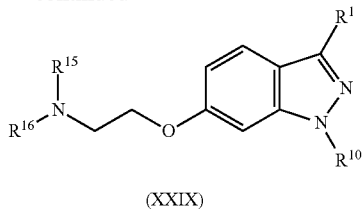

(XXIX)

In each of the formulas in the scheme 6, $R^1$, $R^{10}$, $R^{15}$ and $R^{16}$ have the same meanings as defined above.

Process 6-1 (STEP 6-1)

The compound represented by the formula (XXIX) can be obtained by allowing a compound represented by the formula (XIII) and a compound represented by the formula (XXVII) to react in an inert solvent, in the presence of a phosphine and an azo compound added thereto.

As the inert solvent, ethers such as diethyl ether, tetrahydrofuran or dimethoxyethane; a halogen-based solvent such as methylene chloride; or benzene analogs such as benzene, toluene or xylene may be listed, and toluene or tetrahydrofuran is preferred. The phosphine may be triphenylphosphine or tributylphosphine, and is preferably tirphenylphosphine. The azo compound may be diethyl azodicarboxylate, diisopropyl azodicarboxylate, N,N,N',N'-tetramethylazodicarboxamide, 1,1'-(azodicarbonyl)dipiperidine, N,N,N',N'-tetraisopropylcarboxamide, or the like, and N,N,N',N'-tetramethylazodicarboxamide is preferred.

The amount of use of the phosphine may be 1- to 10-fold the molar amount of the compound represented by the formula (XIII), and is preferably a 1- to 5-fold molar amount. The amount of use of the azo compound may be 1- to 10-fold the molar amount of the compound represented by the formula (XIII), and is preferably a 1- to 5-fold molar amount. The amount of use of the compound represented by the formula (XXVII) may be 1- to 10-fold the molar amount of the compound represented by the formula (XIII), and is preferably a 1- to 5-fold molar amount. The reaction temperature may be usually from −20° C. to the reflux temperature, and is preferably 0° C. to 30° C. The reaction time may be from 1 to 48 hours, and is preferably from 3 to 24 hours.

—$CH_2OMe$ or —$CH_2CH_2CONMe_2$; $X^3$ represents a leaving group, and is preferably a bromine atom, an iodine atom or the like; $R^{10}$ has the same meaning as defined above; and $R^{17}$ is a protective group for a hydroxyl group, and is preferably a methyl group.

In addition, among the compounds represented by the formula (XXXI), only a compound having a methyl group for $R^{17}$ is available from Sigma-Aldrich Co. or the like.

Process 7-1 (STEP 7-1)

A compound represented by the formula (XXXI) is obtained by performing a protection reaction for a hydroxyl group of the compound (XXX), which is available from Tokyo Chemical Industry Co., Ltd. or the like, according to a known method such as, for example, a method described in "Protective Groups in Organic Synthesis", published by John Wiley and Sons (printed in 2007).

Process 7-2 (STEP 7-2)

A compound represented by the formula (XXXII) is obtained by subjecting the compound represented by the formula (XXXI) to a reaction according to a method described in conventional literatures in chemistry, for example, a method described in "Lectures on Experimental Chemistry, $4^{th}$ Edition" (edited by the Chemical Society of Japan, published by Maruzen Co., Ltd.), Vol. 19, pp. 416-482, or a method described in the reference documents cited therein. As a suitable example, there may be mentioned a method of obtaining the compound represented by the formula (XXXII) by reacting the compound represented by the formula (XXXI), with a halogenating reagent and a radical initiating reagent added thereto, in an inert solvent. Furthermore, this reaction may also be performed under irradiation of a radiation, instead of adding a radical initiating reagent.

As the inert solvent, benzene analogs such as benzene or chlorobenzene; a halogen-based hydrocarbon such as carbon tetrachloride; or the like may be used alone, or a solvent mixture of these may be used, and carbon tetrachloride is preferred. The halogenating reagent may be bromine, N-bromosuccinimide, or the like, and N-bromosuccinimide is preferred. The radical initiating reagent may be azobisbutyronitrile, benzoyl peroxide or the like, and benzoyl peroxide is preferred.

Scheme 7

[Chemical Formula 19]

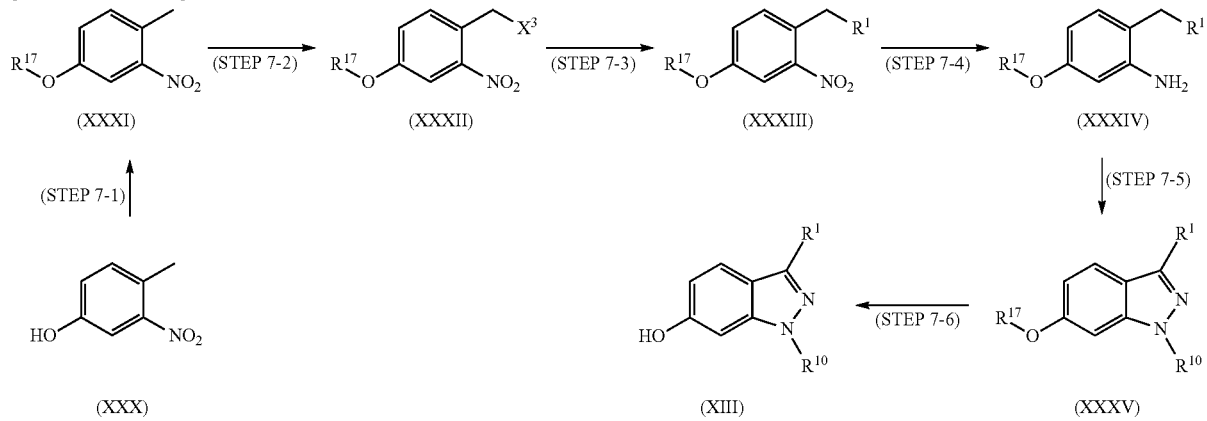

In each of the formulas in the scheme 7, $R^1$ has the same meaning as defined above, and represents a group other than The amount of use of the halogenating reagent is preferably 1- to 10-fold the molar amount of the compound represented by the formula (XXXII). The amount of use of the radical initiating reagent is preferably 1- to 10-fold the molar amount of the compound represented by the formula (XXXII). The reaction temperature may be from −20° C. to the reflux temperature, and is preferably from 40° C. to the reflux temperature. The reaction time may be from 0.1 hours to 48 hours, and is preferably from 5 hours to 48 hours.

Process 7-3 (STEP 7-3)

A compound represented by the-formula (XXXIII) is obtained by allowing the compound represented by the formula (XXXII) to react in an inert solvent, with a nucleophilic reagent for introducing group $R^1$, and if necessary, in the presence of a catalyst added thereto.

The nucleophilic reagent for introducing group $R^1$ can be obtained by purchasing a commercially available product of a Grignard reagent, an organozinc reagent, an organoboronic acid reagent, an organoboronic acid ester reagent, an organolithium reagent, an organocopper reagent, or an organotin reagent, or by preparing the reagent according to a conventional method. The catalyst may be a palladium complex, a nickel complex, a copper complex, a copper salt, a copper powder, a lithium salt, or the like.

Furthermore, in the case of a compound represented by the formula (XXXII) with $R^1$ representing —$CF_3$, the compound represented by the formula (XXXIII) can be obtained by performing the reaction according to a method described in conventional literatures in chemistry, for example, a method described in "OrganoFluorine Chemistry" (written by Kenji Uneyama, published by Blackwell Publishing Co.), pp. 292-300, or a method described in the reference documents cited therein. As a suitable example thereof, there may be mentioned a method of obtaining the compound represented by the formula (XXXIII), by allowing the compound represented by the formula (XXXII) to react in an inert solvent, in the presence of a trifluoromethylating agent and a catalyst added thereto.

Examples of the inert solvent include aprotic polar solvents such as N,N-dimethylformamide, N,N-dimethylacetamide, dimethyl sulfoxide and N-methylpyrrolidone; and the like, and N,N-dimethylformamide is preferred. Examples of the trifluoromethylating reagent include trifluoromethyl iodide, sodium trifluoroacetate, methyl 2,2-difluoro-2-(fluorosulfonyl)acetate, trifluoromethyl-trimethylsilane, trifluoromethyl-triethylsilane, methyl chlorodifluoroacetate-potassium fluoride, and the like, and methyl 2,2-difluoro-2-(fluorosulfonyl) acetate is preferred. The catalyst may be a copper complex, a copper salt such as copper iodide or copper bromide, or a copper powder, and copper iodide is preferred.

The amount of use of the trifluoromethylating reagent is preferably 1- to 10-fold the molar amount of the compound represented by the formula (XXXII). The amount of use of the catalyst may be 0.001- to 10-fold the molar amount of the compound represented by the formula (XXXII), and is preferably a 0.1- to 1-fold molar amount. The reaction temperature may be from 0° C. to the reflux temperature, and is preferably from 40° C. to 130° C. The reaction time may be from 0.1 to 48 hours, and is preferably from 1 to 12 hours.

Process 7-4 (STEP 7-4)

A compound represented by the formula (XXXIV) is obtained by subjecting the compound represented by the formula (XXXIII) to a reaction according to a method described in conventional literatures in chemistry, for example, a method described in "Lectures on Experimental Chemistry, $4^{th}$ Edition" (edited by the Chemical Society of Japan, published by Maruzen Co., Ltd.), Vol. 26, pp. 159-266, or a method described in the reference documents cited therein. As a suitable example, there may be mentioned a method of obtaining the compound represented by the formula (XXXIV) by allowing the compound represented by the formula (XXXIII) to react in an inert solvent, in the presence of a catalyst and a hydrogen source added thereto.

The inert solvent may be an alcohol such as methanol or ethanol, and methanol is preferred. The catalyst may be Raney nickel, palladium on carbon, or the like, and palladium on carbon is preferred. The hydrogen source may be hydrogen gas, ammonium formate, or the like, and hydrogen gas is preferred.

The amount of use of the catalyst may be 0.1 to 10% by weight, and preferably 1 to 10% by weight, based on the compound represented by the formula (XXXIII). The amount of use of the hydrogen source may be an equimolar amount to a large excess with respect to the compound represented by the formula (XXXIII), and is preferably 2- to 40-fold molar amount. When hydrogen gas is used as the hydrogen source, the gas is preferably at normal pressure or under pressure. The reaction temperature maybe from −20° C. to the reflux temperature, and is preferably from 0° C. to the reflux temperature. The reaction time may be from 0.1 hours to 24 hours, and is preferably from 0.5 hours to 12 hours.

Process 7-5 (STEP 7-5)

A compound represented by the formula (XXXV) is obtained by subjecting the compound represented by the formula (XXXIV) to a reaction according to a method described in conventional literatures in chemistry, for example, a method described in "Heterocyclic Compounds, New Edition: Applications" (written by Hiroshi Yamanaka, Tohru Hino, Masako Nakagawa and Takao Sakamoto; published by Kodansha, Ltd.), pp. 41-63, or a method described the reference documents cited therein. As a suitable example, there may be mentioned a method of obtaining the compound represented by the formula (XXXV) by allowing the compound represented by the formula (XXXIV) to react in an inert solvent with a diazotizing reagent or a nitrosofying reagent, and if necessary, in the presence of acetic anhydride added thereto.

As the inert solvent, acetic acid; benzene analogs such as benzene, toluene or monochlorobenzene; or the like may be used alone, or a solvent mixture of these may be used, and monochlorobenzene is preferred. The diazotizing reagent or a nitrosofying reagent may be sodium nitrite, tert-butyl nitrite, isoamyl nitrite, or the like, and isoamyl nitrite is preferred.

The amount of use of the diazotizing reagent or nitrosofying reagent is preferably 1- to 10-fold the molar amount of the compound represented by the formula (XXXIV). The amount of use of the acetic anhydride may be 0 to 10-fold the molar amount, and is preferably a 1- to 10-fold molar amount. The reaction temperature may be from −20° C. to the reflux temperature, and is preferably from 40° C. to the reflux temperature. The reaction time may be from 0.1 hours to 24 hours, and is preferably from 1 hour to 20 hours.

Process 7-6 (STEP 7-6)

When removal of the protective group in the compound represented by the formula (XXXV) is necessary, the removal may be carried out according to a known method, for example, a method described in "Protective Groups in Organic Synthesis", published by John Wiley and Sons (printed in 2007), and thus a compound represented by the formula (XIII) is obtained. As a suitable example, the method described in Reference Example 38 or the like may be mentioned.

The compound represented by the formula (XXXV) can also be obtained, for example, according to the method described in scheme 8 below.

[Chemical Formula 20]

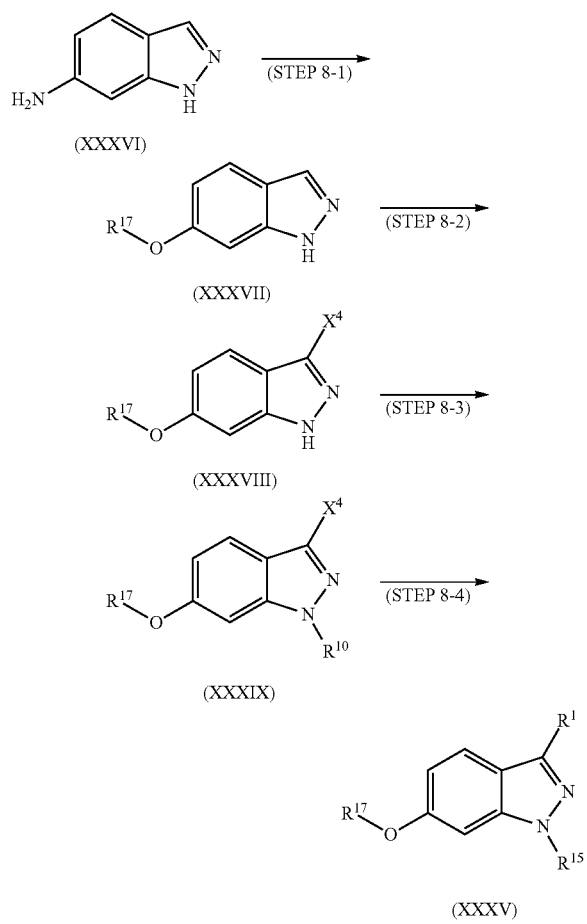

In each of the formulas in the scheme 8, $R^1$ has the same meaning as defined above; $X^4$ may be a chlorine atom, a bromine atom, an iodine atom, or the like, and is preferably a bromine atom or an iodine atom; $R^{10}$ has the same meaning as defined above; $R^{17}$ is a protective group for a hydroxyl group, and is preferably an acetyl group or a tert-butyldiphenylsilyl group.

Process 8-1 (STEP 8-1)

A compound represented by the formula (XXXVII) is obtained by subjecting a compound (XXXVI) that is available from Tokyo Chemical Industry Co., Ltd., to a reaction according to a method described in conventional literatures in chemistry, for example, a method described in "Lectures on Experimental Chemistry, $4^{th}$ Edition" (edited by the Chemical Society of Japan, published by Maruzen Co., Ltd.), Vol. 20, pp. 112-114, or a method described in the reference documents cited therein. As a suitable example, there may be mentioned a method of obtaining the compound represented by the formula (XXXVII) by reacting the compound (XXXVI) with a diazotizing reagent or a nitrosofying reagent in an inert solvent, in the presence of an acid added thereto, or by converting the compound (XXXVI) to a diazonium salt, and then reacting the salt with acetic acid or the like.

The inert solvent is preferably water or the like. The diazotizing reagent or the nitrosofying reagent may be sodium nitrite, tert-butyl nitrite, isoamyl nitrite, or the like, and sodium nitrite is preferred. The acid may be hydrochloric acid, sulfuric acid, tetrafluoroboric acid, or the like, and tetrafluoroboric acid is preferred.

The amount of use of the diazotizing reagent or the nitrosofying reagent is preferably 1- to 10-fold the molar amount of the compound (XXXVI). The amount of use of the acid is preferably an equimolar amount to a large excess with respect to the compound (XXXVI). The reaction temperature is preferably from −20° C. to 100° C. The reaction time may be from 0.1 hours to 48 hours, and is preferably from 1 hour to 24 hours.

If $R^{17}$ is a hydrogen atom, protection of the hydroxyl group can be carried out. The protection reaction may be carried out according to a known method, for example, a method described in "Protective Groups in Organic Synthesis", published by John Wiley and Sons (printed in 2007).

Process 8-2 (STEP 8-2)

A compound represented by the formula (XXXVIII) is obtained by allowing the compound represented by the formula (XXXVII) to react with a halogenating reagent in an inert solvent, and if necessary, in the presence of a base added thereto.

As the inert solvent, ethers such as diethyl ether, tetrahydrofuran or dimethoxyethane; a halogen-based hydrocarbon such as dichloromethane, chloroform or 1,2-dichloroethane; benzene analogs such as benzene, toluene or xylene; acetonitrile; or the like may be used alone, or a solvent mixture of these may be used, and tetrahydrofuran or acetonitrile is preferred. The halogenated reagent may be chlorine gas, bromine, iodine, N-bromosuccinimide, N-chlorosuccinimide, N-iodosuccinimide or the like, and N-bromosuccinimide or iodine is preferred. Examples of the base include alkali metal compounds such as potassium carbonate, sodium carbonate, cesium carbonate, sodium hydrogen carbonate, potassium hydroxide, sodium hydroxide, sodium methoxide, and potassium t-butoxide; and organic tertiary amines such as pyridine, 4-dimethylaminopyridine, 1,8-diazabicyclo[5,4,0]undecene, trimethylamine and triethylamine, and potassium t-butoxide is preferred.

The amount of use of the halogenating reagent is preferably 1- to 10-fold the molar amount of the compound represented by the formula (XXXVII). The amount of use of the base may be 0 to 10-fold the molar amount of the compound represented by the formula (XXXVII), and is preferably a 0 to 5-fold molar amount. The reaction temperature may be from −20° C. to the reflux temperature, and is preferably from 0° C. to the reflux temperature. The reaction time may be from 0.1 to 24 hours, and is preferably from 1 to 12 hours.

Process 8-3 (STEP 8-3)

When a protective group for indazole in the compound represented by the formula (XXXVIII) is necessary, the protective groups for indazole mentioned above are selected, and protection is carried out according to a known method, for example, a method described in "Protective Groups in Organic Synthesis", published by John Wiley and Sons (printed in 2007), and thus the compound represented by the formula (XXXIX) can be obtained. As a suitable example, there may be mentioned a method of obtaining the compound represented by the formula (XXXIX) by allowing the compound represented by the formula (XXXVIII) to react with a protective reagent in an inert solvent, and if necessary, in the presence of a base or a catalyst added thereto.

As the inert solvent, ethers such as diethyl ether, tetrahydrofuran or dimethoxyethane; a halogen-based hydrocarbon such as dichloromethane or 1,2-dichloroethane; a benzene analogs such as benzene, toluene or xylene; acetonitrile; or the like may be used alone, or a solvent mixture of these may be used. The protective reagent may be dihydropyran, di-tert-butyl carbonate or the like. Examples of the base include alkali metal compounds such as potassium carbonate, sodium carbonate, cesium carbonate, sodium hydrogen carbonate, potassium hydroxide, sodium hydroxide, sodium methoxide and potassium t-butoxide; and organic tertiary amine such as pyridine, 4-dimethylaminopyridine, 1,8-diazabicyclo[5,4,0]undecene, trimethylamine and triethylamine. As for the catalyst, an acid catalyst or a base catalyst may be used properly in accordance with the protection reaction. The acid catalyst may be hydrochloric acid, p-toluenesulfonic acid, or the like. The base catalyst may be 4-dimethylaminopyridine, or the like.

The amount of use of the protective reagent may be 1- to 10-fold the molar amount of the compound represented by the formula (XXXVIII), and is preferably a 1- to 5-fold molar amount. The amount of use of the base may be 0 to 10-fold the molar amount of the compound represented by the formula (XXXVIII), and is preferably 0 to a 5-fold molar amount. The amount of use of the catalyst may be 0.001- to 1-fold the molar amount of the compound represented by the formula (XXXVIII), and is preferably a 0.01- to 0.5-fold molar amount. The reaction temperature may be from −20° C. to the reflux temperature, and is preferably from 0° C. to 100° C. The reaction time may be from 0.1 hour to 48 hours, and is preferably from 1 hour to 24 hours.

Process 8-4 (STEP 8-4)

The compound represented by the formula (XXXV) is obtained by allowing the compound represented by the formula (XXXIX) to react with a nucleophilic reagent for introducing $R^1$ in an inert solvent, and if necessary, in the presence of a catalyst added thereto.

The nucleophilic reagent for introducing $R^1$ can be obtained by purchasing a commercially available product of a Grignard reagent, an organozinc reagent, an organoboronic acid reagent, an organoboronic acid ester reagent, an organolithium reagent, an organocopper reagent, or an organotin reagent, or by preparing the reagent according to a conventional method. The catalyst may be a palladium complex, a nickel complex, a copper complex, a copper salt, a copper powder, a lithium salt, or the like.

Furthermore, in the case of a compound represented by the formula (XXXIX) with $R^1$ representing —$CF_3$, the compound represented by the formula (XXXV) can be obtained by performing the reaction according to a method described in conventional literatures in chemistry, for example, a method described in "OrganoFluorine Chemistry" (written by Kenji Uneyama, published by Blackwell Publishing Co.), pp. 292-300, or a method described in the reference documents cited therein. As a suitable example, there may be mentioned a method of obtaining the compound represented by the formula (XXXV), by allowing the compound represented by the formula (XXXIX) to react in an inert solvent, in the presence of a trifluoromethylating agent and a catalyst added thereto. Examples of the inert solvent include aprotic polar solvents such as N,N-dimethylformamide, N,N-dimethylacetamide, dimethyl sulfoxide and N-methylpyrrolidone; and the like, and N-methylpyrrolidone is preferred. Examples of the trifluoromethylating reagent include trifluoromethyl iodide, sodium trifluoroacetate, methyl 2,2-difluoro-2-(fluorosulfonyl)acetate, trifluoromethyl-trimethylsilane, trifluoromethyl-triethylsilane, methyl chlorodifluoroacetate-potassium fluoride, and the like, and methyl 2,2-difluoro-2-(fluorosulfonyl)acetate is preferred. The catalyst may be a copper complex, a copper salt such as copper iodide or copper bromide, or a copper powder, and copper iodide is preferred.

The amount of use of the trifluoromethylating reagent is preferably 1- to 10-fold the molar amount of the compound represented by the formula (XXXIX), and is preferably a 1- to 5-fold molar amount. The amount of use of the catalyst may be 0.001- to 10-fold the molar amount of the compound represented by the formula (XXXIX), and is preferably a 0.1- to 5-fold molar amount. The reaction temperature may be from 0° C. to the reflux temperature, and is preferably from 60° C. to the reflux temperature. The reaction time may be from 0.1 to 48 hours, and is preferably from 1 to 24 hours.

A compound represented by the formula (XIII) with $R^1$ representing —$CH(R^2)OMe$ or —$CH_2CH_2CON(R^{3-1})(R^{3-2})$, can also be obtained according to the method described in scheme 9 or scheme 10.

Scheme 9

[Chemical Formula 21]

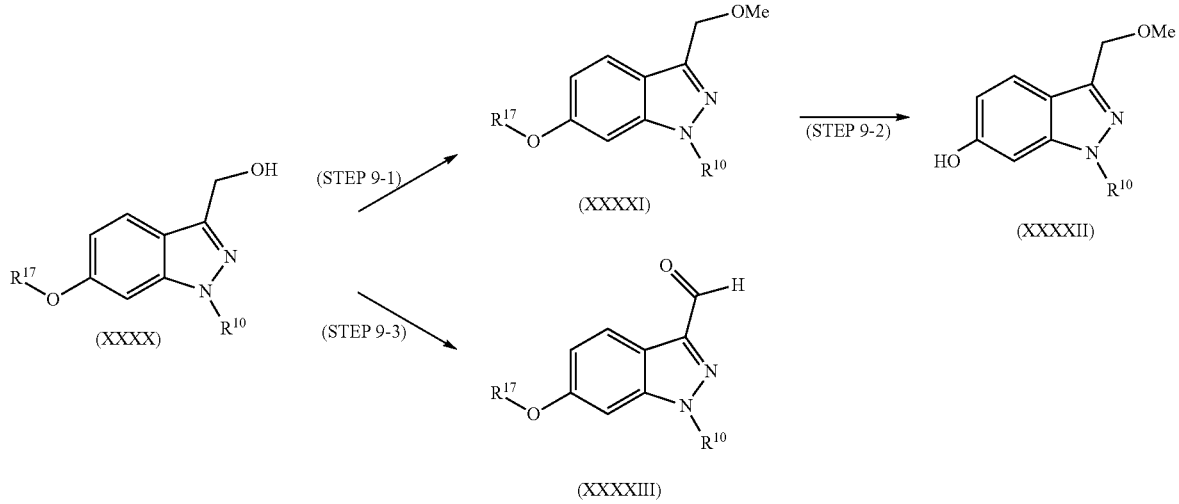

In each of the formulas in the scheme 9, $R^{10}$ is a protective group for indazole, and is preferably a tetrahydropyranyl group; and $R^{17}$ is a protective group for a hydroxyl group, and is preferably a benzyl group. In addition, a compound represented by the formula (XXXX) can be obtained by the method described in scheme 12.

Process 9-1 (STEP 9-1)

A compound represented by the formula (XXXXI) is obtained by subjecting a compound represented by the formula (XXXX) to a reaction according to a method described in conventional literatures in chemistry, for example, a method described in "Lectures on Experimental Chemistry, 4th Edition" (edited by the Chemical Society of Japan, published by Maruzen Co., Ltd.) Vol. 20, pp. 187-200, or a method described in the reference documents cited therein. As a suitable example, there may be mentioned a method of obtaining the compound represented by the formula (XXXXI) by allowing a compound represented by the formula (XXXX) to react with a base and a methylating agent added thereto, in an inert solvent.

As the inert solvent, ethers such as diethyl ether, tetrahydrofuran, 1,4-dioxane or dimethoxyethane; an aprotic polar solvent such as N,N-dimethylformamide; or the like may be used alone, or a solvent mixture of these may be used, and N,N-dimethylformamide is preferred. Examples of the base include alkali metal compounds such as potassium carbonate, sodium carbonate, cesium carbonate, sodium hydrogen carbonate, potassium hydroxide, cesium hydroxide, sodium hydroxide, barium hydroxide, sodium methoxide, sodium hydride, potassium hydride, and potassium t-butoxide; and organic tertiary amines such as pyridine, 4-dimethylaminopyridine, 1,8-diazabicyclo[5,4,0]undecene, trimethylamine and triethylamine, and sodium hydride is preferred. The methylating agent may be dimethyl sulfate, methyl iodide, or the like, and methyl iodide is preferred.

The amount of use of the base is preferably 1- to 5-fold the molar amount of the compound represented by the formula (XXXX). The amount of use of the methylating agent is preferably 1- to 5-fold the molar amount of the compound represented by the formula (XXXX). The reaction temperature may be from −20° C. to the reflux temperature, and is preferably from −20° C. to 40° C. The reaction time may be from 0.1 hours to 48 hours, and is preferably from 0.1 hours to 12 hours.

Process 9-2 (STEP 9-2)

When removal of the protective group of the compound represented by the formula (XXXXI) is necessary, the removal may be carried out according to a known method, for example, a method described in "Protective Groups in Organic Synthesis", published by John Wiley and Sons (printed in 2007), and thus a compound represented by the formula (XXXXII) is obtained. As a suitable example, the method described in Reference Example 55 may be mentioned.

Process 9-3 (STEP 9-3)

A compound represented by the formula (XXXXIII) is obtained by subjecting the compound represented by the formula (XXXX) to a reaction according to a method described in conventional literatures in chemistry such as, for example, a method described in "Lectures on Experimental Chemistry, 4th Edition" (edited by the Chemical Society of Japan, published by Maruzen Co., Ltd.), Vol. 21, pp. 1-23, or a method described in the reference documents cited therein. As a suitable example, there may be mentioned a method of obtaining the compound represented by the formula (XXXXIII) by allowing the compound represented by the formula (XXXX) with an oxidizing agent added thereto, in an inert solvent.

As the inert solvent, ethers such as diethyl ether, tetrahydrofuran, 1,4-dioxane or dimethoxyethane; benzene analogs such as benzene, toluene or xylene; a halogen-based hydrocarbon such as dichloromethane, chloroform or 1,2-dichloroethane; or the like maybe used alone, or a solvent mixture of these may be used, and a mixed solvent of dichloromethane and tetrahydrofuran is preferred.

Examples of the oxidizing agent include 1,1,1-triacetoxy-1,1-dihydro-1,2-benziodoxol-3(1H)-one, 2-iodoxybenzoic acid, pyridinium chlorochromate, activated manganese dioxide, dimethyl sulfoxide-dicyclohexylcarbodiimide, dimethyl sulfoxide-acetic anhydride, dimethyl sulfoxide-trifluoroacetic anhydride, dimethyl sulfoxide-thionyl chloride, dimethyl sulfoxide-oxalyl chloride, dimethyl sulfide-N-chlorosuccinimide, dimethyl sulfoxide-chlorine gas, an oxoammonium salt and tetrapropylammonium perruthenate, and activated manganese dioxide is preferred.

The amount of the oxidizing agent required may be 1- to 10-fold the molar amount of the compound represented by the formula (XXXX). The reaction temperature may be from −20° C. to the reflux temperature, and is preferably from −20 to 40° C. The reaction time may be from 0.1 hours to 48 hours, and is preferably from 0.1 hours to 12 hours.

Furthermore, the amount of the oxidizing agent can be reduced to a catalytic amount by co-incorporating the oxidizing agent and a reoxidizing agent such as 4-methylmorpholine-N-oxide.

Scheme 10

[Chemical Formula 22]

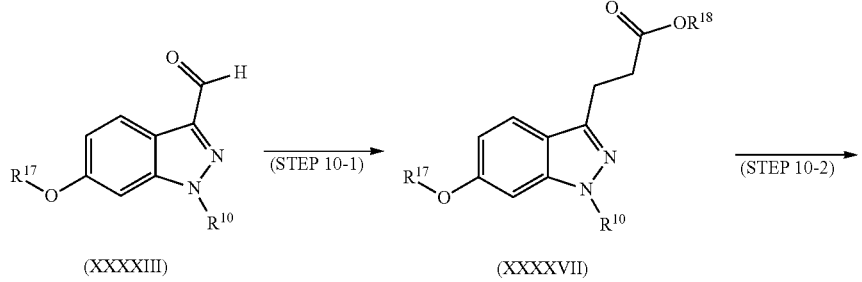

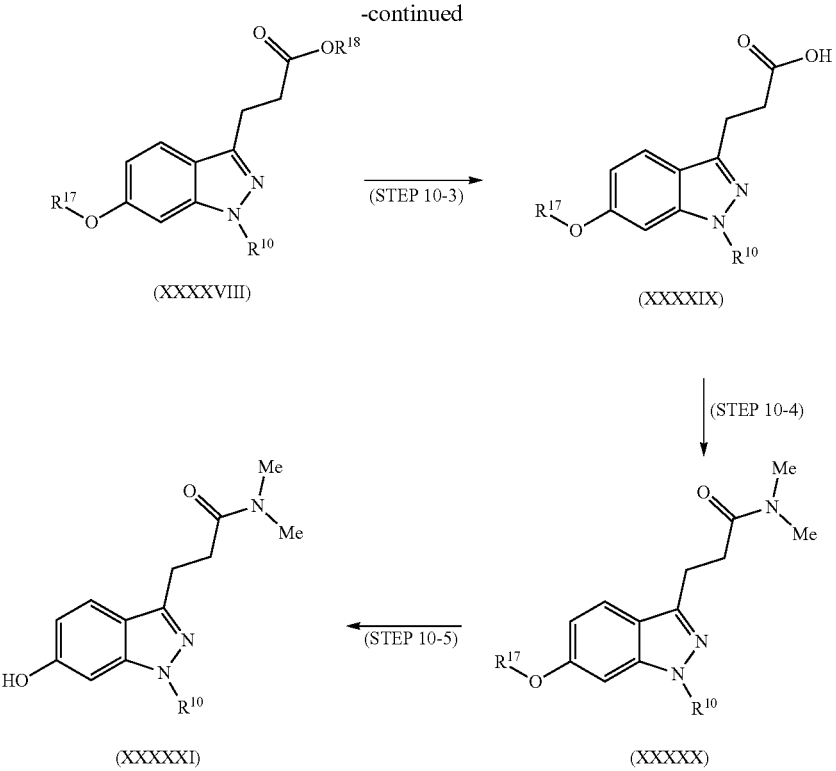

In each of the formulas in the scheme 10, $R^{10}$ represents a protective group for indazole, and is preferably a tetrahydropyranyl group or a tert-butoxycarbonyl group; $R^{17}$ represents a protective group for a hydroxyl group, and is preferably a benzyl group; and $R^{18}$ represents a linear alkyl group such as a methyl group, an ethyl group or an n-propyl group, or a tert-butyl group, and is preferably an ethyl group. In addition, the compound represented by the formula (XXXXIII) can be obtained by the method described in the scheme 9.

Process 10-1 (STEP 10-1)

A compound represented by the formula (XXXXVII) can be obtained by subjecting the compound represented by the formula (XXXXIII) to a reaction according to a method described in conventional literatures in chemistry such as, for example, a method described in "Lectures on Experimental Chemistry, 4$^{th}$ Edition" (edited by the Chemical Society of Japan, published by Maruzen Co., Ltd.), Vol. 19, pp. 53-101, or a method described in the reference documents cited therein. As a suitable example, the compound represented by the formula (XXXXVII) can be obtained by allowing the compound represented by the formula (XXXXIII) to react with a phosphorus ylide or a phosphonate that will be described below in an inert solvent, and if necessary, in the presence of a base added thereto.

As the inert solvent, ethers such as diethyl ether, tetrahydrofuran or dimethoxyethane; benzene analogs such as benzene, toluene or xylene; a halogen-based hydrocarbon such as dichloromethane, chloroform or 1,2-dichloroethane; an aprotic polar solvent such as dimethyl sulfoxide; or the like may be used alone, or a solvent mixture of these may be used, and tetrahydrofuran is preferred. The phosphorus ylide can be produced according to a conventional method. For example, a phosphorus ylide can be produced according to a conventional method such as adding, among the inert solvents described above, an α-bromoacetic acid ester such as methyl α-bromoacetate, ethyl α-bromoacetate, benzyl α-bromoacetate, tert-butyl α-bromoacetate or n-propyl α-bromoacetate, and triphenylphosphine. The phosphonate is preferably ethyl 2-(diethoxyphosphoryl)acetate. Examples of the base include alkali metal compounds such as potassium carbonate, sodium carbonate, cesium carbonate, sodium hydrogen carbonate, potassium hydroxide, cesium hydroxide, sodium hydroxide, barium hydroxide, sodium methoxide, sodium hydride, potassium hydride and potassium t-butoxide, and sodium hydride is preferred.

The amount of use of the phosphorus ylide or phosphonate may be 1- to 10-fold the molar amount of the compound represented by the formula (XXXXVII), and is preferably a 1- to 5-fold molar amount. The amount of use of the base may be 0 to 10-fold the molar amount of the compound represented by the formula (XXXXIII), and is preferably 0 to a 5-fold molar amount. The reaction temperature may be from −20° C. to the reflux temperature, and is preferably from −20° C. to 40° C. The reaction time may be from 0.1 hours to 48 hours, and is preferably from 0.1 hours to 12 hours.

Process 10-2 (STEP 10-2)

A compound represented by the formula (XXXXVIII) can be obtained by subjecting the compound represented by the formula (XXXXVII) to a reaction according to a method described in conventional literatures in chemistry such as, for example, a method described in "Lectures on Experimental Chemistry, 4$^{th}$ Edition" (edited by the Chemical Society of Japan, published by Maruzen Co., Ltd.), Vol. 26, pp. 159-266, or a method described in the reference documents cited therein. As a suitable example, the compound represented by the formula (XXXXVIII) can be obtained by allowing the compound represented by the formula (XXXXVII) to react with a reducing agent in an inert solvent, and if necessary, in the presence of a base added thereto.

As the inert solvent, water; ethers such as diethyl ether, tetrahydrofuran or dimethoxyethane; or the like may be used alone, or a solvent mixture of these may be used, and a mixed solvent of dimethoxyethane and water is preferred. The reducing agent is preferably p-toluenesulfonyl hydrazide. The base is preferably sodium acetate.

The amount of use of the reducing agent maybe 1- to 30-fold the molar amount of the compound represented by the formula (XXXXVII), and is preferably a 1- to 20-fold molar amount. The amount of use of the base may be 1- to 30-fold the molar amount of the compound represented by the formula (XXXXVII), and is preferably a 1- to 20-fold molar amount. The reaction temperature may be from −20° C. to the reflux temperature, and is preferably from 40° C. to the reflux temperature. The reaction time may be from 0.1 hours to 48 hours, and is preferably from 1 hour to 24 hours.

Process 10-3 (STEP 10-3)

A compound represented by the formula (XXXXIX) can be obtained by subjecting the compound represented by the formula (XXXXVIII) to a reaction according to a method described in conventional literatures in chemistry such as, for example, a method described in "Lectures on Experimental Chemistry, 4$^{th}$ Edition" (edited by the Chemical Society of Japan, published by Maruzen Co., Ltd.), Vol. 22, pp. 1-43, or a method described in the reference documents cited therein. Furthermore, the compound represented by the formula (XXXXIX) can be obtained, also by subjecting the compound represented by the formula (XXXXVIII) to a reaction according to a method described in "Protective Groups in Organic Synthesis", published by John Wiley and Sons (printed in 2007), or the like. As a suitable example, there may be mentioned a method of obtaining the compound represented by the formula (XXXXIX) by subjecting the compound represented by the formula (XXXXVIII) to a reaction with a base in an inert solvent.

As the inert solvent, water, an alcohol such as methanol or ethanol, or the like may be used alone, or a solvent mixture of these may be used, and a mixed solvent of methanol and water is preferred. Examples of the base include alkali metal compounds such as potassium carbonate, cesium carbonate, potassium hydroxide, cesium hydroxide, sodium hydroxide, barium hydroxide, sodium methoxide, sodium hydride, potassium hydride and potassium t-butoxide, and sodium hydroxide is preferred.

The amount of use of the base may be 1- to 20-fold the molar amount of the compound represented by the formula (XXXXVIII), and is preferably a 1- to 10-fold molar amount. The reaction temperature maybe from −20° C. to the reflux temperature, and is preferably from 0° C. to the reflux temperature. The reaction time may be from 0.1 to 48 hours, and is preferably from 0.1 to 12 hours.

Process 10-4 (STEP 10-4)

A compound represented by the formula (XXXXX) can be obtained by subjecting the compound represented by the formula (XXXXIX) to a reaction according to a method described in conventional literatures in chemistry such as, for example, a method described in "Lectures on Experimental Chemistry, 4$^{th}$ Edition" (edited by the Chemical Society of Japan, published by Maruzen Co., Ltd.), Vol. 22, pp. 137-173 or pp. 258-309, or a method described in the reference documents cited therein. As a suitable example, there may be mentioned a method of obtaining the compound represented by the formula (XXXXX) by allowing the compound represented by the formula (XXXXIX) to react with an alkyloxy chloride or acid chloride and a base in an inert solvent to form a mixed acid anhydride, and then adding Me$_2$NH thereto.

As the inert solvent, ethers such as diethyl ether, tetrahydrofuran or dimethoxyethane; benzene analogs such as benzene, toluene or xylene; a halogen-based hydrocarbon such as dichloromethane, chloroform or 1,2-dichloroethane; an aprotic polar solvent such as dimethyl sulfoxide, N,N-dimethyl formamide, N,N-dimethylacetamide or acetonitrile; or the like may be used alone, or a solvent mixture of these may be used, and tetrahydrofuran is preferred. The alkyloxy chloride or acid chloride may be isobutyloxycarbonyl chloride, diethylacetyl chloride, pivaloyl chloride or the like, and pivaloyl chloride is preferred.

The amount of use of the alkyloxy chloride or acid chloride is preferably 1- to 5-fold the molar amount of the compound represented by the formula (XXXXIX). The amount of use of the base is preferably 1- to 10-fold the molar amount of the compound represented by the formula (XXXXIX). The amount of use of Me$_2$NH is preferably a 1- to 10-fold amount. The reaction temperature may be from −20° C. to the reflux temperature, and is preferably from 0° C. to 40° C. The reaction time may be from 0.1 to 48 hours, and is preferably from 0.1 to 12 hours.

Process 10-5 (STEP 10-5)

When removal of the protective group in the compound represented by the formula (XXXXX) is necessary, the removal may be carried out according to a known method, for example, a method described in "Protective Groups in Organic Synthesis", published by John Wiley and Sons (printed in 2007), and thus a compound represented by the formula (XXXXXI) is obtained. As a suitable example, the method described in Reference Example 52 may be mentioned.

The compound represented by the formula (XIII) can also be obtained, for example, according to the method shown in scheme 11.

Scheme 11

[Chemical Formula 23]

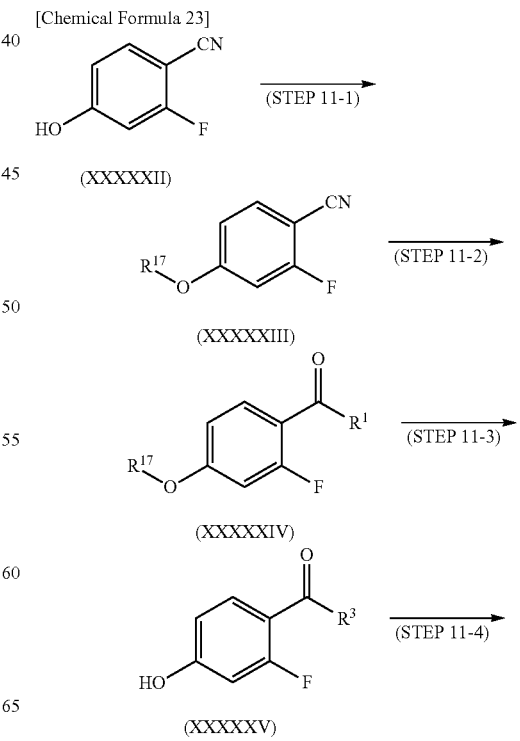

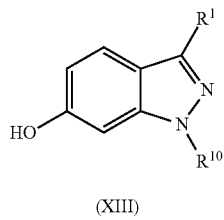

(XIII)

In each of the formulas in the scheme 11, $R^1$ represents the groups other than —$CF_3$, —$CH_2OMe$ and —$CH_2CH_2ONMe_2$ among the groups previously defined; and $R^{17}$ is a protective group for a hydroxyl group, and is preferably a methoxymethyl group, a benzyl group or a tert-butyldimethylsilyl group.

Process 11-1 (STEP 11-1)

The protection reaction for a hydroxyl group of a compound (XXXXXII), which is available from Wako Pure Chemical Industries, Ltd. or the like, may be carried out according to a known method such as, for example, a method described in "Protective Groups in Organic Synthesis", published by John Wiley and Sons (printed in 2007). As a suitable example, there may be mentioned a method of obtaining a compound represented by the formula (XXXXXIII) by allowing the compound (XXXXXII) to react with a base and a protective reagent in an inert solvent.

As the inert solvent, a halogen-based hydrocarbon such as dichloromethane, chloroform or 1,2-dichloroethane; an aprotic polar solvent such as N,N-dimethylformamide; or the like may be used alone, or a solvent mixture of these may be used. Examples of the base include triethylamine, diisopropylethylamine, and 1,8-diazabicyclo[5,4,0]undecene; alkali metal compounds such as potassium carbonate, sodium carbonate, cesium carbonate and sodium hydrogen carbonate; and the like, and triethylamine, diisopropylethylamine, potassium carbonate or imidazole is preferred. The protective reagent maybe tert-butyldimethylchlorosilane, methoxymethyl chloride, benzyl chloride, benzyl bromide or the like.

The amount of use of the base may be 1- to 5-fold the molar amount of the compound (XXXXXII). The protective reagent may be 1- to 5-fold the molar amount of the compound (XXXXXII). The reaction temperature may be from –20° C. to the reflux temperature, and is preferably from 0° C. to 40° C. The reaction time may be from 0.1 to 48 hours, and is preferably 0.1 to 12 hours.

Process 11-2 (STEP 11-2)

A compound represented by the formula (XXXXXIV) can be obtained by subjecting a compound represented by the formula (XXXXXIII) to a reaction according to a method described in conventional literatures in chemistry such as, for example, a method described in "Lectures on Experimental Chemistry, 4$^{th}$ Edition" (edited by the Chemical Society of Japan, published by Maruzen Co., Ltd.), Vol. 25, pp. 59-82, or a method described in the reference documents cited therein. As a suitable example, there may be mentioned a method of obtaining the compound represented by the formula (XXXXXIV) by reacting the compound represented by the formula (XXXXXIII) with a Grignard reagent for introducing group $R^1$ in an inert solvent, and if necessary, in the presence of a catalyst added thereto, to thereby form an imine, and then hydrolyzing the product in the presence of an acidic aqueous solution.

As the inert solvent, ethers such as diethyl ether, tetrahydrofuran or dimethoxyethane; benzene analogs such as benzene, toluene or xylene; or the like may be used alone, or a solvent mixture of these may be used, and diethyl ether or tetrahydrofuran is preferred. The Grignard reagent for $R^1$ may be a commercially available Grignard reagent, a Grignard reagent prepared according to a method described in the previously mentioned chemistry literature or in the reference documents described in the previously mentioned chemistry literature, or a Grignard reagent prepared using a known method other than these methods. For example, cyclobutyl-magnesium bromide can be prepared by adding magnesium, a small amount of iodine, and bromocyclobutane in a dehydrated diethyl ether solvent. The catalyst may be a lithium salt such as lithium chloride; or a copper salt or copper complex such as copper cyanate, copper chloride, copper bromide, copper bromide-dimethyl sulfide complex, or copper iodide, and copper bromide is preferred.

The amount of use of the Grignard reagent may be from 1- to 5-fold the molar amount of the compound represented by the formula (XXXXXIII). The ratio of the catalyst may be such that compound represented by formula (XXXXXIII)/catalyst=S/C=1 to 10000 by mole, and a ratio of S/C=10 to 1000 by mole is preferred. The reaction temperature may be usually from –20° C. to the reflux temperature, and is preferably from 0° C. to the reflux temperature. The reaction time may be from 0.1 to 48 hours, and is preferably from 0.1 to 12 hours.

Process 11-3 (STEP 11-3)

When removal of the protective group in the compound represented by the formula (XXXXXIV) is necessary, the removal may be carried out according to a known method, for example, a method described in "Protective Groups in Organic Synthesis", published by John Wiley and Sons (printed in 2007), and thus a compound represented by the formula (XXXXXV) is obtained. When $R^{17}$ is appropriately selected, the process 11-2 and the process 11-3 may be carried out in succession.

Process 11-4 (STEP 11-4)

A compound (XIII) is obtained by allowing the compound represented by the formula (XXXXXV) to react with a hydrazine in an inert solvent, and if necessary, in the presence of a base added thereto.

As the inert solvent, an alcohol such as methanol, ethanol, 1-butanol or 2-butanol; ethers such as tetrahydrofuran or dimethoxyethane; benzene analogs such as benzene, toluene or xylene; or the like may be used alone, or a solvent mixture of these maybe used, and xylene is preferred. The hydrazine may be benzylhydrazine, benzylhydrazine monohydrochloride, benzylhydrazine dihydrochloride, hydrazine monohydrate or hydrazine hydrate, and benzylhydrazine monohydrochloride is preferred. The base may be an alkali metal compound such as sodium acetate, potassium carbonate, sodium carbonate, cesium carbonate, or sodium hydrogen carbonate; or the like, and sodium acetate is preferred.

The amount of use of the hydrazine may be 1- to 5-fold the molar amount of the compound represented by the formula (XXXXXV), and is preferably a 1- to 3-fold molar amount. The amount of use of the base may be from 0 to 10-fold the molar amount of the compound represented by the formula (XXXXXV), and is preferably a 1- to 5-fold molar amount. The reaction temperature may be from 0° C. to the reflux temperature, and is preferably from 50° C. to the reflux temperature. The reaction time may be from 0.1 to 48 hours, and is preferably from 3 to 24 hours.

If the reaction progress is slow, the inside of the reaction system may be brought to a pressurized state by sealing the reaction vessel. In this case, the reaction can be performed at a temperature greater than the reflux temperature of the solvent, and the reaction temperature may be from the reflux temperature to 250° C., and preferably from the reflux temperature to 200° C.

The alcohol solvent may be selected from methanol, ethanol, n-propanol, n-butanol and the like, in accordance with the type of $R^{19}$ that is intended to be introduced. The acid catalyst may be hydrochloric acid, sulfuric acid, p-toluenesulfonic acid, trifluoroacetic acid, or the like.

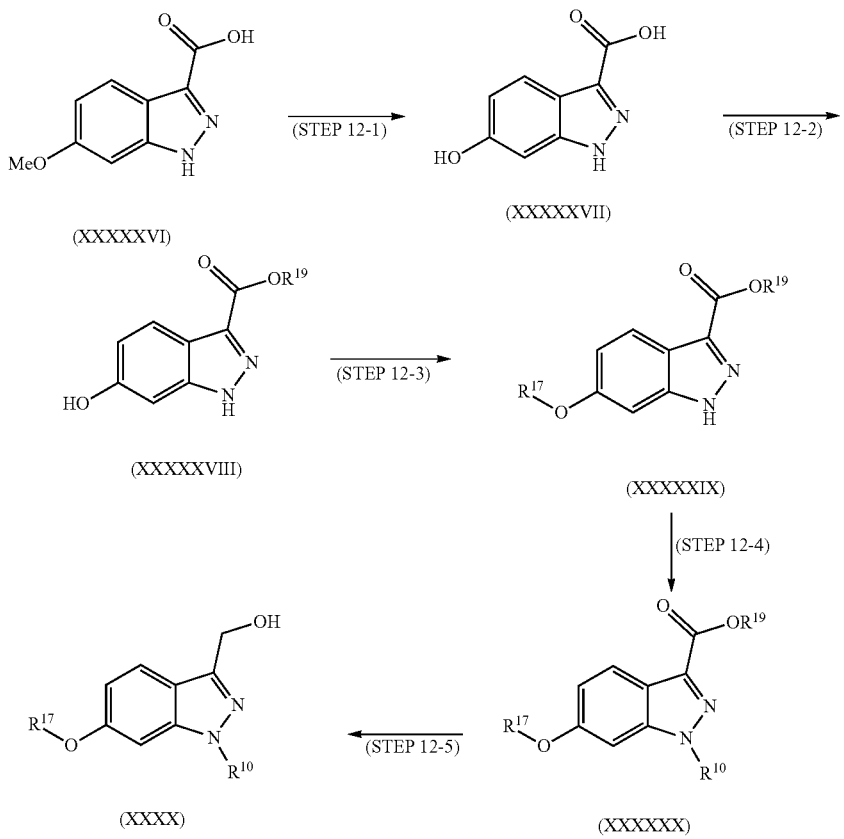

Scheme 12

[Chemical Formula 24]

In each of the formulas in the scheme 12, $R^{10}$ has the same meaning as defined above; $R^{17}$ is a protective group for a hydroxyl group, and is preferably a tert-butyldiphenylsilyl group, or a benzyl group; and $R^{19}$ represents a methyl group, an ethyl group, an n-propyl group, an n-butyl group or the like, and is preferably a methyl group or an ethyl group.

Process 12-1 (STEP 12-1)

A compound (XXXXXVII) is obtained by allowing a compound (XXXXXVI) that is available from ChemPacific Corp., to react according to a known method such as, for example, a method described in "Protective Groups in Organic Synthesis", published by John Wiley and Sons (printed in 2007). As a suitable example, the method described in Reference Example 40 may be mentioned.

Process 12-2 (STEP 12-2)

A compound represented by the formula (XXXXXVIII) can be obtained by allowing the compound (XXXXXVII) to react according to a known method such as, for example, a method described in "Protective Groups in Organic Synthesis", published by John Wiley and Sons (printed in 2007). As a suitable example, there may be mentioned a method of obtaining the compound represented by the formula (XXXXXVIII) by allowing the compound (XXXXXVII) to react in an alcohol solvent in the presence of an acid catalyst or thionyl chloride added thereto.

The amount of use of the acid catalyst may be 0.01- to 10-fold the molar amount of the compound (XXXXXVII). The amount of use of thionyl chloride may be 1- to 10-fold the molar amount of the compound (XXXXXVII), and is preferably a 1- to 5-fold molar amount. The reaction temperature may be from 0° C. to the reflux temperature, and is preferably from 40° C. to the reflux temperature. The reaction time may be from 0.1 hours to 48 hours, and is preferably from 1 to 24 hours.

Process 12-3 (STEP 12-3)

When protection of a hydroxyl group in the compound represented by the formula (XXXXXVIII) is necessary, a protective group for the hydroxyl group is selected, and the protection reaction for a hydroxyl group may be carried out according to a known method, for example, a method described in "Protective Groups in Organic Synthesis", published by John Wiley and Sons (printed in 2007), to thereby obtain a compound represented by the formula (XXXXXIX). As a suitable example, there may be mentioned a method of obtaining the compound represented by the formula (XXXXXIX) by allowing the compound represented by the formula (XXXXXVIII) to react with a silylating agent in an inert solvent in the presence of a base added thereto.

The inert solvent may be N,N-dimethylformamide or the like. The base may be imidazole or the like. The silylating agent may be triethylchlorosilane, tert-butyldimethylchlorosilane or the like.

The amount of use of the silylating agent may be from 1- to 10-fold the molar amount of the compound represented by the formula (XXXXXVIII), and is preferably a 1- to 5-fold molar amount. The amount of use of the base may be from 1- to 10-fold the molar amount of the compound represented by the formula (XXXXXVIII), and is preferably a 1- to 5-fold molar amount. The reaction temperature may be from −20° C. to the reflux temperature, and is preferably from 0° C. to 40° C. The reaction time may be from 0.1 hours to 48 hours, and is preferably from 0.1 hours to 12 hours.

Process 12-4 (STEP 12-4)

When a protective group for the indazole of the compound represented by the formula (XXXXXIX) is necessary, the protective group for indazole is selected, and the protection reaction may be carried out according to a known method, for example, a method described in "Protective Groups in Organic Synthesis", published by John Wiley and Sons (printed in 2007), to thereby obtain a compound represented by the formula (XXXXXX). As a suitable example, there may be mentioned a method of obtaining the compound represented by the formula (XXXXXX) by allowing the compound represented by the formula (XXXXXIX) to react with a protective reagent in an inert solvent, and if necessary, in the presence of a base or an acid catalyst added thereto.

As the inert solvent, ethers such as diethyl ether, tetrahydrofuran or dimethoxyethane; a halogen-based hydrocarbon such as dichloromethane or 1,2-dichloroethane; benzene analogs such as benzene, toluene or xylene; acetonitrile; or the like may be used alone, or a solvent mixture of these may be used. The protective reagent may be dihydropyran, chloromethyl methyl ether, 2-(chloromethoxy)ethoxytrimethylsilane, or the like. Examples of the base include alkali metal compounds such as potassium carbonate, sodium carbonate, cesium carbonate, sodium hydrogen carbonate, potassium hydroxide, sodium hydroxide, sodium methoxide and potassium t-butoxide; and organic tertiary amines such as pyridine, 4-dimethylaminopyridine, 1,8-diazabicyclo[5,4,0]undecene, trimethylamine and triethylamine.

The acid catalyst may be hydrochloric acid, trifluoroacetic acid, p-toluenesulfonic acid, or the like.

The amount of use of the protective reagent may be 1- to 10-fold the molar amount of the compound represented by the formula (XXXXXIX), and is preferably from a 1- to 5-fold molar amount. The amount of use of the base may be from 0 to 10-fold the molar amount of the compound represented by the formula (XXXXXIX), and is preferably from 0 to a 5-fold molar amount. The amount of use of the catalyst may be 0.001- to 1-fold the molar amount of the compound represented by the formula (XXXXXIX), and is preferably a 0.01- to 0.5-fold molar amount. The reaction temperature may be from −20° C. to the reflux temperature, and is preferably from 0° C. to 100° C. The reaction time may be from 0.1 hours to 48 hours, and is preferably from 1 hour to 24 hours.

Process 12-5 (STEP 12-5)

The compound represented by the formula (XXXX) is obtained by subjecting a compound represented by the formula (XXXXXX) to a reaction according to a method described in conventional literatures in chemistry such as, for example, a method described in "Lectures on Experimental Chemistry, 4$^{th}$ Edition" (edited by the Chemical Society of Japan, published by Maruzen Co., Ltd.), Vol. 26, pp. 159-266, or a method described in the reference documents cited therein. As a suitable example, there may be mentioned a method of obtaining the compound represented by the formula (XXXX) by allowing the compound represented by the formula (XXXXXX) to react with a reducing agent in an inert solvent.

As the inert solvent, ethers such as diethyl ether, tetrahydrofuran, or dimethoxyethane; benzene analogs such as benzene, toluene or xylene; a halogen-based hydrocarbon such as dichloromethane, chloroform, or 1,2-dichloroethane; or the like may be used alone, or a solvent mixture of these may be use. The reducing agent may be lithium aluminum hydride, diisobutylaluminum hydride, lithium borohydride, sodium bis(2-methoxyethoxy)aluminum hydride, or the like.

The amount of use of the reducing agent may be 1- to 10-fold the molar amount of the compound represented by the formula (XXXXXX), and is preferably a 1- to 5-fold molar amount. The reaction temperature may be from −20° C. to the reflux temperature, and is preferably from 0° C. to 50° C. The reaction time may be from 0.1 hours to 48 hours, and is preferably from 0.1 hours to 12 hours.

Hereinafter, the method for producing the compound represented by formula (A-1) according to an embodiment of the present invention will be described in detail with scheme 13 to scheme 17.

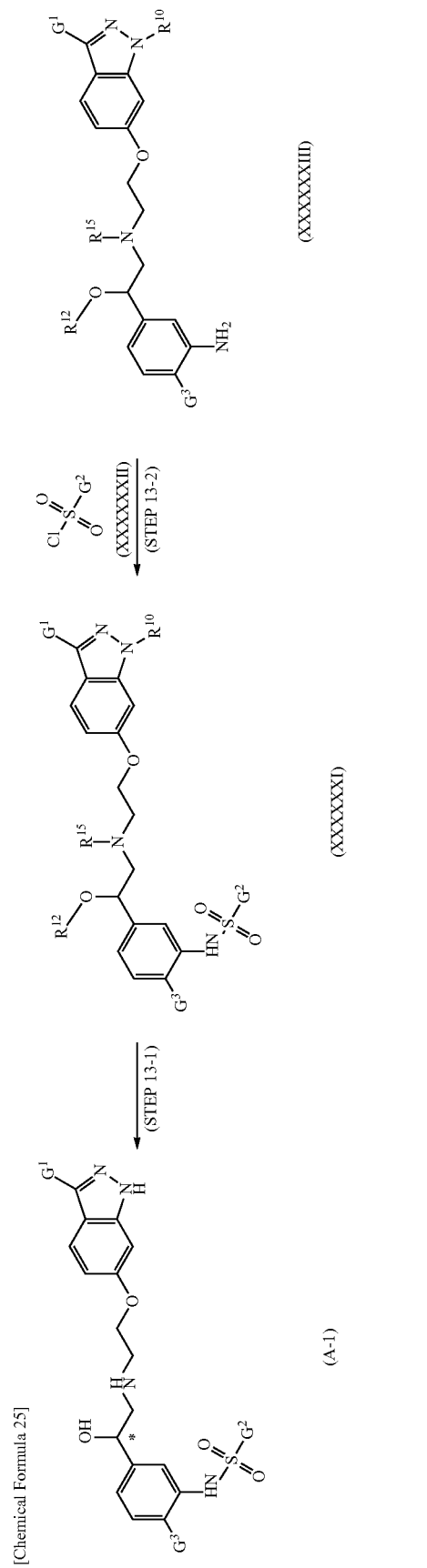

In each of the formulas in the scheme 13, $G^1$, $G^2$ and $G^3$ have the same meaning as defined above; $R^{10}$ has the same meaning as defined above, and is preferably a benzyl group, a tert-butoxycarbonyl group, or a tetrahydropyranyl group, and more preferably a tert-butoxycarbonyl group; $R^{12}$ has the same meaning as defined above, and is preferably a triethylsilyl group; $R^{15}$ has the same meaning as defined above, and is preferably a tert-butoxycarbonyl group.

Process 13-1 (STEP 13-1)

The compound represented by the formula (A-1) can be produced by subjecting a compound represented by the formula (XXXXXXI) to a deprotection reaction according to a known method such as, for example, a method described in "Protective Groups in Organic Synthesis", published by John Wiley and Sons (printed in 2007). As a suitable example, a deprotection reaction under acidic conditions may be performed, the deprotection reaction based on hydrogenolysis described above may be performed alone, or these reactions are used in combination. At any rate, an appropriate deprotection reaction may be selected for various protective groups present in the compound represented by the formula (XXXXXXI).

As the inert solvent, a ketone-based organic solvent such as methyl isobutyl ketone; a hydrocarbon-based solvent such as toluene; a halogen-based hydrocarbon such as dichloromethane, chloroform, or 1,2-dichloroethane; acetonitrile; or the like are exemplified, and dichloromethane is preferred. Examples of the base include organic tertiary amines such as 1,8-diazabicyclo[5,4,0]undecene, trimethylamine, N,N-diisopropylethylamine, and triethylamine; organic bases such as pyridine and 4-dimethylaminopyridine; and inorganic bases such as potassium carbonate and sodium hydrogen carbonate. Among them, pyridine or 1,8-diazabicyclo[5,4,0]undecene is preferred.

The amount of use of the base may be 1- to 10-fold the molar amount of the compound represented by the formula (XXXXXXIII), and is preferably a 1- to 5-fold molar amount. The amount of use of the compound represented by the formula (XXXXXXII) may be usually from 1- to 10-fold the molar amount of the compound represented by the formula (XXXXXXIII), and is preferably a 1- to 5-fold molar amount.

The reaction temperature may be from −10° C. to 60° C., and is preferably −10° C. to 30° C. The reaction time may be from 0.1 to 48 hours, and is preferably from 0.2 to 24 hours.

Scheme 14

[Chemical Formula 26]

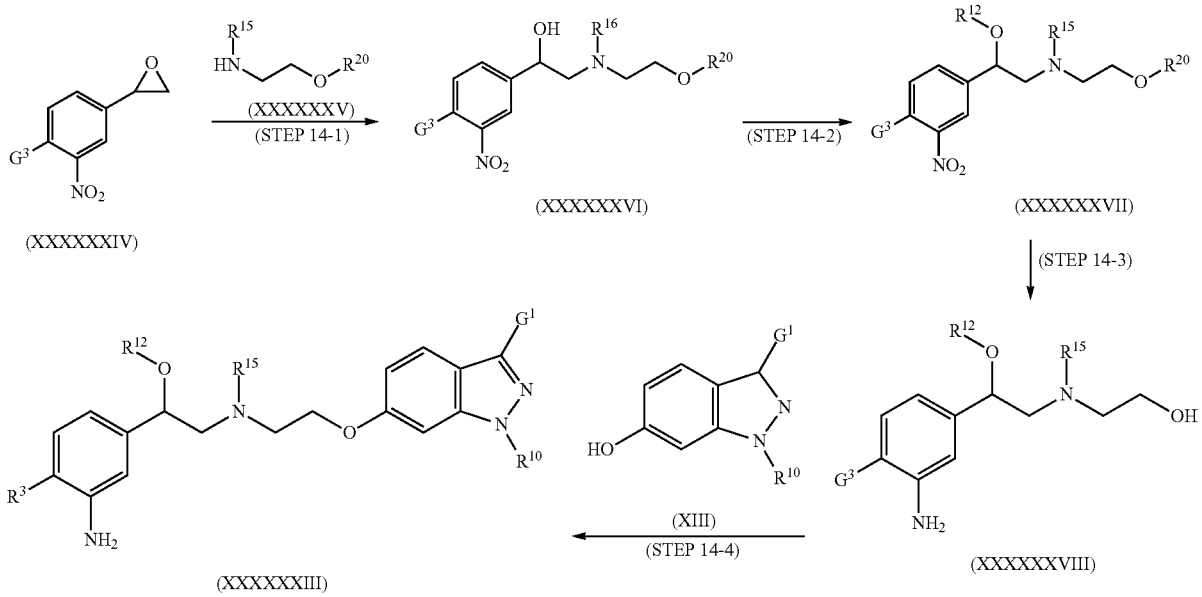

For example, the compound represented by the formula (A-1) is obtained by performing the deprotection reaction under acidic conditions, in an inert solvent in the presence of an acid added thereto.

The inert solvent may be ethyl acetate, 1,4-dioxane, or MTBE. The acid may be a hydrochloric acid-1,4-dioxane solution, or a hydrochloric acid-ethyl acetate solution. The reaction temperature may be from −20° C. to 60° C., and is preferably from 0° C. to 40° C. The reaction time may be from 0.1 hours to 24 hours, and is preferably from 1 to 20 hours.

Process 13-2 (STEP 13-2)

The compound represented by the formula (XXXXXXI) is obtained by allowing a compound represented by the formula (XXXXXXII) and a compound represented by the formula (XXXXXXIII) to react in an inert solvent in the presence of a base added thereto.

In each of the formulas in the scheme 14, $G^1$ and $G^3$ have the same meanings as defined above; $R^{10}$ has the same meaning as defined above, and is preferably a benzyl group, a tert-butoxycarbonyl group or a tetrahydropyranyl group, and more preferably a tert-butoxycarbonyl group; $R^{12}$ has the same meaning as defined above, and is preferably a triethylsilyl group; $R^{15}$ has the same meaning as defined above, and is preferably a benzyl group or a tert-butoxycarbonyl group; and $R^{20}$ is the protective group for a hydroxyl group as described above, and is preferably a benzyl group.

Process 14-1 (STEP 14-1)

A compound represented by the formula (XXXXXXVI) is obtained by allowing a compound represented by the formula (XXXXXXIV) and a compound represented by the formula (XXXXXXV) to react in an inert solvent.

As the inert solvent, an alcohol such as methanol, ethanol, 1-butanol, 2-butanol or 2-propanol; N,N-dimethylformamide, N,N-dimethylacetamide, dimethyl sulfoxide, acetonitrile, or the like may be used alone, or a solvent mixture of these may be used, but 2-propanol is preferred.

The molar ratio of the compound represented by the formula (XXXXXXIV) and the compound represented by the formula (XXXXXXV) may be such that compound represented by formula (XXXXXXIV)/compound represented by formula (XXXXXXV)=0.2 to 5, and is preferably 0.75 to 1.5. The reaction temperature may be from −10° C. to the reflux temperature, and is preferably from 60° C. to the reflux temperature. The reaction time may be from 0.5 to 48 hours, and is preferably from 12 to 48 hours.

If necessary, a Lewis acid catalyst may also be added.

Process 14-2 (STEP 14-2)

A compound represented by the formula (XXXXXXVII) can be obtained by carrying out the protection reaction for a hydroxyl group of the compound represented by the formula (XXXXXXVI) according to a known method such as, for example, a method described in "Protective Groups in Organic Synthesis", published by John Wiley and Sons (printed in 2007).

As a suitable example, there may be mentioned a method of obtaining the compound represented by the formula (XXXXXXVII) by allowing the compound represented by the formula (XXXXXXVI) to react with a silylating agent in an inert solvent in the presence of a base added thereto.

The inert solvent may be N,N-dimethylformamide, or the like. The base may be imidazole or the like. The silylating agent may be triethylchlorosilane, tert-butyldimethylchlorosilane, or the like. The reaction temperature may be from −20° C. to 60° C., and is preferably from 0° C. to 30° C. The reaction time may be from 0.5 to 48 hours, and is preferably from 1 to 24 hours.

Process 14-3 (STEP 14-3)

A compound represented by the formula (XXXXXXVIII) is obtained by allowing the compound represented by the formula (XXXXXXVII) to react in an inert solvent, in the presence of hydrogen gas and a catalyst added thereto.

As the inert solvent, an alcohol such as methanol, ethanol, 1-butanol, 2-butanol or 2-propanol; ethers such as tetrahydrofuran or diethyl ether; or the like may be used alone, or a solvent mixture of these may be used, but ethanol is preferred. The catalyst may be a palladium on carbon powder, platinum oxide ($PtO_2$), activated nickel, or the like, but a palladium on carbon powder is preferred. The reaction temperature may be from 0° C. to the reflux temperature, and is preferably from 0° C. to 60° C. The reaction time may be from 0.5 to 48 hours, and is preferably from 1 to 24 hours.

The compound may also be modified with an appropriate protective group as shown in Reference Example 84.

Process 14-4 (STEP 14-4)

The compound represented by the formula (XXXXXXIII) can be obtained by allowing the compound represented by the formula (XXXXXXVIII) and the compound represented by the formula (XIII) to react in an inert solvent, with a phosphine and an azo compound added thereto.

The inert solvent may be ethers such as diethyl ether, tetrahydrofuran, or dimethoxyethane; a halogen-based solvent such as methylene chloride; or benzene analogs such as benzene, toluene or xylene, and toluene or tetrahydrofuran is preferred. The phosphine may be triphenylphosphine or tributylphosphine, and is preferably triphenylphosphine. The azo compound may be diethyl azodicarboxylate, diisopropyl azodicarboxylate, N,N,N',N'-tetramethylazodicarboxamide, 1,1'-(azodicarbonyl)dipiperidine, N,N,N',N'-tetraisopropylcarboxamide, or the like, and diisopropyl azodicarboxylate or N,N,N',N'-tetramethylazodicarboxamide is preferred.

The amount of use of the phosphine may be 1- to 10-fold the molar amount of the compound represented by the formula (XIII), and is preferably a 1- to 5-fold molar amount. The amount of use of the azo compound may be 1- to 10-fold the molar amount of the compound represented by the formula (XIII), and is preferably a 1- to 5-fold molar amount. The molar ratio of the compound represented by the formula (XXXXXXVIII) and the compound represented by the formula (XIII) may be such that compound represented by formula (XXXXXXVIII)/compound represented by formula (XIII)=0.2 to 5, and preferably 0.75 to 1.5. The reaction temperature may be usually from −20° C. to the reflux temperature, and is preferably from 0° C. to 50° C. The reaction time may be from 0.5 to 48 hours, and is preferably from 1 to 24 hours.

Scheme 15

[Chemical Formula 27]

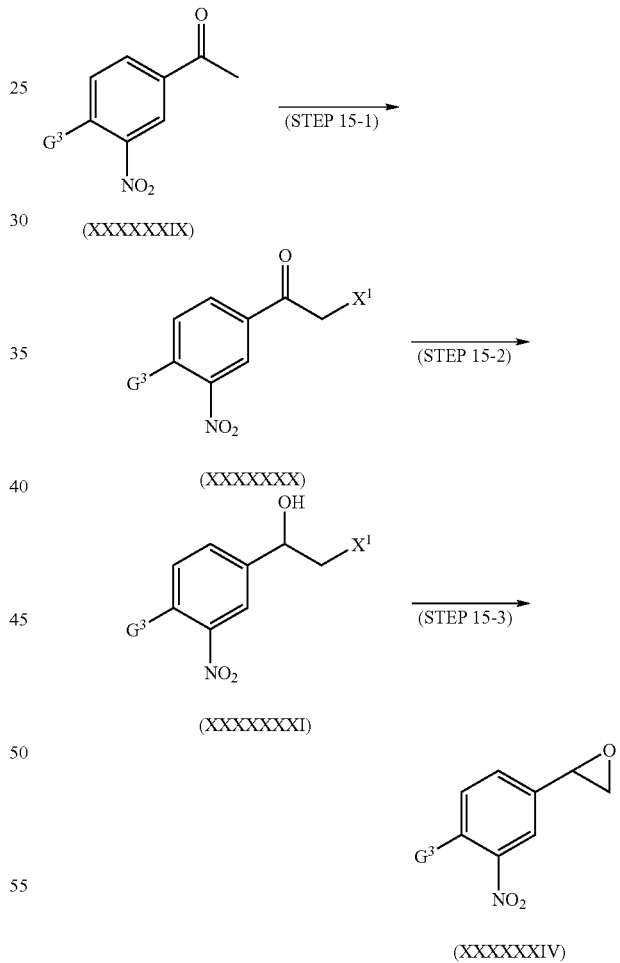

In each of the formulas in the scheme 15, $G^3$ and $X^1$ have the same meanings as defined above.

Process 15-1 (STEP 15-1)

A compound represented by the formula (XXXXXXX) is obtained by allowing a compound represented by the formula (XXXXXXIX) to react in an inert solvent with a halogenating agent added thereto, and if necessary, in the presence of methanol further added thereto.

The inert solvent may be a halogen-based hydrocarbon such as dichloromethane, 1,2-dichloroethane or chloroform, and dichloromethane is preferred. The halogenating agent may be chlorine gas, bromine gas, sulfuryl chloride, or the like, and sulfuryl chloride is preferred.

The amount of use of the halogenating agent is preferably 1- to 3-fold the molar amount of the compound represented by the formula (XXXXXXIX). The amount of use of methanol may be 0 to 5-fold the molar amount of the compound represented by the formula (XXXXXXIX), and is preferably a 0.1- to 3-fold molar amount. The reaction temperature is preferably from −10° C. to 50° C. The reaction time is preferably from 1 to 10 hours, including the time for dropwise addition of the halogenating agent and methanol.

Process 15-2 (STEP 15-2)

A compound represented by the formula (XXXXXXXI) is obtained by reacting the compound represented by the formula (XXXXXXX) with a reducing agent in an organic solvent.

The organic solvent may be, for example, an alcohol solvent such as methanol or ethanol; or ethers solvent such as tetrahydrofuran. The reducing agent may be, for example, sodium borohydride.

Unless an asymmetrical reduction reaction is particularly carried out, the compound represented by the formula (XXXXXXXI) obtainable by the present reduction reaction is obtained as a racemic mixture.

In regard to the technique for obtaining an optically active form, there may be mentioned a technique of performing an asymmetrical reduction reaction. The asymmetrical reduction reaction can be carried out according to a method described in conventional literatures in chemistry such as, for example, a method described in "Lectures on Experimental Chemistry, 5$^{th}$ Edition" (edited by the Chemical Society of Japan, published by Maruzen Co., Ltd.), Vol. 19, pp. 65-171, or a method described in the reference documents cited therein.

As a suitable example, the compound represented by the formula (XXXXXXXI) can be obtained by allowing the compound represented by the formula (XXXXXXX) to react with an optically active ligand and a reducing agent added thereto, in an inert solvent.

As the inert solvent, a halogen-based solvent such as dichloromethane; a hydrocarbon-based solvent such as toluene; an ether-based solvent such as tetrahydrofuran; or the like may be used alone, or a solvent mixture of these may be used, and a mixed solvent of toluene and tetrahydrofuran is preferred. The optically active ligand may be (R)-2-methyl-CBS-oxazaborolidine, (R)-2-n-butyl-CBS-oxazoborolidine, or the like, but a (R)-2-methyl-CBS-oxazaborolidine-toluene solution available from Sigma-Aldrich Co. is preferred. The reducing agent may be a borane-tetrahydrofuran complex, a borane-dimethyl sulfide complex; catecholborane, or the like, but a borane-dimethyl sulfoxide is preferred.

The amount of use of the optically active ligand is preferably 0.05- to 1-fold the molar amount of the compound represented by the formula (XXXXXXX). The amount of use of the reducing agent is preferably 1- to 10-fold the molar amount of the compound represented by the formula (XXXXXXX). The reaction temperature may be from −78° C. to 50° C., and is preferably from −10° C. to 30° C. The reaction time maybe from 0.1 hours to 12 hours, and is preferably from 1 hour to 12 hours.

Process 15-3 (STEP 15-3)

The compound represented by the formula (XXXXXXIV) is obtained by allowing the compound represented by the formula (XXXXXXXI) in an inert solvent, with a base added thereto.

As the inert solvent, water; an alcohol solvent such as methanol, 2-propanol or ethanol; N,N-dimethylformamide, tetrahydrofuran, 1,4-dioxane, acetone, 2-butanone dimethyl sulfoxide, acetonitrile, or the like may be used alone, or a solvent mixture of these may be used, and 2-propanol is preferred. Examples of the base include alkali metal compounds such as potassium carbonate, sodium carbonate, cesium carbonate, sodium hydrogen carbonate, potassium hydroxide, sodium hydroxide, sodium methoxide, a 28% sodium methoxide-methanol solution, and potassium t-butoxide; and organic tertiary amines such as pyridine, 4-dimethylaminopyridine, 1,8-diazabicyclo[5,4,0]undecene, trimethylamine and triethylamine, and sodium hydroxide is preferred.

The amount of use of the base is preferably 1- to 10-fold the molar amount of the compound represented by the formula (XXXXXXXI). The reaction temperature may be from −40° C. to the reflux temperature, and is preferably from −10° C. to 50° C. The reaction time may be from 0.1 hours to 48 hours, and is preferably from 0.1 hours to 12 hours.

Scheme 16

[Chemical Formula 28]

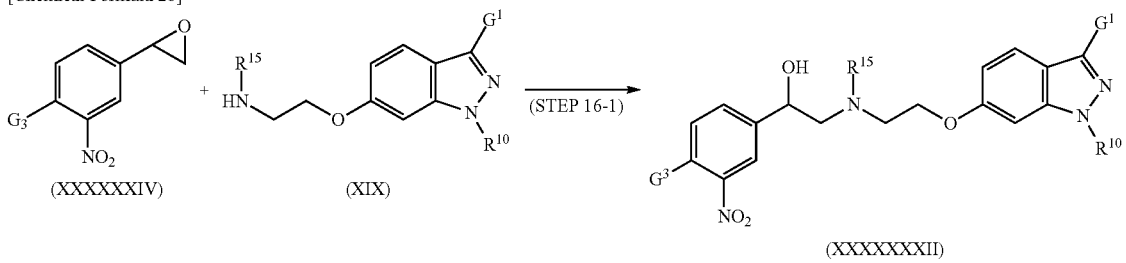

(STEP 16-2)

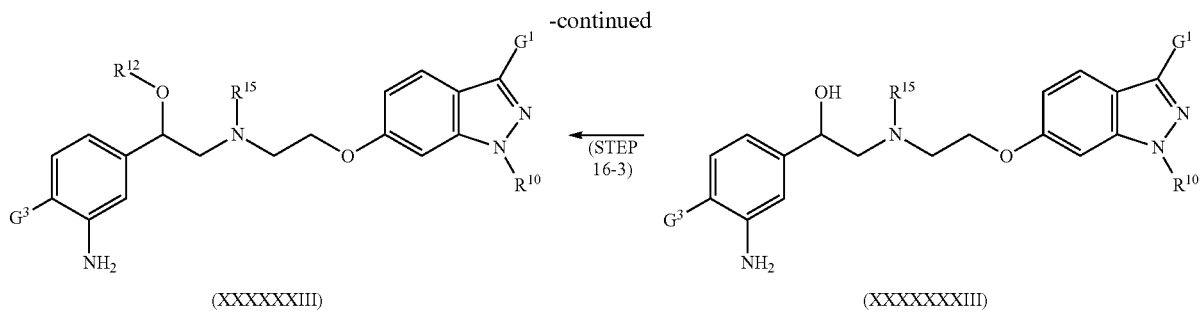

(XXXXXXXIII)        (XXXXXXXIII)

In each of the formulas in the scheme 16, $G^1$ and $G^3$ have the same meanings as defined above; $R^{10}$ has the same meaning as defined above, and is preferably a benzyl group, a tert-butoxycarbonyl group, or a tetrahydropyranyl group, and more preferably a tert-butoxycarbonyl group; $R^{12}$ has the same meaning as defined above, and is preferably a triethylsilyl group; and $R^{15}$ has the same meaning as defined above, and is preferably a benzyl group or a tert-butoxycarbonyl group.

Process 16-1 (STEP 16-1)

A compound represented by the formula (XXXXXXXII) is obtained by allowing the compound represented by the formula (XXXXXXIV) and the compound represented by the formula (XIX) to react in an inert solvent.

As the inert solvent, an alcohol such as methanol, ethanol, 1-butanol, 2-butanol or 2-propanol; N,N-dimethylformamide, N,N-dimethylacetamide, dimethyl sulfoxide, acetonitrile or the like may be used alone, or a solvent mixture of these may be used, but 2-propanol is preferred.

The molar ratio of the compound represented by the formula (XXXXXXIV) and the compound represented by the formula (XIX) is preferably such that compound represented by formula (XXXXXXIV)/compound represented by formula (XIX)=0.2 to 5, and more preferably 0.75 to 1.5. The reaction temperature may be from −10° C. to the reflux temperature, and is preferably from 60° C. to the reflux temperature. The reaction time may be from 0.5 to 48 hours, and is preferably from 12 to 48 hours.

Process 16-2 (STEP 16-2)

A compound represented by the formula (XXXXXXXIII) is obtained by allowing the compound represented by the formula (XXXXXXXII) to react in an inert solvent, in the presence of a catalyst and hydrogen gas added thereto.

As the inert solvent, an alcohol such as methanol, ethanol, 1-butanol 2-butanol or 2-propanol; ethers such as tetrahydrofuran or diethyl ether; or the like may be used alone, or a solvent mixture of these may be used, but ethanol or a mixed solvent of tetrahydrofuran-methanol is preferred. The catalyst may be a palladium on carbon powder, platinum oxide (Pt $O_2$), a CM-101 catalyst available from N.E. Chemcat Corp., activated nickel or the like, but a palladium on carbon powder or a CM-101 catalyst is preferred. The reaction temperature may be from 0° C. to the reflux temperature, and is preferably from 0° C. to 60° C. The reaction time may be from 0.5 hours to 3 days, and is preferably from 1 hour to 3 days.

Furthermore, the compound may also be modified with an appropriate protective group as shown in Reference Example 96.

Process 16-3 (STEP 16-3)

The compound represented by the formula (XXXXXXIII) can be obtained by performing the protection reaction for a hydroxyl group of the compound represented by the formula (XXXXXXXIII) according to a known method such as, for example, a method described in "Protective Groups in Organic Synthesis", published by John Wiley and Sons (printed in 2007).

As a suitable example, there may be mentioned a method of obtaining the compound represented by the formula (XXXXXXIII) by reacting the compound represented by the formula (XXXXXXXIII) with a silylating agent in an inert solvent in the presence of a base added thereto.

The inert solvent may be N,N-dimethylformamide or the like. The base may be imidazole or the like. The silylating agent may be triethylchlorosilane, tert-butyldimethylchlorosilane, or the like.

The reaction temperature may be from −20° C. to 60° C., and is preferably from 0° C. to 30° C. The reaction time may be from 0.5 to 48 hours, and is preferably from 1 to 24 hours.

Scheme 17

[Chemical Formula 29]

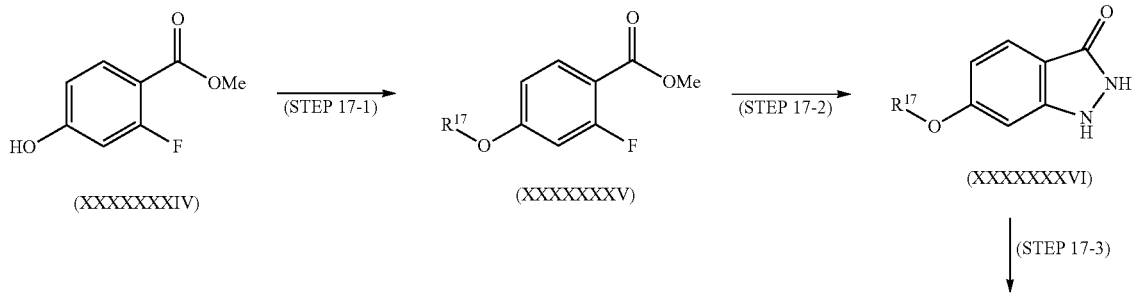

(XXXXXXXIV)        (XXXXXXXV)        (XXXXXXXVI)

(STEP 17-3)

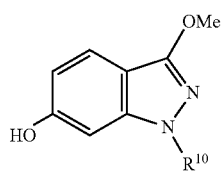 (XIII) 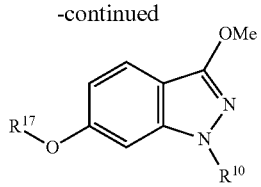 (XXXXXXXVIII) 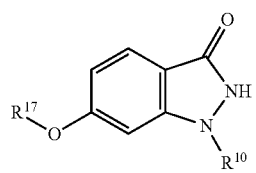 (XXXXXXXVII)

In each of the formulas in the scheme 17, $R^{10}$ has the same meaning as defined above, and is preferably a tert-butoxycarbonyl group; and $R^{17}$ has the same meaning as defined above, and is preferably a benzyl group.

Process 17-1 (Step 17-1)

When protection of a hydroxyl group of the compound (XXXXXXXIV) that is available from Changzou Fine Chemical Co., Ltd. is necessary, the protection reaction may be performed according to a known method such as, for example, a method described in "Protective Groups in Organic Synthesis", published by John Wiley and Sons (printed in 2007), and thereby a compound (XXXXXXXV) is obtained.

As a suitable example, the compound represented by the formula (XXXXXXXV) is obtained by allowing the compound (XXXXXXXIV) to react with a benzylating reagent and a base in an inert solvent.

As the inert solvent, a ketone such as acetone or methyl ethyl ketone; ethers such as tetrahydrofuran or diethyl ether; N,N-dimethylformamide or the like may be used alone, or a solvent mixture of these may be used, and acetone is preferred. The benzylating agent may be benzyl chloride, benzyl bromide or the like, but benzyl bromide is preferred. Examples of the base include inorganic bases such as potassium carbonate, sodium carbonate, cesium carbonate, sodium hydrogen carbonate, potassium hydroxide, sodium hydroxide, sodium methoxide and potassium t-butoxide; and organic amines such as pyridine, 4-dimethylaminopyridine, 1,8-diazabicyclo[5,4,0]undecene trimethylamine and triethylamine, and potassium carbonate is preferred. The benzylating agent is preferably added in an amount of 1- to 10-fold the molar amount of the compound (XXXXXXXIV).

The amount of use of the base is preferably 1- to 10-fold the molar amount of the compound (XXXXXXXIV). The reaction temperature may be from −20° C. to the reflux temperature, and is preferably from 0° C. to 70° C. The reaction time may be from 0.1 hours to 48 hours, and is preferably from 1 to 24 hours Process 17-2 (Step 17-2)

A compound represented by the formula (XXXXXXXVI) is obtained by allowing the compound represented by the formula (XXXXXXXV) to react with a hydrazine in an inert solvent, and if necessary, in the presence of a base added thereto.

As the inert solvent, an alcohol such as methanol, ethanol, 1-butanol or 2-butanol; ethers such as tetrahydrofuran or dimethoxyethane; benzene analogs such as benzene, toluene or xylene; or the like may be used alone, or a solvent mixture of these may be used, and 1-butanol is preferred. The hydrazine may be hydrazine monohydrate, hydrazine monohydrochloride, hydrazine dihydrochloride, or hydrazine hydrate, and hydrazine monohydrate is preferred. The base may be an inorganic base such as sodium acetate, potassium carbonate, sodium carbonate, cesium carbonate or sodium hydrogen carbonate; or the like.

The amount of use of the hydrazine may be 1- to 20-fold the molar amount of the compound represented by the formula (XXXXXXXV), and is preferably a 1- to 15-fold molar amount. The reaction temperature may be from 0° C. to the reflux temperature. When the reaction is carried out in a sealed reaction vessel under microwaves, the reaction may be carried out at a temperature greater than the reflux temperature of the solvent, and in this case, the temperature is preferably from 100° C. to 200° C. The reaction time may be from 0.1 hours to 48 hours, and is preferably from 0.1 to 12 hours.

Process 17-3 (Step 17-3)

When a protective group for the amine of the compound represented by the formula (XXXXXXXVI) is necessary, the protection reaction may be carried out according to a known method, for example, a method described in "Protective Groups in Organic Synthesis", published by John Wiley and Sons (printed in 2007), and thereby a compound represented by the formula (XXXXXXXVII) is obtained. As a suitable example; there may be mentioned a method of obtaining the compound represented by the formula (XXXXXXXVII) by allowing the compound represented by the formula (XXXXXXXVI) to react with $Boc_2O$ and a base added in an inert solvent, and if necessary, in the presence of a catalyst added thereto.

As the inert solvent, ethers such as diethyl ether, tetrahydrofuran or dimethoxyethane; a halogen-based hydrocarbon such as dichloromethane or 1,2-dichloroethane; benzene analogs such as benzene, toluene or xylene; acetonitrile; or the like may be used alone, or a solvent mixture of these may be used, and dichloromethane is preferred. Examples of the base include inorganic bases such as potassium carbonate, sodium carbonate, cesium carbonate, sodium hydrogen carbonate, potassium hydroxide, sodium hydroxide, sodium methoxide and potassium t-butoxide; and organic tertiary amines such as pyridine, 4-dimethylaminopyridine 1,8-diazabicyclo[5,4,0] undecene, trimethylamine and triethylamine, and triethylamine is preferred. The catalyst may be 4-N,N-dimethylaminopyridine, or the like.

The amount of use of $Boc_2O$ is preferably 1- to 10-fold the molar amount of the compound represented by the formula (XXXXXXXVI). The amount of use of the base is preferably 1- to 10-fold the molar amount of the compound represented by the formula (XXXXXXXVI). The amount of use of the catalyst is preferably 0.001- to 1-fold the molar amount of the compound represented by the formula (XXXXXXXVI). The reaction temperature may be from −20° C. to 100° C., and is preferably from 0° C. to 50° C. The reaction time may be from 0.1 hours to 48 hours, and is preferably from 1 hour to 24 hours.

Process 17-4 (Step 17-4)

A compound represented by the formula (XXXXXXXVIII) is obtained by allowing the compound represented by the formula (XXXXXXXVII) to react in an inert solvent, with a base and a methylating reagent added thereto.

As the inert solvent, ethers such as diethyl ether, tetrahydrofuran or dimethoxyethane; a halogen-based hydrocarbon such as dichloromethane or 1,2-dichloroethane; benzene analogs such as benzene, toluene or xylene; an aprotic polar solvent such as acetonitrile, N,N-dimethylformamide, dimethyl sulfoxide or N-methylpyrrolidin-2-one; or the like may be used alone, or a solvent mixture of these may be used, and toluene is preferred. Examples of the base include inorganic bases such as potassium carbonate, sodium carbonate, cesium carbonate, sodium hydrogen carbonate, silver(I) carbonate, potassium hydroxide, sodium hydroxide, sodium methoxide and potassium t-butoxide; and organic tertiary amines such as pyridine, 4-dimethylaminopyridine, 1,8-diazabicyclo[5,4,0]undecene, trimethylamine and triethylamine, and silver(I) carbonate is preferred. The methylating reagent may be methyl iodide, dimethyl sulfate, or the like, and methyl iodide is preferred.

The amount of use of the base is preferably 1- to 20-fold the molar amount of the compound represented by the formula (XXXXXXXVI). The amount of use of the methylating reagent is 1- to 20-fold the molar amount of the compound represented by the formula (XXXXXXXVI). The reaction temperature may be from −20° C. to 100° C., and is preferably from 20° C. to 120° C. The reaction time may be from 0.1 hours to 48 hours, and is preferably from 1 hour to 24 hours.

If necessary, a catalyst such as silver oxide may also be added.

Process 17-5 (Step 17-5)

When removal of the protective group in the compound represented by the formula (XXXXXXXVIII) is necessary, the removal may be carried out according to a known method, for example, a method described in "Protective Groups in Organic Synthesis", published by John Wiley and Sons (printed in 2007). Preferably, if the deprotection reaction under acidic conditions, deprotection reaction based on hydrogenolysis or deprotection of a silyl group, as described above, is carried out, and more preferably, if the deprotection reaction based on hydrogenolysis is carried out, the compound represented by the formula (XIII) is obtained.

As a suitable example, the compound represented by the formula (XIII) is obtained by allowing the compound represented by the formula (XXXXXXXVIII) to react in an inert solvent in the presence of a catalyst and hydrogen gas.

As the inert solvent, an alcohol such as methanol, ethanol, 1-butanol, 2-butanol or 2-propanol; ethers such as tetrahydrofuran or diethyl ether; or the like may be used alone, or a solvent mixture of these may be used, and tetrahydrofuran is preferred. The catalyst may be a palladium on carbon powder. The reaction temperature may be from 0° C. to the reflux temperature, and is preferably from 0° C. to 60° C. The reaction time may be from 0.5 hours to 48 hours, and is preferably from 1 hour to 24 hours.

The compounds of the present invention thus obtainable, and various raw material compounds as well as their intermediates can be isolated and purified according to conventional methods such as extraction, distillation, chromatography and recrystallization.

As an example of the method for producing a compound containing an asymmetric carbon atom among the compounds of the present invention, there may be mentioned the production method based on asymmetrical reduction discussed previously, as well as a method of using a commercially available (or producible according to a known method or a method equivalent to a known method) raw material compound in which the moiety corresponding to the asymmetric carbon atom is already optically active. There is also a method of separating a compound of the present invention or a precursor thereof by a conventional method, as optically active isomers. Examples of the method include a method involving high performance liquid chromatography (HPLC) using an optically active column; a classical optically fractionated crystallization method of forming a salt with an optically active reagent, separating the salt using fractionated crystallization or the like, and then releasing the formation of the salt; a method of separating and purifying a diastereomer that is generated by condensing with an optically active reagent, and then resolving the diastereomer again; and the like. When an optically active form is obtained by separating the precursor, an optically active compound of the present invention can be produced by carrying out the production method after the separation of the precursor.

The compound of the present invention is not recognized of toxicity and is useful as a medicine. For example, since the compound has a β3 adrenergic receptor agonist activity, the compound can be used as a medicine used for the treatment and prevention of β3 adrenergic receptor-associated diseases. The term β3 adrenergic receptor-associated diseases is a generic name of those diseases that can be improved by the agonistic activity mediated by the subject receptor, and examples thereof include overactive bladder, urinary incontinence, interstitial cystitis, diabetes mellitus, obesity, hyperlipidemia, fatty liver, diseases in the digestive system (preferably, abnormal movement of the digestive system or ulcers), depression, diseases caused by gallstones or hypermotility of the biliary tract, diseases accompanying decreased tears, and the like. In particular, it is preferable to use the medicine of the present invention for the treatment and/or prevention of overactive bladder or urinary incontinence, and it is particularly preferable to use the medicine of the present invention for the treatment of overactive bladder. In other particularly preferred embodiments, the medicine of the present invention is used for the treatment of urinary incontinence.

According to the International Continence Society (ICS), overactive bladder is defined as "urgency of urination as a main symptom, with or without urgency incontinence, usually with frequency and nocturia." Furthermore, according to the International Continence Society, urinary incontinence is defined as "a condition where involuntary loss of urine is a social or hygienic problem and is objectively demonstrable."

Furthermore, the compound of the present invention is useful as a β3/α1 adrenergic receptor selective agonist. Particularly, the compound of the present invention is desirable in the aspect that even when the compound is administered to a patient in whom the activation of β3 adrenergic receptor is intended, the compound does not substantially activate α1 adrenergic receptor in that patient.

Here, according to a preferred embodiment of the compound which allows "β3/α1 adrenergic receptor selective activation," there may be mentioned a compound for which the Intrinsic Activity [I.A. (%)] ratio in regard to [Test Example 4] that will be described later, that is, the value obtained by dividing the I.A. (t) of the compound for α1 adrenergic receptor by the I.A. (%) of the compound for β3 adrenergic receptor, is 0.8 or less. Preferably, a compound having an I.A. (%) ratio of 0.7 or less, more preferably 0.5 or less, and particularly preferably 0.3 or less, may be mentioned. Furthermore, a compound having an I.A. ratio of 0.15 or less is even more preferable.

According to another preferred embodiment of the compound which allows "β3/α1 adrenergic receptor selective activation," there may be mentioned a compound for which the I.A. ratio is 0.8 or less, and the EC50 ratio, that is, the value obtained by dividing the EC50 of the compound for α1 adrenergic receptor by the EC50 of the compound for β3 adrenergic receptor, is 5 times or more. According to another preferred embodiment, there may be mentioned a compound for which the I.A. ratio is 0.5 or less, and the EC50 ratio is 5 times or more. According to another preferred embodiment, a compound for which the I.A ratio is 0.3 or less, and the EC50 ratio is 5 times or more, may be mentioned. According to another preferred embodiment, a compound for which the I.A. ratio is 0.15 or less, and the EC50 ratio is 5 times or more.

According to another preferred embodiment of the compound which allows "β3/α1 adrenergic receptor selective activation," there may be mentioned a compound for which the I.A. ratio is 0.8 or less, and the EC50 ratio is 10 times or more. According to another preferred embodiment, there may be mentioned a compound for which the I.A. ratio is 0.5 or less, and the EC50 ratio is 10 times or more. According to another preferred embodiment, there may be mentioned a compound for which the I.A. ratio is 0.3 or less, and the EC50 ratio is 10 times or more. According to another preferred embodiment, there may be mentioned a compound for which the I.A. ratio is 0.15 or less, and the EC50 ratio is 10 times or more.

According to another preferred embodiment of the compound which allows "β3/α1 adrenergic receptor selective activation," there may be mentioned a compound for which the I.A. ratio is 0.8 or less, and the EC50 ratio is 15 times or more. According to another preferred embodiment, there may be mentioned a compound for which the I.A. ratio is 0.5. or less, and the EC50 ratio is 15 times or more. According to another preferred embodiment, there may be mentioned a compound for which the I.A. ratio is 0.3 or less, and the EC50 ratio is 15 times or more. According to another preferred embodiment, there may be mentioned a compound for which the I.A. ratio is 0.15 or less, and the EC50 ratio is 15 times or more.

The expression "does not substantially activate α1 adrenergic receptor" means that similarly in regard to the [Test Example 4] that will be described later, a compound exhibits an I.A. of 55% or less, preferably 45% or less, more preferably 35% or less, even more preferably 25% or less, particularly preferably 15% or less, and particularly more preferably 5% or less.

To further the explanation, the compound of the present invention is excellent in safety (various toxicities and safety effects of drug), pharmacokinetic performance and the like, and thus the usefulness of the compound as an active ingredient of medicines can be verified.

Tests related to safety include, for example, those listed in the following, but are not intended to be limited to these examples. They include cytotoxicity tests (test using HL60 cells or liver cells, and the like), genotoxicity testa (Ames test, mouse lymphoma TK test, chromosomal aberration test, micronucleus test, and the like), skin sensitization tests (Buehler method, GPMT method, APT method, LLNA test, and the like), skin photosensitization tests (Adjuvant and Strip method, and the like), eye irritancy tests (single instillation, short-period continuous instillation, repeated instillations, and the like), safety pharmacology tests on the cardiovascular system (measurement of electrocardiogram, heart rate, blood pressure and the like according to a telemetric method, APD method, hERG inhibition evaluation method, and the like), safety pharmacology testa on the central nervous system (FOB method, Irwin method, and the like), safety pharmacology tests on the respiratory system (measurement method using a respiratory function measuring apparatus (plethysmography method), measurement method using a blood gas analysis apparatus, and the like), general toxicity tests, reproductive and developmental toxicity tests, and the like.

Tests related to the pharmacokinetic performance include, for example, those listed in the following, but are not intended to be limited to these examples. They include tests on inhibition or induction of cytochrome P450 enzyme, cell permeability tests (tests using CaCO-2 cells, MDCK cells or the like), drug transporter ATPase assay, oral absorbability tests, blood concentration profile measurement test, metabolic tests (stability test, metabolite molecular species tests, reactivity tests, and the like), solubility teats (solubility tests according to turbidity method, and the like), and the like.

Usefulness of the compound of the present invention as an active ingredient of medicines can be confirmed by, for example, performing a cytotoxicity teat. Cytotoxicity tests include methods using various cultured cells, for example, HL-60 cells which are human preleukemic cells, primary isolated cultured cells of hepatic cells, a neutrophil traction prepared from human peripheral blood, or the like. These tests can be carried out by the method that will be described below, but the tests are not intended to be limited to this disclosure. A cellular suspension at a concentration of $10^6$ to $10^7$ cells/ml is prepared from cells, and 0.01 mL to 1 mL of the suspension is dispensed into a microtube or a microplate. To this, a solution containing a test compound dissolved therein is added in an amount of 1/100-fold to 1-fold the amount of the cellular suspension, and the cells are cultured for 30 minutes to several days at 37° C. under 5% $CO_2$. After completion of the culture, the survival rate of the cells is assessed using an MTT method or a WST-1 method (Ishiyama, M. et al., In Vitro Toxicology, 8, p. 187, 1995). Measurement of the cytotoxicity of the compound of the present invention against cells can verify the usefulness of the compound as an active ingredient of medicines.

Usefulness of the compound of the present invention as an active ingredient of medicines can be verified by, for example, performing a genotoxicity test. Genotoxicity tests include the Ames test, a mouse lymphoma TK test, a chromosomal aberration test, a micronucleus test and the like. The Ames test is a method of determining mutant or revertant by using a *Salmonella bacterium* or *Escherichia bacterium* of predefined species, and culturing the bacterial cells on a culture plate or the like incorporated with a test compound (II-1. Genotoxicity Test, from the "Genotoxicity Test Guidelines," Pharmaceutical Affairs Bureau Notification of year 1999, No. 1604). The mouse lymphoma TK test is a genetic mutagenicity detection test targeting thymidine kinase gene of mouse lymphoma L5178Y cells (II-3. Mouse lymphoma TK Test, from the "Genotoxicity Test Guidelines," Pharmaceutical Affairs Bureau Notification of year 1999, No. 1604; Clive, D. et al., Mutat. Res., 31, pp. 17-29, 1975; and Cole, J. et al., Mutat. Res., 111, pp. 371-386, 1983). The chromosomal aberration test is a method of judging the activity causing chromosomal aberrations by co-culturing mammalian cultured cells and a test compound, subsequently immobilizing the cells, staining the chromosomes and making an observation (II-2. Chromosomal Aberration Test Using Mammalian Cultured Cells, from the "Genotoxicity Test Guidelines," Pharmaceutical Affairs Bureau Notification of year 1999, No. 1604). Furthermore, the micronucleus test includes a method of using rodents in evaluating the ability to form micronucleus that is attributable to chromosomal aberrations (in vivo test) (II-4. Micronucleus Test Using Rodent, from the "Genotoxicity Test Guidelines," Pharmaceutical Affairs Bureau Notification of year 1999, No. 1604; Hayashi, M. et al., Mutat. Res., 312, pp. 293-304, 1994; and Hayashi, M. et al., Environ. Mol. Mutagen., 35, pp. 234-252, 2000), a method of using cultured cells (in vitro test) (Fenech, M. et al., Mutat. Res., 147, pp. 29-36, 1985; and Miller, B. et al., Mutat. Res., 392, pp. 45-59, 1997), and the like. Elucidation of the genotoxicity of the compound of the present invention using any one or two or more of these methods can verify the usefulness of the compound as an active ingredient of medicines.

Usefulness of the compound of the present invention as an active ingredient of medicines can be verified by, for example, performing a skin sensitization test. Skin sensitization tests include, as skin sensitization tests using guinea pig, the Buehler method (Buehler, E. V., Arch. Dermatol., 91, pp. 171-177, 1965), the GPMT method (Maximization method (Magnusson, B. et al., J. Invest. Dermatol., 52, pp. 268-276, 1969), the APT method (Adjuvant & Patch method (Sato, Y. et al., Contact Dermatitis, 7, pp. 225-237, 1981)), and the like. The skin sensitization tests also include, as skin sensitization tests using mouse, the LLNA (Local Lymph Node Assay) method (OECD Guideline for the testing of chemicals 429, skin sensitization 2002; Takeyoshi, M. et al., Toxicol. Lett., 119(3), pp. 203-8, 2001; and Takeyoshi, M. et al., J. Appl. Toxicol., 25(2), pp. 129-34, 2005), and the like. Elucidation of the skin sensitizability of the compound of the present invention using any one or two or more of these methods can verify the usefulness of the compound as an active ingredient of medicines.

Usefulness of the compound of the present invention as an active ingredient of medicines can be verified by, for example, performing a skin photosensitization teat. Skin photosensitization tests include skin photosensitization tests using guinea pig (1-9: Skin Photosensitization Test, "Japanese Guidelines for Nonclinical Studies of Drugs manual 2002," Yakuji Nippo, Ltd., published in 2002), and methods thereof include the Adjuvant and Strip method (Ichikawa, H. et al., J. Invest. Dermatol., 76, pp. 498-501, 1981), the Harber method (Harber, L. C., Arch. Dermatol., 96, pp. 646-653, 1967), the Horio method (Horio, T., J. Invest. Dermatol., 67, pp. 591-593, 1976), the Jordan method (Jordan, W. P., Contact Dermatitis, 8,pp. 109-116, 1982), the Kochever method (Kochever, I. E. et al., J. Invest. Dermatol., 73, pp. 144-146, 1979), the Maurer method (Maurer, T. et al., Br. J. Dermatol., 63, pp. 593-605, 1980), the Morikawa method (Morikawa, F. et al., "Sunlight and man", Tokyo Univ. Press, Tokyo, pp. 529-557, 1974), the Vinson method (Vinson, L. J., J. Soc. Cosm. Chem., 17, pp. 123-130, 1966), and the like. Elucidation of the skin photosensitizability of the compound of the present invention using any one or two or more of these methods can verify the usefulness of the compound as an active ingredient of medicines.

Usefulness of the compound of the present invention as an active ingredient of medicines can be verified by, for example, performing an eye irritancy test. Eye irritancy tests include a single instillation test method (ocular instillation for once only), a short-period continuous instillation test method (ocular instillation for a number of times at a constant interval within a short period of time), a repeated instillation test method (ocular instillation intermittently repeated over several days to several ten days), all using the rabbit eye, the monkey eye and the like, and also includes a method of evaluating the symptoms of eye irritancy for a defined period of time after ocular instillation according to an improved Draize score (Fukui, N. et al., Gendai no Rinsho, 4(7), pp. 277-289, 1970) or the like. Elucidation of the eye irritancy of the compound of the present invention using any one or two or more of these methods can verify the usefulness of the compound as an active ingredient of medicines.

Usefulness of the compound of the present invention as an active ingredient of medicines can be verified by, for example, performing safety pharmacology tests for the cardiovascular system. Safety pharmacology tests for the cardiovascular system include a telemetric method (method of measuring the effect of the administration of a test compound in an unanesthetized state, on the electrocardiogram, heart rate, blood pressure, blood flow and the like (Shigeru Kanno, Hirokazu Tsubone and Yoshikata Nakada, ed., "Cardiographic, Echocardiographic, Blood pressure, Pathological Examination in Animals for Fundamentals and Clinical Applications," published in 2003, Maruzen Co., Ltd.), the APD method (a method for measuring the time for suspension of the action potential of cardiomyocytes (Muraki, K. et al., AM. J. Physiol., 269, H524-532, 1995; an Ducic, I. et al., J. Cardiovasc. Pharmacol., 30(1), pp. 42-54, 1997)), the hERG inhibition assays (a patch clamping method (Chachin, M. et al., Nippon Yakurigaku Zasshi, 119, pp. 345-351, 2002), a binding assay (Gilbert, J. D. et al., J. Pharm. Tox. Methods, 50, pp. 187-199, 2004), an Rb+ efflex assay (Cheng, C. S. et al., Drug Develop. Indust. Pharm., 28, pp. 177-191, 2002), a membrane potential assay (Dorn, A. et al., J. Biomol. Screen, 10, pp. 339-347, 2005)), and the like. Elucidation of the action of the compound of the present invention on the cardiovascular system using any one or two or more of these methods can verify the usefulness of the compound as an active ingredient of medicines.

Usefulness of the compound of the present invention as an active ingredient of medicines can be verified by, for example, performing a safety pharmacology test for the central nervous system. Safety pharmacology tests for the central nervous system include the FOB method (Functional Observational Battery method (Mattson, J. L. et al., J. American College of Technology, 15(3), pp. 219-254, 1996)), Irwin's modified method (a method of evaluating general symptoms and behavioral observations (Irwin, S. Comprehensive Observational Assessment (Berl.) 13, pp. 222-257, 1968), and the like. Elucidation of the action of the compound of the present invention on the central nervous system using any one or two or more of these methods can verify the usefulness of the compound as an active ingredient of medicines.

Usefulness of the compound of the present invention as an active ingredient of medicines can be verified by, for example, performing a safety pharmacology test on the respiratory system. Safety pharmacology testa on the respiratory system include a measurement method using a respiratory function measuring apparatus (measurement of the respiration rate, tidal volume and minute ventilation volume) (Drorbaugh, J. E. et al., Pediatrics, 16, pp. 81-87, 1955; Epstein, M. A. et al., Respir. Physiol. 32, pp. 105-120, 1978), a measurement method using a blood gas analysis apparatus (measurement of blood gas and hemoglobin oxygen saturation level) (Matsuo, S., Medicina, 40, pp. 188-, 2003), and the like. Elucidation of the action of the compound of the present invention on the respiratory system using any one or two or more of these methods can verify the usefulness of the compound as an active ingredient of medicines.

Usefulness of the compound of the present invention as an active ingredient of medicines can be verified by, for example, performing a general toxicity test. General toxicity tests include a method of making observations of general conditions, and evaluations of clinical chemical changes, pathological tissue changes and the like, in animals administered with a test compound, by using a rodent such as rat or mouse, or a non-rodent such as monkey or dog, and administering the test compound which has been dissolved or suspended in an appropriate solvent, to the animal orally or intravenously once or repeatedly (for multiple days). Elucidation of the general toxicity of the compound of the present invention using these methods can verify the usefulness of the compound as an active ingredient of medicines.

Usefulness of the compound of the present invention as an active ingredient of medicines can be verified by, for example, performing a reproductive and developmental toxicity test. The reproductive and developmental toxicity test is a test for investigating the induction of adverse effects of a test compound in the reproduction process using a rodent such as rat or mouse or a non-rodent such as monkey or dog (see, 1-6: Reproductive and developmental toxicity Tests, "Japanese Guidelines for Nonclinical Studies of Drugs Manual 2002," Yakuji Nippo, Ltd., published in 2002). Reproductive and developmental toxicity tests include a test on fertility and the early embryonic development up to nidation, a test on the prenatal and post-natal development and maternal function, a test on embryo-fetal development (see [3] Reproductive and developmental toxicity Tests, from "Guidelines for Toxicity Studies of Drugs" appended to Pharmaceutical Affairs Bureau Notification of year 2000, No. 1834, and the like), and the like. Elucidation of the reproductive and developmental toxicity of the compound of the present invention using these test methods can verify the usefulness of the compound as an active ingredient of medicines.

Usefulness of the compound of the present invention as an active ingredient of medicines can be verified by, for example, performing a cytochrome P450 enzyme inhibition or induction test (Gomez Lechon, M. J. et al., Curr. Drug Metab., 5(5), pp. 443-462, 2004). Examples of such a test include a method of determining in vitro as to whether a test compound inhibits the activity of a cytochrome P450 enzyme, by using cytochrome P450 enzymes of various molecular species purified from cells or prepared using genetic recombinants, or a human P450 expression system microsome (Miller, V. P. et al., Ann. N.Y. Acad. Sci., 919, pp. 26-32, 2000), a method of measuring changes in the expression and enzymatic activity of cytochrome P450 enzymes of various molecular species, using human liver microsomes or disrupted cell suspensions (Hengstler, J. G. et al., Drug Metab. Rev., 32, pp. 81-118, 2000), a method of extracting RNA from human hepatocytes exposed to a test compound, and comparing the amount of mRNA expression with that of a control, to thereby investigate the enzyme induction ability of the test compound (Kato, M. et al., Drug Metab. Pharmacokinet., 20(4), pp. 236-243, 2005), and the like. Elucidation of the action of the compound of the present invention on the inhibition or induction of cytochrome P450 enzyme using any one or two or more of these methods can verify the usefulness of the compound as an active ingredient of medicines.

Usefulness of the compound of the present invention as an active ingredient of medicines can be verified by, for example, performing a cell permeability test. There are available a method of measuring the cellular membrane permeability of a test compound in an in vitro cell culture system using CaCO-2 cells (Delie, F. et al., Crit. Rev. Ther. Drug Carrier Syst., 14, pp. 221-286, 1997; Yamashita S. et al., Eur. J. Pharm. Sci. 10, pp. 195-204, 2000; and Ingels, F. M. et al., J. Pharm. Sci., 92, pp. 1545-1558, 2003), a method of measuring the cellular membrane permeability of a test compound in an in vitro cell culture system using MDCK cells (Irvine, J. D. et al., J. Pharm. Sci., 88, pp. 28-33, 1999), and the like. Elucidation of the cell permeability of the compound of the present invention using any one or two or more of these test methods can verify the usefulness of the compound as an active ingredient of medicines.

Usefulness of the compound of the present invention as an active ingredient of medicines can be verified by, for example, performing a drug transporter ATPase assay as an ATP-Binding Cassette (ABC) transporter. Drug transporter ATPase assays include a method of-examining whether a test compound is a substrate of P-glycoprotein (P-gp), using a P-gp baculovirus expression system (Germann, U. A., Methods Enzymol., 292, pp. 427-41, 1998), and the like. Furthermore, the usefulness can also be verified by performing, for example, a transport test using oocytes collected from African clawed frog (Xenopus laevis) as a solute carrier (SLC) transporter. Transport tests include a method of examining whether a test compound is a substrate of OATP2, using OATP2-expressing oocytes (Tamai I. et al., Pharm. Res., 2001 September; 18(9), 1262-1269), and the like. Elucidation of the action of the compound of the present invention on the ABC transporter or SLC transporter using these test methods, can verify the usefulness of the compound as an active ingredient of medicines.

Usefulness of the compound of the present invention as an active ingredient of medicines can be verified by, for example, performing an oral absorbability test. Oral absorbability tests include a method of orally administering a certain amount of a test compound dissolved or suspended in an appropriate solvent, to a rodent, monkey, dog or the like, measuring the blood concentration after oral administration of the compound over time, and thereby evaluating the blood migration of the test compound by oral administration using an LC-MS/MS method (Kenichi Harada et al., ed., "Newest mass Spectrometry for Life Science", Kodansha Scientific, 2002), and the like. Elucidation of the oral absorbability of the compound of the present invention using these test methods can verify the usefulness of the compound as an active ingredient of medicines.

Usefulness of the compound of the present invention as an active ingredient of medicines can be verified by, for example, performing a blood concentration profile measurement test. Blood concentration profile measurement tests include a method of administering a test compound to a rodent, monkey, dog or the like, and measuring the blood concentration profile after administration of the test compound using an LC-MS/MS method (Kenichi Harada et al., ed., "Newest mass Spectrometry for Life Science", Kodansha Scientific, 2002), and the like. Elucidation of the blood concentration profile of the compound of the present invention using these test methods can verify the usefulness of the compound as an active ingredient of medicines.

Usefulness of the compound of the present invention as an active ingredient of medicines can be verified by, for example, performing a metabolic test. Metabolic teats include a blood stability teat method (a method of predicting the metabolic clearance in vivo of a test compound from the metabolic rate in hepatic microsomes of human or other animal species (Shou, W. Z. et al., J. Mass Spectrom., 40(10), pp. 1347-1356, 2005; and Li, C. et al., Drug Metab. Dispos., 34(6), 901-905, 2006)), a metabolite molecular species method, a reactive metabolite test method, and the like. Elucidation of the metabolic profile of the compound of the present invention using any one or two or more of these test methods can verify the usefulness of the compound as an active ingredient of medicines.

Usefulness of the compound of the present invention as an active ingredient of medicines can be verified by, for example, performing a solubility test. Solubility tests include a solubility test method based on turbidimetry (Lipinski, C. A. et al., Adv. Drug Deliv. Rev., 23, pp. 3-26, 1997; and Bevan, C. D. et al., Anal. Chem., 72, pp. 1781-1787, 2000), and the like. Elucidation of the solubility of the compound of the present invention using any one or two or more of these test methods can verify the usefulness of the compound as an active ingredient of medicines.

Usefulness of the compound of the present invention as an active ingredient of medicines can be verified by, for example, by investigating the upper digestive tract disorders, renal functional disorders, and the like. In a pharmacology test concerning the upper digestive tract, the action of the compound on gastric mucosa can be investigated using a food-deprived rat gastric mucosa injury model. Pharmacology tests concerning the renal function include a method of measuring the renal blood flow and the glomerular filtration rate [Physiology, 18$^{th}$ Edition (Bunkodo Co., Ltd.), 1986, Chapter 17], and the like. Elucidation of the action of the compound of the present invention on the upper digestive tract and renal function using any one or two or more of these methods can verify the usefulness of the compound as an active ingredient of medicines.

When the medicine of the present invention is administered to human being, the medicine can be orally administered in the form of tablets, powders, granules, capsules, sugar-coated tablets, liquids, syrups or the like, or can also be parenterally administered in the form of injectable preparations, infusion preparations, suppositories, transdermal or absorbable preparations. Inhalation in the form of sprayable preparations such as aerosol or dry powder may also be mentioned as a preferred mode of administration.

The period of administration of the medicine of the present invention is not particularly limited, but when the medicine is administered for a treatment purpose, the time period in which the clinical symptoms of each disease are considered to be expressed, can be in principle selected as the administration period. Usually, it is general to continue the administration for a period of several weeks to one year, but further continuous administration is possible in accordance with the disease condition, and it is also possible to continue administration even after the recovery from clinical symptoms. Furthermore, even if clinical symptoms are not being expressed, the medicine of the present invention can be administered for prophylactic purposes under a physician's decision. The dose of the medicine of the present invention is not particularly limited, but for example, 0.01 to 2000 mg in terms of the active ingredient can be administered to an adult, once or in several divided portions in a day. The frequency of administration may range from once a month to daily administration, and is preferably from once a week to three times a week, five times a week, or everyday administration. The daily dose, duration of administration and frequency of administration may be all appropriately increased or decreased in accordance with the age, body weight and degree of physical healthiness of the patient, and the disease to be treated, severity of the disease, or the like.

It is definitely obvious that the medicine of the present invention can also be administered together with a prophylactic drug or therapeutic drug for various abnormalities or diseases, in addition to the prophylactic and/or therapeutic purposes of the medicine of the present invention.

Examples

The present invention will be further explained based on Examples, Reference Examples and Test Examples, but the scope of the invention is not intended to be limited to the following Examples.

In the following Examples, various analyses were performed as follows.

(1) Thin layer chromatography (TLC) was carried out using Precoated silica gel 60 F254 (manufactured by Merck GmbH, product No. 5715-1M). After development with chloroform:methanol (1:0 to 1:1), ethyl acetate:hexane (1:0 to 0:1) or the like, spots were confirmed by irradiation with UV (254 nm or 365 nm) and staining with a iodine solution, an aqueous solution of potassium permanganate, phosphorus molybdate (ethanol solution), ninhydrin, a dinitrophenylhydrazine-hydrochloric acid solution or the like.

(2) Column chromatography was performed by the following method.

Indication with "COLUMN-A" means that a Multi Prep YFLC (manufactured by Yamazen Corp.) was used, and a Hi-Flash™ Column-Silica gel series manufactured by the same company was used as the column.

Indication with "COLUMN-B" means that a Multi Prep YFLC (manufactured by Yamazen Corp.) was used, and a Purifpack-Si series manufactured by Moritex Corp. was used as the column.

Indication with "COLUMN-C" means that a 2ch parallel purification system "Purif-α2 (50F)" manufactured by Moritex Corp. was used, and a PurifPack-Si series manufactured by the same company was used as the column.

Indication with "COLUMN-D" means that a 2ch parallel purification system "Purif-α2 (50F)" manufactured by Moritex Corp. was used, and a Hi-Flash™ Column-Silica gel series manufactured Yamazen Corp. was used as the column.

Indication with "COLUMN-E" means that a Silica Gel 60N (spherical, neutral, 40 to 100 μm, manufactured by Kanto Chemical Co., Inc.) was used.

Indication with "COLUMN-F" means that a BOND ELUT series (MEGA BE-Si; manufactured by Varian, Inc.) was used.

Indication with "COLUMN-G" means that a Quad1 preparative isolation system (manufactured by Biotage AB) was used, and one or a few cartridge columns were selected from several columns of KP-Sil-12M, 40S and 40M manufactured by the same company, and used in accordance with the amount of sample.

Indication with "COLUMN-H" means that silica gel (manufactured by Merck, Inc.) was use.

Indication with "COLUMN-I" means that a BONDESIL-SCX 40UM (manufactured by Varian, Inc.) was used.

(3) In HPLC purification, an LCMS preparative isolation system (manufactured by Waters Corp.) was used. Indication with "HPLC-A" means that a Develosil C30-UG-5 (manufactured by Nomura Chemical Co., Ltd.) was used, and indication with "HPLC-B" means that an ODS column was used. A water-acetonitrile solvent containing 0.1% of acetic acid was used as the eluent. In the case of HPLC purification, unless particularly stated otherwise, a target substance was collected using the molecular weight as a trigger, and the solvent was removed by a freeze-drying method.

(4) In the measurement of nuclear magnetic resonance spectrum (NMR), measurement was carried out using AL-300 (FT-NMR, manufactured by JEOL, Ltd.), Gemini-300 (FT-NMR, manufactured by Varian, Inc.) or LA-400 (FT-NMR, manufactured by JEOL, Ltd.). The chemical shift, which was calibrated using tetramethylsilane (TMS) as an internal standard, was expressed as δ (ppm), and the coupling constant was expressed J (Hz). The symbols of splitting pattern are as follows: s; singlet, d; doublet, t; triplet, q; quartet, qu; quintet, dd; doublet doublet, td; triplet doublet, ddd; doublet doublet doublet, m; multiplet, bra; broad singlet, brd; broad doublet, brdd; broad doublet doublet, and brddd; broad doublet doublet doublet.

(5) In regard to the "LCMS," a mass spectrum was measured by liquid chromatography-mass spectrometry (LC-MS). In terms of analysis, indication with "LCMS Condition; A" means that measurement was performed under the conditions described below under the title (LCMS-A). Indication with "LCMS Condition; B" means that measurement was performed under the conditions described below under the title (LCMS-B). Indication with "LCMS Condition; C" means that measurement was performed under the conditions described below under the title (LCMS-C). Indication with "LCMS Condition; D" means that measurement was performed under the conditions described below under the title (LCMS-D).

(LCMS-A) A platform-LC type mass spectrometer [manufactured by Micromass, Ltd.] was used as the mass spectrometer, and measurement was made by an electrospray ionization (ESI) method. A liquid chromatography apparatus manufactured by Gilson, Inc. was used. The separating column used was a Davelosil C30-UG-5 (50×4.6 mm) [manufactured by Nomura Chemical Co., Ltd.]. Elution was generally carried out at a flow rate of 2 ml/min, using solution A=water [containing 0.1% (v/v) of acetic acid] and solution B=acetonitrile [containing 0.1% (v/v) of acetic acid] as solvents. Measurement was made under the conditions in which a linear gradient of the solution B was run from 5 to 98% (v/v) over a period of 0 to 4 minutes, and then elution was carried out at 98% solution B up to 6 minutes.

(LCMS-B) A platform-LC type mass spectrometer [manufactured by Micromass, Ltd.] was used as the mass spectrometer, and measurement was made by an electrospray ionization (ESI) method. A liquid chromatography apparatus manufactured by Gilson, Inc. was used. The separating column used was a DeveloSil C30-UG-5 (50×4.6 mm) [manufactured by Nomura Chemical Co., Ltd.]. Elution was generally carried out at a flow rate of 2 ml/min, using solution A=water [containing 0.1% (v/v) of acetic acid] and solution B=acetonitrile [containing 0.1% (v/v) of acetic acid] as solvents. Measurement was made under the conditions in which a linear gradient of the solution B was run from 5 to 100% (v/v) over a period of 0 to 5 minutes, subsequently elution was carried out at 100% solution B up to 9 minutes, and then elution was carried out at 5% solution B from 9.01 to 10 minutes.

(LCMS-C) A single quadrupole type mass spectrometer; UPLC/SQD system [manufactured by Waters Corp.] was used as the mass spectrometer, and measurement was made by an electrospray ionization (ESI) method. An Acquity Ultra Performance LC system manufactured by Waters Corp. was used as the liquid chromatography apparatus. The separating column used was ACQUITY UPLC BEH C18 2.1×50 mm, 1.7 μm [manufactured by waters Corp.]. Elution was generally carried out at a flow rate of 0.6 ml/min, using solution A=water [containing 0.1% (v/v) of acetic acid] and solution B=acetonitrile [containing 0.1% (v/v) of acetic acid] as solvents. Measurement was made under the conditions in which a linear gradient of the solution B was run from 5 to 90% (v/v) over a period of 0 to 2.0 minutes, a linear gradient of the solution B was run from 90 to 98% (v/v) over a period of 2.0 minutes to 2.5 minutes, and then elution was carried out at 5% solution B from 2.6 minutes to 2.8 minutes.

(LCMS-D) A single quadrupole type mass spectrometer; UPLC/SQD system [manufactured by Waters Corp.] was used as the mass spectrometer, and measurement was made by an electrospray ionization (ESI) method. An Acquity Ultra Performance LC system manufactured by Waters Corp. was used as the liquid chromatography apparatus. The separating column used was ACQUITY UPLC BEH C18 2.1×50 mm, 1.7 μm [manufactured by Waters Corp.]. Elution was generally carried out at a flow rate of 0.6 ml/min, using solution A=water [containing 0.1% (v/v) of acetic acid] and solution B=acetonitrile [containing 0.1% (v/v) of acetic acid] as solvents. Measurement was made under the conditions in which a linear gradient of the solution B was run from 50 to 90% (v/v) over a period of 0 to 2.0 minutes, a linear gradient of the solution B was run from 90 to 98% (v/v) over a period of 2.0 minutes to 2.5 minutes, and then elution was carried out at 50% solution B from 2.6 minutes to 2.8 minutes.

(LCMS-E) A single quadrupole type mass spectrometer; UPLC/SQD system [manufactured by Waters Corp.] was used as the mass spectrometer, and measurement was made by an electrospray ionization (ESI) method. An Acquity Ultra Performance LC system manufactured by Waters Corp. was used as the liquid chromatography apparatus. The separating column used was ACQUITY UPLC BEH C18 2.1×50 mm, 1.7 μm [manufactured by Waters Corp.] Elution was generally carried out at a flow rate of 0.6 ml/min, using solution A water [containing 0.1% (v/v) of acetic acid] and solution B acetonitrile [containing 0.1% (v/v) of acetic acid] as solvents. Measurement was made under the conditions in which a linear gradient of the solution B was run from 70 to 90% (v/v) over a period of 0 to 2.0 minutes, a linear gradient of the solution B was run from 90 to 98% (v/v) over a period of 2.0 minutes to 2.5 minutes, and then elution was carried out at 50% solution B from 2.6 minutes to 2.8 minutes.

(6) In regard to the ion chromatography, anion measurement was carried out using IonPac AS14 (manufactured by Nippon Dionex Kabushiki Kaisha) as the column. The eluent used was a 1.0 mmol/L aqueous solution of sodium hydrogen carbonate containing 3.5 mmol/L sodium carbonate at a flow rate of 1.2 mL/min, the column temperature was 30° C., and the detector used was an electrical conductivity detector. Mixed Anion Standard Solution IV (manufactured by Kanto Chemical Industry Co., Ltd.) was used as the standard solution. Cation measurement was carried out using IonPac CS14 (manufactured by Nippon Dionex Kabushiki Kaisha) as the column. The eluent used was a 10 mmol/L aqueous solution of methanesulfonic acid at a flow rate of 1.0 mL/min, the column temperature was 30° C., and the detector used was an electrical conductivity detector. Mixed Cation Standard Solution II (manufactured by Kanto Chemical Industry Co., Ltd.) was used as the standard solution.

(7) The sealed reaction under microwaves was carried out using Discover (manufactured by CEM Corp.).

In the following Examples, abbreviations and words as shown below will be used.

THF: tetrahydrofuran
$Boc_2O$: di-tert-butyl carbonate
DMF: N,N-dimethylformamide
TBDMSCl: tert-butyldimethylsilyl chloride
TBDPSCl: tert-butyldiphenylsilyl chloride
DMAP: 4-dimethylaminopyridine
TBAF: tetra-n-butylammonium fluoride
TMAD: N,N,N',N'-tetramethylazodicarboxamide
MTBE: methyl tert-butyl ether
NBS: N-bromosuccinimide
DBU: 1,8-diazabicyclo[5,4,0]-7-undecene
DIAD: diisopropyl azodicarboxylate
$Et_2O$: diethyl ether
(R)-CBS:
(R)-5,5-diphenyl-2-methyl-3,4-propano-1,3,2-oxazaborolidine In the chemical formulas representing chemical structural formulas, abbreviations and words as shown below will be used.

Bn; benzyl group
Boc: tert-butoxycarbonyl group
TBDMSO: tert-butyldimethylsilyloxy group
TBDPSO: tert-butyldiphenylsilyloxy group
THP: tetrahydro-2H-pyranyl group
Cbz: benzyloxycarbonyl group Intermediates that are not described with the synthesis method and cited reference in the Examples or Reference Examples, will be listed below together with the documents that describe the synthesis method.

(R)-N-benzyl-N-(3-(2-(benzyl-(2-hydroxyethyl)amino)-1-(triethylsilyioxy)ethyl)phenyl)methanesulfonamide: Reference Example 1 of WO 03/035620

[Chemical Formula 30]

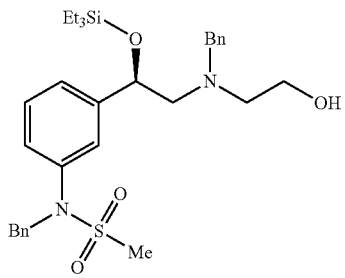

(R)-N-benzyl-N-(3-(oxiran-2-yl)phenyl)methanesulfonamide: Synthesis method of Example 3 of WO 01/0409212 (the disclosure of which is incorporated herein) or production scheme 3 of the present specification

[Chemical Formula 31]

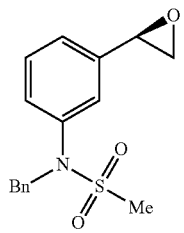

(R)-2-(3-nitrophenyl)oxirane: Example 6 of WO 01/17962 (the disclosure of which is incorporated herein)

[Chemical Formula 32]

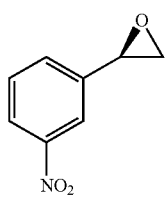

(R)-2-(4-chloro-3-nitrophenyl)oxirane: Example 19 of WO 01/17962

[Chemical Formula 28]

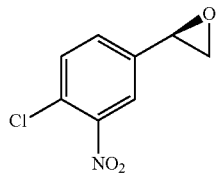

(R)-N-(2-fluoro-5-(2-iodo-1-(triethylsilyloxy)ethyl)phenyl)methanesulfonamide: Intermediate 101 of WO 97/25311 (the disclosure of which is incorporated herein)

[Chemical Formula 34]

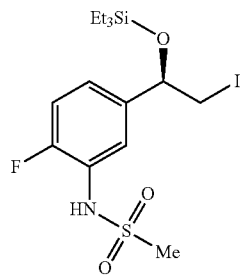

(R)-N-(2-chloro-5-(2-iodo-1-(triethylsilyloxy)ethyl)phenyl)methanesulfonamide: Intermediate 107 of WO 97/25311

[Chemical Formula 35]

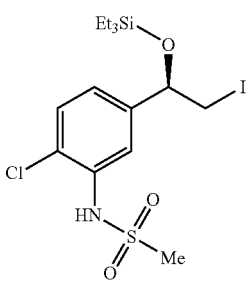

1-Benzyl-3-methylindazol-6-ol: Reference Example 11 of WO 03/035620

[Chemical Formula 36]

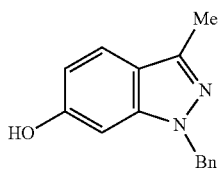

Reference Example 1

4-(Tert-butyldimethylsilyloxy)-2-fluorobenzonitrile

[Chemical Formula 37]

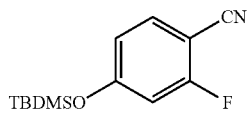

2-Fluoro-4-hydroxybenzonitrile (30.1 g; manufactured by Wako Pure Chemical Industries, Ltd.) and imidazole (18.3 g; manufactured by Tokyo Chemical Industry Co., Ltd.) were dissolved in dehydrated DMF (436 mL; manufactured by Kanto Chemical Co., Inc.), and the solution was cooled to 0° C. Subsequently, TBDMSCl (48.3 g; manufactured by Tokyo Chemical Industry Co., Ltd.) was added thereto, and the mixture was stirred for one hour while the temperature was raised to room temperature. The solvent was evaporated under reduced pressure from the reaction solution, subsequently water was added thereto, and the mixture was extracted two times with ethyl acetate. The organic layer was washed two times with water and with brine, and was dried over anhydrous sodium sulfate. The solvent was evaporated under reduced pressure, and then the residue was purified by column chromatography ("COLUMN-A."; n-hexane:ethyl acetate=100:0→94:6). Thus, the title compound (40.3 g) was obtained.

$^1$H-NMR (300 MHz, CDCl$_3$); δ (ppm) 0.25 (3H, s), 0.25 (3H, s), 0.98 (9H, s), 6.62-6.70 (2H, m), 7.44-7.50 (1H, m)

Reference Example 2

1-(2-Fluoro-4-hydroxyphenyl)-2-methylpropan-1-one

[Chemical Formula 38]

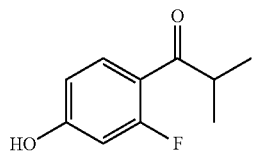

Under an argon atmosphere, dehydrated THF (5 mL; Manufactured by Kanto Chemical Co., Inc.) was added to 4-(tert-butyldimethylsilyloxy)-2-fluorobenzonitrile (14.02 g) that can be produced by the method described in Reference Example 1 or the like, and the mixture was cooled to 0° C. Subsequently, a 0.78 mol/L isopropylmagnesium bromide-THF solution (89 mL; manufactured by Kanto Chemical Co., Inc.) was added dropwise thereto. After completion of the dropwise addition, the reaction solution was stirred for 20 minutes while the temperature was raised to room temperature, copper bromide (140 mg; manufactured by Wako Pure Chemical Industries, Ltd.) was added thereto, and the reaction solution was stirred for 1.5 hours at 60° C. The reaction solution was cooled to 0° C., water (21.4 mL) and 5 mol/L hydrochloric acid (21.4 mL) were added thereto, and the reaction solution was stirred to 6 hours at 60° C. 5 mol/L hydrochloric acid (21 mL) was further added, and the reaction solution was stirred for 13 hours at 60° C. The reaction solution was cooled to room temperature, and was extracted three times with ethyl acetate. The organic layer was washed with water and brine, and was dried over anhydrous sodium sulfate. The solvent was evaporated under reduced pressure, and n-hexane was added to the residue. Precipitates were filtered, and thus the title compound (8.69 g) was obtained.

$^1$H-NMR (300 MHz, DMSO-d$_6$); δ (ppm) 1.06 (6H, d, J=6.6), 3.27-3.33 (1H, m), 6.62 (1H, dd, J=2.2, 13.6), 6.70 (1H, dd, J=2.2, 8.6), 7.66-7.72 (1H, m)

LCMS: 181.1 [M+H]; Retention time: 3.70 minutes; LCMS condition: A

Reference Example 3

1-Benzyl-3-isopropylindazol-6-ol

[Chemical Formula 39]

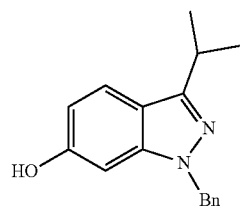

1-(2-Fluoro-4-hydroxyphenyl)-2-methylpropan-1-one (8.69 g) that can be produced by the method described in Reference Example 2, sodium acetate (18.90 g; manufactured by Kanto Chemical Co., Inc.) and benzylhydrazine dihydrochloride (13.97 g; manufactured by Sigma-Aldrich Co.) were suspended in xylene (200 mL; manufactured by Wako Pure Chemical Industries, Ltd.). The suspension was stirred overnight at reflux using a Dean-Stark apparatus. The reaction solution was cooled to room temperature, subsequently water was added thereto, and the mixture was extracted two times with ethyl acetate. The organic layer was washed two times with water and with brine, and was dried over anhydrous sodium sulfate. Subsequently, the solvent was evaporated under reduced pressure, and n-hexane was added to the residue. Precipitates were filtered, and thus a crude product of the title compound (14.09 g) was obtained.

$^1$H-NMR (300 MHz, DMSO-d$_6$); δ (ppm) 1.35 (6H, d, J=6.8), 3.25-3.29 (1H, m), 5.42 (2H, s), 6.61 (1H, dd, J=2.0, 8.6), 6.70 (1H, d, J=1.6), 7.12-7.57 (5H, m), 7.56 (1H, d, J=8.6), 10.32 (1H, brs)

LCMS: 267.4 [M+H]; Retention time: 3.99 minutes; LCMS condition: A

Reference Example 4

3-Isopropylindazol-6-ol

[Chemical Formula 40]

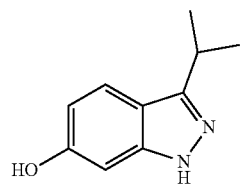

1-Benzyl-3-isopropylindazol-6-ol (6.51 g) that can be produced by the method described in Reference Example 3 or the like, and 10% palladium on carbon-PE-type-50% wet with water, (2.69 g; manufactured by N.E. Chemcat Corp.) were suspended in ethanol (244 mL; manufactured by Wako Pure Chemical Industries, Ltd.), and concentrated hydrochloric acid (2.03 mL; manufactured by Wako Pure Chemical Industries, Ltd.) was added thereto. The reaction system was purged with hydrogen, and under a hydrogen atmosphere, the reaction solution was stirred for 1.5 hours at 60° C. The reaction solution was cooled to room temperature, and was purged with nitrogen. The reaction solution was filtered, and the filtrate was concentrated under reduced pressure. Thus, hydrochloride of the title compound was obtained as a crude product (6.17 g).

$^1$H-NMR (300 MHz, DMSO-$d_6$); δ (ppm) 1.35 (6H, d, J=7.0), 3.32-3.36 (1H, m), 6.69 (1H, dd, J=2.0, 8.8), 6.75 (1H, d, J=2.0), 7.64 (1H, d, J=8.8)

LCMS: 177.1 [M+H]; Retention time: 2.83 minutes; LCMS condition: A

Reference Example 5

6-(Tert-butyldiphenylsilyloxy)-3-isopropylindazole

[Chemical Formula 41]

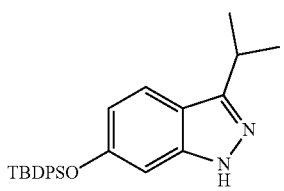

3-Isopropylindazol-6-ol hydrochloride (6.17 g) that can be produced by the method described in Reference Example 4 or the like, and imidazole (4.15 g; manufactured by Tokyo Chemical Industry Co., Ltd.) were dissolved in DMF (122 mL; manufactured by Kanto Chemical Co., Inc.), and the solution was cooled to 0° C. TBDPSCl (15.67 mL; manufactured by Tokyo Chemical Industry Co., Ltd.) was added to the solution, and while the temperature was raised to room temperature, and the mixture was stirred overnight. Subsequently, imidazole (2.47 g; manufactured by Tokyo Chemical Industry Co., Ltd.) and TBDPSCl (9.4 mL; manufactured by Tokyo Chemical Industry Co., Ltd.) were further added thereto, and the mixture was stirred for 3 hours at 20° C. Water was added to the reaction solution, and the mixture was extracted two times with ethyl acetate. The organic layer was washed two times with water and one time with brine. The organic layer was dried over anhydrous sodium sulfate, and then the solvent was evaporated under reduced pressure. The residue was purified by column chromatography ("COLUMN-A"; n-hexane:ethyl acetate=95:5→74:26), and thus the title compound (6.65 g) was obtained.

$^1$H-NMR (300 MHz, CDCl$_3$); δ (ppm) 1.11 (9H, s), 1.39 (6H, d, J=7.0), 3.24-3.38 (1H, m), 6.61 (1H, d, J=8.8), 6.73 (1H, dd, J=2.0, 8.8), 7.34-7.48 (7H, m), 7.72-7.76 (4H, m)

LCMS: 415.2 [M+H]; Retention time: 6.40 minutes; LCMS condition: B

Reference Example 6

Tert-butyl 6-(tert-butyldiphenylsilyloxy)-3-isopropylindazole-1-carboxylate

[Chemical Formula 42]

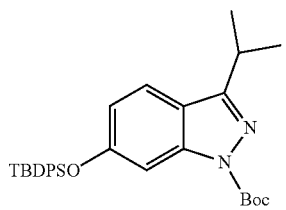

6-(Tert-butyl diphenylsilyloxy)-3-isopropylindazole (6.65 g) that can be produced by the method described in Reference Example 5, was dissolved in dehydrated acetonitrile (160 mL; manufactured by Kanto Chemical Co., Inc.), and triethylamine (2.68 mL; manufactured by Kokusan Chemical Co., Ltd.), DMAP (0.98 g; manufactured by Wako Pure Chemical Industries, Ltd.) and Boc$_2$O (4.426 g; manufactured by Peptide Institute, Inc.) were added to the solution. The mixture was stirred for 13 hours at room temperature. The reaction solution was concentrated under reduced pressure, and then the residue was crudely purified by column chromatography ("COLUMN-B"; n-hexane:ethyl acetate=100:0→90:10). Thus, a crude product (8.12 g) of the title compound was obtained.

$^1$H-NMR (300 MHz, CDCl$_3$); 1.11 (9H, s), 1.39-1.52 (15H, m), 3.26-3.35 (1H, m), 6.89 (1H, dd, J=2.2, 8.6), 7.33-7.46 (8H, m), 7.71-7.74 (4H, m)

LCMS: 515.4 [M+H]; Retention time: 7.93 minutes; LCMS condition: B

Reference Example 7

Tert-butyl 6-hydroxy-3-isopropylindazole-1-carboxylate

[Chemical Formula 43]

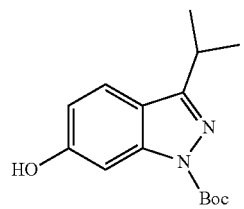

Tert-butyl 6-(tert-butyldiphenylsilyloxy)-3-isopropylindazole-1-carboxylate (8.12 g) that can be produced by the method described in Reference Example 6, was dissolved in dehydrated THF (56.4 mL; manufactured by Kanto Chemical Co., Inc.), and the solution was cooled to 0° C. Subsequently, a 1 mol/L TBAF-THF solution (31.5 mL; manufactured by Sigma-Aldrich Co.) was added thereto, and the mixture was stirred for one hour at room temperature. Water and brine were added to the reaction solution, and the mixture was extracted three times with ethyl acetate. The organic layer was washed with water and brine, and was dried over anhydrous sodium sulfate. Subsequently, the solvent was evaporated under reduced pressure, and the residue was purified by column chromatography ("COLUMN-B"; n-hexane: ethyl acetate=95:5→74:26). Thus, the title compound (3.39 g) was obtained.

$^1$H-NMR (300 MHz, CDCl$_3$); δ (ppm) 1.43 (6H, d, J=7.0), 1.64 (9H, s), 3.28-3.40 (1H, m), 6.22 (1H, brs), 6.86 (1H, dd, J=2.2, 8.4), 7.53-7.54 (1H, m), 7.59 (1H, d, J=8.4)

LCMS: 277.1 [M+H]; Retention time: 4.08 minutes; LCMS condition: B

Reference Example 8

(R)-tert-butyl 6-(2-(tert-butoxycarbonyl (2-(3-(N-(tert-butoxycarbonyl)methylsulfonamido)phenyl)-2-(triethylsilyloxy)ethyl)amino)ethoxy)-3-isopropylindazole-1-carboxylate

[Chemical Formula 44]

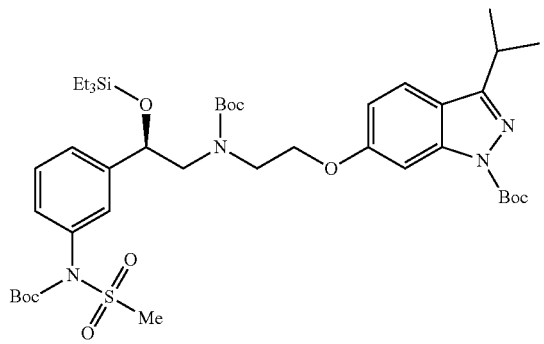

Tert-butyl 6-hydroxy-3-isopropylindazole-1-carboxylate (0.2565 g) that can be produced by the method described in Reference Example 7 or the like, was dissolved in dehydrated toluene (10 mL; manufactured by Kanto Chemical Co., Inc.), and (R)-(3-(2-(N-tart-butoxycarbonyl-N-(2-hydroxyethyl)amino)-1-triethylsilyloxy)ethyl)phenyl)-N-tert-butoxycarbonylmethanesulfonamide (2.0878 g) that can be produced by the method described in Reference Example 58 or the like, triphenylphosphine (0.9016 g; manufactured by Sigma-Aldrich Co.) and TMAD (1.61 g; manufactured by Masuda Chemical Industries, Co., Ltd.) were added to the solution. The mixture was stirred overnight at room temperature. The reaction solution was purified by column chromatography ("COLUMN-A"; n-hexane:ethyl acetate=99:1→67:33), and thus the title compound (0.7071 g) was obtained.

$^1$H-NMR (300 MHz, CDCl$_3$); δ (ppm) 0.54 (6H, q, J=8.1), 0.90 (9H, t, J=8.1), 1.26-1.65 (24H, m), 1.70 (9H, s), 3.43 (3H, s), 3.30-3.61 (5H, m), 4.04-4.11 (2H, m), 4.96-5.14 (1H, m), 6.85 (1H, dd, J=1.8, 8.8), 7.29-7.59 (6H, m)

LCMS: 847.2 [M+H]; Retention time: 8.27 minutes; LCMS condition: B

Example 1

(R)-N-(3-(1-hydroxy-2-(2-(3-isopropylindazol-6-yloxy)ethylamino)ethyl)phenyl)methanesulfonamide

[Chemical Formula 45]

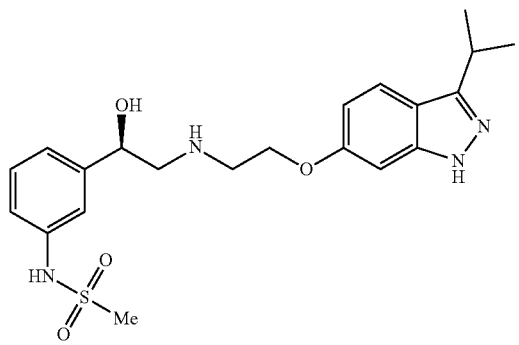

(R)-tert-butyl 6-(2-(tert-butoxycarbonyl(2-(3-(N-(tert-butoxycarbonyl)methylsulfonamido)phenyl)-2-(triethylsilyloxy)ethyl)amino)ethoxy)-3-isopropylindazole-1-carboxylate (3.85 g) that can be produced by the method described in Reference Example 8 or the like, was dissolved in 1,4-dioxane (9 mL), and a 4 mol/L hydrogen chloride-1,4-dioxane solution (20 mL; manufactured by Kokusan Chemical Co., Ltd.) was added thereto. The mixture was stirred overnight at room temperature. Precipitates were filtered, and the obtained solids were dissolved in water (20 mL). The solution was freeze-dried, and then was dissolved in ethanol (85 mL) added thereto. Then, the solvent was evaporated under reduced pressure. The residue was dissolved again in ethanol (85 mL), and evaporating of the solvent under reduced pressure was repeated two times. The resulting residue was added to water (80 mL) to dissolve therein, and the solution was freeze-dried. Thus, the title compound was obtained in the form of hydrochloride (2.24 g).

$^1$H-NMR (300 MHz, DMSO-d$_6$); δ (ppm) 1.35 (6H, d, J=7.0), 3.00 (3H, s), 3.06-3.09 (1H, m), 3.26-3.46 (4H, m), 4.37-4.49 (2H, m), 5.02 (1H, d, J=8.99), 6.78 (1H, dd, J=2.0, 8.8) 6.92 (1H, d, J=1.5), 7.12-7.17 (2H, m), 7.30-7.37 (2H, m), 7.70 (1H, d, J=8.8), 9.05 (1H, brs), 9.38 (1H, brs), 9.86 (1H, s)

LCMS: 433.1 [M+H]; Retention time: 2.32 minutes; LCMS condition: B

Reference Example 9

1-(2-Fluoro-4-hydroxyphenyl)propan-1-one

[Chemical Formula 46]

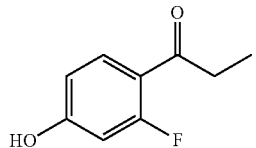

Under an argon atmosphere, 4-(tert-butyldimethylsilyloxy)-2-fluorobenzonitrile (10.06 g) that can be produced by the method of Reference Example 1 or the like, was dissolved in dehydrated diethyl ether (100 mL; manufactured by Kanto Chemical Co., Inc.), and a 3 mol/L ethylmagnesium bromide-diethyl ether solution (35 mL; manufactured by Kanto Chemical Co., Inc.) was added dropwise thereto. After completion of the dropwise addition, the reaction solution was stirred for 20 minutes at room temperature, and was stirred for 1.5 hours at reflux. The reaction solution was cooled to 0° C., and water (35.98 mL) and 5 mol/L hydrochloric acid (35.98 mL) were added thereto. The mixture was stirred overnight at reflux, and then the reaction solution cooled to room temperature and was extracted three times with ethyl acetate. The organic layer was washed with water and brine, and was dried over anhydrous sodium sulfate. The solvent was evaporated under reduced pressure, and the residue was dissolved in dehydrated THF (100 mL; manufactured by Kanto Chemical Co., Inc.). A 1 mol/L TBAF-THF solution (31.5 mL; manufactured by Tokyo Chemical Industry Co., Ltd.) was added to the solution, and the mixture was stirred for 20 minutes at room temperature. Water and brine were added to the reaction solution, and the mixture was extracted three times with ethyl acetate. The organic layer was washed with water and brine, and was dried over anhydrous sodium sulfate. The solvent was evaporated under reduced pressure, and the residue was dissolved in diethyl ether. The solution was extracted with a 2 mol/L aqueous solution of sodium hydroxide, and the aqueous layer was washed with diethyl ether. 2 mol/L hydrochloric acid was added to the aqueous layer, and the mixture was extracted two times with ethyl acetate. The organic layer was washed with water and brine, and was dried over anhydrous sodium sulfate. The solvent was evaporated under reduced pressure, and thus the title compound (5.63 g) was obtained.

$^1$H-NMR (300 MHz, CDCl$_3$); δ (ppm) 1.14 (3H, t, J=7.3), 2.86-2.95 (2H, m), 6.55 (1H, dd, J=2.2, 13.2), 6.67 (1H, dd, J=2.2, 8.8), 7.71-7.77 (1H, m), 10.22 (1H, brs)

LCMS: 166.9 [m-H]; Retention time: 3.31 minutes; LCMS condition: B

Reference Example 10

1-Benzyl-3-ethylindazol-6-ol

[Chemical Formula 47]

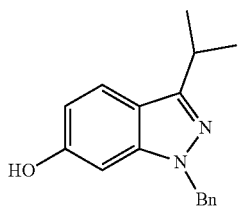

1-(2-Fluoro-4-hydroxyphenyl)propan-1-one (5.37 g) that can be produced by the method described in Reference Example 9 or the like, sodium acetate (12.75 g; manufactured by Wako Pure Chemical Industries, Ltd.) and benzylhydrazine dihydrochloride (9.452 g; manufactured by Sigma-Aldrich Co.) were suspended in xylene (76 mL). The suspension was stirred overnight at reflux using a Dean-Stark apparatus. The reaction solution was cooled to room temperature, subsequently water was added thereto, and the mixture was extracted two times with ethyl acetate. The organic layer was washed two times with water and with brine, and was dried over anhydrous sodium sulfate. Subsequently, the solvent was evaporated under reduced pressure. Before completely evaporating the solvent, precipitates were filtered, and the solids were washed with n-hexane. Thus, the title compound (4.76 g) was obtained. Furthermore, the filtrate was concentrated under reduced pressure, and the solids precipitating in the middle of the concentrating process were also filtered. Thus, the title compound (3.44 g) was obtained.

$^1$H-NMR (300 MHz, DMSO-d$_6$); δ (ppm) 1.28 (3H, t, J=7.7), 2.84 (2H, q, J=7.7), 5.42 (2H, s), 6.62 (1H, dd, J=1.8, 8.4), 6.72 (1H, d, J=1.8) 7.14-7.33 (5H, m), 7.51 (1H, d, J=8.8), 9.58 (1H, brs)

LCMS: 253.2 [M+H]; Retention time: 3.78 minutes; LCMS condition: A

Reference Example 11

3-Ethylindazol-6-ol

[Chemical Formula 48]

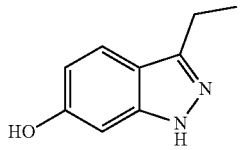

1-Benzyl-3-ethylindazol-6-ol (4.780 g) that can be produced by the method described in Reference Example 10 or the like, and 10% palladium on carbon-PE-type-50% wet with water (1.953 g; manufactured by N.E. Chemcat Corp.) were suspended in ethanol (189 mL; manufactured by Wako Pure Chemical Industries, Ltd.), and concentrated hydrochloric acid (1.579 mL; manufactured by Kanto Chemical Co., Inc.) was added thereto. The reaction system was purged with hydrogen, and under a hydrogen atmosphere, the mixture was stirred for 1.2 hours at 60° C. The reaction solution was cooled to room temperature and then was subjected to nitrogen purging and filtration. The filtrate was concentrated under reduced pressure, and thus the title compound was obtained in the hydrochloride form (3.918 g).

$^1$H-NMR (300 MHz, DMSO-d$_6$); 1.31 (3H, t, J=7.7), 2.95 (2H, q, J=7.7), 6.68-6.78 (2H, m), 7.59-7.67 (1H, m)

LCMS: 163.1 [M+H]; Retention time: 2.76 minutes; LCMS condition: A

Reference Example 12

6-(Tert-butyldiphenylsilyloxy)-3-ethylindazole

[Chemical Formula 49]

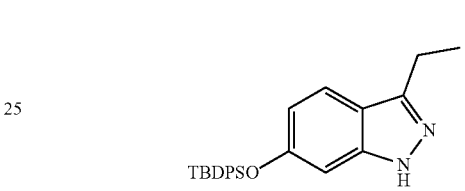

3-Ethylindazol-6-ol hydrochloride (3.76 g) that can be produced by the method described in Reference Example 11 or the like, and imidazole (4.510 g; manufactured by Tokyo Chemical Industry Co., Ltd.) were dissolved in dehydrated DMF (122 mL; manufactured by Kanto Chemical Co., Inc.), and the solution was cooled to 0° C. TBDPSCl (17.01 mL; manufactured by Tokyo Chemical Industry Co., Ltd.) was added thereto, and the mixture was stirred overnight while the temperature was raised to room temperature. Subsequently, the mixture was stirred for one hour at 30° C. Imidazole (1.289 g; manufactured by Tokyo Chemical Industry Co., Ltd.) and TBDPSCl (4.862 mL; manufactured by Tokyo Chemical Industry Co., Ltd.) were further added thereto, and the mixture was stirred for 2.5 hours at 30° C. Water was added to the reaction solution, and the mixture was extracted two times with ethyl acetate. The organic layer was washed two times with water and once with brine. The organic layer was dried over anhydrous sodium sulfate, and the solvent was evaporated under reduced pressure. The residue was purified by column chromatography ("COLUMN-A"; n-hexane:ethyl acetate=88:12→67:33), and thus the title compound (5.9788 g) was obtained.

$^1$H-NMR (300 MHz, CDCl$_3$); δ (ppm) 1.11 (9H, s), 1.35 (3H, t, J=7.7), 2.90 (2H, q, J=7.7), 6.61 (1H, d, J=1.5), 6.74 (1H, dd, J=2.2, 8.8) 7.33-7.45 (7H, m), 7.72-7.76 (4H, m)

LCMS: 401.2[M+H]; Retention time: 6.23 minutes; LCMS condition:B

Reference Example 13

Tert-butyl 6-(tert-butyldiphenylsilyloxy)-3-ethylindazole-1-carboxylate

[Chemical Formula 50]

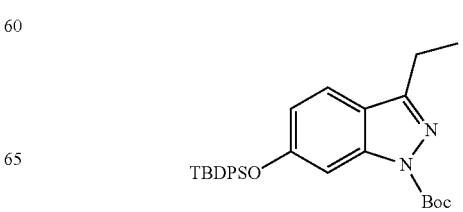

6-(Tert-butyldiphenylsilyloxy)-3-ethylindazole (5.98 g) that can be produced by the method described in Reference Example 12 or the like, was dissolved in dehydrated THF (150 mL; manufactured by Kanto Chemical Co., Inc.), and triethylamine (2.50 mL; manufactured by Kokusan Chemical Co., Ltd.), DMAP (1.01 g; manufactured by Wako Pure Chemical Industries, Ltd.) and Boc$_2$O (4.11 mL; manufactured by Peptide Institute, Inc.) were added to the solution. The mixture was stirred overnight at room temperature. The reaction solution was concentrated under reduced pressure, ethyl acetate was then added to the residue, and the mixture was washed two times with 1 mol/L hydrochloric acid. The organic layer was dried over anhydrous sodium sulfate, and then the solvent was evaporated under reduced pressure. Thus, the title compound (8.02 g) was obtained.

LCMS: 501.2 [M+H]; Retention time: 7.48 minutes; LCMS condition: B

Reference Example 14

Tert-butyl 6-hydroxy-3-ethylindazole-1-carboxylate

[Chemical Formula 51]

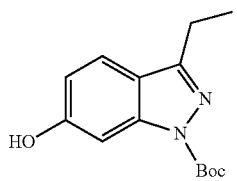

Tert-butyl 6-(tert-butyldiphenylsilyloxy)-3-ethylindazole-1-carboxylate (8.02 g) that can be produced by the method described in Reference Example 13 or the like, was dissolved in dehydrated THF (53 mL), and a 1 mol/L TBAF-THF solution (31.5 mL; manufactured by Tokyo Chemical Industry Co., Ltd.) was added to the solution. The mixture was stirred for 0.5 hours at room temperature. Water and brine were added to the reaction solution, and the mixture was extracted three times with ethyl acetate. The organic layer was washed with water and brine, and was dried over anhydrous sodium sulfate. Subsequently, the solvent was evaporated under reduced pressure, and the residue was purified by column chromatography ("COLUMN-B"; n-hexane:ethyl acetate=95:5→74:26). Thus, the title compound (3.269 g) was obtained.

$^1$H-NMR (300 MHz, CDCl$_3$); δ (ppm) 1.37 (3H, t, J=7.7), 1.63 (9H, s), 2.94 (2H, q, J=7.7), 6.89 (1H, dd, J=2.2, 8.4), 6.91-6.93 (1H, m) 7.47-7.61 (2H, m)

LCMS: 263.1 [M+H]; Retention time: 3.74 minutes; LCMS condition: B

Reference Example 15

(R)-tert-butyl 6-(2-(tert-butoxycarbonyl (2-(3-(N-(tert-butoxycarbonyl)methylsulfonamido)phenyl)-2-(triethylsilyloxy)ethyl)amino)ethoxy)-3-ethylindazole-1-carboxylate

[Chemical Formula 52]

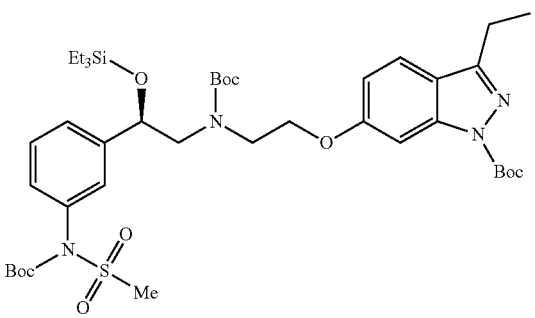

Tert-butyl 6-hydroxy-3-ethylindazole-1-carboxylate (1.326 g) that can be produced by the method described in Reference Example 14 or the like, was dissolved in dehydrated toluene (15 mL; manufactured by Kanto Chemical Co., Inc.), and (R)-(3-(2-(N-tert-butoxycarbonyl-N-(2-hydroxyethyl)amino)-1-triethylsilyloxy)ethyl)phenyl)-N-tert-butoxycarbonylmethanesulfonamide-toluene solution that can be produced by the method described in Reference Example 58 or the like [10 mL; solution prepared by dissolving (R)-(3-(2-(N-tert-butoxycarbonyl-N-(2-hydroxyethyl) amino)-1-triethylsilyloxy)ethyl)phenyl]-N-text-butoxycarbonylmethanesulfonamide (22.4 g) in dehydrated toluene (38 mL)], triphenylphosphine (2.905 g; manufactured by Tokyo Chemical Industry Co., Ltd.) and TMAD (1.953 g; manufactured by Masuda Chemical Industries, Co., Ltd.) were added to the solution. The mixture was stirred overnight at room temperature. Triphenylphosphine (1.344 g; manufactured by Tokyo Chemical Industry Co., Ltd.) and TMAD (0.973 g; manufactured by Masuda Chemical Industries, Co., Ltd.) were further added to the reaction solution, and the mixture was stirred for 2 hours at room temperature. Furthermore, triphenylphosphine (1.24 g; manufactured by Tokyo Chemical Industry Co., Ltd.) and TMAD (0.923 g; manufactured by Masuda Chemical Industries, Co., Ltd.) were further added to the reaction solution, and the mixture was stirred for 0.5 hours at room temperature. The reaction solution was crudely purified by column chromatography ("COLUMN-A"; n-hexane:ethyl acetate=88:12→67:33), and thus a crude product (3.71 g) of the title compound was obtained.

$^1$H-NMR (300 MHz, CDCl$_3$); δ (ppm) 0.54 (6H, q, J=7.7), 0.90 (9H, t, J=7.9), 1.36-1.52 (21H, m), 1.70 (9H, s), 2.91-2.96 (2H, m), 3.22-3.62 (7H, m), 4.02-4.13 (2H, m), 4.93-5.13 (1H, m), 6.77 (1H, dd, 8.6), 7.13-7.60 (6H, m)

LCMS: 833.2 [M+H]; Retention time: 8.10 minutes; LCMS condition: B

Example 2

(R)-N-(3-(1-hydroxy-2-(2-(3-ethylindazol-6-yloxy)ethylamino)ethyl)phenyl)methanesulfonamide

[Chemical Formula 53]

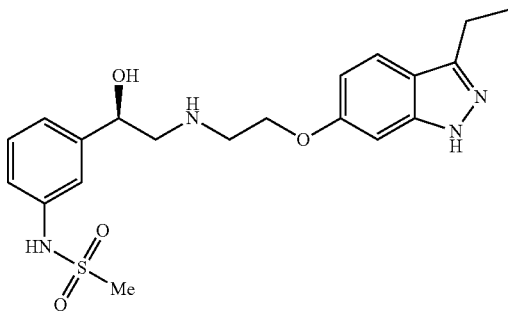

A 4 mol/L hydrogen chloride-ethyl acetate solution (70 mL; manufactured by Kokusan Chemical Co., Ltd.) was added to (R)-tert-butyl 6-(2-(tert-butoxycarbonyl-(2-(3-(N-(tert-butoxycarbonyl)methylsulfonamido)phenyl)-2-(triethylsilyloxy)ethyl)amino)ethoxy)-3-ethylindazole-1-carboxylate (3.56 g) that can be produced by the method described in Reference Example 15 or the like, and the mixture was stirred overnight at room temperature. Precipitates were filtered, and the Solids were washed five times with ethyl acetate (3 mL) and once with diethyl ether (1 mL). Thus, the title compound was obtained in the form of hydrochloride (2.056 g).

$^1$H-NMR (300 MHz, DMSO-$d_6$); δ (ppm) 1.30 (3H, t, J=7.5) 2.92 (2H, q, J=7.5), 3.00 (3H, s), 3.04-3.09 (1H, m), 3.12-3.27 (1H, m), 3.39-3.52 (2H, m), 4.38 (2H, d, J=5.1), 5.03 (1H, dd, J=2.0, 8.1), 6.81 (1H, dd, J=2.0, 8.8) 6.94 (1H, d, J=2.0), 7.12-7.18 (2H, m), 7.30-7.40 (2H, m), 7.69 (1H, d, J=8.8), 9.10 (1H, brs), 9.48 (1H, brs), 9.87 (1H, s)

LCMS: 419.2 [M+H]; Retention time; 2.10 minutes; LCMS condition: B

Reference Example 16

1-(2-Fluoro-4-hydroxyphenyl)butan-1-one

[Chemical Formula 54]

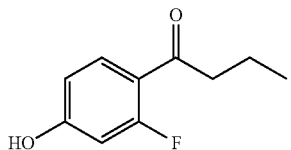

4-(Tert-butyldimethylsilyloxy)-2-fluorobenzonitrile (40.5 g) that can be produced by the method described in Reference Example 1 or the like was dissolved in dehydrated diethyl ether (350 mL; manufactured by Kanto Chemical Co., Inc.) and a 2 mol/L-n-propylmagnesium chloride-diethyl-ether solution (200 mL; manufactured by Sigma-Aldrich Co.) was added dropwise thereto. The mixture was stirred for 1.5 hours at reflux. The reaction solution was cooled to room temperature, and then water (150 mL) and 5 mol/L hydrochloric acid (150 mL) were added thereto. The reaction solution was stirred overnight at reflux. The reaction solution was extracted three times with ethyl acetate, and the organic layer was washed with water and brine, and dried over anhydrous sodium sulfate. Subsequently, the solvent was evaporated under reduced pressure, and the residue (47.17 g) was dissolved in THF (250 mL). A 1 mol/L TBAF-THF solution (40 mL; manufactured by Tokyo Chemical Industry Co., Ltd.) was added the solution, and the mixture was stirred for one hour at room temperature. Water was added to the reaction solution, and the mixture was extracted three times with ethyl acetate. The organic layer was washed with water and saturated brine, and was dried over anhydrous sodium sulfate. Subsequently, the solvent was evaporated under reduced pressure, and the residue was dissolved in diethyl ether. The solution was extracted with a 2 mol/L aqueous solution of sodium hydroxide, and the aqueous layer was washed with diethyl ether. 2 mol/L hydrochloric acid was added to the aqueous layer, and the mixture was extracted two times with ethyl acetate. The organic layer was washed with water and brine, and was dried over anhydrous sodium sulfate. Then, the solvent was evaporated under reduced pressure, and thus the title compound (28.38 g) was obtained.

$^1$H-NMR (300 MHz, CDCl$_3$); δ (ppm) 0.99 (3H, t, J=7.3), 1.70-1.78 (2H, m), 2.90-2.96 (2H, m), 6.64 (1H, dd, J=2.4, 12.8), 6.73 (1H, dd, J=2.4, 8.6), 7.79-7.84 (1H, m), 10.22 (1H, brs)

LCMS: 181.0 [M−H]; Retention time: 3.71 minutes; LCMS condition: B

Reference Example 17

1-Benzyl-3-n-propylindazol-6-ol

[Chemical Formula 55]

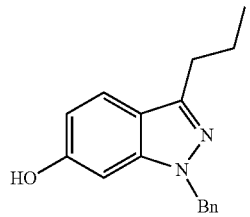

1-(2-Fluoro-4-hydroxyphenyl)butan-1-one (3.468 g) that can be produced by the method described in Reference Example 16 or the like, sodium acetate (7.57 g; manufactured by Wako Pure Chemical Industries, Ltd.), and benzylhydrazine dihydrochloride (5.48 g; manufactured by Wako Pure Chemical Industries, Ltd,) were suspended in xylene (200 mL; manufactured by Kanto Chemical Co., Inc.). The suspension was stirred overnight at reflux using a Dean-Stark apparatus. The reaction solution was cooled to room temperature, subsequently water was added thereto, and the mixture was extracted two times with ethyl acetate. The organic layer was washed two times with water and with brine, and was dried over anhydrous sodium sulfate. Subsequently, the solvent was evaporated under reduced pressure, and n-hexane was added to the residue. Precipitates were filtered, and thus the title compound (5.41 g) was obtained.

$^1$H-NMR (300 MHz, CDCl$_3$); δ (ppm) 0.99 (3H, t, J=7.3), 1.77-1.85 (2H, m), 2.90 (2H, t, J=7.3), 5.40 (2H, s), 5.71 (1H, bra) 6.57 (1H, d, J=2.0), 6.66 (1H, dd, 8.6) 7.10-7.28 (5H, m), 7.52 (1H, d, J=8.6), LCMS: 267.2 [M+H]; Retention time: 4.08 minutes; LCMS condition: B

Reference Example 18

N,N-dibenzyl-2-(1-benzyl-3-n-propylindazol-6-yloxy)ethanamine

[Chemical Formula 56]

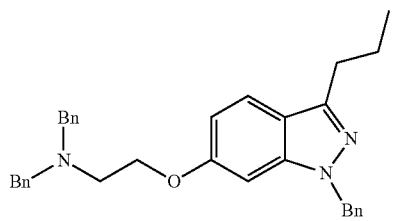

Under a nitrogen atmosphere, 2-(dibenzylamino)ethanol (6.41 mL; manufactured by Tokyo Chemical Industry Co., Ltd.) and triethylamine (4.71 mL; manufactured by Kokusan Chemical Co., Ltd.) were dissolved in dehydrated THF (93 mL; manufactured by Kanto Chemical Co., Inc.), and the solution was stirred for 10 minutes at 0° C. Methanesulfonyl chloride (2.47 mL; manufactured by Tokyo Chemical Industry Co., Ltd.) was added dropwise from a dropping funnel to the reaction solution over 3 minutes, and dehydrated THF (50 mL) was used to wash the dropping funnel and was included to the reaction solution. The mixture was stirred for one hour at 0° c. To the reaction solution, 1-benzyl-3-n-propyl indazol-6-ol (4.98 g) that can be produced by the method described in Reference Example 17 or the like was added, and a 1 mol/L sodium methoxide-methanol solution (56.3 mL) was added dropwise thereto from a dropping funnel over 10 minutes. Dehydrated THF (50 mL) was used to wash the dropping funnel and was included to the reaction solution. The mixture was stirred overnight at 50° C. The reaction solution was cooled to room temperature, and then precipitates were filtered. The solvent in the filtrate was evaporated under reduced pressure, and the residue was purified by column chromatography ("COLUMN-A"; n-hexane:ethyl acetate=100:0→60:10). Thus, the title compound (5.89 g) was obtained.

$^1$H-NMR (300 MHz, CDCl$_3$); δ (ppm) 0.97 (3H, t, J=7.3), 1.78-1.85 (2H, m), 2.87-2.92 (4H, m), 3.70 (4H, s), 3.95-4.00 (2H, m), 5.44 (2H, s), 6.47 (1H, d, J=2.0), 6.69 (1H, dd, J=2.0, 8.8) 7.11-7.52 (16H, m)

LCMS: 490.3 [M+H]; Retention time: 5.23 minutes; LCMS condition: A

Reference Example 19

N-benzyl-2-(1-benzyl-3-propylindazol-6-yloxy)ethanamine

[Chemical Formula 57]

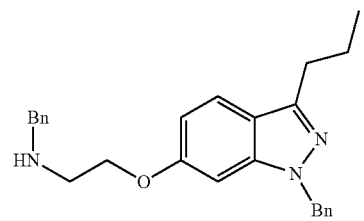

N,N-dibenzyl-2-(1-benzyl-3-n-propylindazol-6-yloxy) ethanamine (16.3 g) that can be produced by the method described in Reference Example 18 or the like, and 5% palladium on carbon-STD-type-54.4% wet with water (3.05 g; manufactured by N.E. Chemcat Corp.) were suspended in methanol (282 mL; manufactured by Wako Pure Chemical Industries, Ltd.), and concentrated hydrochloric acid (4.71 mL; manufactured by Wako Pure Chemical Industries, Ltd.) was added thereto. The reaction system was purged with hydrogen, and under a hydrogen atmosphere, the reaction solution was stirred overnight at room temperature. The reaction solution was filtered, and the filtrate was concentrated under reduced pressure. Water, ethyl acetate and a 20 mol/L aqueous solution of sodium hydroxide were added to the residue to basify the residue, and the mixture was extracted two times with ethyl acetate. The organic layer was washed with water and brine, and was dried over anhydrous sodium sulfate. Subsequently, the solvent was evaporated under reduced pressure, and thus the title compound (20.81 g) was obtained.

$^1$H-NMR (300 MHz, CDCl$_3$); δ (ppm) 1.00 (3H, t, J=7.3), 1.78-1.86 (2H, m), 2.91 (2H, t, J=7.3), 3.01 (2H, t, J=5.1), 3.86 (2H, s), 4.05 (2H, t, J=5.0), 5.46 (2H, s), 6.57 (1H, d, J=2.0), 6.74 (1H, dd, J=2.0, 8.8) 7.12-7.54 (11H, m)

LCMS: 400.3 [M+H]; Retention time: 3.00 minutes; LCMS condition; B

Reference Example 20

(R)-N-benzyl-N-(3-(2-(benzyl-(2-(1-benzyl-3-propylindazol-6-yloxy)ethyl)amino)-1-hydroxyethyl)phenyl)methanesulfonamide

[Chemical Formula 58]

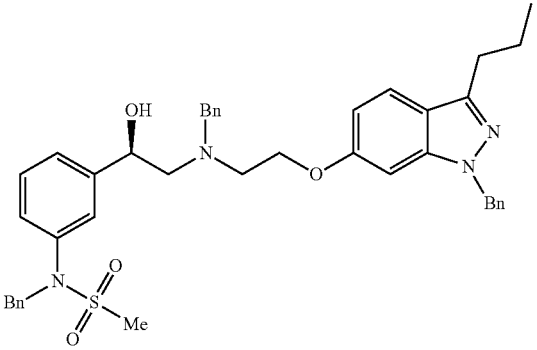

N-benzyl-2-(1-benzyl-3-propylindazol-6-yloxy)ethanamine (20.81 g) that can be produced by the method described in Reference Example 19 or the like, and (R)-N-benzyl-N-(3-(oxiran-2-yl)phenyl)methanesulfonamide (15.83 g; intermediate described in Example 3 of WO 01/0409212) were dissolved in 2-propanol (260 mL; manufactured by Kanto Chemical Co., Inc.). The solution was stirred for 39 hours at reflux. The reaction solution was cooled, and then the solvent was evaporated under reduced pressure. The residue was purified by column chromatography ("COLUMN-A"; n-hexane:ethyl acetate=78:22→57:43), and thus the title compound (23.5 g) was obtained.

$^1$H-NMR (300 MHz, CDCl$_3$); δ (ppm) 1.00 (3H, t, J=7.3), 1.79-1.87 (2H, m), 2.54-2.75 (2H, m), 2.88-3.06 (7H, m), 3.63-3.97 (4H, m), 4.62 (1H, dd, J=3.3, 9.9), 4.79 (2H, s), 5.47 (2H, s), 6.53 (1H, d, J=2.0), 6.76 (1H, dd, J=1.8, 8.8) 7.10-7.30 (19H, m), 7.55 (1H, d, J=8.8)

LCMS: 703.4 [M+H]; Retention time: 4.45 minutes; LCMS condition: A

Example 3

(R)-N-(3-(1-hydroxy-2-(2-(3-propylindazol-6-yloxy)ethylamino)ethyl)phenyl)methanesulfonamide

[Chemical Formula 59]

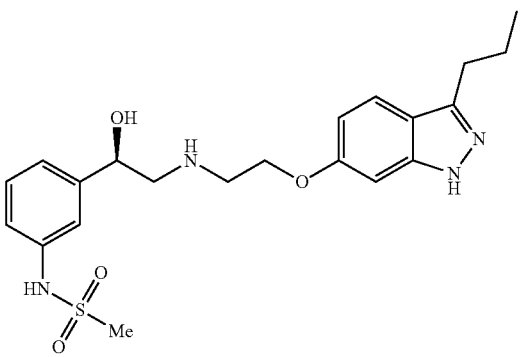

(R)-N-benzyl-N-(3-(2-(benzyl(2-(1-benzyl-3-propylindazol-6-yloxy)ethyl)amino)-1-hydroxyethyl)phenyl)methanesulfonamide (22.0 g) that can be produced by the method described in Reference Example 20 or the like, and 10% palladium on carbon-PE-type-50% wet with water (4.5 g; manufactured by N.E. Chemcat Corp.) were suspended in ethanol (20.9 mL; manufactured by Wako Pure Chemical Industries, Ltd.), and the reaction system was purged with hydrogen. Under a hydrogen atmosphere, the reaction solution was stirred overnight at 60° C. The reaction solution was cooled to room temperature, and then was purged with nitrogen. Concentrated hydrochloric acid (5.21 mL; manufactured by Wako Pure Chemical Industries, Ltd.) was added thereto, and the reaction solution was purged with hydrogen again. Under a hydrogen atmosphere, the reaction solution was stirred for 0.5 hours at 60° C. The reaction solution was cooled to room temperature, and was purged with nitrogen. A portion of the reaction solution was withdrawn and was subjected to hydrogen purging three times. Under a hydrogen atmosphere, the reaction solution was stirred for one hour at 60° C. The reaction solution was cooled to room temperature, and then was subjected to nitrogen purging. The reaction solution was filtered, and the filtrate was concentrated under reduced pressure. The residue was dissolved in ethanol/water=1/3 (86.5 mL), and a 0.2 mol/L aqueous solution of sodium hydroxide was added thereto until the pH reached 8.3. To this solution, ethanol/water=1/3 (2000 mL) was added while the temperature was raised to 70° C. Insoluble matters were filtered, and the filtrate was left to stand still overnight at room temperature. The filtrate was stirred to one hour at 0° C., precipitates were filtered, and thus the title compound (10.92 g) was obtained.

$^1$H-NMR (300 MHz, DMSO-$d_6$); δ (ppm) 0.93 (3H, t, J=7.3), 1.66-1.78 (2H, m), 2.64-2.96 (9H, m), 4.05 (2H, t, J=5.5), 4.61-4.64 (1H, m), 5.38 (1H, brs), 6.68 (1H, dd, J=3.8, 8.8), 6.83 (1H, d, J=1.8), 7.07-7.10 (2H, m), 7.24-7.30 (2H, m), 7.51-7.57 (1H, m), 12.36 (1H, brs)

LCMS: 433.1 [M+H]; Retention time: 2.49 minutes; LCMS condition: B

Reference Example 21

Indazol-6-ol

[Chemical Formula 60]

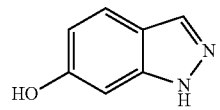

Indazol-6-amine (24.33 g; manufactured by Tokyo Chemical Industry Co., Ltd.) was dissolved in water (100 mL) and a 48 wt % aqueous solution of tetrafluoroboric acid (242 mL; manufactured by Sigma-Aldrich Co.), and the solution was cooled to 0° C. Subsequently, an aqueous solution of sodium nitrite (20 mL (sodium nitrite (13.87 g; manufactured by Kanto Chemical Co., Inc.) was dissolved in water (20 mL)) was added dropwise to the solution over 10 minutes, and the resulting mixture was stirred for 30 minutes at 0° C. Precipitates of the reaction solution were filtered, and were washed with chloroform. The obtained precipitates were dissolved in acetic acid (250 mL), and the solution was stirred for 10 minutes at 50° C., for 10 minutes at 110° C., and for 10 minutes at 130° C. The reaction solution was cooled, a saturated aqueous solution of sodium carbonate was added thereto, and the mixture was extracted with ethyl acetate. The organic layer was washed with brine, and was dried over anhydrous magnesium sulfate. The solvent was evaporated under reduced pressure, and the resulting residue was dissolved in ethanol (240 mL). A 2 mol/L aqueous solution of sodium hydroxide (365 mL) was added to the solution, and the mixture was stirred for one hour at room temperature. The reaction solution was concentrated under reduced pressure, and 2 mol/L hydrochloric acid (200 mL), water and a saturated aqueous solution of ammonium chloride were added to the residue to adjust the pH to about 7. The mixture was then extracted with ethyl acetate. The organic layer was washed with brine, and was dried over anhydrous magnesium sulfate. Subsequently, the solvent was evaporated under reduced pressure, and chloroform was added to the residue. Insoluble matters were filtered, and were washed with chloroform. Thus, a crude product (13.5401 g) of the title compound was obtained.

$^1$H-NMR (300 MHz, DMSO-$d_6$); δ (ppm) 6.64 (1H, dd, J=1.8, 8.8), 6.78(1H, dd, J=0.7, 1.8), 7.52(1H, d, J=8.8), 7.86(1H, d, J=0.7), 9.54(1H, s), 12.56 (1H, s)

LCMS: 134.9 [M+H]; Retention time: 0.72 minutes; LCMS condition: C

Reference Example 22

6-Tert-butyldiphenylsilyloxyindazole

[Chemical Formula 61]

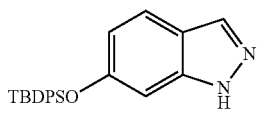

Indazol-6-ol (4.029 g) that can be produced by the method described in Reference Example 21 or the like, was dissolved in dehydrated DMF (60 mL; manufactured by Kanto Chemical Co., Inc.), and imidazole (4.49 g; manufactured by Tokyo Chemical Industry Co., Ltd.) and TBDPSCl (17.1 mL; manufactured by Tokyo Chemical Industry Co., Ltd.) were added to the solution. The mixture was stirred overnight at room temperature. The reaction solution was poured into water, and the mixture was extracted three times with ethyl acetate. The organic layer was washed three times with water, and was dried over anhydrous magnesium sulfate. Subsequently, the solvent was evaporated under reduced pressure, and the residue was purified by column chromatography ("COLUMN-A"; n-hexane:ethyl acetate=92:8→71:29). Thus, the title compound (9.214 g) was obtained.

$^1$H-NMR (300 MHz, CDCl$_3$); δ (ppm) 1.11 (9H, s), 6.66-6.67(1H, m), 6.78(1H, dd, J=2.0, 8.8), 7.33-7.45(6H, m), 7.48(1H, dd, J=0.5, 8.8), 7.71-7.74(4H, m), 7.88(1H, s)

LCMS: 373.3 [M+H]; Retention time: 5.88 minutes; LCMS condition: A

Reference Example 23

6-(Tert-butyldiphenylsilyloxy)-3-iodoindazole

[Chemical Formula 62]

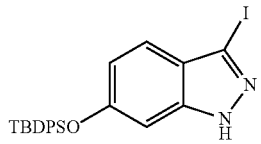

6-Tert-butyldiphenyleilyloxyindazole (9.124 g) that can be produced by the method described in Reference Example 22 or the like, was dissolved in dehydrated THF (247 mL; manufactured by Kanto Chemical Co., Inc.), and the solution was purged with nitrogen. The solution was cooled to 0° C., and then potassium tert-butoxide (5.560 g; manufactured by Kanto Chemical Co., Inc.) and iodine (12.621 g) were added thereto. The mixture was stirred for 40 minutes while the temperature was raised to room temperature. The reaction solution was poured into an aqueous solution of sodium thiosulfate, and the mixture was extracted two times with ethyl acetate. The organic layer was washed two times with brine, and was dried over anhydrous magnesium sulfate. Subsequently, the solvent was evaporated under reduced pressure, and the residue was purified by column chromatography ("COLUMN-A"; n-hexane:ethyl acetate=88:12→67:33). Thus, the title compound (11.046 g) was obtained.

$^1$H-NMR (300 MHz, CDCl$_3$); δ (ppm) 1.10 (9H, s), 6.71 (1H, d, J=1.8), 6.84 (1H, dd, J=1.8, 8.8), 7.23 (1H, d, J=9.1), 7.32-7.44 (6H, m), 7.69-7.74 (4H, m), 10.68 (1H, brs)

LCMS: 499.2 [m+H]; Retention time: 6.60 minutes; LCMS condition: B

Reference Example 24

Tert-butyl 6-(tert-butyldiphenylsilyloxy)-3-iodoindazole-1-carboxylate

[Chemical Formula 63]

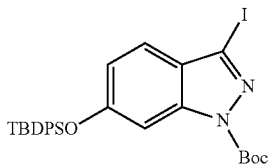

6-(Tert-butyldiphenylsilyloxy)-3-iodoindazole (2.432 g) that can be produced by the method described in Reference Example 23 or the like, was dissolved in dehydrated acetonitrile (25 mL; manufactured by Kanto Chemical Co., Inc.), and triethylamine (0.766 mL; manufactured by Kokusan Chemical Co., Ltd.), DMAP (0.609 g; manufactured by Wako Pure Chemical Industries, Ltd.) and Boc$_2$O (1.37 mL; manufactured by Wako Pure Chemical Industries, Ltd.) were added to the solution. The mixture was stirred overnight at room temperature. The reaction solution was concentrated under reduced pressure, and then the residue was purified by column chromatography ("COLUMN-B"; n-hexane:ethyl acetate=100:0→87:13). Thus, the title compound (2.302 g) was obtained.

$^1$H-NMR (300 MHz, CDCl$_3$); δ (ppm) 1.11 (9H, s) 1.46 (9H, s), 6.82 (1H, dd, J=2.0, 8.6), 7.17 (1H, d, J=8.8), 7.32-7.45 (6H, m), 7.69-7.72 (5H, m)

Reference Example 25

Tert-butyl 6-hydroxy-3-iodoindazole-1-carboxylate

[Chemical Formula 64]

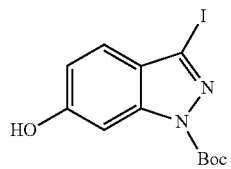

Tert-butyl 6-(tert-butyldiphenylsilyloxy)-3-iodoindazole-1-carboxylate (596 mg) that can be produced by the method described in Reference Example 24 or the like, was dissolved in dehydrated THF (10 mL), and a 1 mol/L TBAF-THF solution (1.5 mL; manufactured by Sigma-Aldrich Co.) was added thereto. The mixture was stirred for one hour at room temperature. The reaction solution was poured into water, and the mixture was extracted two times with ethyl acetate. The organic layer was washed three times with water, and was dried over anhydrous sodium sulfate. Subsequently, the solvent was evaporated under reduced pressure, and hexane was added to the residue. Precipitates were filtered, and thus the title compound (291 mg) was obtained.

$^1$H-NMR (300 MHz, CDCl$_3$); δ (ppm) 1.68 (9H, s), 5.73 (1H, s), 6.93 (1H, dd, J=2.0, 8.6), 7.33 (1H, d, J=8.9), 7.56 (1H, d, J=2.0)

LCMS: 361.2 [M+H]; Retention time: 4.25 minutes; LCMS condition; A

Reference Example 26

Tert-butyl 3-iodo-6-methylsulfonyloxyindazole-1-carboxylate

[Chemical Formula 65]

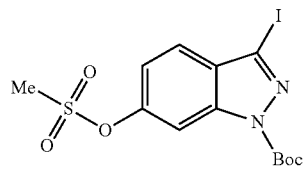

Tert-butyl 6-hydroxy-3-iodoindazole-1-carboxylate (248.6 mg) that can be produced by the method described in Reference Example 25 or the like, was dissolved in dehydrated dichloromethane (120 mL), and the solution was cooled to 0° C. Subsequently, diisopropylethylamine (133 µL; manufactured by Wako Pure Chemical Industries, Ltd.), and methanesulfonyl chloride (75.2 µL; manufactured by Wako Pure Chemical Industries, Ltd.) were added to the solution, and the mixture was stirred overnight while the temperature was raised to room temperature. To the reaction solution, diisopropylethylamine (20 µL; manufactured by Wako Pure Chemical Industries, Ltd.) and methanesulfonyl chloride (10 µL; manufactured by Wako Pure Chemical Industries, Ltd.) were added, and the mixture was stirred for 9 hours at room temperature. To the reaction solution, diisopropylethylamine (66.5 µL; manufactured by Wako Pure Chemical Industries, Ltd.) and methanesulfonyl chloride (37.6 µL; manufactured by Wako Pure Chemical Industries, Ltd.) were added, and the mixture was stirred overnight at room temperature. The reaction solution was washed three times with water, and the organic layer was dried over anhydrous sodium sulfate. Subsequently, the solvent was evaporated under reduced pressure, and the residue was purified by column chromatography ("COLUMN-A"; n-hexane:ethyl acetate=82:18→61:39). Thus, the title compound (275.9 mg) was obtained.

$^1$H-NMR (300 MHz, CDCl$_3$); δ (ppm) 1.71 (9H, s), 3.22 (3H, s), 7.31 (1H, dd, J=2.2, 8.8), 7.53 (1H, dd, J=0.5, 8.8), 8.12 (1H, d, J=2.0)

LCMS: 439.1 [M+H]; Retention time: 4.81 minutes; LCMS condition: A

Reference Example 27

3-Trifluoromethylindazol-6-yl methanesulfonate

[Chemical Formula 66]

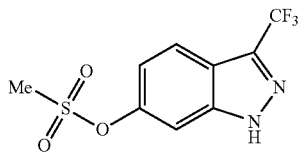

A dehydrated NMP solution of tert-butyl 3-iodo-6-methylsulfonyloxyindazole-1-carboxylate that can be produced by the method described in Reference Example 26 or the like [1 mL (tert-butyl 3-iodo-6-methylsulfonyloxyindazole-1-carboxylate (535.4 mg) was dissolved in dehydrated NMP (12.2 mL; manufactured by Kanto Chemical Co., Inc.))], copper iodide (4.0 mg; manufactured by Wako Pure Chemical Industries, Ltd.), and methyl 2,2-difluoro-2-(fluorosulfonyl) acetate (50.5 µL; manufactured by Tokyo Chemical Industry Co., Ltd.) were added, and the mixture was purged with nitrogen and then stirred for 4 hours at 160° C. The same reaction was carried out 12 times in total. The twelve reaction solutions were poured into a sodium hydrogen carbonate solution, and the mixture was extracted two times with ethyl acetate. The organic layer was washed three times with water, and was dried over anhydrous magnesium sulfate. The solvent was evaporated under reduced pressure, and the residue was purified by column chromatography ("COLUMN-A"; n-hexane:ethyl acetate=75:25→54:46). Thus, the title compound (146 mg) was obtained.

$^1$H-NMR (300 MHz, CDCl$_3$)); δ (ppm) 3.23 (3H, s), 7.22 (1H, dd, J=2.0, 9.0), 7.56 (1H, d, J=0.5), 7.89 (1H, dd, J=0.7, 8.8), 10.67 (1H, brs)

LCMS: 279.0 [M−H]; Retention time: 3.81 minutes; LCMS condition: A

Reference Example 28

1-(Tetrahydro-2H-pyran-2-yl)-3-trifluoromethylindazol-6-yl methanesulfonate

[Chemical Formula 67]

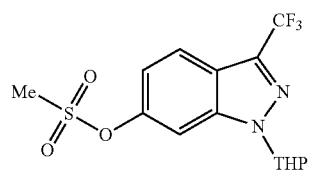

3-Trifluoromethylindazol-6-yl methanesulfonate (281.5 mg) that can be produced by the method described in Reference Example 27 or the like, was dissolved in toluene (10 mL), and 3,4-dihydro-2H-pyrane (0.182 mL; manufactured by Kanto Chemical Co., Inc.) and toluenesulfonic acid monohydrate (37.1 mg; manufactured by Tokyo Chemical Industry Co., Ltd.) were added to the solution. Under a nitrogen atmosphere, the mixture was stirred overnight at 60° C. Ethyl acetate was added to the reaction solution, and the reaction solution was washed once with a saturated aqueous solution of sodium hydrogen carbonate, twice with water, and once with brine. The organic layer was dried over anhydrous sodium sulfate, and then the solvent was evaporated under reduced pressure. The residue was purified by column chromatography ("COLUMN-A"; n-hexane:ethyl acetate=88:12→67:33), and thus the title compound (320 mg) was obtained.

$^1$H-NMR (300 MHz, CDCl$_3$); δ (ppm) 1.66-1.84 (3H, m), 2.07-2.13 (2H, m), 2.44-2.57 (1H, m), 3.21 (1H, s), 3.72-3.80 (1H, m), 3.96-4.02 (1H, m), 5.57 (1H, dd, J=2.7, 8.8), 7.22 (1H, dd, J=2.0, 8.8), 7.65 (1H, dd, J=0.5, 2.0), 7.85 (1H, d, J=8.8)

LCMS: Retention time: 4.88 minutes; LCMS condition: A

Reference Example 29

1-(Tetrahydro-2H-pyran-2-yl)-3-trifluoromethylindazol-6-ol

[Chemical Formula 68]

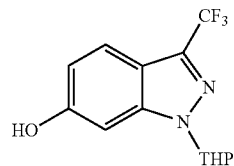

1-(Tetrahydro-2H-pyran-2-yl)-3-trifluoromethylindazol-6-yl methanesulfonate (490 mg) that can be produced by the method described in Reference Example 28 or the like, was dissolved in ethanol (13 mL), and a 2 mol/L aqueous solution of sodium hydroxide (3.9 mL) was added thereto. The mixture was stirred for 2 hours at reflux. The reaction solution was cooled to room temperature, and then 1 mol/L hydrochloric acid (7.8 mL) was added thereto. The solvent was evaporated under reduced pressure to the extent that the residue would not become solid dry, and the residue was poured into a saturated aqueous solution of sodium hydrogen carbonate. The mixture was extracted two times with ethyl acetate. The organic layer was washed with water, and was dried over anhydrous sodium sulfate. Subsequently, the solvent was evaporated under reduced pressure, and thus the title compound (379 mg) was obtained.

$^1$H-NMR (300 MHz, CDCl$_3$); δ (ppm) 1.64-1.82 (3H, m), 2.03-2.18 (2H, m), 2.44-2.56 (1H, m), 3.68-3.76 (1H, m), 3.97-4.03 (1H, m), 5.37 (1H, s), 5.66 (1H, dd, J=2.7, 9.0), 6.84 (1H, dd, J=2.2, 8.8), 7.02 (1H, dd, J=0.5, 2.2), 7.64 (1H, dt, J=0.7, 0.9, 8.8)

LCMS: 287.2 [M+H]; Retention time: 4.39 minutes; LCMS condition: A

Reference Example 30

(R)-6-(2-(tert-butoxycarbonyl (2-(3-(N-(tert-butoxycarbonyl)methylsulfonamido)phenyl)-2-(triethylsilyloxy)ethyl)amino)ethoxy)-1-(tetrahydro-2H-pyran-2-yl)-3-trifluoromethylindazole

[Chemical Formula 69]

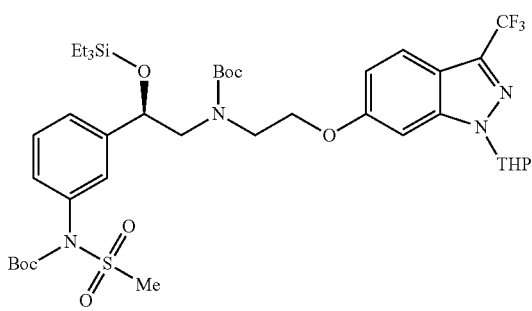

1-(Tetrahydro-2H-pyran-2-yl)-3-trifluoromethylindazol-6-ol (230.2 mg) that can be produced by the method described in Reference Example 29 or the like, was dissolved in toluene (8.5 mL; manufactured by Kanto Chemical Co., Inc.), and a (R)-(3-(2-(N-tert-butoxycarbonyl-N-(2-hydroxyethyl) amino)-1-triethylsilyloxy)ethyl)phenyl)-N-tert-butoxycarbonylmethanesulfonamide-toluene solution [4.25 mL; solution prepared by dissolving (R)-(3-(2-(N-tert-butoxycarbonyl-N-(2-hydroxyethyl)amino)-1-triethylsilyloxy)ethyl)phenyl]-N-tert-butoxycarbonylmethanesulfonamide (1.1458 g) in dehydrated toluene (4.89 mL)], triphenylphosphine (459.0 mg; manufactured by Kanto Chemical Co., Inc.) and TMAD (297.7 mg; manufactured by Masuda Chemical Industries, Co., Ltd.) were added to the solution. The mixture was stirred overnight at room temperature. The reaction solution was purified by column chromatography ("COLUMN-B"; n-hexane:ethyl acetate=88:12→67:33), and thus the title compound (502.7 mg) was obtained.

$^1$H-NMR (300 MHz, CDCl$_3$); δ (ppm) 0.50-0.58 (6H, m), 0.86-0.92 (9H, m), 1.43-1.57 (18H, m), 1.67-1.78 (3H, m); 2.03-2.15 (2H, m), 2.51-2.57 (1H, m), 3.22-4.98 (10H, m), 5.10-5.14 (1H, m), 6.67 (1H, dd, J=3.1, 9.3), 6.86-7.43 (6H, m), 7.56-7.65 (1H, m)

Reference Example 31

1-(Bromomethyl)-4-methoxy-2-nitrobenzene

[Chemical Formula 70]

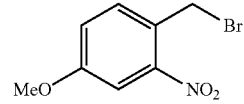

4-Methyl-3-nitroanisole (2.7 mL; manufactured by Sigma-Aldrich Co.) was dissolved in carbon tetrachloride (20 mL; manufactured by Wako Pure Chemical Industries, Ltd.), and NBS (4.0520 g; manufactured by Tokyo Chemical Industry Co., Ltd.) and hydrated benzoyl peroxide (348 mg; manufactured by Sigma-Aldrich Co.) were added to the solution. The mixture was purged with nitrogen, and was stirred for 3 hours at reflux. The reaction solution was filtered, and then the filtrate was washed with an aqueous solution of NaHSO$_3$ and water and dried over anhydrous sodium sulfate. The solvent was evaporated under reduced pressure, and the residue was purified by column chromatography ("COLUMN-B"; n-hexane:ethyl acetate=94:6→73:27). Thus, the title compound (3.2549 g) was obtained.

$^1$H-NMR (300 mHz, CDCl$_3$); δ (ppm) 3.88 (3H, s), 4.80 (2H, s), 7.13 (1H, dd, J=2.5, 8.9), 7.45 (1H, d, J=8.4), 7.55 (1H, d, J=2.5)

Reference Example 32

4-Methoxy-2-nitro-1-(2,2,2-trifluoroethyl)benzene

[Chemical Formula 71]

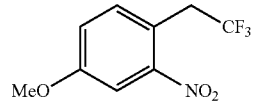

1-(Bromomethyl)-4-methoxy-2-nitrobenzene (2.7123 g) that can be produced by the method described in Reference Example 31 or the like, was dissolved in dehydrated DMF (22 mL; manufactured by Kanto Chemical Co., Inc.), and copper iodide (524 mg; manufactured by Wako Pure Chemical Industries, Ltd.) and methyl 2,2-difluoro-2-(fluorosulfonyl) acetate (3.06 mL; manufactured by Tokyo Chemical Industry Co., Ltd.) were added to the solution. The mixture was purged with nitrogen, and was stirred for 4 hours at 100° C. Ethyl acetate was added to the reaction solution, and the organic layer was washed with aqueous ammonia, water and brine and dried over anhydrous magnesium sulfate. The solvent was evaporated under reduced pressure. The residue was purified by column chromatography ("COLUMN-B"; n-hexane:ethyl acetate=97:3→77:23), and thus the title compound (1.579 g) was obtained.

¹H-NMR (300 MHz, CDCl₃); δ (ppm) 3.83 (2H, q, J=10.2), 3.88 (3H, s), 7.14 (1H, dd, J=2.5, 8.4), 7.35 (1H, d, J=8.4), 7.51 (1H, d, J=2.9)

Reference Example 33

5-Methoxy-2-(2,2,2-trifluoroethyl)benzenamine

[Chemical Formula 72]

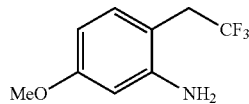

4-Methoxy-2-nitro-1-(2,2,2-trifluoroethyl)benzene (1.8153 g) that can be produced by the method described in Reference Example 32 or the like, and 5% palladium on carbon-STD-type-50% wet with water (926 mg; Manufactured by N.E. Chemcat Corp.) were suspended in methanol (30 mL; manufactured by Kanto Chemical Co., Inc.), and the reaction system was purged with hydrogen. Under a hydrogen atmosphere, the suspension was stirred overnight at room temperature. The reaction solution was purged with nitrogen, and then 5% palladium on carbon-STD-type-50% wet with water (926 mg; manufactured by N.E. Chemcat Corp.) was added thereto. The reaction system was purged with hydrogen, and under a hydrogen atmosphere, the reaction solution was stirred for 9 hours at room temperature. The reaction solution was purged with nitrogen, and then was filtered. The filtrate was concentrated under reduced pressure. The residue was dissolved in chloroform, and was dried over anhydrous magnesium sulfate. The solvent was evaporated under reduced pressure, and thus the title compound (1.4096 g) was obtained.

LCMS: 206.2 [M+H]; Retention time: 1.41 minutes; LCMS condition: C

Reference Example 34

1-(6-Methoxy-3-trifluoromethylindazol-1-yl)ethanone

[Chemical Formula 73]

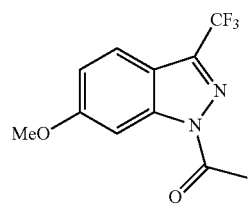

5-Methoxy-2-(2,2,2-trifluoroethyl)benzenamine (1.4013 g) that can be produced by the method described in Reference Example 33 or the like, was dissolved in monochlorobenzene (23 mL; manufactured by Kanto Chemical Co., Inc.), and potassium acetate (1.6994 g; manufactured by Wako Pure Chemical Industries, Ltd.) and acetic anhydride (3.26 mL; manufactured by Wako Pure Chemical Industries, Ltd.) were added to the solution. The mixture was stirred for 5 minutes at 80° C. Isoamyl nitrite (2.75 mL; manufactured by Tokyo Chemical Industry Co., Ltd.) was added to the reaction solution; and the mixture was stirred for 15 hours at 80° C. The reaction solution was cooled to room temperature, and was left to stand for 2 days. Subsequently, isoamyl nitrite (1 mL; manufactured by Tokyo Chemical Industry Co., Ltd.) was added thereto, and the mixture was stirred for 4 hours at 80° C. The reaction solution was cooled to room temperature, and ethyl acetate was added thereto. The organic layer was washed with a saturated aqueous solution of sodium hydrogen carbonate and brine, and was dried over anhydrous sodium sulfate. The solvent was evaporated under reduced pressure, and the residue was purified by column chromatography ("COLUMN-B"; n-hexane:ethyl acetate=100:0→80:20). Thus, the title compound (1.6105 g) was obtained.

¹H-NMR (300 MHz, CDCl₃); δ (ppm) 2.81 (3H, s), 3-93 (3H, s), 7.06 (1H, dd, 8.7), 7.67 (1H, d, J=8.7), 7.90 (1H, d, J=2.2)

LCMS: 259.2 [M+H]; Retention time: 1.90 minutes; LCMS condition: C

Reference Example 35

3-Trifluoromethylindazol-6-ol

[Chemical Formula 74]

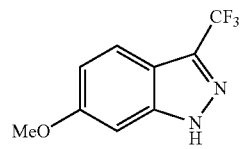

Hydrobromic acid (100 mL; manufactured by Wako Pure Chemical Industries, Ltd.) was added to 1-(6-methoxy-3-trifluoromethylindazol-1-yl)ethanone (2.5826 g) that can be produced by the method described in Reference Example 34 or the like, and the mixture was stirred overnight at 110° C. The reaction solution was cooled to 0° C., and then was neutralized with a 5 mol/L aqueous solution of sodium hydroxide to adjust the pH to about 7. The reaction solution was extracted once with ethyl acetate. The organic layer was washed with brine, and was dried over anhydrous magnesium sulfate. The solvent was evaporated under reduced pressure, and thus the title compound (1.8583 g) was obtained.

¹H-NMR (300 MHz, DMSO-d₆); δ (ppm) 6.85 (1H, dd, J=1.8, 8.7), 6.87 (1H, d, J=1.8), 7.57 (1H, d, J=8.7), 9.98 (1H, brs), 13.45 (1H, brs)

LCMS: 202.9 [M+H]; Retention time: 1.23 minutes; LCMS condition: C

Reference Example 36

6-(Tert-butyldiphenylsilyloxy)-3-trifluoromethylindazole

[Chemical Formula 75]

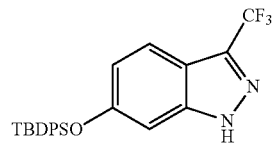

3-Trifluoromethylindazol-6-ol (1.818 g) that can be produced by the method described in Reference Example 35 or the like, and imidazole (1.363 g; manufactured by Tokyo Chemical Industry Co., Ltd.) were dissolved in dehydrated DMF (22 mL; manufactured by Kanto Chemical Co., Inc.), and TBDPSCl (5.14 mL; manufactured by Tokyo Chemical Industry Co., Ltd.) was added to the solution. The mixture was stirred overnight at room temperature. Ethyl acetate was added to the reaction solution, and the organic layer was washed twice with water and once with brine. The organic layer was dried over anhydrous magnesium sulfate, and then the solvent was evaporated under reduced pressure. The residue was purified by column chromatography ("COLUMN-A"; n-hexane:ethyl acetate=97:3→76:24), and a fraction with low purity was purified again by column chromatography ("COLUMN-A"; n-hexane:ethyl acetate=97:3→76:24). A fraction with low purity was purified again by column chromatography ("COLUMN-B"; n-hexane:ethyl acetate=97:3→76:24), and thus the title compound (3.367 g) was obtained.

$^1$H-NMR (300 MHz, DMSO-$d_6$); δ (ppm) 6.75 (1H, d, J=1.8), 6.93 (1H, dd, J=2.2, 8.7), 7.37-7.53 (6H, m), 7.62 (1H, d, J=8.7), 7.69-7.72 (4H, m), 13.49 (1H, brs)

Reference Example 37

Tert-butyl 6-(tert-butyldiphenylsilyloxy)-3-trifluoromethylindazole-1-carboxylate

[Chemical Formula 76]

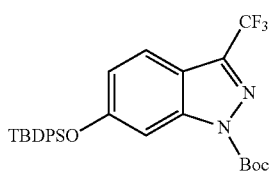

6-(Tert-butyldiphenylsilyloxy)-3-trifluoromethylindazole (3.3513 g) that can be produced by the method described in Reference Example 36 or the like, was dissolved in dehydrated THF (35 mL; manufactured by Kanto Chemical Co., Inc.), and $Boc_2O$ (2.09 mL; manufactured by Wako Pure Chemical Industries, Ltd.), triethylamine (1.28 mL; manufactured by Kokusan. Chemical Co., Ltd.) and DMAP (93.1 mg; manufactured by Wako Pure Chemical Industries, Ltd.) were added to the solution. The mixture was stirred overnight at room temperature. Ethyl acetate was added to the reaction solution, and the organic layer was washed twice with 1 mol/L hydrochloric acid, once with water and once with brine. The organic layer was dried over anhydrous magnesium sulfate, and then the solvent was evaporated under reduced pressure. Thus, a crude product (4.4773 g) of the title compound was obtained.

$^1$H-NMR (300 MHz, DMSO-$d_6$); δ (ppm) 1.06 (9H, s), 1.36 (9H, s), 7.11 (1H, dd, J=2.2, 8.7), 7.33 (1H, d, 7.38-7.53 (6H, m), 7.63-7.72 (4H, m), 7.75 (1H, d, J=8.7)

LCMS: Retention time: 7.67 minutes; LCMS conditions B

Reference Example 38

Tert-butyl 6-hydroxy-3-trifluoromethylindazole-1-carboxylate

[Chemical Formula 77]

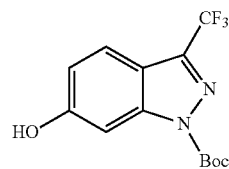

A crude product of tert-butyl 6-(tert-butyldiphenylsilyloxy)-3-trifluoromethylindazole-1-carboxylate (4.4773 g) that can be produced by the method described in Reference Example 37 or the like, was dissolved in dehydrated THF (40 mL; manufactured by Kanto Chemical Co., Inc.) and a 1 mol/L TBAF-THF solution (12 mL; manufactured by Tokyo Chemical Industry Co., Ltd.) was added to the solution. The mixture was stirred for 20 minutes at room temperature. The reaction solution was poured into brine, and the mixture was extracted once with ethyl acetate. The organic layer was washed twice with water and once with brine, and was dried over anhydrous magnesium sulfate. Subsequently, the solvent was evaporated under reduced pressure, and the residue was purified by column chromatography ("COLUMN-"; n-hexane:ethyl acetate=86:14→65:35). Thus, the title compound (1.6508 g) was obtained.

$^1$H-NMR (300 MHz, $CDCl_3$); δ (ppm) 1.72 (9H, s), 5.39 (1H, s), 6.98 (1H, dd, J=2.1, 8.7), 7.62 (1H, d, J=2.1), 7.68 (1H, d, J=8.7)

LCMS: 300.9 [M−H]; Retention time: 1.73; LCMS condition: C

Reference Example 39

(R)-tert-butyl 6-(2-(tert-butoxycarbonyl (2-(3-(N-(tert-butoxycarbonyl)methylsulfonamido)phenyl)-2-(triethylsilyloxy)ethyl)amino)ethoxy)-3-trifluoromethyl-1-carboxylate

[Chemical Formula 78]

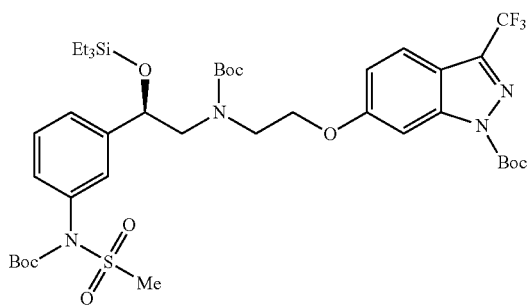

Tert-butyl 6-hydroxy-3-trifluoromethylindazole-1-carboxylate (1.5110 g) that can be produced by the method described in Reference Example 38 or the like, was dissolved in dehydrated toluene (15 mL; manufactured by Kanto Chemical Co., Inc.), and a toluene solution of (R)-(3-(2-(N-tert-butoxycarbonyl-N-(2-hydroxyethyl)amino)-1-triethylsilyloxy)ethyl)phenyl)-N-tert-butoxycarbonylmethanesulfonamide that can be produced by the method described in Reference Example 58 or the like [10 mL; solution prepared by dissolving (R)-(3-(2-(N-tent-butoxycarbonyl-N-(2-hydroxyethyl)amino)-1-triethylsilyloxy)ethyl)phenyl)-N-tert-butoxycarbonylmethanesulfonamide (16.56 g) in dehydrated toluene (28 mL; manufactured by Kanto Chemical Co., Inc.)], triphenylphosphine (2.5996 g; manufactured by Kanto Chemical Co., Inc.) and TMAD (1.7325 g; manufactured by Masuda Chemical Industries, Co., Ltd.) were added to the solution. The mixture-was stirred overnight at room temperature. The reaction solution was purified by column chromatography ("COLUMN-A"; n-hexane:ethyl acetate=82:18→61:39), and thus the title compound (3.5441 g) was obtained.

$^1$H-NMR (300 MHz, CDCl$_3$); δ (ppm) 0.54 (6H, q, J=7.6), 0.89 (9H, t, J=8.0), 1.43-1.71 (18H, m), 3.22-3.63 (7H, m), 4.03-4.12 (2H, m), 5.10-5.14 (1H, m), 6.98 (1H, dd, J=2.2, 8.7), 7.14-7.44 (4H, m) 7.59 (1H, d, J=1.8), 7.64 (1H, dd, J=4.0, 8.7)

LCMS: 873.5 [M+H]; Retention time: 8.12 minutes; LCMS condition: B

Example 4

(R)-N-(3-(1-hydroxy-2-(2-(3-trifluoromethylindazol-6-yloxy)ethylamino)ethyl)phenyl)methanesulfonamide

[Chemical Formula 79]

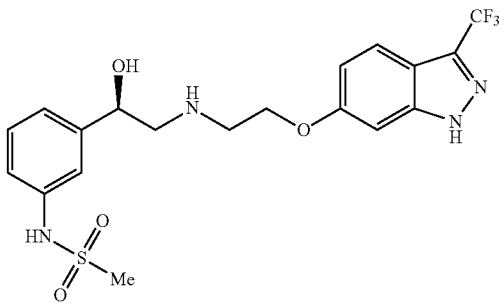

[Method 1] (R)-6-(2-(tert-butoxycarbonyl(2-(3-(N-(tert -butoxycarbonyl)methylsulfonamido)phenyl)-2-(triethylsilyloxy)ethyl)amino)ethoxy)-1-(tetrahydro -2H -pyran-2-yl)-3-trifluoromethylindazole (85.6 mg) that can be produced by the method described in Reference Example 30 or the like, was dissolved in a 10% hydrogen chloride-methanol solution (1.5 mL; manufactured by Tokyo Chemical Industry Co., Ltd.), and the solution was purged with nitrogen and stirred for 39 hours at 50° C. The reaction solution was cooled to room temperature, and then nitrogen gas was blown into the reaction solution to evaporate the solvent. The operation of adding diethyl ether to the residue, and blowing nitrogen gas into the reaction solution to evaporate the solvent, was repeated three times. The resulting residue was purified by HPLC, and then the purified product was dissolved in methanol (2 mL). A 10% hydrogen chloride-methanol solution (0.2 mL; manufactured by Tokyo Chemical Industry Co., Ltd.) was added to the solution, and nitrogen gas was blown into the solution to evaporate the solvent. The residue was dissolved in water (1 mL), and the solution was freeze-dried. Thus, the title compound was obtained in the form of hydrochloride (31 mg).

[Method 2] (R)-tert-butyl 6-(2-(tert-butoxycarbonyl(2-(3-(N-(tert-butoxycarbonyl)methylsulfonamido)phenyl)-2-(triethylsilyloxy)ethyl)amino)ethoxy)-3-trifluoromethyl-1-carboxylate (3.5143 g) that can be produced by the method described in Reference Example 39 or the like, was dissolved in a 4 mol/L hydrogen chloride-ethyl acetate solution (80 mL; manufactured by Kokusan Chemical Co., Ltd.), and the solution was stirred for 7 hours at room temperature. Precipitates in the reaction solution were filtered, and then were washed ethyl acetate. Thus, the title compound was obtained in the form of hydrochloride (1.9304 g). The hydrochloride (0.3792 mg) was dissolved in pure water (3.5008 g), and anions therein were analyzed by ion chromatography. As a result, chloride ions (10.2 ppm) were detected. Cations therein were analyzed, and as a result, sodium ions (0.01 ppm) were detected.

$^1$H-NMR (300 MHz, DMSO-d$_6$); δ (ppm) 3.00 (3H, s), 3.07-3.12 (1H, m), 3.24-3.26 (1H, m), 3.48 (2H, brs), 4.42 (2H, t, J=4.7), 5.02 (1H, d, J=8.0), 7.02 (1H, dd, J=1.8, 8.7), 7.12-7.17 (3H, m) 7.30-7.37 (2H, m), 7.70 (1H, d, J=8.7), 9.06 (1H, brs), 9.39 (1H, brs), 9.87 (1H, s), 13.94 (1H, brs)

LCMS: 459.2 [M+H]; Retention time: 0.97 minutes; LCMS condition: C

Reference Example 40

6-Hydroxyindazole-3-carboxylic acid

[Chemical Formula 80]

6-Methoxyindazole-3-carboxylic acid (1.015 g; manufactured by ChemPacific Corp.) was dissolved in hydrobromic acid (52 mL; manufactured by Kanto Chemical Co., Inc.), and the solution was stirred overnight at reflux. The solution was cooled to room temperature, and then the loss of raw materials and the presence of the title compound were confirmed using LCMS. The solvent was evaporated under reduced pressure, and thus a crude product (1.504 g) of the title compound was obtained.

LCMS: 179.1 [M+H]; Retention time: 1.94 minutes; LCMS condition: A

Reference Example 41

Ethyl 6-hydroxyindazole-3-carboxylate

[Chemical Formula 81]

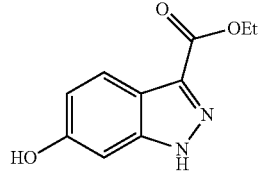

A crude product (1.504 g) of 6-hydroxyindazole-3-carboxylic acid that can be produced by the method described in Reference Example 40 or the like, was dissolved in ethanol, and the solution was cooled to 0° C. Subsequently, thionyl chloride (7.6 mL; manufactured by Wako Pure Chemical Industries, Ltd.) was added dropwise to the solution. The reaction solution was stirred overnight at 60° C., and then was cooled to room temperature. The loss of raw materials and the presence of the title compound were confirmed using LCMS, and the solvent was evaporated under reduced pressure. Ethanol (50 mL) was added to the residue, and the solvent was evaporated under reduced pressure. THF (50 mL) was added to the resulting residue, and the solvent was evaporated under reduced pressure again. Thus, a crude product (1.457 g) of the title compound was obtained.

LCMS; 207.1 [M+H]; Retention time: 2.80 minutes; LCMS condition: A

Reference Example 42

Ethyl 6-tert-butyldiphenylsilyloxyindazole-3-carboxylate

[Chemical Formula 82]

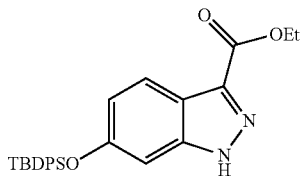

Ethyl 6-hydroxyindazole-3-carboxylate (1.457 g) that can be produced by the method described in Reference Example 41 or the like, was dissolved in dehydrated DMF (15.6 mL; manufactured by Kanto Chemical Co., Inc.), and imidazole (1.425 g; manufactured by Tokyo Chemical Industry Co., Ltd.) and TBDPSCl (4.06 mL) were added to the solution. The mixture was stirred overnight at room temperature. The reaction solution was poured into a saturated aqueous solution of sodium hydrogen carbonate, and the mixture was extracted two times with ethyl acetate. The organic layer was washed with brine, and then insoluble matters were filtered using Celite. The organic layer was washed two times with water, and was dried over anhydrous magnesium sulfate. The solvent was evaporated under reduced pressure, and the residue was purified by column chromatography ("COLUMN-A"; n-hexane:ethyl acetate=81:19→60:40). Thus, the title compound (1.467 g) was obtained.

$^1$H-NMR (300 MHz, CDCl$_3$); δ (ppm) 1.14 (9H, s), 1.42 (3H, t, J=6.9), 1.47-2.18 (5H, m), 3.46-3.54 (1H, m), 3.84-3.87 (1H, m), 4.44 (2H, q, J=7.1), 5.47 (1H, dd, J=2.7, 9.9), 6.86 (1H, d, J=2.0), 7.33-7.46 (6H, m), 7.71-7.76 (4H, m), 7.90 (1H, d, J=8.6)

LCMS: 445.1 [M+H]; Retention time: 6.09 minutes; LCMS condition: B

Reference Example 43

Ethyl 6-(tert-butyldiphenylsilyloxy)-1-(tetrahydro-2H-pyran-2-yl)-indazole-3-carboxylate

[Chemical Formula 83]

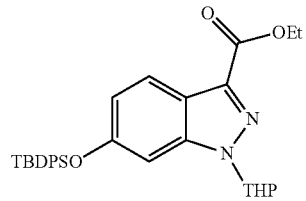

Ethyl 6-tert-butyldiphenylsilyloxyindazole-3-carboxylate (1.461 g) that can be produced by the method described in Reference Example 42 or the like, was dissolved in toluene (16.5 mL; manufactured by Wako Pure Chemical Industries, Ltd.), and 3,4-dihydro-2H-pyrane (0.6 mL; manufactured by Tokyo Chemical Industry Co., Ltd.) and toluenesulfonic acid monohydrate (0.1293 g) were added thereto. Under a nitrogen atmosphere, the mixture was stirred overnight at 60° C. The reaction solution was poured into a saturated aqueous solution of sodium hydrogen carbonate, and the mixture was extracted once with ethyl acetate. The organic layer was washed twice with water and once with brine, and was dried over anhydrous magnesium sulfate. Subsequently, the solvent was evaporated under reduced pressure, and the residue was purified by column chromatography ("COLUMN-A"; n-hexane:ethyl acetate=96:4→75:25). Thus, the title compound (1.334 g) was obtained.

$^1$H-NMR (300 MHz, CDCl$_3$); δ (ppm) 1.14 (9H, s), 1.42 (3H, t, J=6.9), 1.47-2.18 (5H, m), 3.46-3.54 (1H, m), 3.84-3.87 (1H, m), 4.44 (2H, q, J=7.1), 5.47 (1H, dd, J=2.7, 9.9), 6.86 (1H, d, J=2.0), 7.33-7.46 (6H, m), 7.71-7.76 (4H, m), 7.90 (1H, d, J=8.6)

LCMS: 529.2 [M+H]; Retention time: 6.83 minutes; LCMS condition: B

Reference Example 44

Ethyl 6-hydroxy-1-(tetrahydro-2H-pyran-2-yl)-indazole-3-carboxylate

[Chemical Formula 84]

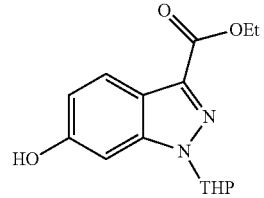

Ethyl 6-(tert-butyldiphenylsilyloxy)-1-(tetrahydro-2H-pyran-2-yl)-indazole-3-carboxylate (1.299 g) that can be produced by the method described in Reference Example 43 or the like, was dissolved in dehydrated THF (12.3 mL; manufactured by Kanto Chemical Co., Inc.), and a 1 mol/L TBAF-THF solution (3.69 mL; manufactured by Sigma-Aldrich Co.) was added to the solution. Under a nitrogen atmosphere, the mixture was stirred for 2 hours at room temperature. Ethyl acetate was added to the reaction solution, and the mixture was washed three times with brine and dried over anhydrous magnesium sulfate. The solvent was evaporated under reduced pressure, and the residue was purified by column chromatography ("COLUMN-A"; n-hexane:ethyl acetate=100:0→81:19). Thus, the title compound (0.660 g) was obtained.

¹H-NMR (300 MHz, CDCl₃); δ (ppm) 1.45 (3H, t, J=7.1), 1.60-1.76 (3H, m), 2.03-2.08 (2H, m), 2.42-2.53 (1H, m), 3.67-3.75 (1H, m), 4.01-4.05 (1H, m), 4.48 (2H, q, J=7.1), 5.40 (1H, brs), 5.71 (1H, dd, J=2.7, 9.7), 6.88 (1H, dd, J=2.0, 8.8), 7.07 (1H, d, J=2.0), 8.03 (1H, d, J=8.8)

LCMS: 291.2 [M+H]; Retention time: 3.69 minutes; LCMS condition: A

Reference Example 45

Ethyl 6-benzyloxy-1-(tetrahydro-2H-pyran-2-yl)-indazole-3-carboxylate

[Chemical Formula 85]

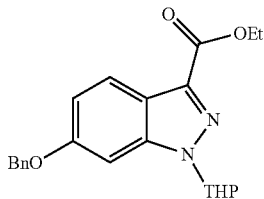

Ethyl 6-hydroxy-1-(tetrahydro-2H-pyran-2-yl)-indazole-3-carboxylate (148 mg) that can be produced by the method described in Reference Example 44 or the like, was dissolved in dehydrated DMF (5.2 mL; manufactured by Kanto Chemical Co., Inc.), and potassium carbonate (227 mg; manufactured by Sigma-Aldrich Co.) and benzyl bromide (73.6 μL; manufactured by Wako Pure Chemical Industries, Ltd.) were added to the solution. The mixture was stirred overnight at 60° C. The reaction solution was cooled to room temperature, and then was poured into water. The mixture was extracted two times with ethyl acetate. The organic layer was washed twice with water and once with brine, and was dried over anhydrous sodium sulfate. The solvent was evaporated under reduced pressure, and the residue was purified by column chromatography ("COLUMN-A"; n-hexane:ethyl acetate=95:5→74:26). Thus, the title compound (187 mg) was obtained.

¹H-NMR (300 MHz, CDCl₃); δ (ppm) 1.46 (3H, t, J=7.2), 1.67-1.78 (3H, 2.04-2.12 (2H, m), 2.42-2.49 (1H, m), 3.69-3.75 (1H, m), 4.01-4.05 (1H, m), 4.49 (2H, q, J=7.2), 5.16 (2H, s), 5.75 (1H, dd, J=2.6, 9.2), 7.04 (1H, dd, J=2.2, 8.8), 7.11 (1H, d, J=1.7), 7.32-7.49 (5H, m), 8.06 (1H, d, J=8.9)

Reference Example 46

(6-(Benzyloxy)-1-(tetrahydro-2H-pyran-2-yl)-indazol-3-yl)methanol

[Chemical Formula 86]

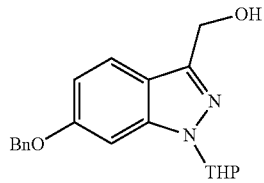

Ethyl 6-benzyloxy-1-(tetrahydro-2H-pyran-2-yl)-indazole-3-carboxylate (182 mg) that can be produced by the method described in Reference Example 45 or the like, was dissolved in dehydrated THF (4.78 mL; manufactured by Kanto Chemical Co., Inc.), and the solution was purged with nitrogen. LiAlH₄ (54 mg) was added to the solution at 0° C., and the mixture was stirred for one hour while the temperature was raised to room temperature. The reaction solution was cooled to 0° C., and then THF/water=1/1 (5 mL), Rochelle salt (manufactured by Kanto Chemical Co., Inc.) and a saturated aqueous solution of sodium hydrogen carbonate were added thereto. The mixture was extracted two times with ethyl acetate. The organic layer was washed twice with water and once with brine, and was dried over anhydrous sodium sulfate. Subsequently, the solvent was evaporated under reduced pressure, and hexane was added to the residue. The solvent was evaporated under reduced pressure, and thus the title compound (155 mg) was obtained.

¹H-NMR (300 MHz, CDCl₃); δ (ppm) 1.54-1.79 (3H, m), 1.98-2.14 (2H, m), 2.05 (1H, t, J=5.9), 2.46-2.59 (1H, m), 3.72-3.77 (1H, m), 4.02-4.06 (1H, m), 4.98 (2H, d, J=5.9), 5.15 (2H, s), 5.58 (1H, dd, J=2.8, 9.5), 6.91 (1H, dd, J=2.2, 8.8), 6.98 (1H, d, J=2.0), 7.32-7.49 (5H, m), 7.65 (1H, d, J=8.6)

LCMS: 339.0 [M+H]; Retention time: 4.02 minutes; LCMS condition: A

Reference Example 47

(6-(Benzyloxy)-1-(tetrahydro-2H-pyran-2-yl)-indazole-3-carbaldehyde

[Chemical Formula 87]

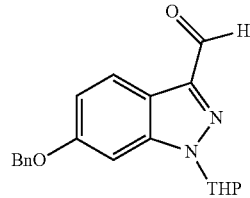

(6-(Benzyloxy)-1-(tetrahydro-2H-pyran-2-yl)-indazol-3-yl)methanol (1.70 g) that can be produced by the method described in Reference Example 46 or the like, was dissolved in dichloromethane (25 mL; manufactured by Kanto Chemical Co., Inc.) and THF (25 mL; manufactured by Kanto Chemical Co., Inc.), and activated manganese dioxide (7.48 g; manufactured by Sigma-Aldrich Co.) was added to the solution. The mixture was stirred overnight at room temperature. The reaction solution was filtered through a thin pad of anhydrous magnesium sulfate, and the filtrate was filtered again using a membrane filter (0.2 μm, manufactured by Advantec MFS, Inc.). Subsequently, the solvent was evaporated under reduced pressure, and the residue was purified by column chromatography ("COLUMN-B"; n-hexane:ethyl acetate=100:0→82:18). Thus, the title compound (1.20 g) was obtained.

¹H-NMR (300 MHz, CDCl₃); δ (ppm) 1.66-1.87 (3H, m) 2.04-2.22 (2H, m), 2.49-2.61 (1H, m), 3.71-3.79 (1H, m), 3.96-4.01 (1H, m), 5.16 (2H, s), 5.74 (1H, dd, J=3.1, 8.8), 7.06-7.10 (2H, m), 7.32-7.49 (5H, m), 8.15 (1H, d, J=9.4), 10.19 (1H, s)

LCMS: 337.3 [M+H]; Retention time 5.14 minutes; LCMS condition: A

Reference Example 48

(E)-ethyl 3-(6-(benzyloxy)-1-(tetrahydro-2H-pyran-2-yl)-indazol-3-yl)acrylate

[Chemical Formula 88]

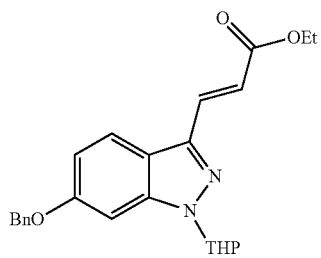

Ethyl 2-(diethoxyphosphoryl)acetate (0.595 mL; manufactured by Tokyo Chemical Industry Co., Ltd.) was dissolved in dehydrated THF (10 mL; manufactured by Kanto Chemical Co., Inc.), and sodium hydride-60% oil (126 mg; manufactured by Kanto Chemical Co., Inc.) was added to the solution. The mixture was stirred for 10 minutes at room temperature, and then (6-(benzyloxy)-1-(tetrahydro-2H-pyran-2-yl)-indazole-3-carbaldehyde (849 mg) that can be produced by the method described in Reference Example 47 or the like, was added to the reaction solution. The mixture was stirred for 5 hours at room temperature. Water was added to the reaction solution, and the mixture was extracted two times with ethyl acetate. The organic layer was washed twice with water and once with brine, and was dried over anhydrous sodium sulfate. The solvent was evaporated under reduced pressure, and thus a crude product (1.10 g) of the title compound was obtained.

$^1$H-NMR (300 MHz, CDCl$_3$); δ (ppm) 1.35 (3H, t, J=7.2), 1.68-1.75 (3H, m), 2.07-2.16 (2H, m), 2.50-2.54 (1H, m), 3.70-3.77 (1H, m), 3.96-4.00 (1H, m), 4.28 (2H, q, J=7.2), 5.15 (2H, s), 5.66 (1H, dd, J=2.9, 8.8), 6.73 (1H, d, J=16.3), 6.99 (1H, dd, J=2.2, 8.8), 7.05 (1H, d, J=1.8), 7.32-7.49 (5H, m), 7.79 (1H, d, J=9.0), 7.94 (1H, d, J=16.3)

LCMS: 407.4 [M+H]; Retention time: 5.72 minutes; LCMS condition: B

Reference Example 49

Ethyl 3-(6-(benzyloxy)-1-(tetrahydro-2H-pyran-2-yl)-indazol-3-yl)propanoate

[Chemical Formula 89]

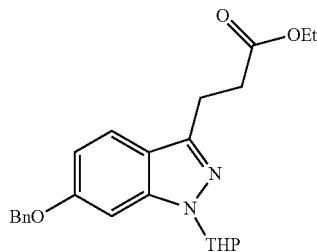

(E)-ethyl 3-(6-(benzyloxy)-1-(tetrahydro-2H-pyran-2-yl)-indazol-3-yl)acrylate (1.02 g) that can be produced by the method described in Reference Example 48, and p-toluenesulfonyl hydrazide (4.70 g; manufactured by Tokyo Chemical Industry Co., Ltd.) were dissolved in ethylene glycol dimethyl ether (12.5 mL; manufactured by Sigma-Aldrich Co.), and the temperature was raised to 95° C. Subsequently, an aqueous solution of sodium acetate [prepared from sodium acetate (4.11 g; manufactured by Wako Pure Chemical Industries, Ltd.) and water (6.25 mL)] was added dropwise to the solution, and the mixture was stirred for 5.5 hours at 95° C. The reaction solution was cooled to room temperature, and then was poured into a saturated aqueous solution of sodium hydrogen carbonate containing ice. The mixture was extracted two times with ethyl acetate. The organic layer was washed twice with water and once with brine, and was dried over anhydrous sodium sulfate. Subsequently, the solvent was evaporated under reduced pressure, and the residue was purified by column chromatography ("COLUMN-A"; n-hexane:ethyl acetate=96:4→75:25). Thus, the title compound (0.809 g) was obtained.

$^1$H-NMR (300 MHz, CDCl$_3$); δ (ppm) 1.24 (3H, t, J=7.2), 1.54-1.76 (3H, m), 1.96-2.01 (1H, m), 2.11-2.14 (1H, m), 2.45-2.56 (1H, m), 2.81-2.86 (2H, m), 3.20-3.25 (2H, m), 3.67-3.75 (1H, m), 4.00-4.03 (1H, m), 4.13 (2H, q, J=7.2), 5.13 (2H, s), 5.54 (1H, dd, J=2.8, 9.4), 6.87 (1H, dd, J=2.2, 8.8), 6.96 (1H, d, J=2.0), 7.31-7.55 (6H, m)

LCMS: 409.3 [M+H]; Retention time: 2.04 minutes; LCMS condition: C

Reference Example 50

3-(6-(Benzyloxy)-1-(tetrahydro-2H-pyran-2-yl)-indazol-3-yl)propanoic acid

[Chemical Formula 90]

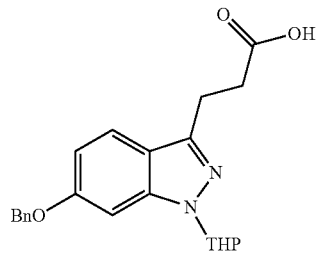

Ethyl 3-(6-(benzyloxy)-1-(tetrahydro-2H-pyran-2-yl)-indazol-3-yl)propanoate (0.809 g) that can be produced by the method described in Reference Example 49 or the like, was dissolved in methanol (8 mL; manufactured by Kanto Chemical Co., Inc.). and a 2 mol/L aqueous solution of sodium hydroxide (1.68 mL) was added thereto. The mixture was stirred overnight at 40° C. The reaction solution was cooled to room temperature, and then the solvent was evaporated under reduced pressure water (10 mL), 2 mol/L hydrochloric acid (1.78 mL) and water (20 mL) were added to the residue, and precipitates were filtered. Thus, the title compound (0.630 g) was obtained.

$^1$H-NMR (300 MHz, CDCl$_3$); δ (ppm) 1.64-1.76 (3H, m), 1.99-2.12 (2H, m), 2.43-2.54 (1H, m), 2.92 (2H, t, J=7.3), 3.24 (2H, t, J=7.3), 3.68-3.75 (1H, m), 4.00-4.03 (1H, m), 5.14 (2H, s), 5.56 (1H, dd, J=2.6, 9.4), 6.88 (1H, dd, J=2.2, 8.4), 6.96 (1H, d, J=1.5), 7.31-7.54 (6H, m)

LCMS: 381.4 [M+H]; Retention time: 4.34 minutes; LCMS condition: A

Reference Example 51

3-(6-(Benzyloxy)-1-(tetrahydro-2H-pyran-2-yl)-indazole-N,N-dimethylpropanamide

[Chemical Formula 91]

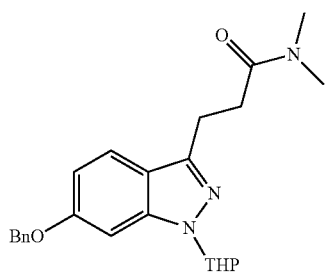

3-(6-(Benzyloxy)-1-(tetrahydro-2H-pyran -2-yl)-indazol-3-yl) propanoic acid (570 mg) that can be produced by the method described in Reference Example 50 or the like was dissolved in dehydrated THF (7 mL; manufactured by Kanto Chemical Co., Inc.), and triethylamine (0.289 mL; manufactured by Wako Pure Chemical Industries, Ltd.) and pivaloyl chloride (0.204 mL; manufactured by Kanto Chemical Co., Inc.) were added to the solution. The mixture was stirred for 15 minutes at room temperature. A 2 mol/L dimethylamine-THF solution (24.84 mL) was added to the reaction solution, and the mixture was stirred overnight at room temperature. The reaction solution was poured into water, and the mixture was extracted two times with ethyl acetate. The organic layer was washed twice with water and once with brine, and was dried over anhydrous sodium sulfate. Subsequently, the solvent was evaporated under reduced pressure, and the residue was purified by column chromatography ("COLUMN-B"; n-hexane: ethyl acetate=54:46→33:67). Thus, the title compound (597 mg) was obtained.

$^1$H-NMR (300 MHz, CDCl$_3$); δ (ppm) 1.61-1.77 (3H, m), 1.96-2.13 (2H, m), 2.50-2.53 (1H, m), 2.81-2.86 (2H, m), 2.95 (3H, s), 2.97 (3H, s), 3.24-3.29 (2H, m), 3.72-3.75 (1H, m), 4.04-4.08 (1H, M), 5.14 (2H, s), 5.53 (1H, dd, J=2.6, 9.7), 6.86 (1H, dd, J=2.2, 8.8), 6.95 (1H, d, J=2.0), 7.31-7.57 (6H, m)

LCMS: 408.4 [M+H]; Retention time: 4.28 minutes; LCMS condition: B

Reference Example 52

3-(6-Hydroxy-1-(tetrahydro-2H-pyran-2-yl)-indazole-N,N-dimethylpropanamide

[Chemical Formula 92]

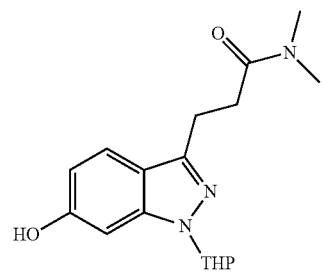

5% palladium on carbon-STD-type-50% wet with water (224 mg; manufactured by N.E. Chemcat Corp.), and a THF solution of 3-(6-(benzyloxy)-1-(tetrahydro-2H-pyran-2-yl)-indazole-N,N-dimethylpropanamide that can be produced by the method described in Reference Example 51 or the like [6.3 mL; prepared by dissolving 3-(6-(benzyloxy)-1-(tetrahydro-2H-pyran-2-yl)-indazole-N,N-dimethylpropanamide (596 mg) in dehydrated THF (7.3 mL)) were mixed, and the reaction system was purged with hydrogen. Under a hydrogen atmosphere, the reaction solution was stirred overnight at room temperature. The reaction solution was purged with nitrogen, and then was filtered. The solvent was evaporated under reduced pressure from the filtrate, and thus the title compound (383 mg) was obtained.

$^1$H-NMR (300 MHz, CDCl$_3$); δ (ppm) 1.63-1.73 (3H, m), 1.92-2.08 (2H, m), 2.43-2.53 (1H, m), 2.76-2.95 (2H, m), 2.96 (3H, s), 3.01 (3H, s), 3.19-3.28 (2H, m), 3.62-3.70 (1H, m), 4.00-4.05 (1H, m), 5.45 (1H, dd, J=2.4, 9.9), 6.58 (1H, dd, J=2.2, 8.6), 6.85 (1H, d, J=2.0), 6.98 (1H, brs), 7.32 (1H, d, J=8.6)

LCMS: 318.3 [M+H]; Retention time: 2.76 minutes; LCMS condition: A

Reference Example 53

3-(6-(2-(Text-butoxycarbonyl(2-(3-(N-(tert-butoxycarbonyl)methylsulfonamido)phenyl)-2-(triethylsilyloxy)ethyl)amino)ethoxy)-1-(tetrahydro-2H-pyran-2-yl)-indazole-N,N-dimethylpropanamide

[Chemical Formula 93]

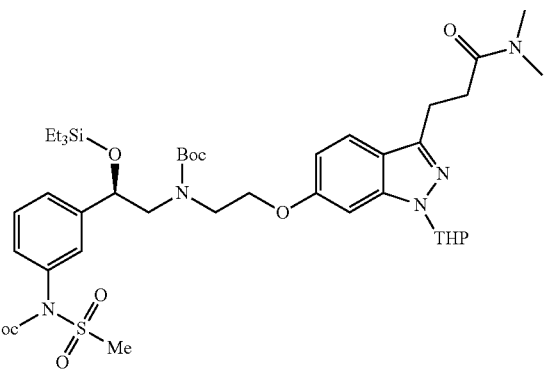

3-(6-Hydroxy-1-(tetrahydro-2H-pyran-2-yl)-indazole-N,N-dimethylpropanamide (0.400 mg) that can be produced by the method described in Reference Example 52 or the like, and a toluene solution of (R)-(3-(2-(N-tert-butoxycarbonyl-N-(2-hydroxyethyl)amino)-1-triethylsilyloxy)ethyl)phenyl)-N-tert-butoxycarbonylmethanesulfonamide that can be produced by the method described in Reference Example 58 or the like [3.78 mL; solution prepared by dissolving (R)-(3-(2-(N-tert-butoxycarbonyl-N-(2-hydroxyethyl)amino)-1-triethylsilyloxy)ethyl)phenyl]-N-tert-butoxycarbonylmethanesulfonamide (4.78 g) in dehydrated toluene (8.12 mL)] were dissolved in dehydrated toluene (5 mL; manufactured by Kanto Chemical Co., Inc.). Triphenylphosphine (1.016 g; manufactured by Tokyo Chemical Industry Co., Ltd.) and TMAD (0.705 g; manufactured by Masuda Chemical Industries, Co., Ltd.) were added to the solution, and the mixture was stirred overnight at room temperature. Triphenylphosphine (1.015 g; manufactured by Tokyo Chemical Industry Co., Ltd.) and TMAD (0.643 g; manufactured by Masuda Chemical Industries, Co., Ltd.) were added to the reaction solution, and the mixture was stirred for 3 hours at room temperature. The reaction solution was purified by column chromatography ("COLUMN-B"; n-hexane:ethyl acetate=32:68→11:89) to obtain a crude product. This crude product was purified again by column chromatography ("COLUMN-B"; n-hexane:ethyl acetate=32;68→11:89), and thus the title compound (455.7 mg) was obtained.

LCMS: 888.9 [M+H]; Retention time: 6.63 minutes; LCMS condition: B

Example 5

(R)-3-(6-(2-(2-hydroxy-2-(3-(methylsulfonamido) phenyl)ethylamino)ethoxy)-indazol-3-yl)-N,N-dimethylpropanamide

[Chemical Formula 94]

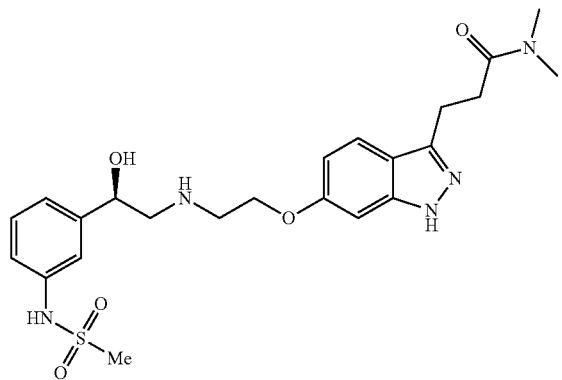

3-(6-(2-(Tert-butoxycarbonyl-(2-(3-(N-(tert-butoxycarbonyl)methylsulfonamido)phenyl)-2-(triethylsilyloxy) ethyl)amino)ethoxy)-1-(tetrahydro-2H-pyran-2-yl)-indazole-N,N-dimethylpropanamide (276 mg) that can be produced by the method described in Reference Example 53 or the like, was dissolved in MTBE (0.3 mL; manufactured by Wako Pure Chemical Industries, Ltd.), and a 4 mol/L hydrogen chloride-1,4-dioxane solution (2 mL; manufactured by Kokusan Chemical Co., Ltd.) was added to the solution. The mixture was shaken (600 min$^{-1}$) for 2 hours at room temperature. Ethanol (1.5 mL) was added to the reaction solution, and the mixture was shaken (600 min$^{-1}$) overnight at room temperature. Nitrogen gas was blown into the reaction solution to evaporate the solvent. The residue was designated as "THP-1". Furthermore, 3-(6-(2-(tert-butoxycarbonyl-(2-(3-(N-(tert-butoxycarbonyl)methylsulfonamido)phenyl)-2-(triethylsilyloxy)ethyl)amino)ethoxy)-1-(tetrahydro-2H-pyran-2-yl)-indazole-N,N-dimethylpropanamide (254 mg) that can be produced by the method described in Reference Example 53 or the like, was dissolved in MTBE (0.3 mL; manufactured by Wako Pure Chemical Industries, Ltd.), and a 4 mol/L hydrogen chloride-1,4-dioxane solution (2 mL; manufactured by Kokusan Chemical Co.,. Ltd.) was added to the solution. The mixture was shaken (600 min$^{-1}$) for 2 hours at room temperature. Ethanol (1.5 mL) was added to the reaction solution, and the mixture was shaken (600 min$^{-1}$) overnight at room temperature. Nitrogen gas was blown into the reaction solution to evaporate the solvent. The residue was designated as "THP-2". The "THP-1" and "THP-2" were combined and dissolved in ethanol (1 mL). A 4 mol/L hydrogen chloride-1,4-dioxane solution (1 mL; manufactured by Kokusan Chemical Co., Ltd.) was added thereto, and the mixture was shaken (600 min$^{-1}$) at room temperature. Nitrogen gas was blown into the reaction solution to evaporate the solvent, and a 5 to 10% hydrogen chloride-methanol solution (1 mL; manufactured by Tokyo Chemical Industry Co., Ltd.) was added to the reaction solution. The reaction solution was shaken for one hour at (600 min$^{-1}$), and nitrogen gas was blown into the reaction solution to evaporate the solvent. Ethanol was added thereto, and nitrogen gas was blown into the reaction solution to evaporate the solvent. Subsequently, diethyl ether was added thereto, and nitrogen as was blown into the reaction solution to evaporate the solvent. Water was added to dissolve the residue, and the solution was freeze-dried. Thus, the title compound was obtained in the form of hydrochloride (216 mg). This hydrochloride (0.5531 mg) was dissolved in pure water (5.0380 g), and anions were analyzed by ion chromatography. As a result, chloride ions (14.2 ppm) were detected.

$^{1}$H-NMR (300 MHz, DMSO-d$_6$); δ (ppm) 2.76-2.81 (5H, m), 2.95 (3H, s), 3.00 (3H, s), 3.08-3.13 (1H, m), 3.23-3.25 (1H, m), 3.46-3.47 (2H, m), 3.66-3.70 (2H, m), 4.35-4.50 (2H, m), 5.04 (1H, d, J=8.1), 6.81 (1H, dd, J=1.8, 8.8) 6.93 (1H, d, J=1.8), 7.12-7.17 (2H, m), 7.30-7.37 (2H, m), 7.69 (1H, d, J=8.8), 9.09 (1H, brs), 9.47 (1H, brs), 9.87 (1H, s)

LCMS: 490.2 [M+H]; Retention time: 0.29 minutes, 0.78 minutes (detected as a double-peak); LCMS condition: C Reference Example 54

6-(Benzyloxy)-3-(methoxymethyl)-1-(tetrahydro-2H-pyran-2-yl)indazole

[Chemical Formula 95]

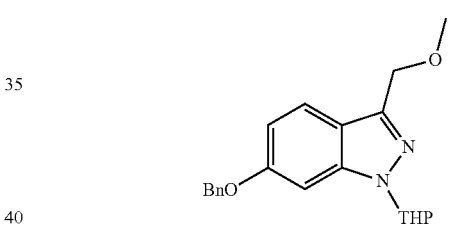

(6-(Benzyloxy)-1-(tetrahydro-2H-pyran-2-yl)indazol-3-yl)methanol (145 mg) that can be produced by the method described in Reference Example 46 or the like, was dissolved in dehydrated DMF (1.7 mL; manufactured by Kanto Chemical Co., Inc.), and the solution was cooled to 0° C. Subsequently, 40% oil-containing sodium hydride (12 mg; manufactured by Kanto Chemical Co., Inc.) was added to the solution, and the mixture was stirred for 15 minutes at 0° C. Methyl iodide (30.3 μL) was added to the reaction solution, and the mixture was stirred overnight while the temperature was raised to room temperature. The reaction solution was cooled again to 0° C., and then 40% oil-containing sodium hydride (8.9 mg; manufactured by Kanto Chemical Co., Inc.) was added thereto. The mixture was stirred for 5 minutes at 0° C. Methyl iodide (20 μL) was added thereto, and the mixture was stirred for 5 hours while the temperature was raised to room temperature. The reaction solution was cooled again to 0° C., and then 40% oil-containing sodium hydride (9.1 mg; manufactured by Kanto Chemical Co., Inc.) was added thereto. The mixture was stirred for 5 minutes at 0° C., methyl iodide (20 μL) was added thereto, and the mixture was stirred for one hour while the temperature was raised to room temperature. Water was added to the reaction solution, and then the mixture was extracted two times with ethyl acetate. The organic layer was washed twice with water and once with brine, and was dried over anhydrous sodium sulfate. Then, the solvent was evaporated under reduced pressure. The residue was purified by column chromatography ("COLUMN-F"; n-hexane:ethyl acetate=1:0→5:1), and thus the title compound (138 mg) was obtained.

$^1$H-NMR (300 MHz, CDCl$_3$); δ (ppm) 1.63-1.78 (3H, m), 1.99-2.13 (2H, m), 2.45-2.58 (1H, m), 3.40 (3H, s), 3.72-3.76 (1H, m), 4.02-4.07 (1H, m), 4.77 (2H, d, J=0.7), 5.14 (2H, s), 5.59 (1H, dd, J=2.6, 9.5), 6.90 (1H, dd, J=2.2, 8.8), 6.99 (1H, d, J=2.0), 7.34-7.49 (5H, m), 7.68 (1H, d, J=8.8)

LCMS: 353.4 [M+H]; Retention time: 4.86 minutes; LCMS condition: A

Reference Example 55

3-(Methoxymethyl)-1-(tetrahydro-2H-pyran-2-yl) indazol-6-ol

[Chemical Formula 96]

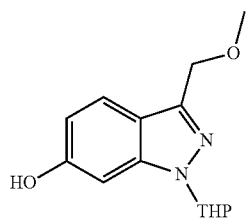

5% Palladium on carbon-STD-type-50% wet with water (199 mg; manufactured by N.E. Chemcat Corp.) and 6-(benzyloxy)-3-(methoxymethyl)-1-(tetrahydro-2H-pyran-2-yl) indazole (450 mg) that can be produced by the method described in Reference Example 54 or the like, were dissolved in THF (12.7 mL; manufactured by Kanto Chemical Co., Inc.). The reaction system was purged with hydrogen, and under a hydrogen atmosphere, the reaction solution was stirred overnight at room temperature. The reaction solution was purged with nitrogen, and then was filtered. The filtrate was concentrated under reduced pressure, and thus the title compound (337.4 mg) was obtained.

$^1$H-NMR (300 MHz, CDCl$_3$); δ (ppm) 1.61-1.77 (3H, m), 1.99-2.13 (2H, m), 2.49-2.53 (1H, m), 3.40 (3H, s), 3.67-3.76 (1H, m), 4.03-4.07 (1H, m), 4.77 (2H, s), 5.44 (1H, brs), 5.55 (1H, dd, J=2.7, 9.5), 6.72 (1H, dd, J=2.0, 8.6), 6.92 (1H, d, J=2.0), 7.66 (1H, dd, J=0.6, 8.6)

LCMS: 263.3 [M+H]; Retention time: 2.99 minutes; LCMS condition: A

Reference Example 56

(R)-6-(2-(tert-butoxycarbonyl-(2-(3-(N-(tert-butoxycarbonyl)methylsulfonamido)phenyl)-2-hydroxyethyl)amino)ethoxy)-1-(tetrahydro-2H-pyran-2-yl)-3-methoxymethylindazole

[Chemical Formula 97]

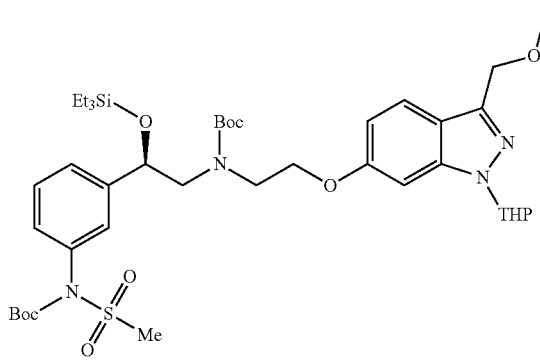

3-(Methoxymethyl)-1-(tetrahydro-2H-pyran-2-yl)-indazol-6-ol (185 mg) that can be produced by the method described in Reference Example 55 or the like, was dissolved in toluene (7 mL; manufactured by Kanto Chemical Co., Inc.), and a toluene solution of (R)-(3-(2-(N-tert-butoxycarbonyl-N-(2-hydroxyethyl)amino)-1-triethylsilyloxy)ethyl) phenyl)-N-tert-butoxycarbonylmethanesulfonamide that can be produced by the method described in Reference Example 58 or the like [2.00 mL; solution prepared by dissolving (R)-(3-(2-(N-tert-butoxycarbonyl-N-(2-hydroxyethyl) amino)-1-triethylsilyloxy)ethyl)phenyl]-N-tert-butoxycarbonylmethanesulfonamide (4.78 g) in dehydrated toluene (8.12 mL)], triphenylphosphine (588 mg) and TMAD (376 mg) were added to the solution. The mixture was stirred overnight at room temperature. The reaction solution was purified by column chromatography ("COLUMN-B"; n-hexane:ethyl acetate=32:68→11:89) to obtain the title compound as a crude product (738 mg). Subsequently, the crude product was dissolved in THF (4 mL), and a 1 mol/L TBAF-THF solution (1.06 mL; manufactured by Sigma-Aldrich Co.) was added to the solution. The mixture was stirred for 10 minutes at room temperature. Water and brine were added to the reaction solution, and the mixture was extracted three times with ethyl acetate. The organic layer was washed with water and brine, and was dried over anhydrous sodium sulfate. Subsequently, the solvent was evaporated under reduced pressure, and the residue was purified by column chromatography ("COLUMN-B"; n-hexane:ethyl acetate=61:39→40: 60). Thus, the title compound (472 mg) was obtained.

$^1$H-NMR (300 MHz, CDCl$_3$); δ (ppm) 1.43-1.78 (21H, m), 2.00-2.13 (2H, m), 2.52-2.56 (1H, m), 3.39-4.42 (8H, m), 3.55-3.78 (4H, m), 4.06-4.17 (2H, m), 4.60-4.81 (3H, m), 5.06 (1H, brs), 6.18-6.84 (2H, m), 7.15-7.40 (4H, m), 7.67 (1H, d, J=8.8)

LCMS: 719.6 [M+H]; Retention time: 4.98 minutes; LCMS condition: B

Example 6

(R)-N-(3-(1-hydroxy-2-(2-(3-methoxymethylindazol-6-yloxy)ethylamino)ethyl)phenyl)methanesulfonamide

[Chemical Formula 98]

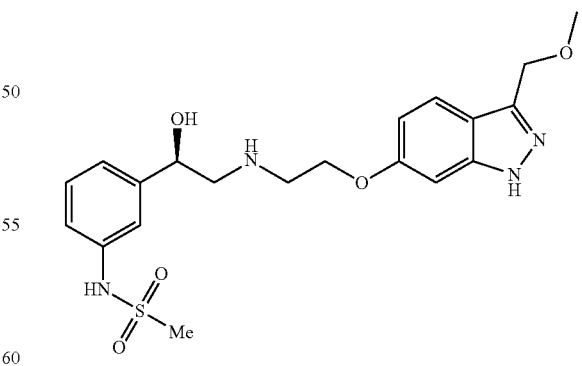

(R)-6-(2-(tert-butoxycarbonyl-(2-(3-(N-(tert-butoxycarbonyl)methylsulfonamido)phenyl)-2-hydroxyethyl)amino) ethoxy)-1-(tetrahydro-2H-pyran-2-yl)-3-methoxymethylindazole (472 mg) that can be produced by the method described in Reference Example 56 or the like was dissolved in MTBE (2.5 mL), and a 4 mol/L hydrogen chloride-1,4- dioxane solution (2 mL; manufactured by Kokusan Chemical Co., Ltd.) was added thereto. The mixture was shaken (600 min$^{-1}$) overnight at room temperature. A 4 mol/L hydrogen chloride-1,4-dioxane solution (2 mL; manufactured by Kokusan Chemical Co., Ltd.) was added to the reaction solution, and the mixture was shaken (600 min$^{-1}$) for 7 hours at room temperature. Ethanol (6 mL) was added to the reaction solution, and nitrogen gas was blown into the reaction solution to evaporate the solvent. A 4 mol/L hydrogen chloride-1,4-dioxane solution (6 mL; manufactured by Kokusan Chemical Co., Ltd.) and ethanol (10 mL) were added to the residue, and the mixture was shaken (600 min$^{-1}$) overnight at room temperature. Nitrogen gas was blown into the reaction solution to evaporate the solvent. The operation of adding diethyl ether to the reaction solution, and blowing nitrogen gas again into the reaction solution to evaporate the solvent, was repeated two times. Water was added to the residue, and the mixture was freeze-dried. Thus, the title compound was obtained in the form of hydrochloride (292 mg).

$^1$H-NMR (300 MHz, DMSO-d$_6$); δ (ppm) 3.00 (3H, s), 3.04-3.08 (2H, m), 3.28 (3H, s), 3.46-3.49 (2H, m), 4.37 (2H, d, J=5.0), 4.67 (2H, s), 5.02 (1H, d, J=8.1), 6.82 (1H, dd, J=2.0, 8.8) 6.96 (1H, d, J=2.0), 7.11-7.17 (2H, m), 7.30-7.34 (2H, m), 7.67 (1H, d, J=8.8), 9.05 (1H, brs), 9.38 (1H, brs), 9.86 (1H, s)

LCMS: 435.3 [M+H]; Retention time: 2.04 minutes; LCMS condition: B

Reference Example 57

(R)-N-(3-(2-(2-hydroxyethylamino)-1-(triethylsilyloxy)ethyl)phenyl)methanesulfonamide

[Chemical Formula 99]

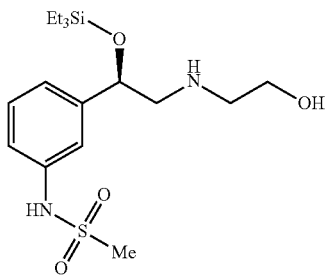

(R)-N-benzyl-N-(3-(2-(benzyl-(2-hydroxyethyl)amino)-1-(triethylsilyloxy)ethyl)phenyl)methanesulfonamide (500 mg; an intermediate described in Reference Example 1 of WO 03/035620) was dissolved in THF (1.76 mL; manufactured by Wako Pure Chemical Industries, Ltd.) and methanol (1.76 mL; manufactured by Wako Pure Chemical Industries, Ltd.) under a nitrogen atmosphere, and 20% palladium hydroxide on carbon-49.94% wet with water (102.7 mg; manufactured by N.E. Chemcat Corp.) was added thereto. Subsequently, the reaction system was purged with hydrogen, and under a hydrogen atmosphere, the reaction solution was stirred for 15 hours at 50° C. The reaction solution was cooled to room temperature, purged with nitrogen, and then filtered. The filtrate was concentrated under reduced pressure, and thus the title compound (364 mg) was obtained.

$^1$H-NMR (300 MHz, CDCl$_3$); δ (ppm) 0.50-0.58 (6H, m), 0.81-0.91 (9H, m), 1.81-1.87 (2H, m), 2.99 (3H, s), 3.53-3.61 (2H, m), 3.72-3.76 (2H, m), 4.77-4.81 (1H, m), 7.11-7.33 (4H, m)

LCMS: 389.2 [M+H]; Retention time: 2.65 minutes; LCMS condition: A

Reference Example 58

(R)-(3-(2-(N-tert-butoxycarbonyl-N-(2-hydroxyethyl)amino)-1-triethylsilyloxy)ethyl)phenyl)-N-tert-butoxycarbonylmethanesulfonamide

[Chemical Formula 100]

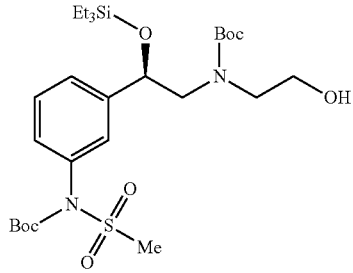

(R)-N-(3-(2-(2-hydroxyethylamino)-1-(triethylsilyloxy)ethyl)phenyl)methanesulfonamide (337 mg) that can be produced by the method described in Reference Example 57 or the like, was dissolved in dehydrated THF (4.3 mL; manufactured by Kanto Chemical Co., Inc.), and triethylamine (0.12 mL; manufactured by Wako Pure Chemical Industries, Ltd.), (Boc)$_2$O (0.437 mL; manufactured by Wako Pure Chemical Industries, Ltd.), and 4-N,N-dimethylaminopyridine (21 mg; manufactured by Wako Pure Chemical Industries, Ltd.) were added to the solution. Under a nitrogen atmosphere, the mixture was stirred for 16 hours at room temperature. Ethyl acetate was added to the reaction solution, and the mixture was washed twice with water and once with brine, and then was dried over anhydrous sodium sulfate. The solvent was evaporated under reduced pressure, and the residue was purified by column chromatography ("COLUMN-A"; n-hexane:ethyl acetate=71:29→50:50), to obtain a crude product. Subsequently, the crude product was purified again by column chromatography ("COLUMN-A"; n-hexane:ethyl acetate=71:29→50:50), and thus the title compound (254 mg) was obtained.

$^1$H-NMR (300 MHz, CDCl$_3$); δ (ppm) 0.49-0.57 (6H, m), 0.85-0.90 (9H, m), 1.44 (9H, s), 1.44-1.53 (9H, m), 3.03-4.83 (9H, m), 5.00-5.29 (1H, m), 7.10-7.42 (4H, m)

LCMS: 589.2 [M+H]; Retention time: 5.98 minutes; LCMS condition; A

Reference Example 59

3-Methylindazol-6-ol

[Chemical Formula 101]

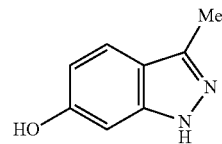

1-Benzyl-3-methylindazol-6-ol (16.7410 g) and 10% palladium-carbon-PE-type-50% wet with water (5.1164 g; manufactured by N.E. Chemcat Corp.) were suspended in ethanol (166 mL), and then concentrated hydrochloric acid (5.83 mL; manufactured by Kanto Chemical Co., Inc.) was added thereto. The reaction system was purged with hydrogen, and under a hydrogen atmosphere, the reaction solution was stirred for 10 hours at 60° C. The reaction solution was cooled to room temperature, and then the reaction system was purged with nitrogen. 10% Palladium on carbon-PE-type-50% wet with water (1.5059 g; manufactured by N.E. Chemcat Corp.) was added to the reaction solution, and the reaction system was purged with hydrogen. Under a hydrogen atmosphere, the reaction solution was stirred for 5 hours at 60° C. The reaction solution was cooled to room temperature, and the reaction system was purged with nitrogen. Subsequently, the reaction solution was filtered, and the solvent was evaporated under reduced pressure from the filtrate. Ethyl acetate was added to the resulting residue, and the mixture was washed once with a saturated aqueous solution of sodium hydrogen carbonate. The organic layer was washed once with a saturated sodium hydrogen carbonate solution, and then was dried over sodium sulfate. The solvent was evaporated under reduced pressure from the organic layer, and thus the title compound was obtained as a crude product (10.816 g).

$^1$H-NMR (300 MHz, DMSO-d$_6$); δ (ppm) 2.38 (3H, s), 6.58 (1H, dd, J=2.2, 8.4), 6.67 (1H, d, J=2.2), 7.44 (1H, d, J=8.4), 9.47 (1H, brs), 12.09 (1H, brs)

LCMS: 149 [M+H]; Retention time: 7.48 minutes; LCMS condition: A

Reference Example 60

Tert-butyl 6-hydroxy-3-methylindazole-1-carboxylate

[Chemical Formula 102]

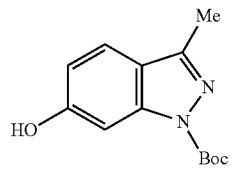

3-Methylindazol-6-ol (10.72 g) that can be produced by the method described in Reference Example 59 or the like, and imidazole (9.5492 g; manufactured by Tokyo Chemical Industry Co., Ltd.) were dissolved in dehydrated DMF (140 mL), and TBDPSCl (38.5301 g; manufactured by Wako Pure Chemical Industries, Ltd.) was added to the solution. The mixture was stirred overnight at room temperature. The reaction solution was poured into water, and the mixture was extracted two times with ethyl acetate. The organic layer was washed twice with water and once with brine, and was dried over sodium sulfate. The solvent was evaporated under reduced pressure, and the resulting residue (41.3621 g) was dissolved in CH$_2$Cl$_2$ (350 mL). Triethylamine (8.5155 g; manufactured by Kokusan Chemical Co., Ltd.), Boc$_2$O (18.3611 g; manufactured by Wako Pure Chemical Industries, Ltd.) and 4-N,N-dimethylaminopyridine (846.7 mg) were added to the solution, and the mixture was stirred overnight at room temperature. The reaction solution was washed twice with a 1 mol/L aqueous solution of hydrochloric acid and once with brine, and was dried over anhydrous sodium sulfate. The solvent was evaporated under reduced pressure, and the resulting residue (52.566 g) was dissolved in dehydrated THF (350 mL). A 1 mol/L TBAF-THF solution (140 mL; manufactured by Tokyo Chemical Industry Co., Ltd.) was added thereto, and the mixture was stirred for one hour at room temperature. Ethyl acetate was added to the reaction solution, and the mixture was washed once with brine, once with water and once with brine. The organic layer was dried over magnesium sulfate, and then the solvent was evaporated under reduced pressure. The resulting residue was purified by column chromatography ("COLUMN-A"; n-hexane:ethyl acetate=74:26→47:53), and thus the title compound (10.934 g) was obtained.

$^1$H-NMR (300 MHz, CDCl$_3$); δ (ppm) 1.66 (9H, s), 2.52 (3H, s), 6.42 (1H, brs), 6.88 (1H, dd, J=2.2, 8.4), 7.48 (1H, d, J=8.4), 7.57 (1H, s)

LCMS: 249 [M+H]; Retention time: 1.29 minutes; LCMS condition: C

Reference Example 61

Methyl 4-(benzyloxy)-2-fluorobenzoate

[Chemical Formula 103]

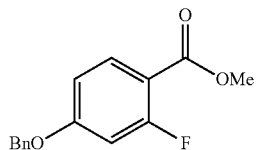

Methyl 2-fluoro-4-hydroxybenzoate (1.4685 g; manufactured by Changzou Fine Chemical Co., Ltd.) and potassium carbonate (3.6-917 g; manufactured by Sigma-Aldrich Co.) were suspended in dehydrated DMF (21 mL; manufactured by Kanto Chemical Co., Inc.), and benzyl bromide (1.22 mL; manufactured by Wako Pure Chemical Industries, Ltd.) was added thereto. The mixture was stirred overnight at 50° C. The reaction solution was cooled to room temperature, and then was poured into water. The mixture was extracted two times with ethyl acetate. The organic layer was washed twice with water and once with brine, and was dried over anhydrous sodium sulfate. Subsequently, the solvent was evaporated under reduced pressure, and the residue was purified by column chromatography ("COLUMN-B"; n-hexane:ethyl acetate=97:3→77:23). Thus, the title compound (2.2207 g) was obtained.

$^1$H-NMR (300 MHz, CDCl$_3$); δ (ppm) 3.89 (3H, s), 5.09 (2H, s), 6.70 (1H, dd, J=2.3, 12.6), 6.78 (1H, dd, J=2.3, 8.8), 7.31-7.41 (5H, m), 7.89 (1H, t, J=8.6)

Reference Example 62

6-(Benzyloxy)-1,2-dihydroindazol-3-one

[Chemical Formula 104]

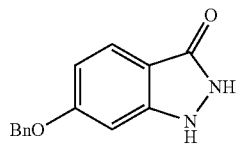

Methyl 4-(benzyloxy)-2-fluorobenzoate (52.4 mg) that can be produced by the method described in Reference Example 61 or the like, was dissolved in n-butanol (1 mL; manufac-

Reference Example 63

Tert-butyl 6-(benzyloxy)-3-oxo-2,3-dihydroindazole-1-carboxylate

[Chemical Formula 105]

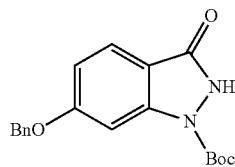

6-(Benzyloxy)-1,2-dihydroindazol-3-one (1.9209 g) that can be produced by the method described in Reference Example 62 or the like, was suspended in dichloromethane (80 mL; manufactured by Wako Pure Chemical Industries, Ltd.), and triethylamine (2.78 mL; manufactured by Kokusan Chemical Co., Ltd.), Boc$_2$O (4.6 mL;, manufactured by Wako Pure Chemical Industries, Ltd.) and DMAP (0.4947 g; manufactured by Wako Pure Chemical Industries, Ltd.) were added to the suspension. The mixture was purged with nitrogen, and was stirred overnight at room temperature. The reaction solution was washed twice with 1 mol/L hydrochloric acid and once with water, and the organic layer was dried over magnesium sulfate. Then, the solvent was evaporated under reduced pressure. The residue was dissolved in methanol (64 mL; manufactured by Wako Pure Chemical Industries, Ltd.), and a 7 mol/L ammonia-methanol solution (16 mL; manufactured by Sigma-Aldrich Co.) was added thereto. The reaction solution was stirred for 4 hours at room temperature and was concentrated under reduced pressure. Subsequently, ethanol was added to the residue, and precipitates were filtered, to thereby obtain the title compound (1.5822 g). The filtrate was concentrated under reduced pressure, and then ethanol was added to the residue. Precipitates were filtered again, and thus the title compound (0.3956 g) was obtained.

$^1$H-NMR (300 MHz, CDCl$_3$); δ (ppm) 1.70 (9H, s), 5.15 (2H, s), 6.96 (1H, dd, J=2.0, 8.6), 7.32-7.60 (6H, m), 7.68 (1H, d, J=8.6)

LCMS: 341 [M+H]; Retention time 4.57 minutes; LCMS condition: A

Reference Example 64

Tert-butyl 6-(benzyloxy)-3-methoxyindazole-1-carboxylate

[Chemical Formula 106]

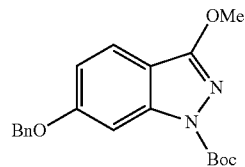

Tert-butyl 6-(benzyloxy)-3-oxo-2,3-dihydroindazole-1-carboxylate (207.1 mg) that can be produced by the method described in Reference Example 63 or the like, and Ag$_2$CO$_3$ (509.1 mg; manufactured by Kanto Chemical Co., Inc.) were suspended in dehydrated toluene (6 mL), and then methyl iodide (373 μL; manufactured by Tokyo Chemical Industry Co., Ltd.) was added thereto. The mixture was stirred in a sealed reaction vessel under microwaves for 2 hours at 60° C. The reaction solution was cooled to room temperature, and then insoluble matters were filtered. The filtrate was concentrated under reduced pressure, and then the resulting residue was purified by column chromatography ("COLUMN-B"; n-hexane:ethyl acetate=99:1→78:22). Thus, the title compound (153.5 mg) was obtained.

$^1$H-NMR (300 MHz, CDCl$_3$); δ (ppm) 1.68 (9H, s), 4.14 (3H, s), 5.14 (2H, s), 6.94 (1H, dd, J=2.2, 8.6), 7.31-7.46 (5H, m), 7.51 (1H, d, J=8.6), 7.60 (1H, brs)

LCMS; 355 [M+H]; Retention time 5.79 minutes; LCMS condition: A

Reference Example 65

Tert-butyl 6-hydroxy-3-methoxyindazole-1-carboxylate

[Chemical Formula 107]

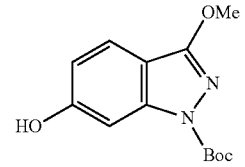

Tert-butyl 6-(benzyloxy)-3-methoxyindazole-1-carboxylate (206 mg) that can be produced by the method described in Reference Example 64 or the like, and 5% palladium on carbon-STD-type-50% hydrate (113 mg; manufactured by N.E. Chemcat Corp.) were suspended in THF (5.8 mL), and then the reaction system was purged with hydrogen. Under a hydrogen atmosphere, the mixture was stirred overnight at room temperature. The reaction system was purged with nitrogen, and then was filtered. The filtrate was concentrated under reduced pressure, and thus the title compound (163.5 mg) was obtained.

¹H-NMR (300 MHz, CDCl₃); δ (ppm) 1.64 (9H, s), 4.10 (3H, s), 6.60 (1H, brs), 6.83 (1H, dd, J=1.8, 8.4), 7.43 (1H, brs), 7.48 (1H, d, J=8.4)

LCMS: 265 [M+H]; Retention time: 3.74 minutes; LCMS condition: A

Reference Example 66

Benzyl 2-bromoethylcarbamate

[Chemical Formula 108]

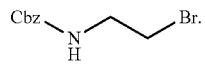

To a solution prepared by adding 1,4-dioxane (50 mL) to benzyl chloroformate (17.5729 g; manufactured by Wako Pure Chemical Industries, Ltd.), an aqueous solution of 2-bromoethanamine hydrobromide-1,4-dioxane [104 mL; solution prepared by dissolving 2-bromoethanamine hydrobromide (21.3617 g; manufactured by Tokyo Chemical Industry Co., Ltd.) in water (54 mL) and 1,4-dioxane (54 mL)]and a 2 mol/L aqueous solution of sodium hydroxide (104 mL; manufactured by Kanto Chemical Co., Inc.) were simultaneously added dropwise. The mixture was stirred for 2 hours at 0° C. Water was added to the reaction solution, and the mixture was extracted two times with ethyl acetate. The organic layer was washed with a saturated solution of sodium hydrogen carbonate, and was dried over magnesium sulfate. The organic layer was concentrated under reduced pressure. The resulting residue was purified by column chromatography ("COLUMN-A"; n-hexane:ethyl acetate=94:6→73:27), and thus the title compound (19.2014 g) was obtained.

¹H-NMR (300 MHz, CDCl₃); δ (ppm) 3.47 (2H, t, J=5.8), 3.60 (2H, t, J=5.8), 5.11 (2H, s), 7.27-7.40 (5H, m)

LCMS: 258 [M+H]; Retention time: 1.42 minutes; LCMS condition; C

Reference Example 67

Benzyl 2-(1-benzyl-3-isopropylindazol-6-yloxy)ethylcarbamate

[Chemical Formula 109]

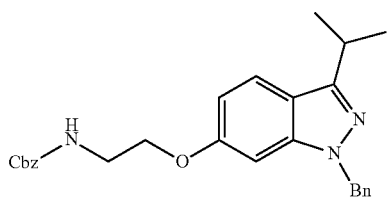

To a solution prepared by adding benzyl 2-bromoethylcarbamate (1.0546 g) that can be produced by the method described in Reference Example 66 or the like to dehydrated DMF (5 mL), 1-benzyl-3-isopropylindazol-6-ol (0.5365 g) that can be produced by the method described in Reference Example 3 or the like and potassium carbonate (0.8565 g; manufactured by Sigma-Aldrich Co.) were added. The mixture was stirred overnight at 50° C. under a nitrogen atmosphere. The reaction solution was poured into water, and the mixture was extracted twice with ethyl acetate. The organic layer was washed two times with water and with brine, and then was dried over anhydrous sodium sulfate. The organic layer was concentrated under reduced pressure. The resulting residue was purified by column chromatography ("COLUMN-B"; n-hexane:ethyl acetate=81:19→60:40), and thus the title compound (0.6727 g) was obtained.

¹H-NMR (300 MHz, CDCl₃); δ (ppm) 1.44 (6H, d, J=6.9), 3.36 (1H, septet, J=6.9), 3.58 (2H, q, J=4.9), 3.98 (2H, t, J=4.9), 5.09 (2H, s), 5.20 (1H, brs), 5.46 (2H, s), 5.46 (1H, s), 6.70 (1H, dd, J=2.2, 8.8), 7.11-7.35 (10H, m), 7.59 (1H, dd, J=0.3, 8.8)

LCMS: 444 [M+H]; Retention time: 5.18 minutes; LCMS condition: A

Reference Example 68

2-(3-Isopropylindazol-6-yloxy)ethanamine

[Chemical Formula 110]

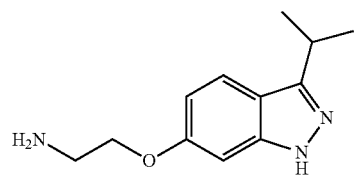

Benzyl 2-(1-benzyl-3-isopropylindazol-6-yloxy)ethylcarbamate (0.655 g) that can be produced by the method described in Reference Example 67 or the like, and 10% palladium on carbon-PE-type-50% wet with water (133 mg; manufactured by N.E. Chemcat Corp.) were suspended in ethanol (15 mL), and then concentrated hydrochloric acid (0.25 mL; manufactured by Wako Pure Chemical Industries, Ltd.) was added thereto. The reaction system was purged with hydrogen, and under a hydrogen atmosphere, the mixture was stirred for one hour at 60° C. The reaction solution was purged with nitrogen, and was filtered. MP-Carbonate [2.2276 g (2.73 mmol/g); manufactured by Argonaut Technologies, Inc.] was added to the filtrate, and the mixture was stirred for one hour at room temperature. The reaction solution was filtered, and then the filtrate was concentrated under reduced pressure. Thus, the title compound (0.3064 g) was obtained.

LCMS: 220 [M+H]; Retention time: 0.47 and 1.82 minutes (double peak); LCMS condition: A Reference Example 69

(R)-N-(2-chloro-5-(oxiran-2-yl)phenyl)methanesulfonamide

[Chemical Formula 111]

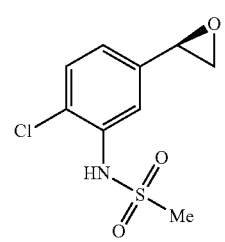

(R)-N-(2-chloro-5-(2-iodo-1-(triethylsilyloxy)ethyl)phenyl)methanesulfonamide (2.2308 g) was dissolved in dehydrated THF (40 mL), and a 1 mol/L TBAF-THF solution (10 mL; manufactured by Sigma-Aldrich Co.) was added thereto. The mixture was purged with nitrogen, and then was stirred for one hour at room temperature. The reaction solution was poured into brine, and the mixture was extracted with once with ethyl acetate. The organic layer was washed once with water, and then was dried over magnesium sulfate. The solvent was evaporated under reduced pressure. The resulting residue was purified by column chromatography ("COLUMN-B"; n-hexane:ethyl acetate 71:29→50:50), and thus the title compound (0.564 g) was obtained.

$^1$H-NMR (300 MHz, CDCl$_3$); δ (ppm) 3.03 (3H, s), 3.38 (1H, dd, J=8.0, 10.4), 3.50 (1H, dd, J=3.8, 10.4), 4.80 (1H, dt, J=3.8, 10.4), 6.81 (1H, brs), 7.20 (1H, dd, J=1.8, 8.4 ), 7.43 (1H, d, J=8.4), 7.65 (1H, d, J=1.6)

LCMS: 248 [M+H]; Retention time: 1.09 minutes; LCMS condition: C

Example 7

(R)-N-(2-chloro-5-(1-hydroxy-2-(2-(3-isopropylindazol-6-yloxy)ethylamino)ethyl)phenyl)methanesulfonamide

[Chemical Formula 112]

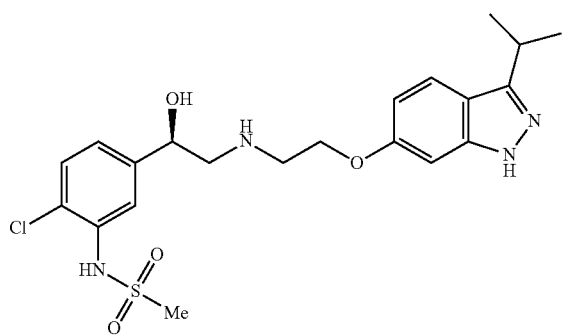

2-Propanol (1.5 mL) was added to (R)-N-(2-chloro-5-(oxiran-2-yl)phenyl)methanesulfonamide (28.6 mg) that can be produced by the method described in Reference Example 69 or the like, and a 2-(3-isopropylindazol-6-yloxy)ethanamine-2-propanol solution [37.5 µL; solution prepared by dissolving 2-(3-isopropylindazol-6-yloxy)ethanamine (306.4 mg) that can be produced by the method described in Reference Example 68 or the like, in 2-propanol (347.5 µL)]. The mixture was stirred overnight at reflux. The reaction solution was cooled to room temperature, and then nitrogen gas was blown into the reaction solution to evaporate the solvent. The resulting residue was purified by HPLC, and then the purification product was dissolved in water (1 mL) and a 1 mol/L aqueous solution of hydrochloric acid (150 µL; manufactured by Kanto Chemical Co., Inc.). The solution was freeze-dried, and thus the title compound was obtained in the form of hydrochloride (18.1 mg).

LCMS: 467 [M+H]; Retention time: 1.01 minutes; LCMS condition: C

Reference Example 70

(R)-tert-butyl 5-(2-(benzyl(2-hydroxyethyl)amino)-1-(triethylsilyloxy)ethyl)-2-fluorophenyl(methanesulfonyl)carbamate

[Chemical Formula 113]

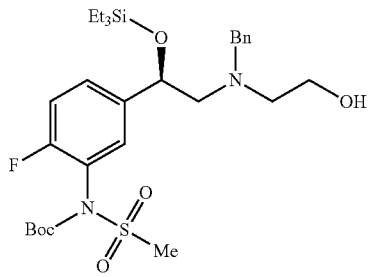

(R)-N-(2-fluoro-5-(2-iodo-1-(triethylsilyloxy)ethyl)phenyl)methanesulfonamide (500 mg) and 2-(benzylamino)ethanol (1.6 g) were mixed, and the mixture was stirred overnight at 100° C. The reaction solution was cooled to room temperature, and then was purified by column chromatography ("COLUMN-H"; n-hexane:ethyl acetate=2:1). Thus, (R)-N-(5-(2-(benzyl-(2-hydroxyethyl)amino)-1-(triethylsilyloxy)ethyl) -2-fluorophenyl)methanesulfonamide (477.5 mg) was obtained. Subsequently,4-N,N-dimethylaminopyridine (12 mg), triethylamine (163 µL) and THF (15 mL) were added thereto, and a Boc$_2$O-THF solution [10 mL; solution prepared by dissolving Boc$_2$O (230 mg) in THF (10 mL)] was added dropwise. The mixture was stirred for 3 hours at room temperature. The reaction solution was concentrated under reduced pressure, and then the residue was purified by column chromatography ("COLUMN-H"; n-hexane:ethyl acetate=3:1). Thus, the title compound (500.3 mg) was obtained.

$^1$1.1-NMR (300 MHz, CDCl$_3$); δ (ppm) 0.41-0.63 (6H, m), 0.82-0.99 (9H, m), 1.42-1.44 (9H, m), 2.59-2.83 (4H, m), 3.42-3.43 (3H, m), 3.45-3.86 (4H, m), 4.54-4.67 (1H, m), 7.04-7.12 (1H, m), 7.19-7.37 (7H, m)

LCMS: 597 [M+H]; Retention time: 0.76 minutes; LCMS condition: D

Reference Example 71

(R)-tert-butyl 2-fluoro-5-(2-(2-hydroxyethylamino)-1-(triethylsilyloxy)ethyl)phenyl(methylsulfonyl)carbamate

[Chemical Formula 114]

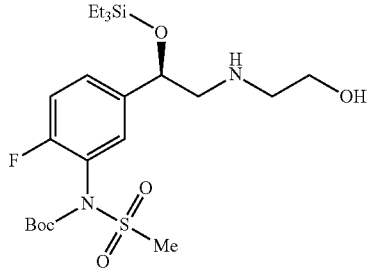

(R)-tert-butyl 5-(2-(benzyl(2-hydroxyethyl)amino)-1-(triethylsilyloxy)ethyl)-2-fluorophenyl(methanesulfonyl)carbamate (1.1717 g) that can be produced by the method described in Reference Example 70 or the like, and 10% palladium on carbon-PE-type-50% wet with water (374 mg; manufactured by N.E. Chemcat Corp,) were suspended in ethanol (5 mL), and then the reaction system was purged with hydrogen. Under a hydrogen atmosphere, the suspension as stirred for 2.5 hours at 50° C. The reaction solution was purged with nitrogen, and was filtered. The filtrate was concentrated under reduced pressure, and thus the title compound (0.8781 g) was obtained.

$^1$H-NMR (300 MHz, CDCl$_3$); δ (ppm) 0.55 (6H, q, J=7.6), 0.88 (9H, t, J=7.6), 1.43 (9H, s), 2.68-2.83 (4H, m), 3.42 (3H, s), 3.57 (2H, t, J=5.1), 4.77 (1H, dt, J=2.5, 4.7), 7.11 (1H, t, J=9.1), 7.34-7.36 (2H, m)

LCMS: 507 [M+H]; Retention time: 1.56 minutes; LCMS condition: C

Reference Example 72

(R)-(2-fluoro-5-(2-(N-tert-butoxycarbonyl-N-(2-hydroxyethyl)amino)-1-triethylsilyloxy)ethyl)phenyl)-N-tert-butoxycarbonylmethanesulfonamide

[Chemical Formula 115]

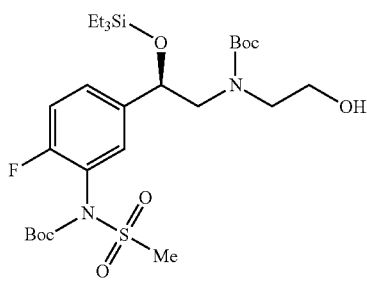

(R)-tert-butyl 2-fluoro-5-(2-(2-hydroxyethylamino)-1-(triethylsilyloxy)ethyl)phenyl(methylsulfonyl)carbamate (0.861 mg) that can be produced by the method described in Reference Example 71 or the like, was dissolved in dehydrated THF (8 mL), and Boc$_2$O (459 μL; manufactured by Wako Pure Chemical Industries, Ltd.) was added thereto. The mixture was stirred overnight at room temperature. The reaction solution was concentrated under reduced pressure, and then the residue was purified by column chromatography ("COLUMN-B"; n-hexane:ethyl acetate=88:12→67:33). Thus, the title compound (755.3 mg) was obtained.

$^1$H-NMR (300 MHz, CDCl$_3$); δ (ppm) 0.53 (6H, q, J=8.0), 0.87 (9H, t, J=8.0), 1.44 (9H, s), 1.48-1.58 (9H, m), 3.08-3.65 (6H, m), 3.42 (3H, s), 4.98-5.24 (1H, m), 7.12 (1H, t, J=9.1), 7.31-7.38 (2H, m)

Reference Example 73

(R)-tert-butyl 6-(2-(tert-butoxycarbonyl(2-(3-(N-(tert-butoxycarbonyl)methylsulfonamido)-4-fluorophenyl)-2-(triethylsilyloxy)ethyl)amino)ethoxy)-3-ethylindazole-1-carboxylate

[Chemical Formula 116]

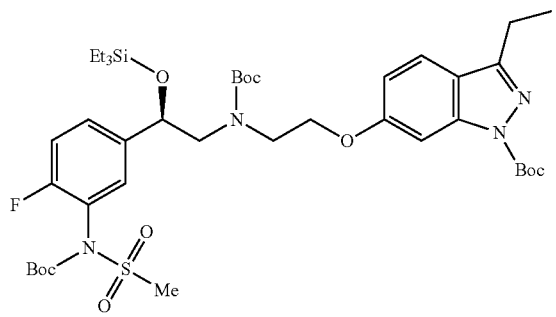

Tert-butyl 3-ethyl-6-hydroxyindazole-1-carboxylate (27.7 mg) that can be produced by the method described in Reference Example 14 or the like, and a (R)-(2-fluoro-5-(2-(N-tert-butoxycarbonyl-N-(2-hydroxyethyl)amino)-1-triethylsilyloxy)ethyl)phenyl)-N-tert-butoxycarbonylmethanesulfonamide-toluene solution [0.5 mL; solution prepared by dissolving (R)-(2-fluoro-5-(2-(N-tert-butoxycarbonyl-N-(2-hydroxyethyl)amino)-1-triethylsilyloxy)ethyl)phenyl)-N-tert-butoxycarbonylmethanesulfonamide (755.3 mg) that can be produced by the method described in Reference Example 72 in dehydrated toluene (3.15 mL)] were dissolved in dehydrated toluene (0.5 mL). Triphenylphosphine (59. 1 mg; manufactured by Wako Pure Chemical Industries, Ltd.) and TMAD (38.7 mg; manufactured by Masuda Chemical Industries, Co., Ltd.) were added to the solution, and the solution was stirred for 3 days at room temperature. The reaction solution was purified by column chromatography ("COLUMN-B"; n-hexane:ethyl acetate=88:12→67:33), and thus the title compound (85.3 mg) was obtained.

$^1$H-NMR (300 MHz, CDCl$_3$); δ (ppm) 0.49-0.57 (6H, m), 0.88 (9H, t, J=8.0), 1.38 (3H, t, J=7.6), 1.43-1.56 (18H, m), 1.70 (9H, s), 2.94 (2H, q, J=7.6), 3.26-3.57 (4H, m), 3.42 (3H, s), 4.03-4.10 (2H, m), 4.89-5.11 (1H, m), 6.86 (1H, d, J=8.4), 7.11 (1H, dt, J=4.3, 9.1), 7.34-7.36 (1H, m), 7.50-7.52 (2H, m)

LCMS: 851 [M+H]; Retention time: 2.35 minutes; LCMS condition: E

Example 8

(R)-N-(5-(2-(2-(3-ethylindazol-6-yloxy)ethylamino)-1-hydroxyethyl)-2-fluorophenyl)methanesulfonamide

[Chemical Formula 117]

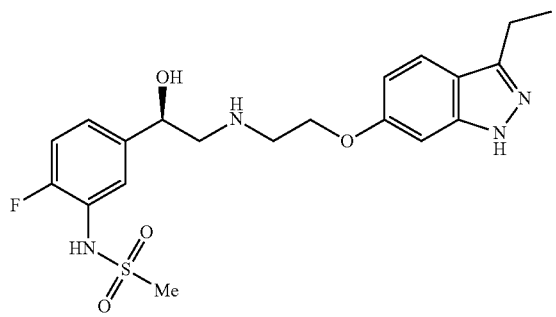

(R)-tert-butyl 6-(2-(tert-butoxycarbonyl(2-(3-(N-(tert-butoxycarbonyl)methylsulfonamido)-4-fluorophenyl)-2-(triethylsilyloxy)ethyl)amino)ethoxy)-3-ethylindazole-1-carboxylate (85.3 mg) that can be produced by the method described in Reference Example 73 or the like, was dissolved in ethyl acetate (200 μL), and a 4 mol/L hydrogen chloride-ethyl acetate solution (1.5 mL; manufactured by Kokusan Chemical Co., Ltd.) was added thereto. The mixture was shaken (600 min$^{-1}$) overnight at room temperature. Nitrogen gas was blown into the reaction solution to evaporate the solvent, and ethyl acetate was added thereto. Insoluble matters were filtered, and thus the title compound was obtained in the form of hydrochloride (40.9 mg).

LCMS: 437 [M+H]; Retention time: 0.92 minutes; LCMS condition: C

Reference Example 74

(R)-N-(5-(2-(benzyl(2-hydroxyethyl)amino)-1-(triethylsilyloxy)ethyl)-2-chlorophenyl)methanesulfonamide

[Chemical Formula 118]

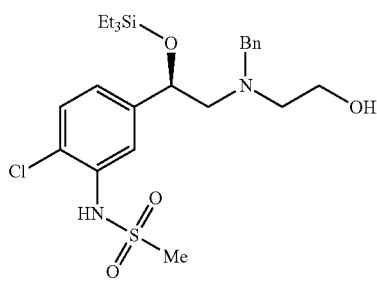

(R)-N-(2-chloro-5-(2-iodo-1-(triethylsilyloxy)ethyl)phenyl)methanesulfonamide (3 g) and 2-(benzylamino)ethanol (6 mL; manufactured by Tokyo Chemical Industry Co., Ltd.) were mixed, and the mixture was stirred overnight at 100° C. The reaction solution was cooled to room temperature, and then toluene and Et$_2$O were added thereto. The mixture was washed three times with water, and the organic layer was dried over magnesium sulfate. Then, the solvent was evaporated under reduced pressure. The residue was purified by column chromatography ("COLUMN-B"; n-hexane:ethyl acetate=84:16→64:36), and thus the title compound (2.1894 g) was obtained.

$^1$H-NMR (300 MHz, CDCl$_3$); δ (ppm) 0.44-0.53 (6H, m), 0.85 (9H, t, J=8.0), 2.53-2.84 (4H, m), 2.99 (3H, s), 3.37 (2H, t, J=5.4), 3.68 (2H, d, J=2.1), 4.55 (1H, t, J=6.5), 7.08 (1H, dd, J=1.8, 8.4), 7.19-7.34 (5H, m), 7.36 (1H, d, J=8.4), 7.58 (1H, d, J=1.8)

LCMS: 513 [M+H]; Retention time: 1.54 minutes; LCMS condition: C

Reference Example 75

(R)-tert-butyl 5-(2-(benzyl(2-hydroxyethyl)amino)-1-(triethylsilyloxy)ethyl)-2-chlorophenyl(methylsulfonyl)carbamate

[Chemical Formula 119]

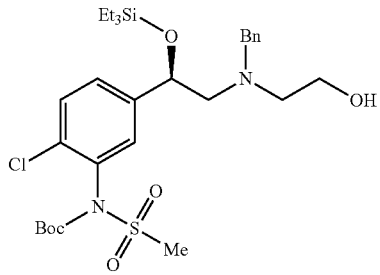

(R)-N-(5-(2-(benzyl(2-hydroxyethyl)amino)-1-(triethylsilyloxy)ethyl)-2-chlorophenyl)methanesulfonamide (2.1515 g) that can be produced by the method described in Reference Example 74 or the like, was dissolved in dehydrated THF (20 mL), and triethylamine (0.884 mL; manufactured by Kokusan Chemical Co., Ltd.) was added thereto. The mixture was cooled to 0° C. To this solution, Boc$_2$O (1.14 mL; manufactured by Wako Pure Chemical Industries, Ltd.) and 4-N,N-dimethylaminopyridine (51.4 mg; manufactured by Wako Pure Chemical Industries, Ltd.) were added, and the mixture was stirred overnight while the temperature was raised to room temperature. The reaction solution was concentrated under reduced pressure, and the residue was purified by column chromatography ("COLUMN-B"; n-hexane:ethyl acetate=88:12→67:33). Thus, the title compound (1.5265 g) was obtained.

$^1$H-NMR (300 MHz, CDCl$_3$); δ (ppm) 0.42-0.53 (6H, m), 0.82-0.90 (9H, m), 1.41-1.43 (9H, m), 2.51-2.80 (4H, m), 3.42-3.50 (2H, m), 3.51-3.53 (3H, m), 4.51-4.59 (1H, m), 7.12-7.37 (8H, m)

LCMS: 613 [M+H]; Retention time: 1.03 minutes; LCMS condition: D

Reference Example 76

(R)-tert-butyl 6-(2-(benzyl-(2-(3-(N-(tert-butoxycarbonyl)methylsulfonamido)-4-chlorophenyl)-2-(triethylsilyloxy)ethyl)amino)ethoxy)-3-ethylindazole-1-carboxylate

[Chemical Formula 120]

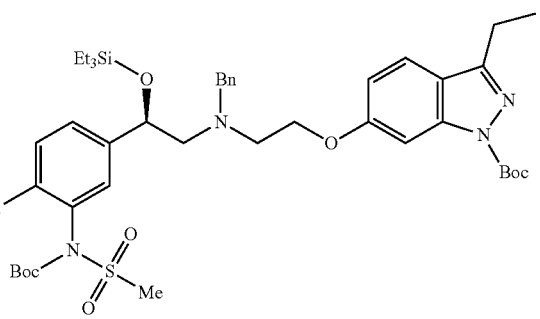

Tert-butyl 3-ethyl-6-hydroxyindazole-1-carboxylate (27.9 mg) that can be produced by the method described in Reference Example 14 or the like, and a (R)-tert-butyl 5-(2-(benzyl(2-hydroxyethyl)amino)-1-(triethylsilyloxy)ethyl)-2-chlorophenyl(methylsulfonyl)carbamate-toluene solution [0.5 mL; solution prepared by dissolving (R)-tert-butyl 5-(2-(benzyl(2-hydroxyethyl)amino)-1-(triethylsilyloxy)ethyl)-2-chlorophenyl(methylsulfonyl)carbamate (1.5265 g) that can be produced by the method described in Reference Example 75 or the like in dehydrated toluene (10 mL)] were dissolved in dehydrated toluene (0.5 mL), and triphenylphosphine (54.9 mg; manufactured by Wako Pure Chemical Industries, Ltd.) and TMAD (41.4 mg; manufactured by Masuda Chemical Industries, Co., Ltd.) were added to the solution. The mixture was stirred for 3 days at room temperature. The reaction solution was purified by column chromatography ("COLUMN-B"; n-hexane:ethyl acetate=85:15→64:36), and thus the title compound (85.6 mg) was obtained.

$^1$H-NMR (300 MHz, CDCl$_3$); δ (ppm) 0.42-0.50 (6H, m), 0.80-0.88 (9H, m), 1.37-1.53 (12H, m), 1.70 (9H, s), 2.80-2.99 (4H, m), 3.47-3.50 (3H, m), 3.71-3.78 (2H, m), 3.83-4.00 (2H, m), 4.59 (1H, brs), 6.82-6.87 (1H, m), 7.16-7.31 (8H, m), 7.42-7.53 (2H, m)

LCMS: 857 [M+H]; Retention time: 8.67 minutes; LCMS condition: B

Reference Example 77

(R)-tert-butyl 6-(2-(tert-butoxycarbonyl(2-(3-(N-(tert-butoxycarbonyl)methylsulfonamido)-4-chlorophenyl)-2-(triethylsilyloxy)ethyl)amino)ethoxy)-3-ethylindazole-1-carboxylate

[Chemical Formula 121]

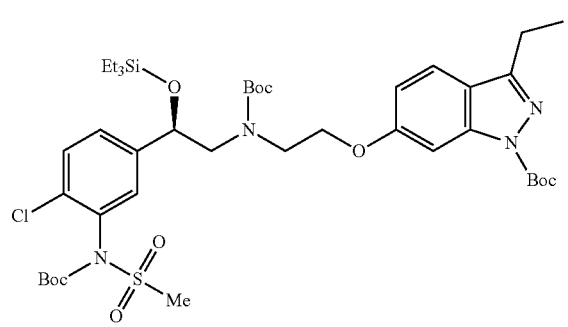

(R)-tert-butyl 6-(2-(benzyl(2-(3-(N-(tert-butoxycarbonyl)methylsulfonamido)-4-chlorophenyl)-2-(triethylsilyloxy)ethyl)amino)ethoxy)-3-ethylindazole-1-carboxylate (83.2 mg) that can be produced by the method described in Reference Example 76 or the like, and 10% palladium on carbon-PE-type-50% wet with water (18.1 mg; manufactured by N.E. Chemcat Corp.) were suspended in ethanol (0.5 mL), and then a 0.1 mol/L hydrochloric acid-ethanol solution (1 mL; manufactured by Kanto Chemical Co., Inc.) was added to the suspension. The reaction system was purged with hydrogen, and under a hydrogen atmosphere, the reaction solution was stirred for one hour at room temperature. The reaction solution was purged with nitrogen, and was filtered. Triethylamine (20 μL; manufactured by Kokusan Chemical Co., Ltd.) was added to the filtrate, and the mixture was concentrated under reduced pressure. The residue was dissolved in CH$_2$Cl$_2$ (1.5 mL), and Boc$_2$O (30 μL; manufactured by Wako Pure Chemical Industries, Ltd.) was added thereto. The mixture was stirred overnight at room temperature. Triethylamine (20 μL; manufactured by Kokusan Chemical Co., Ltd.) and Boc$_2$O (30 μL; manufactured by Wako Pure Chemical Industries, Ltd.) were added to the reaction solution, and the mixture was stirred overnight at room temperature. Nitrogen gas was blown into the reaction solution to evaporate the solvent, and the resulting residue was purified by column chromatography ("COLUMN-B"; n-hexane:ethyl acetate=77:23→56:44). Thus, the title compound (73.3 mg) was obtained.

$^1$H-NMR (300 MHz, CDCl$_3$); δ (ppm) 0.49-0.58 (6H, m), 0.85-0.91 (9H, m), 1.38 (3H, t, J=7.3), 1.42-1.63 (18H, m), 1.70 (9H, s), 2.91-2.98 (2H, q, J=7.3), 3.21-3.62 (4H, m), 3.50 (3H, s), 4.04-4.10 (2H, m), 4.90-5.09 (1H, m), 6.84-6.88 (1H, m), 7.26-7.51 (5H, m)

LCMS: 867 [M+H]; Retention time: 8.11 minutes; LCMS condition: B

Example 9

(R)-N-(2-chloro-5-(2-(2-(3-ethylindazol-6-yloxy)ethylamino)-1-hydroxyethyl)phenyl)methanesulfonamide

[Chemical Formula 122]

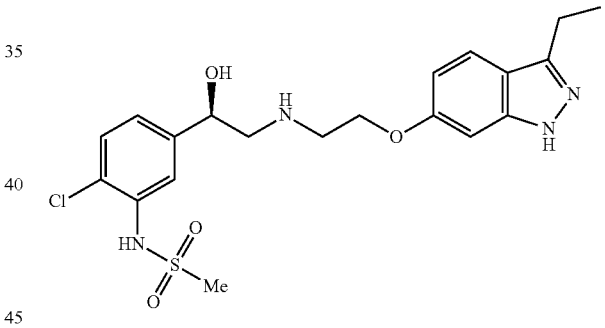

(R)-tert-butyl 6-(2-(tert-butoxycarbonyl(2-(3-(N-(tert-butoxycarbonyl)methylsulfonamido)-4-chlorophenyl)-2-(triethylsilyloxy)ethyl)amino)ethoxy)-3-ethylindazole-1-carboxylate (70.2 mg) that can be produced by the method described in Reference Example 77 or the like, was dissolved in MTBE (200 μL), and a 4 mol/L hydrogen chloride-1,4-dioxane solution (1.5 mL; manufactured by Kokusan Chemical Co., Ltd.) was added thereto. The mixture was shaken (600 min$^{-1}$) overnight at room temperature. Nitrogen gas was blown into the reaction solution to evaporate the solvent, and MTBE (1.5 mL) was added thereto. Nitrogen gas was blown into the suspension to evaporate the solvent, and thus the title compound was obtained in the form of hydrochloride (52.5 mg).

LCMS: 453 [M+H]; Retention time 0.95 minutes; LCMS condition: C

Reference Example 78

(R)-tert-butyl 6-(2-(tert-butoxycarbonyl(2-(3-(N-(tert-butoxycarbonyl)methylsulfonamido)-4-fluorophenyl)-2-(triethylsilyloxy)ethyl)amino)ethoxy)-3-(trifluoromethyl)indazole-1-carboxylate

[Chemical Formula 123]

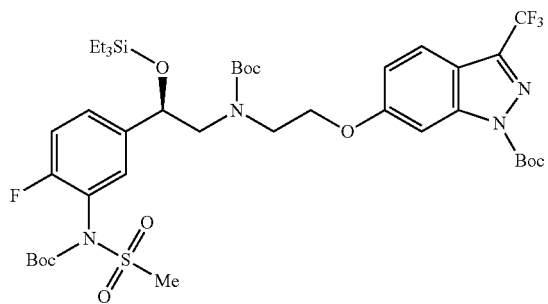

The title compound (75.5 mg) was obtained by the same method as that used in Reference Example 73, using tert-butyl 3-(trifluoromethyl)-6-hydroxyindazole-1-carboxylate (34.8 mg) that can be produced by the method described in Reference Example 38, instead of tert-butyl 3-ethyl-6-hydroxyindazole-1-carboxylate.

$^1$H-NMR (300 MHz, CDCl$_3$); δ (ppm) 0.49-0.57 (6H, m), 0.88 (9H, t, J=7.6), 1.43-1.64 (18H, m), 1.71 (9H, s), 3.27-3.60 (4H, m), 3.42 (3H, s), 4.05-4.11 (2H, m), 4.90-5.11 (1H, m), 6.98 (1H, d, J=8.4), 7.11 (1H, d, J=5.1-9.5), 7.37 (2H, brs), 7.60 (1H, s), 7.65 (1H, dd, J=2.1, 8.4)

LCMS: 891 [M+H]; Retention time: 8.10 minutes; LCMS condition: B

Example 10

(R)-N-(2-fluoro-5-(1-hydroxy-2-(2-(3-(trifluoromethyl)indazol-6-yloxy)ethylamino)ethyl)phenyl)methanesulfonamide

[Chemical Formula 124]

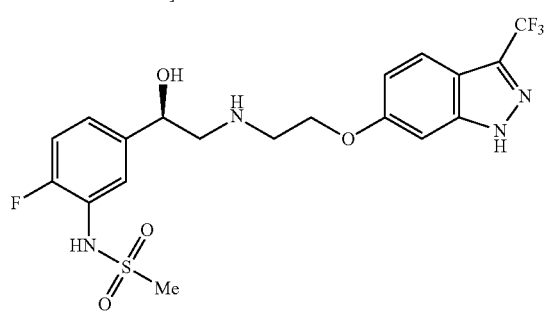

(R)-tert-butyl 6-(2-(tert-butoxycarbonyl-(2-(3-(N-(tert-butoxycarbonyl)methylsulfonamido)-4-fluorophenyl)-2-(triethylsilyloxy)ethyl)amino)ethoxy)-3-(trifluoromethyl)indazole-1-carboxylate (75.5 mg) that can be produced by the method described in Reference Example 78 or the like, was dissolved in ethyl acetate (200 μL), and a 4 mol/L hydrogen chloride-ethyl acetate solution (1.5 mL; manufactured by Kokusan Chemical Co., Ltd.) was added thereto. The mixture was shaken (600 min$^{-1}$) overnight at room temperature. Nitrogen gas was blown into the reaction solution to evaporate the solvent, and ethyl acetate was added thereto. Insoluble matters were filtered, and thus the title compound was obtained in the form of hydrochloride (21.1 mg).

LCMS: '477 [M+H]; Retention time: 1.04 minutes; LCMS condition: C

Reference Example 79

(R)-tert-butyl 6-(2-(benzyl(2-(3-(N-(tert-butoxycarbonyl)methylsulfonamido)-4-chlorophenyl)-2-(triethylsilyloxy)ethyl)amino)ethoxy)-3-(trifluoromethyl)indazole-1-carboxylate

[Chemical Formula 125]

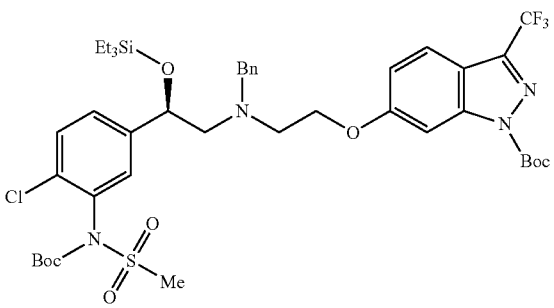

The title compound (92.6 mg) was obtained by the same method as that used in Reference Example 76, using tert-butyl 3-(trifluoromethyl)-6-hydroxyindazole-1-carboxylate (36.5 mg) that can be produced by the method described in Reference Example 38 or the like, instead of tert-butyl 3-ethyl-6-hydroxyindazole-1-carboxylate.

$^1$H-NMR (300 MHz, CDCl$_3$); δ (ppm) 0.42-0.53 (6H, 1H) 0.83 (9H, t, J=7.6), 1.38 (9H, s), 1.72 (9H, s), 2.75-2.96 (4H, m), 3, 46-3.51 (3H, m), 3.71-3.98 (4H, m), 4.59 (1H, brs), 6.93-6.98 (1H, m), 7.14-7.44 (8H, m), 7.53 (1H, d, J=2.1), 7.65 (1H, d, J=9.1)

LCMS: 897 [M+H]; Retention time: 9.08 minutes; LCMS condition: B

Reference Example 80

(R)-tert-butyl 6-(2-(tert-butoxycarbonyl(2-(3-(N-(tert-butoxycarbonyl)methylsulfonamido)-4-chlorophenyl)-2-(triethylsilyloxy)ethyl)amino)ethoxy)-3-trifluoromethylindazole-1-carboxylate

[Chemical Formula 126]

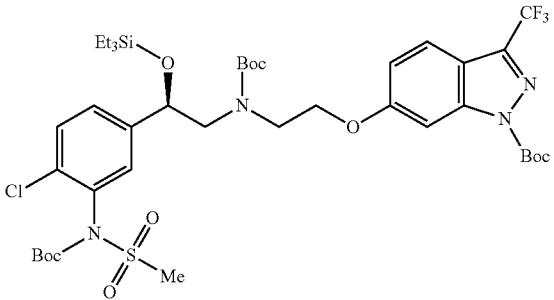

The title compound (77.5 mg) was obtained by the same method as that used in Reference Example 77, using (R)-tert-butyl 6-(2-(benzyl-(2-(3-(N-(tert-butoxycarbonyl)methylsulfonamido)-4-chlorophenyl)-2-(triethylsilyloxy)ethyl)amino)ethoxy)-3-(trifluoromethyl)indazole-1-carboxylate (87.1 mg) that can be produced by the method described in Reference Example 79 or the like, instead of (R)-tert-butyl 6-(2-(benzyl(2-(3-(N-(tert-butoxycarbonyl)methylsulfonamido)-4-chlorophenyl)-2-(triethylsilyloxy)ethyl)amino)ethoxy)-3-ethylindazole-1-carboxylate.

$^1$H-NMR (300 MHz, CDCl$_3$); δ (ppm) 0.49-0.59 (6H, m), 0.85-0.91 (9H, m), 1.42-1.57 (18H, m), 1.71 (9H, s), 3.21-1.65 (4H, m), 3.50 (3H, s), 4.06-4.09 (2H, m), 4.91-5.13 (1H, m), 6.96-7.00 (1H, m), 7.26-7.46 (3H, m), 7.58-7.66 (2H, m)

Example 11

(R)-N-(2-chloro-5-(1-hydroxy-2-(2-(3-(trifluoromethyl)indazol-6-yloxy)ethylamino)ethyl)phenyl)methanesulfonamide

[Chemical Formula 127]

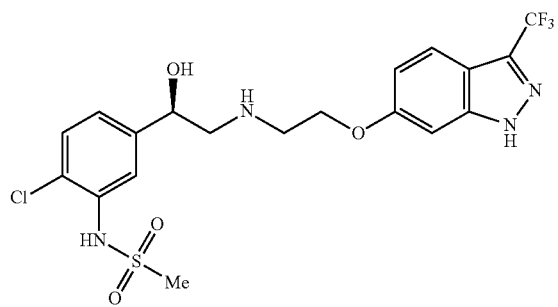

(R)-tert-butyl 6-(2-(tert-butoxycarbonyl(2-(3-(N-(tert-butoxycarbonyl)methylsulfonamido)-4-chlorophenyl)-2-(triethylsilyloxy)ethyl)amino)ethoxy)-3-trifluoromethylindazole-1-carboxylate (74.5 mg) that can be produced by the method described in Reference Example 80 or the like, was dissolved in MTBE (200 μL), and a 4 mol/L hydrogen chloride-1,4-dioxane solution (1.5 mL; manufactured by Kokusan Chemical Co., Ltd.) was added thereto. The mixture was shaken (600 min$^{-1}$) overnight at room temperature. Nitrogen gas was blown into the reaction solution to evaporate the solvent, and MTBE was added thereto. Nitrogen gas was blown into the suspension to evaporate the solvent, and thus the title compound was obtained in the form of hydrochloride (52.5 mg).

$^1$H-NMR (300 MHz, DMSO-d$_6$); δ (ppm) 3.06 (3H, s), 3.09-3.56 (4H, m), 4.35-4.43 (3H, m), 5.06 (1H, d, J=9.8), 6.36 (1H, d, J=4.0), 7.02 (1H, dd, J=1.8, 8.7), 7.14 (1H, d, J=1.8), 7.29 (1H, dd, J=2.1, 8.4), 7.51 (1H, d, J=1.8), 7.55 (1H, d, J=8.4), 7.71 (1H, d, J=8.7), 9.31 (2H, brs), 13.90 (1H, s)

LCMS; 493 [M+H]; Retention time: 1.10 minutes; LCMS condition: C

Example 12

(R)-N-(3-(1-hydroxy-2-(2-(3-methylindazol-6-yloxy)ethylamino)ethyl)phenyl)propane-2-sulfonamide

[Chemical Formula 128]

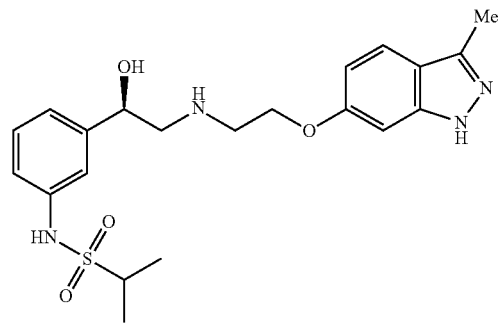

(R)-tert-butyl 6-(2-((2-(3-aminophenyl)-2-(triethylsilyloxy)ethyl)(tert-butoxycarbonyl)amino)ethoxy-3-methylindazole-1-carboxylate (96 mg) that can be produced by the Reference Example 85 or the like, was dissolved in dehydrated CH$_2$Cl$_2$ (0.5 mL), and dehydrated pyridine (18 μL), propane-2-sulfonyl chloride (26 mg) and dehydrated CH$_2$Cl$_2$ (1.5 mL) were added to the solution. The mixture was stirred overnight at room temperature. DBU (134 μL) and propane-2-sulfonyl chloride (20 μL) were added to the reaction solution, and the mixture was stirred overnight at room temperature. DBU (33.5 μL) and propane-2-sulfonyl chloride (20 μL) were added to the reaction solution, and the mixture was stirred for 4 days at room temperature. DBU (33.5 μL) and propane-2-sulfonyl chloride (20 μL) were added to the reaction solution, and the mixture was stirred overnight at room temperature. The reaction solution was crudely purified by column chromatography ("COLUMN-B"; n-hexane:ethyl acetate=81:19→60:40), and the crude purification product was dissolved in dehydrated CH$_2$Cl$_2$ (1.5 mL). MP-Isocyanate (118 mg; manufactured by Argonaut Technologies, Inc., 1.7 mmol/g) was added to the solution, and the mixture was stirred overnight at room temperature. The reaction solution was filtered, and then was concentrated under reduced pressure. A 4 mol/L hydrochloric acid-1,4-dioxane solution (1.5 mL) was added to the resulting residue (39.7 mg), and the mixture was shaken (600 min$^{-1}$) overnight at room temperature. Nitrogen gas was blown into the reaction solution to evaporate the solvent, and MTBE was added thereto. Nitrogen gas was blown into the suspension to evaporate the solvent, and the title compound was obtained in the form of hydrochloride (27.6 mg).

LCMS: 433 [M+H]; Retention time: 0.89 minutes; LCMS condition: C

Example 13

(R)-N-(3-(2-(2-(3-ethylindazol-6-yloxy)ethylamino)-1-hydroxyethyl)phenyl)propane-2-sulfonamide

[Chemical Formuls 129]

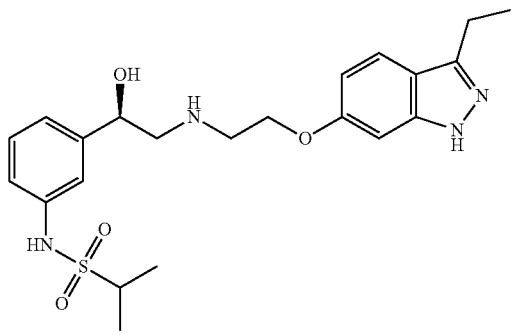

(R)-tert-butyl 6-(2-((2-(3-aminophenyl)-2-(triethylsilyloxy)ethyl)(tert-butoxycarbonyl)amino)ethoxy-3-ethylindazole-1-carboxylate (97 mg) that can be produced by the method described in Reference Example 86 or the like, was dissolved in dehydrated CH$_2$Cl$_2$ (0.5 mL), and dehydrated pyridine (18 μL), propane-2-sulfonyl chloride (26 mg) and dehydrated CH$_2$Cl$_2$ (1.5 mL) were added to the solution. The mixture was stirred overnight at room temperature. DBU (134 μL) and propane-2-sulfonyl chloride (20 μL) were added to the reaction solution, and the mixture was stirred overnight at room temperature. DBU (33.5 μL) and propane-2-sulfonyl chloride (20 μL) were added to the reaction solution, and the mixture was stirred for 4 days at room temperature. DBU (33.5 μL) and propane-2-sulfonyl chloride (20 μL) were added to the reaction solution, and the mixture was stirred overnight at room temperature. The reaction solution was purified by column chromatography ("COLUMN-B"; n-hexane:ethyl acetate=81:19→60:40). A 4 mol/L hydrochloric acid-1,4-dioxane solution (1.5 mL) was added to the purification product (47.9 mg), and the mixture was shaken (600 min$^{-1}$) overnight at room temperature. Nitrogen gas was blown into the reaction solution to evaporate the solvent, and MTBE was added. Nitrogen gas was blown into the suspension to evaporate the solvent, and thus the title compound was obtained in the form of hydrochloride (33.3 mg).

LCMS: 447 [M+H]; Retention time: 0.96 minutes; LCMS condition: C

Example 14

(R)-N-(3-(1-hydroxy-2-(2-(3-methylindazol-6-yloxy)ethylamino)ethyl)phenyl)benzenesulfonamide

[Chemical Formula 130]

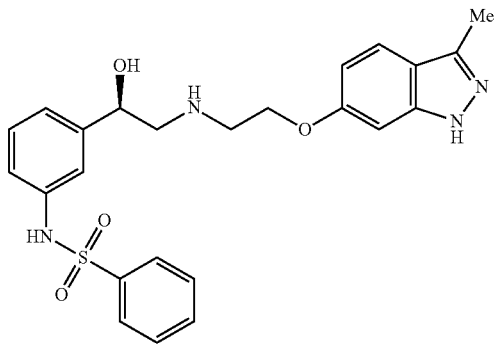

(R)-tert-butyl 6-(2-((2-(3-aminophenyl)-2-(triethylsilyloxy)ethyl)(tert-butoxycarbonyl)amino)ethoxy-3-methylindazole-1-carboxylate (96 mg) that can be produced by the method described in Reference Example 85 or the like, was dissolved in dehydrated CH$_2$Cl$_2$ (0.5 mL), and dehydrated pyridine (18 μL), benzenesulfonyl chloride (32 mg) and dehydrated CH$_2$Cl$_2$ (1.5 mL) were added to the solution. The mixture was stirred overnight at room temperature. The reaction solution was purified by column chromatography ("COLUMN-G"; n-hexane:ethyl acetate=4:3). The purification product was dissolved in 1,4-dioxane (0.2 mL), and a 4 mol/L hydrochloric acid-1,4-dioxane solution (1.5 mL) was added thereto. The mixture was shaken (600 min$^{-1}$) overnight at room temperature. Nitrogen gas was blown into the reaction solution to evaporate the solvent, and the title compound was obtained in the form of hydrochloride (67.3 mg).

LCMS: 467 [M+H]; Retention time: 0.94 minutes; LCMS condition: C

Example 15

(R)-N-(3-(2-(2-(3-ethylindazol-6-yloxy)ethylamino)-1-hydroxyethyl)phenyl)benzenesulfonamide

[Chemical Formula 131]

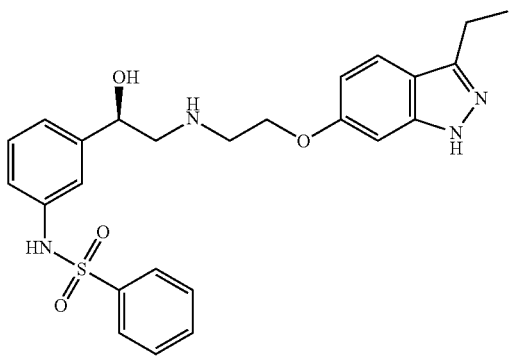

The title compound was obtained in the form of hydrochloride (79.5 mg) by the same method as that used in Example 14, using (R)-tert-butyl 6-(2-((2-(3-aminophenyl)-2-(triethylsilyloxy)ethyl)(tert-butoxycarbonyl)amino)ethoxy-3-ethylindazole-1-carboxylate (97 mg) that can be produced by the method described in Reference Example 86 or the like, instead of (R)-tert-butyl 6-(2-((2-(3-aminophenyl)-2-(triethylsilyloxy)ethyl)(tert-butoxycarbonyl)amino)ethoxy-3-methylindazole-1-carboxylate.

LCMS: 481 [M+H]; Retention time: 1.00 minutes; LCMS condition: C

Example 16

(R)-N-(3-(1-hydroxy-2-(2-(3-methoxyindazol-6-yloxy)ethylamino)ethyl)phenyl)benzenesulfonamide

[Chemical Formula 132]

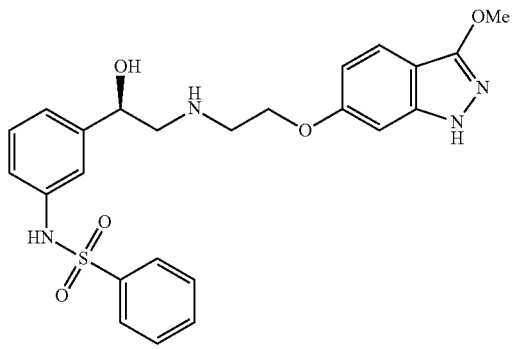

The title compound was obtained in the form of hydrochloride (62.8 mg) by the same method as that used in Example 14, using (R)-tert-butyl 6-(2-((2-(3-aminophenyl)-2-(triethylsilyloxy)ethyl)(tert-butoxycarbonyl)amino)ethoxy-3-methoxyindazole-1-carboxylate (99 mg) that can be produced by the method described in Reference Example 88 or the like, instead of (R)-tert-butyl 6-(2-((2-(3-aminophenyl)-2-(triethylsilyloxy)ethyl)(tert-butoxycarbonyl)amino)ethoxy-3-methylindazole-1-carboxylate.

LCMS: 483 [M+H]; Retention time: 1.04 minutes; LCMS condition: C

Example 17

(R)-N-(3-(1-hydroxy-2-(2-(3-(trifluoromethyl)indazol-6-yloxy)ethylamino)ethyl)phenyl)benzenesulfonamide

[Chemical Formula 133]

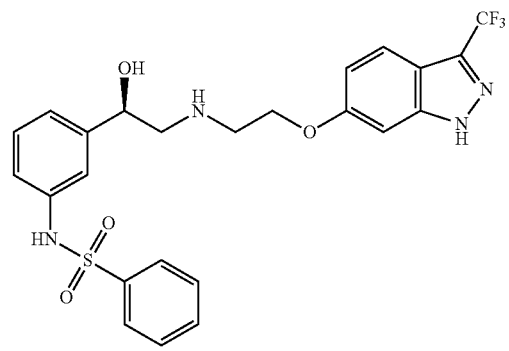

The title compound was obtained in the form of hydrochloride (43.7 mg) by the same method as that used in Example 14, using (R)-tert-butyl 6-(2-((2-(3-aminophenyl)-2-(triethylsilyloxy)ethyl)(tert-butoxycarbonyl)amino)ethoxy-3-(trifluoromethyl)indazole-1-carboxylate (69 mg) that can be produced by the method described in Reference Example 87 or the like, instead of (R)-tert-butyl 6-(2-((2-(3-aminophenyl)-2-(triethylsilyloxy)ethyl)(tert-butoxycarbonyl)amino)ethoxy-3-methylindazole-1-carboxylate.

LCMS: 521 [M+H]; Retention time: 1.15 minutes; LCMS condition: C

Example 18

(R)-N-(3-(1-hydroxy-2-(2-(3-isopropylindazol-6-yloxy)ethylamino)ethyl)phenyl)benzenesulfonamide

[Chemical Formula 134]

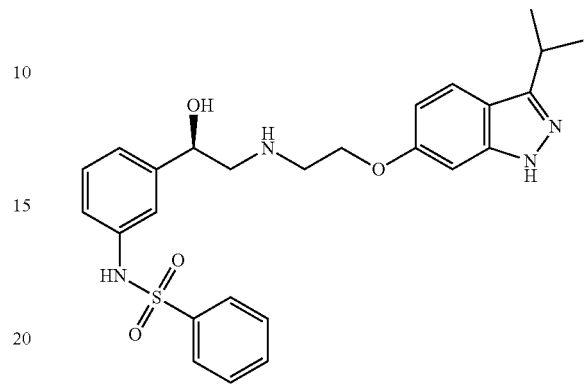

The title compound was obtained in the form of hydrochloride (48.4 mg) by the same method as that used in Example 14, using (R)-tert-butyl 6-(2-((2-(3-aminophenyl)-2-(triethylsilyloxy)ethyl)(tert-butoxycarbonyl)amino)ethoxy-3-isopropylindazole-1-carboxylate (67 mg) that can be produced by the method described in Reference Example 89 or the like, instead of (R)-tert-butyl 6-(2-((2-(3-aminophenyl)-2-(triethylsilyloxy)ethyl)(tert-butoxycarbonyl)amino)ethoxy-3-methylindazole-1-carboxylate.

LCMS: 495 [M+H]; Retention time: 1.07 minutes; LCMS condition: C

Example 19

(R)-3-(6-(2-(2-hydroxy-2-(3-(phenylsulfonamido)phenyl)ethylamino)ethoxy)indazol-3-yl)-N,N-dimethylpropanamide

[Chemical Formula 135]

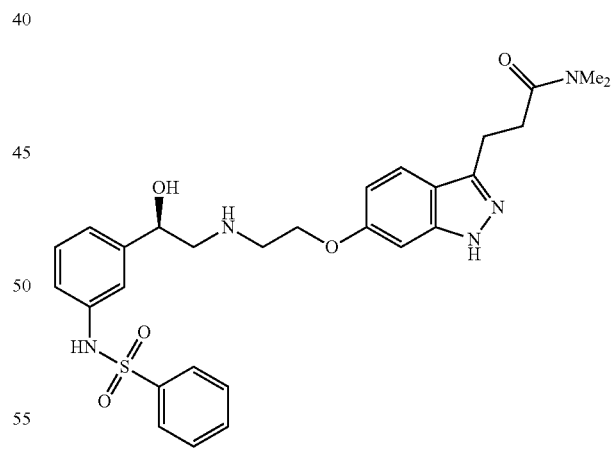

The title compound was obtained in the form of hydrochloride (41.5 mg) by the same method as that used in Example 14, using (R)-tert-butyl 6-(2-((2-(3-aminophenyl)-2-(triethylsilyloxy)ethyl)(tert-butoxycarbonyl)amino)ethoxy-3-(3-(dimethylamino)-3-oxopropyl)indazole-1-carboxylate (73 mg) that can be produced by the method described in Reference Example 90 or the like, instead of (R)-tert-butyl 6-(2-((2-(3-aminophenyl)-2-(triethylsilyloxy)ethyl)(tert-butoxycarbonyl)amino)ethoxy-3-methylindazole-1-carboxylate.

LCMS: 552 [M+H]; Retention time: 0.90 minutes; LCMS condition: C

Example 20

(R)-N-(3-(2-(2-(3-ethylindazol-6-yloxy)ethylamino)-1-hydroxyethyl)phenyl)ethanesulfonamide

[Chemical Formula 136]

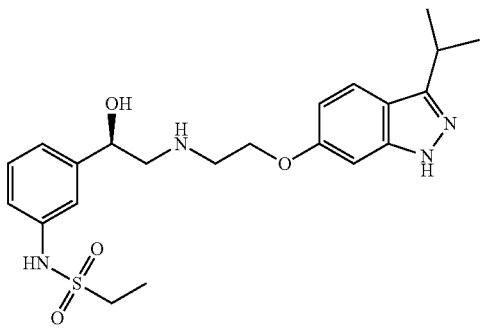

(R)-tert-butyl 6-(2-((2-(3-aminophenyl)-2-(triethylsilyloxy)ethyl)(tert-butoxycarbonyl)amino)ethoxy-3-ethylindazole-1-carboxylate (97 mg) that can be produced by the method described in Reference Example 86 or the like, was dissolved in dehydrated $CH_2Cl_2$ (0.5 mL), and dehydrated pyridine (12 μL), ethanesulfonyl chloride (51 mg) and dehydrated $CH_2Cl_2$ (1.5 mL) were added thereto. The mixture was stirred overnight at room temperature. Dehydrated pyridine (54 μL) and ethanesulfonyl chloride (69 mg) were added to the reaction solution, and the mixture was stirred overnight at room temperature. The reaction solution was purified by column chromatography ("COLUMN-G"; n-hexane:ethyl acetate=4:3). The purification product was dissolved in 1,4-dioxane (0.2 mL), and a 4 mol/L hydrochloric acid-1,4-dioxane solution (1.5 mL) was added thereto. The mixture was shaken (600 $min^{-1}$) overnight at room temperature. Nitrogen gas was blown into the reaction solution to evaporate the solvent, and thus the title compound was obtained in the form of hydrochloride (22.9 mg).

LCMS: 433 [M+]; Retention time 0.90 minutes; LCMS condition:

Example 21

(R)-N-(3-(2-(2-(3-(trifluoromethyl)indazol-6-yloxy)ethylamino)-1-hydroxyethyl)phenyl)ethanesulfonamide

[Chemical Formula 137]

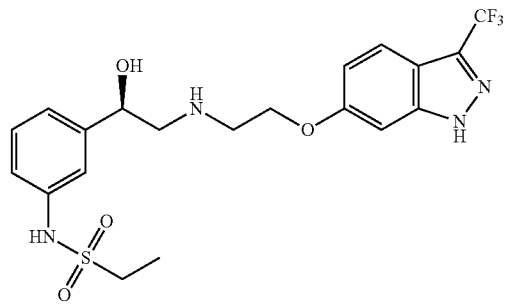

The title compound was obtained in the form of hydrochloride (39.1 mg) by the same method as that used in Example 20, using (R)-tert-butyl 6-(2-((2-(3-aminophenyl)-2-(triethylsilyloxy)ethyl)(tert-butoxycarbonyl)amino)ethoxy-3-(trifluoromethyl)indazole-1-carboxylate (69 mg) that can be produced by the method described in Reference Example 87 or the like, instead of (R)-tert-butyl 6-(2-((2-(3-aminophenyl)-2-(triethylsilyloxy)ethyl)(tert-butoxycarbonyl)amino)ethoxy-3-ethylindazole-1-carboxylate.

LCMS: 473 [M+H]; Retention time; 0.95 minutes; LCMS condition: C

Example 22

(R)-N-(3-(2-(2-(3-isopropylindazol-6-yloxy)ethylamino)-1-hydroxyethyl)phenyl)ethanesulfonamide

[Chemical Formula 138]

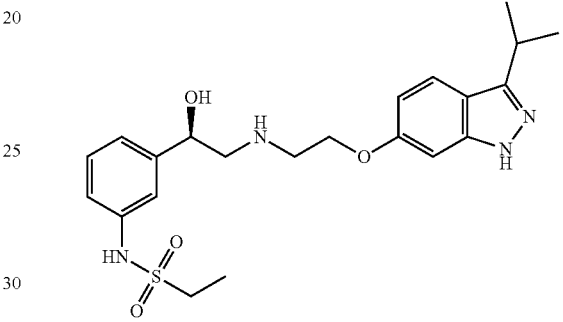

The title compound was obtained in the form of hydrochloride (35.6 mg) by the same method as that used in Example 20, using (R)-tert-butyl 6-(2-((2-(3-aminophenyl)-2-(triethylsilyloxy)ethyl)(tert-butoxycarbonyl)amino)ethoxy-3-isopropylindazole-1-carboxylate (67 mg) that can be produced by the method described in Reference Example 89 or the like, instead of (R)-tert-butyl 6-(2-((2-(3-aminophenyl)-2-(triethylsilyloxy)ethyl)(tert-butoxycarbonyl)amino)ethoxy-3-ethylindazole-1-carboxylate.

LCMS: 447 [M+H]; Retention time: 0.92 minutes; LCMS condition: C

Example 23

(R)-3-(6-(2-(2-(3-(ethylsulfonamido)phenyl)-2-hydroxyethylamino)ethoxy)indazol-3-yl)-N,N-dimethylpropanamide

[Chemical Formula 139]

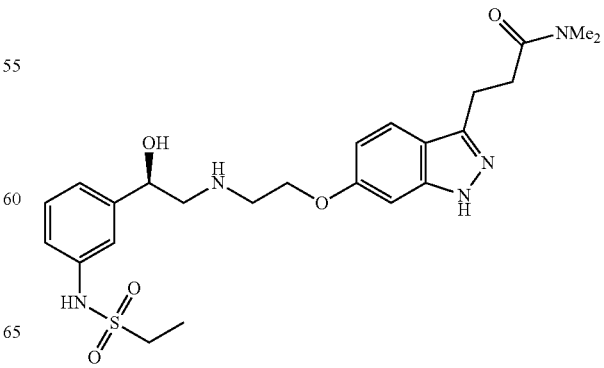

149

The title compound was obtained in the form of hydrochloride (40.5 mg) by the same method as that used in Example 20, using (R)-tert-butyl 6-(2-((2-(3-aminophenyl)-2-(triethylsilyloxy)ethyl)(tert-butoxycarbonyl)amino)ethoxy-3-(3-(dimethylamino)-3-oxopropyl)indazole-1-carboxylate (73 mg) that can be produced by the method described in Reference Example 90 or the like, instead of (R)-tert-butyl 6-(2-((2-(3-aminophenyl)-2-(triethylsilyloxy)ethyl)(tert-butoxycarbonyl)amino)ethoxy-3-ethylindazole-1-carboxylate.

LCMS: 504 [M+H]; Retention time: 0.74 minutes; LCMS condition: C

Example 24

(R)-N-(3-(1-hydroxy-2-(2-(3-methoxyindazol-6-yloxy)ethylamino)ethyl)phenyl)propane-2-sulfonamide

[Chemical Formula 140]

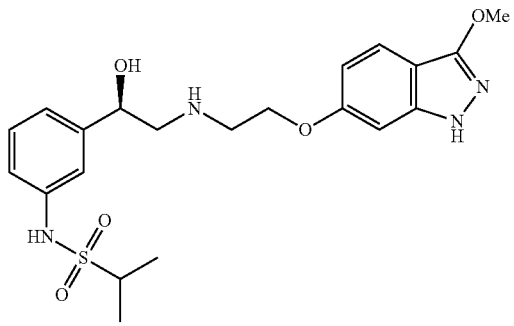

(R)-tert-butyl 6-(2-((2-(3-aminophenyl)-2-(triethylsilyloxy)ethyl)(tert-butoxycarbonyl)amino)-ethoxy-3-methoxyindazole-1-carboxylate (102.7 mg) that can be produced by the method described in Reference Example 88 or the like, was dissolved in dehydrated $CH_2Cl_2$, and DBU (70 µL) and propane-2-sulfonyl chloride (34 µL) were added thereto. The mixture was shaken (600 min$^{-1}$) overnight at room temperature. DBU (90 µL) and propane-2-sulfonyl chloride (68 µL) were added to the reaction solution, and the mixture was shaken (600 min$^{-1}$) overnight at room temperature. The reaction solution was crudely purified by column chromatography ("COLUMN-B"; n-hexane:ethyl acetate=81:19→60:40). The crude purification product was dissolved in dehydrated $CH_2Cl_2$ (1 mL), and MP-Isocyanate (250 mg; manufactured by Argonaut Technologies, Inc., 1.46 mmol/g) was added to the solution. The mixture was stirred overnight at room temperature. The reaction solution was filtered, and then the solvent was evaporated under reduced pressure. The residue was dissolved in MTBE (200 µL). To the MTBE solution, a 4 mol/L hydrochloric acid-1,4-dioxane solution (1.5 mL) was added, and the mixture was shaken (600 min$^{-1}$) overnight at room temperature. Nitrogen gas was blown into the reaction solution to evaporate the solvent, and the MTBE was added to the resulting residue to obtain a suspension. Nitrogen gas was blown into the suspension to evaporate the solvent, and thus the title compound was obtained in the form of hydrochloride (25.5 mg).

LCMS: 449 [M+H]; Retention time: 0.95 minutes; LCMS condition: C

150

Example 25

(R)-N-(3-(1-hydroxy-2-(2-(3-(trifluoromethyl)indazol-6-yloxy)ethylamino)ethyl)phenyl)propane-2-sulfonamide

[Chemical Formula 141]

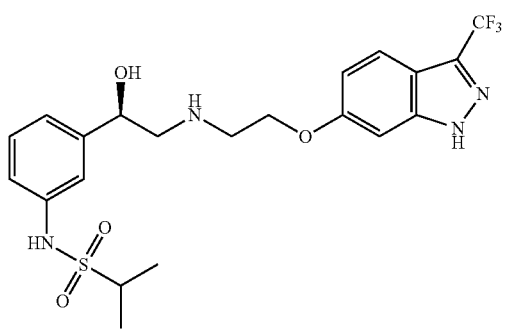

The title compound was obtained in the form of hydrochloride (22.5 mg) by the same method as that used in Example 24, using (R)-tert-butyl 6-(2-((2-(3-aminophenyl)-2-(triethylsilyloxy)ethyl)(tert-butoxycarbonyl)amino)ethoxy-3-(trifluoromethyl)indazole-1-carboxylate (105.9 mg) that can be produced by the method described in Reference Example 87 or the like, instead of (R)-tert-butyl 6-(2-((2-(3-aminophenyl)-2-(triethylsilyloxy)ethyl)(tert-butoxycarbonyl)amino)ethoxy-3-methoxyindazole-1-carboxylate.

LCMS: 487 [M+H]; Retention time: 1.10 minutes; LCMS condition: C

Example 26

(R)-N-(3-(1-hydroxy-2-(2-(3-(trifluoromethyl)indazol-6-yloxy)ethylamino)ethyl)phenyl)propane-1-sulfonamide

[Chemical Formula 142]

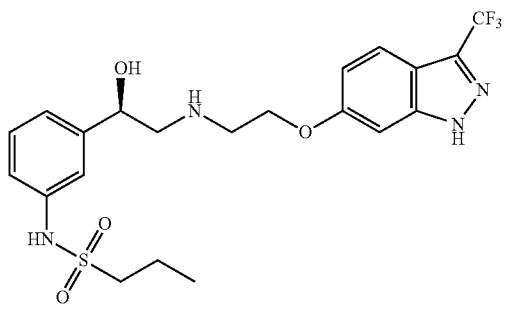

(R)-tert-butyl 6-(2-((2-(3-aminophenyl)-2-(triethylsilyloxy)ethyl)(tert-butoxycarbonyl)amino)ethoxy-3-(trifluoromethyl)indazole-1-carboxylate (104.2 mg) that can be produced by the method described in Reference Example 87 or the like, was dissolved in dehydrated $CH_2Cl_2$ (1 mL), and dehydrated pyridine (75 µL) and a propane-1-sulfonyl chloride-$CH_2Cl_2$ solution [0.5 mL; solution prepared by dissolving propane-1-sulfonyl chloride (607.9 mg) in dehydrated CH₂Cl₂ (3.5 mL)] were added to the solution. The mixture was shaken (600 min⁻¹) overnight at room temperature. The reaction solution was purified by column chromatography. The purification product was dissolved in MTBE (0.1 mL), and a 4 mol/L hydrochloric acid-1,4-dioxane solution (1.5 mL) was added to the solution. The mixture was shaken (600 min⁻¹) overnight at room temperature. Nitrogen gas blown into the reaction solution to evaporate the solvent, and thus the title compound was obtained in the form of hydrochloride (61.1 mg).

LCMS: 487 [M+H]; Retention time: 1.09 minutes; LCMS condition: C

Example 27

(R)-N-(2-chloro-5-(1-hydroxy-2-(2-(3-methylindazol-6-yloxy)ethylamino)ethyl)phenyl)benzenesulfonamide

[Chemical Formula 143]

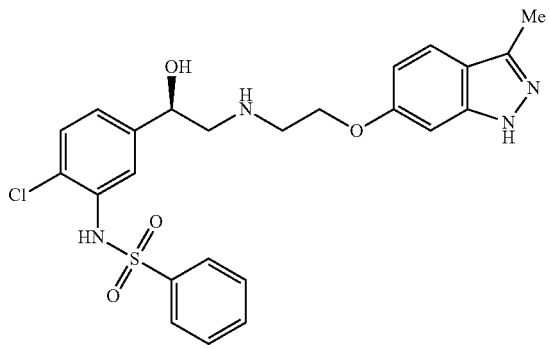

A (R)-tert-butyl 6-(2-((2-(3-amino-4-chlorophenyl)-2-(triethylsilyloxy)ethyl)(tert-butoxycarbonyl)amino)ethoxy)-3-methylindazole-1-carboxylate-CH₂Cl₂ solution [0.5 mL; solution prepared by dissolving (R)-tert-butyl 6-(2-((2-(3-amino-4-chlorophenyl)-2-(triethylsilyloxy)ethyl)(tert-butoxycarbonyl)amino)ethoxy)-3-methylindazole-1-carboxylate (1.324 g) that can be produced by the method described in Reference Example 101 or the like in dehydrated CH₂Cl₂ (10 mL)], dehydrated pyridine (42 µL), a benzenesulfonyl chloride-CH₂Cl₂ solution [0.5 mL; solution prepared by dissolving benzenesulfonyl chloride (466.3 mg; manufactured by Wako Pure Chemical Industries, Ltd.) in dehydrated CH₂Cl₂ (4 mL)], and dehydrated CH₂Cl₂ were added, and the mixture was shaken (600 min⁻¹) overnight at room temperature. PS-Trisamine [300 mg (3.6 mmol/g); manufactured by Argonaut Technologies, Inc.] was added to the reaction solution, and the mixture was shaken (600 min⁻¹) for 5 hours at room temperature. The reaction solution was filtered, and nitrogen gas was blown into the filtrate to evaporate the solvent. The resulting residue was purified by column chromatography ("COLUMN-I"; methanol). The obtained purification product was dissolved in 1,4-dioxane (0.2 mL), and a 4 mol/L hydrochloric acid-1,4-dioxane solution (1.5 mL) was added thereto. The mixture was shaken (600 min⁻¹) overnight at room temperature. Nitrogen gas was blown into the reaction solution to evaporate the solvent, and MTBE was added to the obtained residue to obtain a suspension. Nitrogen gas was blown into the suspension to evaporate the solvent, and thus the title compound was obtained in the form of hydrochloride (46.4 mg).

LCMS: 501 [M+H]; Retention time: 1.00 minutes; LCMS condition: C

Example 28

(R)-N-(2-fluoro-5-(1-hydroxy-2-(2-(3-methylindazol-6-yloxy)ethylamino)ethyl)phenyl)benzenesulfonamide

[Chemical Formula 144]

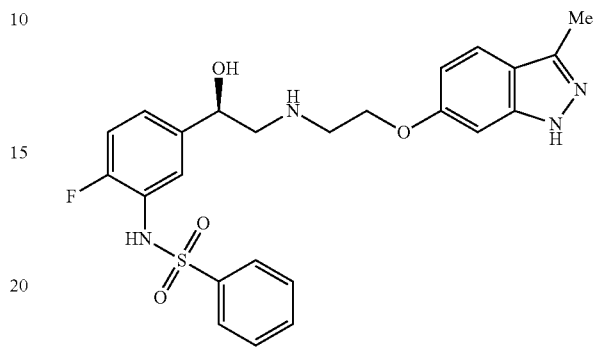

The title compound was obtained in the form of hydrochloride (37.1 mg) by the same method as that used in Example 27, using (R)-tert-butyl 6-(2-((2-(3-amino-4-fluorophenyl)-2-(triethylsilyloxy)ethyl)(tert-butoxycarbonyl)amino)ethoxy)-3-methylindazole-1-carboxylate that can be produced by the method described in Reference Example 97 or the like, instead of (R)-tert-butyl 6-(2-((2-(3-amino-4-chlorophenyl)-2-(triethylsilyloxy)ethyl)(tert-butoxycarbonyl)amino)ethoxy)-3-methylindazole-1-carboxylate.

LCMS: 485 [M+H]; Retention time: 1.00 minutes; LCMS condition: C

Example 29

(R)-N-(2-fluoro-5-(1-hydroxy-2-(2-(3-(trifluoromethyl)indazol-6-yloxy)ethylamino)ethyl)phenyl)benzenesulfonamide

[Chemical Formula 145]

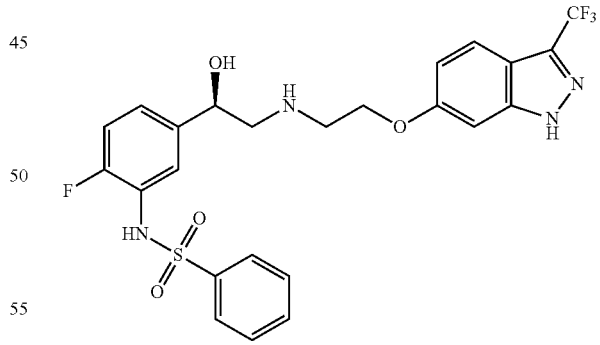

The title compound was obtained in the form of hydrochloride (18.4 mg) by the same method as that used in Example 27, using (R)-tert-butyl 6-(2-((2-(3-amino-4-fluorophenyl)-2-(triethylsilyloxy)ethyl)(tert-butoxycarbonyl)amino)ethoxy)-3-(trifluoromethyl)indazole-1-carboxylate that can be produced by the method described in Reference Example 106 or the like, instead of (R)-tert-butyl 6-(2-((2-(3-amino-4-chlorophenyl)-2-(triethylsilyloxy)ethyl)(tert-butoxycarbonyl)amino)ethoxy)-3-methylindazole-1-carboxylate.

LCMS: 539 [M+H]; Retention time: 1.20 minutes; LCMS condition: C

Example 30

(R)-N-(2-fluoro-5-(1-hydroxy-2-(2-(3-methoxyindazol-6-yloxy)ethylamino)ethyl)phenyl)benzenesulfonamide

[Chemical Formula 146]

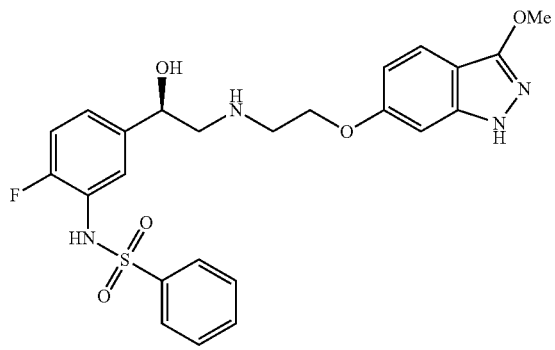

A crude product of the title compound was obtained by the same method as that used in Example 27, using (R)-tert-butyl 6-(2-((2-(3-amino-4-fluorophenyl)-2-(triethylsilyloxy)ethyl)(tert-butoxycarbonyl)amino)ethoxy)-3-methoxyindazole-1-carboxylate that can be produced by the method described in Reference Example 111 or the like, instead of (R)-tert-butyl 6-(2-((2-(3-amino-4-chlorophenyl)-2-(triethylsilyloxy)ethyl)(tert-butoxycarbonyl)amino)ethoxy)-3-methylindazole-1-carboxylate. The crude product was purified by HPLC, and then the purification product was dissolved in ethanol (0.5 mL). A 1 mol/L hydrogen chloride-diethyl ether solution (0.4 mL; manufactured by Tokyo Chemical Industry Co., Ltd.) was added to the solution, and nitrogen gas was blown into the mixture to evaporate the solvent. Thus, the title compound was obtained in the form of hydrochloride (26.5 mg).

LCMS: 501 [M+H]; Retention time: 0.96 minutes; LCMS condition: C

Example 31

(R)-N-(2-chloro-5-(1-hydroxy-2-(2-(3-methoxyindazol-6-yloxy)ethylamino)ethyl)phenyl)benzenesulfonamide

[Chemical Formula 147]

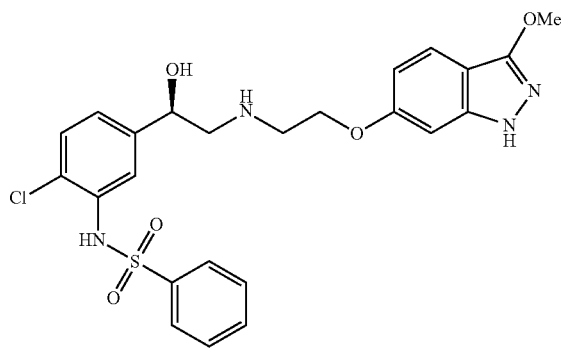

The title compound was obtained in the form of hydrochloride (40.8 mg) by the same method as that used in Example 27, using (R)-tert-butyl 6-(2-((2-(3-amino-4-chlorophenyl)-2-(triethylsilyloxy)ethyl)(tert-butoxycarbonyl)amino)ethoxy)-3-methoxyindazole-1-carboxylate that can be produced by the method described in Reference Example 115 or the like, instead of (R)-tert-butyl 6-(2-((2-(3-amino-4-chlorophenyl)-2-(triethylsilyloxy)ethyl)(tert-butoxycarbonyl)amino)ethoxy)-3-methylindazole-1-carboxylate.

LCMS: 517 [M+H]; Retention time: 1.03 minutes; LCMS condition: C

Reference Example 81

N-benzyl-2-(benzyloxy)ethanamine

[Chemical Formula 148]

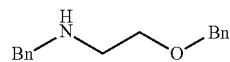

2-(Benzyloxy)ethanamine (12.3146 g; manufactured by Bionet Co., Ltd.) was dissolved in $CH_2Cl_2$ (150 mL), and benzaldehyde (8.7219 g; manufactured by Kanto Chemical Co., Inc.) and anhydrous sodium sulfate (67.7879 g; manufactured by Wako Pure Chemical Industries, Ltd.) were added to the solution. The mixture was stirred overnight at room temperature. The reaction solution was filtered, and the filtrate was concentrated under reduced pressure. The obtained residue was dissolved in methanol (150 mL), and sodium borohydride (3.4129 g; manufactured by Kanto Chemical Co., Inc.) was added thereto. The mixture as stirred for 2 hours at room temperature. The reaction solution was concentrated under reduced pressure, water added thereto, and then the mixture was extracted two times with ethyl acetate. The organic layer was washed twice with water and once with brine, and was dried over anhydrous sodium sulfate. The organic layer was concentrated under reduced pressure, and thus the title compound (20.188 g) was obtained.

$^1$H-NMR (300 MHz, $CDCl_3$); δ (ppm) 2.84 (2H, t, J=5.1), 3.62 (2H, t, J=5.1), 3.80 (2H, s), 4.52 (2H, s), 7.20-7.37 (10H, m)

Reference Example 82

(R)-2-(benzyl-(2-(benzyloxy)ethyl)amino)-1-(3-nitrophenyl)ethanol

[Chemical Formula 149]

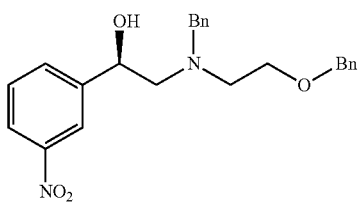

N-benzyl-2-(benzyloxy)ethanamine (13.6532 g) that can be produced by the method described in Reference Example 81 or the like, (R)-2-(3-nitrophenyl)oxirane (20.21 g), and 2-propanol (205 mL) were added, and the mixture was stirred for 36 hours at reflux. The reaction solution was cooled to room temperature, and was concentrated under reduced pressure. Subsequently, toluene (100 mL) was added to the residue, and the mixture was concentrated under reduced pressure. The resulting residue was purified by column chromatography ("COLUMN-D"; n-hexane:ethyl acetate=85:15→80:20), and thus the title compound (30.761 g) was obtained.

$^1$H-NMR (300 MHz, CDCl$_3$); δ (ppm) 2.61 (1H, dd, J=3.2, 10.2), 2.75-3.01 (3H, m), 3.51-3.63 (2H, m), 3.78 (2H, dd, J=13.5, 68.9), 4.53 (2H, s), 4.70 (1H, dd, J=3.2, 10.2), 7.27-7.39 (10H, m), 7.44 (1H, t, J=8.0), 7.59 (1H, d, J=8.0), 8.08 (1H, qd, J=1.1, 8.0), 8.16 (1H, d, J=1.1)

LCMS: 407 [M+H]; Retention time: 1.31 minutes; LCMS condition: C

Reference Example 83

(R)-N-benzyl-N-(2-(benzyloxy)ethyl)-2-(3-nitrophenyl)-2-(triethylsilyloxy)ethanamine

[Chemical Formula 150]

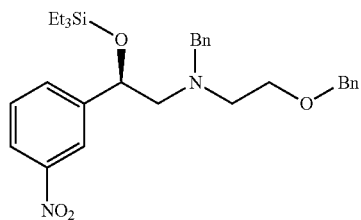

(R)-2-(benzyl-(2-(benzyloxy)ethyl)amino)-1-(3-nitrophenyl)ethanol (30.371 g) that can be produced by the method described in Reference Example 82 or the like, and imidazole (6.1318 g; manufactured by Tokyo Chemical Industry Co., Ltd.) were dissolved in dehydrated DMF (150 mL), and chlorotriethylsilane (15.1 mL; manufactured by Shin-Etsu Chemical Co., Ltd.) was added thereto. The mixture was stirred overnight at room temperature. The reaction solution was poured into water, and the mixture was extracted two times with ethyl acetate. The organic layer was washed twice with water and once with brine, dried over magnesium sulfate, and then concentrated under reduced pressure. The resulting residue was purified by column chromatography ("COLUMN-A"; n-hexane:ethyl acetate=100:0→87:13), and thus the title compound (36.655 g) was obtained.

$^1$H-NMR (300 MHz, CDCl$_3$); δ (ppm) 0.44-0.53 (6H, m), 0.85 (9H, t, J=8.0), 2.67-2.85 (4H, m), 3.40-3.45 (2H, m), 3.62 (2H, dd, J=13.5, 42.8), 4.42 (2H, s), 4.68 (1H, dd, J=7.3), 7.05 -7.36(10H, m), 7.56 (1H, d, J=7.6), 8.02-8.06 (1H, m), 8.11-8.12 (1H, m)

Reference Example 84

(R)-tert-butyl 2-(3-aminophenyl)-2-(triethylsilyloxy)ethyl-(2-hydroxyethyl)carbamate

[Chemical Formula 151]

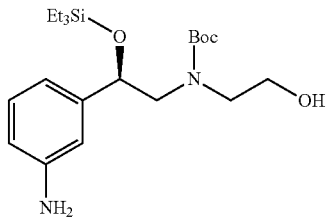

(R)-N-benzyl-N-(2-(benzyloxy)ethyl)-2-(3-nitrophenyl)-2-(triethylsilyloxy)ethanamine (36.455 g) that can be produced by the method described in Reference Example 83 or the like, and 10% palladium on carbon-PE-type-50% wet with water (15.1241 g; manufactured by N.E. Chemcat Corp.) were suspended in ethanol (175 mL), and the reaction system was purged with hydrogen to bring a hydrogen atmosphere. There, the reaction solution was stirred for 9 hours at 50° C. The reaction solution was purged with hydrogen again, and under a hydrogen atmosphere, the reaction solution was stirred for 4 hours at 50° C. The reaction solution was cooled to room temperature, purged with nitrogen, and filtered. The filtrate was concentrated under reduced pressure, and then the resulting residue (25.083 g) was dissolved in THF (175 mL). Boc$_2$O (14.6029 g; manufactured by Wako Pure Chemical Industries, Ltd.) was added to the solution, and the mixture was stirred for 1.5 hours at room temperature. The reaction solution was concentrated under reduced pressure, and 20% palladium hydroxide on carbon-50% wet with water (15.0214 g; manufactured by N.E. Chemcat Corp.), THF (80 mL) and methanol (80 mL) were added to the resulting residue to obtain a suspension. The reaction system was purged with hydrogen to bring a hydrogen atmosphere, and under the atmosphere, the reaction solution was stirred for 8 hours at 50° C. The reaction solution was cooled to room temperature, purged with nitrogen, and then filtered. The filtrate was concentrated under reduced pressure, and then the resulting residue was purified by column chromatography ("COLUMN-A"; n-hexane:ethyl acetate=75:25→54:46). Thus, the title compound (16.918 g) was obtained.

$^1$H-NMR (300 MHz, CDCl$_3$); δ (ppm) 0.43-0.57 (6H, m), 0.87 (9H, t, J=8.0), 1.48-1.50 (9H, m), 2.04-3.86 (6H, m), 4.08-5.19 (1H, m), 6.57-6.77 (3H, m), 7.09 (1H, t, J=7.6)

LCMS: 411 [M+H]; Retention time: 2.03 minutes; LCMS condition: C

Reference Example 85

(R)-tert-butyl 6-(2-((2-(3-aminophenyl)-2-(triethylsilyloxy)ethyl)(tert-butoxycarbonyl)amino)ethoxy-3-methylindazole-1-carboxylate

[Chemical Formula 152]

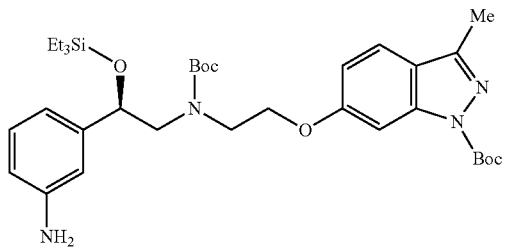

(R)-tert-butyl 2-(3-aminophenyl)-2-(triethylsilyloxy)ethyl-(2-hydroxyethyl)carbamate (3.9587 g) that can be produced by the method described in Reference Example 84 or the like, tert-butyl 6-hydroxy-3-methylindazole-1-carboxylate (2.0894 g) that can be produced by the method described in Reference Example 60, and triphenylphosphine (2.7559 g; manufactured by Kanto Chemical Co., Inc.) were dissolved in dehydrated toluene (50 mL), and DIAD (2.12 mL; manufactured by Sigma-Aldrich Co.) was added thereto. The mixture was stirred overnight at room temperature. The reaction solution was crudely purified by column chromatography ("COLUMN-A"; n-hexane:ethyl acetate=77:23→56:44). The crude purification product (6.3754 g) was dissolved in $CH_2Cl_2$ (50 mL), and MP-Carbonate [8.8 g (2.73 mol/g); manufactured by Argonaut Technologies, Inc.] was added thereto. The mixture was stirred overnight at room temperature. The reaction solution was filtered, and then the filtrate was concentrated under reduced pressure. The resulting residue was purified three times by column chromatography ("COLUMN-A"; n-hexane:ethyl acetate=77:23→56:44), and thus the title compound (3.5065 g) was obtained.

$^1$H-NMR (300 MHz, $CDCl_3$); δ (ppm) 0.48-0.56 (6H, m), 0.84-0.91 (9H, m), 1.48 (9H, s), 1.70 (9H, s); 2.52-2.53 (3H, m), 3.18-3.73 (4H, m), 4.04-4.13 (2H, m), 4.80-4.99 (1H, m), 6.56-6.89 (4H, m), 7.09 (1H, t, J=7.6), 7.46 (1H, dd, J=2.1, 8.7), 7.54 (1H, s)

LCMS: 641 [M+H]; Retention time: 1.71 minutes; LCMS condition: E

Reference Example 86

(R)-tert-butyl 6-(2-((2-(3-aminophenyl)-2-(triethylsilyloxy)ethyl)(tert-butoxycarbonyl)amino)ethoxy-3-ethylindazole-1-carboxylate

[Chemical Formula 153]

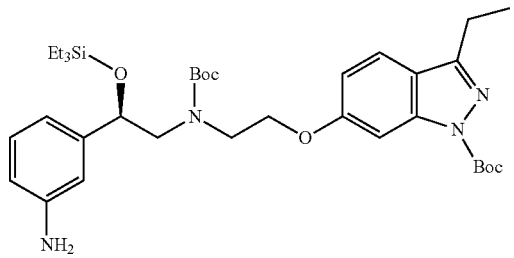

The title compound (4.4487 g) was obtained by the same method as that used in Reference Example 85, using tert-butyl 6-hydroxy-3-ethylindazole-1-carboxylate (2.5983 g) that can be produced by the method described in Reference Example 14 or the like, instead of tert-butyl 6-hydroxy-3-methylindazole-1-carboxylate.

$^1$H-NMR (300 MHz, $CDCl_3$); δ (ppm) 0.53 (6H, q, J=7.6), 0.88 (9H, t, J=7.6), 1.38 (3H, t, J=7.6), 1.48 (9H, s), 1.70 (9H, s), 2.95 (2H, q, J=7.6), 3.20-3.73 (4H, m), 4.04-4.10 (2H, m), 4.86-4.96 (1H, m), 6.56-6.88 (4H, m), 7.09 (1H, t, J=7.6), 7.48-7.52 (2H, m)

LCMS: 655 [M+H]; Retention time: 1.94 minutes; LCMS condition: E

Reference Example 87

(R)-tert-butyl 6-(2-((2-(3-aminophenyl)-2-(triethylsilyloxy)ethyl)(tert-butoxycarbonyl)amino)ethoxy-3-(trifluoromethyl)indazole-1-carboxylate

[Chemical Formula 154]

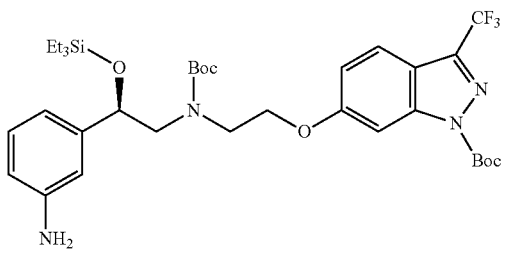

The title compound (1.7128 g) was obtained by the same method as that used in Reference Example 85, using tert-butyl 6-hydroxy-3-(trifluoromethyl)indazole-1-carboxylate (1.6977 g) that can be produced by the method described in Reference Example 38 or the like, instead of tert-butyl 6-hydroxy-3-methylindazole-1-carboxylate.

$^1$H-NMR (300 MHz, $CDCl_3$); δ (ppm) 0.53 (6H, q, J=8.0), 0.88 (9H, t, J=9.0), 1.48 (9H, s), 1.71 (9H, s), 3.15-3.78 (4H, m), 4.03-4.14 (2H, m), 4.80-4.99 (1H, m), 6.58-6.79 (3H, m), 6.99 (1H, dd, J=1.8, 8.7), 7.09 (1H, t, J=7.6), 7.60-7.66 (2H, m)

LCMS: 695 [M+H]; Retention time: 2.03 minutes; LCMS condition: E

Reference Example 88

(R)-tert-butyl 6-(2-((2-(3-aminophenyl)-2-(triethylsilyloxy)ethyl)(tert-butoxycarbonyl)amino)ethoxy-1-methoxyindazole-1-carboxylate

[Chemical Formula 155]

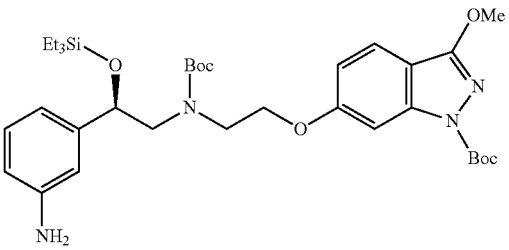

The title compound (1.577 g) was obtained by the same method as that used in Reference Example 85, using tert-butyl 6-hydroxy-3-methoxyindazole-1-carboxylate (1.0539 g) that can be produced by the method described in Reference Example 65 or the like, instead of tert-butyl 6-hydroxy-3-methylindazole-1-carboxylate.

$^1$H-NMR (300 MHz, $CDCl_3$); δ (ppm) 0.48-0.57 (6H, m), 0.88 (9H, t, J=8.0), 1.47-1.48 (9H, m), 1.68 (9H, s), 3.14-3.74 (4H, m), 4.00-4.10 (2H, m), 4.13 (3H, s), 4.79-4.99 (1H, m), 6.56-6.84 (4H, m), 7.08 (1H, t, J=7.6), 7.41 (1H, s), 7.47 (1H, dd, J=2.9, 8.7)

LCMS: 657 [M+H]; Retention time: 1.88 minutes; LCMS condition: E

Reference Example 89

(R)-tert-butyl 6-(2-((2-(3-aminophenyl)-2-(triethylsilyloxy)ethyl)(tert-butoxycarbonyl)amino)ethoxy-3-isopropylindazole-1-carboxylate

[Chemical Formula 156]

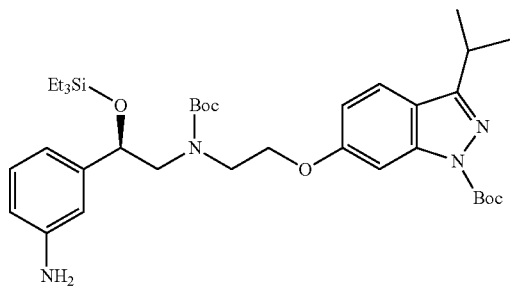

The title compound (633.1 mg) was obtained by the same method as that used in Reference Example 85, using tert-butyl 6-hydroxy-3-isopropylindazole-1-carboxylate (419.7 mg) that can be produced by the method described in Reference Example 7 or the like, instead of tert-butyl 6-hydroxy-3-methylindazole-1-carboxylate.

$^1$H-NMR (300 MHz, CDCl$_3$); δ (ppm) 0.49-0.57 (6H, m), 0.88 (9H, t, J=8.0), 1.44 (6H, d, J=6.9), 1.47 (9H, s), 1.74 (9H, s), 3.15-3.78 (5H, m), 4.02-4.12 (2H, m), 4.79-4.99 (1H, m), 6.56-6.87 (4H, m), 7.08 (1H, t, J=7.6), 7.51 (1H, s), 7.57 (1H, d, J=8.7)

LCMS 669 [M+H]; Retention time: 2.18 minutes; LCMS condition: E

Reference Example 90

(R)-tert-butyl 6-(2-((2-(3-aminophenyl)-2-(triethylsilyloxy)ethyl)(tert-butoxycarbonyl)amino)ethoxy-3-(3-(dimethylamino)-3-oxopropyl)indazole-1-carboxylate

[Chemical Formula 157]

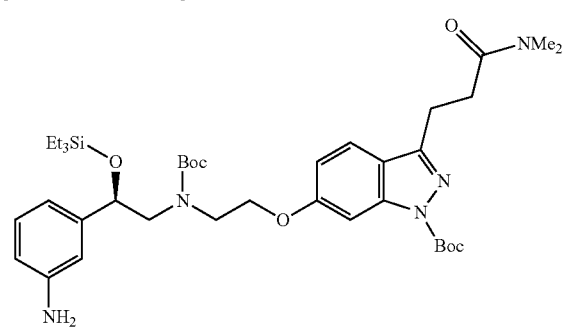

The title compound (453 mg) was obtained by the same method as that used in Reference Example 85, using tert-butyl 3-(3-(dimethylamino)-3-oxopropyl)-6-hydroxyindazole-1-carboxylate (502.1 mg) that can be produced by the method described in Reference Example 118 or the like, instead of tert-butyl 6-hydroxy-3-methylindazole-1-carboxylate.

$^1$H-NMR (300 MHz, CDCl$_3$); δ (ppm) 0.49-0.57 (6H, m), 0.88 (9H, t, J=8.0), 1.47 (9H, s), 1.69 (9H, s), 2.88 (2H, t, J=6.9), 2.95 (3H, s), 3.01 (3H, s), 3.18-3.72 (4H, m), 3.26 (2H, t, J=6.9), 4.03-4.12 (2H, m), 4.79-4.98 (1H, m), 6.56-6.88 (4H, m), 7.08 (1H, t, J=7.3), 7.48 (1H, s), 7.48-7.53 (1H, m)

LCMS: 726 [M+H]; Retention time: 6.46 minutes; LCMS condition: B

Reference Example 91

2-Chloro-1-(4-fluoro-3-nitrophenyl)ethanone

[Chemical Formula 158]

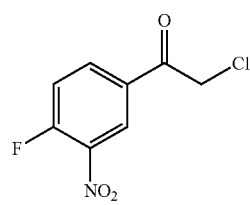

1-(4-Fluoro-3-nitrophenyl)ethanone (18.4249 g; manufactured by Sigma-Aldrich Co.) was dissolved in CH$_2$Cl$_2$ (400 mL), and methanol (3.04 mL) was added thereto. The mixture was purged with nitrogen, and was cooled to 0° C. To this solution, a SO$_2$Cl$_2$—CH$_2$Cl$_2$ Solution [109.32 mL; solution prepared by dissolving SO$_2$Cl$_2$ (9.32 mL; manufactured by Wako Pure Chemical Industries, Ltd.) in CH$_2$Cl$_2$ (100 mL)] was added dropwise over 30 minutes, and the mixture was stirred overnight while the temperature was raised to room temperature. The reaction solution was cooled to 0° C., and methanol (1.52 mL) was added thereto. Subsequently, a SO$_2$Cl$_2$—CH$_2$Cl$_2$ solution [64.66 mL; solution prepared by dissolving SO$_2$Cl$_2$ (4.66 mL; manufactured by Wako Pure Chemical Industries, Ltd.) in CH$_2$Cl$_2$ (60 mL)] was added dropwise to the mixture, and while the temperature was raised to room temperature, the mixture was stirred for 3 hours. The reaction solution was washed once with a saturated aqueous solution of sodium carbonate, and once with brine. The organic layer was dried over anhydrous sodium sulfate, and the solvent was evaporated under reduced pressure. Subsequently, the resulting residue was purified by column chromatography ("COLUMN-A"; n-hexane:ethyl acetate=88:12→67:33), and in the middle of the chromatographic process, crystals solidified in the silica gel were extracted with ethyl acetate and filtered. The solvent of the filtrate was evaporated under reduced pressure, and thus the title compound (6.403 g) was obtained.

$^1$H-NMR (300 MHz, CDCl$_3$); δ (ppm) 4.66 (2H, s), 7.46 (1H, dd, J=8.7, 9.8), 8.28 (1H, ddd, J=2.1, 4.0, 8.7), 8.67 (1H, dd, J=2.1, 7.3)

Reference Example 92

(R)-2-(4-fluoro-3-nitrophenyl)oxirane

[Chemical Formula 159]

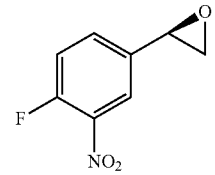

Under a nitrogen atmosphere, 2-chloro-1-(4-fluoro-3-nitrophenyl)ethanone (5.4667 g) that can be produced by the method described in Reference Example 91 or the like was dissolved in dehydrated THF (100 mL), and a 1 mol/L (R)-CBS-toluene solution (7.5 mL; manufactured by Sigma-Aldrich Co.) was added thereto. The mixture was cooled to 0° C. To this solution, BH$_3$.SMe$_2$ (10 mL; manufactured by Sigma-Aldrich Co.) was added dropwise over 10 minutes, and the mixture was stirred for 2 hours at 0° C. An aqueous solution of ammonium chloride was added to the reaction-solution, and the mixture was extracted two times with ethyl acetate. The organic layer was washed once with brine, and then was dried over magnesium sulfate. The solvent was evaporated under reduced pressure. 2-Propanol (100 mL) and a 1 mol/L aqueous solution of sodium hydroxide (25 mL; manufactured by Kanto Chemical Co., Inc.) were added to the resulting residue, and the mixture was stirred for 10 minutes at 0° C. The reaction solution was poured into water, and the mixture was extracted two times with ethyl acetate. The organic layer was washed once with brine, dried over anhydrous sodium sulfate, and then concentrated under reduced pressure. The resulting residue was purified by column chromatography ("COLUMN-B"; n-hexane:ethyl acetate=88:12→67:33), and thus the title compound (4.2885 g, optical purity; 92% ee).

Optical resolution conditions [column; As—H (manufactured by Daicel Chemical Industries, Ltd.), eluent; hexane:ethanol=90:10, flow rate; 0.5 mL/min, detection UV; 254 nM, and temperature; 40° C.].

$^1$H-NMR (300 MHz, CDCl$_3$); δ (ppm) 2.76 (1H, dd, J=2.5, 5.4), 3.20 (1H, dd, J=4.0, 5.4), 3.92 (1H, dd, J=2.5, 4.0), 7.28 (1H, dd, J=8.4, 10.2), 7.54 (1H, ddd, J=2.1, 4.0, 8.4), 7.99 (1H, dd, J=2.1, 6.9)

Reference Example 93

Tert-butyl 6-(2-(dibenzylamino)ethoxy)-3-methylindazole-1-carboxylate

[Chemical Formula 160]

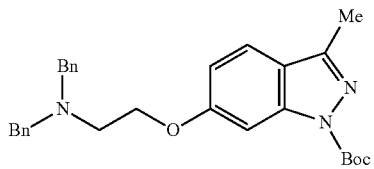

Tert-butyl 6-hydroxy-3-methylindazole-1-carboxylate (4.9962 g) that can be produced by the method described in Reference Example 60 or the like, and 2-(dibenzylamino)ethanol (5.0 mL; manufactured by Tokyo Chemical Industry Co., Ltd.) were dissolved in dehydrated THF (100 mL), and triphenylphosphine (10.5872 g; manufactured by Tokyo Chemical Industry Co., Ltd.) and TMAD (6.9197 g; manufactured by Masuda. Chemical Industries, Co., Ltd.) were added to the solution. The mixture was stirred overnight at room temperature. The reaction solution was filtered, and then the filtrate was concentrated under reduced pressure. Toluene was added to the resulting residue, and insoluble matters were filtered. Subsequently, the filtrate was concentrated under reduced pressure. The resulting residue was purified by column chromatography ("COLUMN-D"; n-hexane:ethyl acetate=90:10→75:25), and thus the title compound (9.6091 g) was obtained.

$^1$H-NMR (300 MHz, CDCl$_3$); δ (ppm) 1.71 (9H, s), 2.53 (3H, s), 2.95 (2H, t, J=5.8), 3.73 (4H, s), 4.13 (2H, t, J=5.8), 6.87 (1H, dd, J=1.4, 8.7), 7.20-7.41 (10H, m), 7.46 (1H, d, J=8.7), 7.56 (1H, d, J=1.4)

LCMS: 472 [M+H]; Retention time: 2.04 minutes; LCMS condition: C

Reference Example 94

Tert-butyl 6-(2-(benzylamino)ethoxy)-3-methylindazole-1-carboxylate

[Chemical Formula 161]

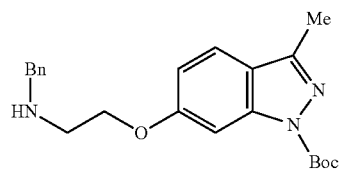

Tert-butyl 6-(2-(dibenzylamino)ethoxy)-3-methylindazole-1-carboxylate (10.84 g) that can be produced by the method described in Reference Example 93 or the like, and 5% palladium on carbon-STD-type-50% wet with water (2.0643 g; manufactured by N.E. Chemcat Corp.) were suspended in methanol (115 mL), and then concentrated hydrochloric acid (1.91 mL; manufactured by Kanto Chemical Co., Inc.) was added to the suspension. The reaction system was purged with hydrogen, and under a hydrogen atmosphere, the mixture was stirred for 3 hours at room temperature. The reaction system was purged with nitrogen, and then the reaction solution was filtered. The filtrate was concentrated under reduced pressure, and thus the title compound (8.4593 g) was obtained $^1$H-NMR (300 MHz, CDCl$_3$); δ (ppm) 1.71 (9H, s), 2.53 (3H, s), 3.07 (2H, t, J=5.4), 3.89 (2H, s), 4.19 (2H, t, J=5.4), 6.91 (1H, dd, J=1.8, 8.4), 7.27-7.37 (5H, m), 7.48 (1H, d, J=8.4), 7.61 (1H, d, J=1.8)

LCMS: 382 [M+H]; Retention time: 1.09 minutes; LCMS condition: C

Reference Example 95

(R)-tert-butyl 6-(2-(benzyl(2-(4-fluoro-3-nitrophenyl)-2-hydroxyethyl)amino)ethoxy)-3-methyl indazole -1-carboxylate

[Chemical Formula 162]

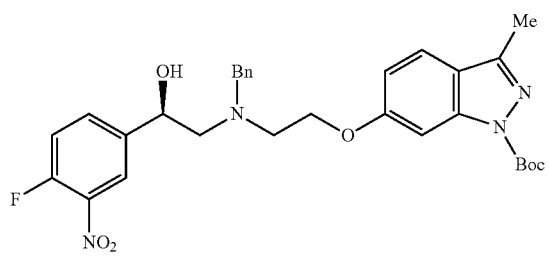

Tert-butyl 6-(2-(benzylamino)ethoxy)-3-methylindazole-1-carboxylate (1.4963 g) that can be produced by the method described in Reference Example 94 or the like, (R)-2-(4- fluoro-3-nitrophenyl)oxirane (723.2 mg) that can be produced by the method described in Reference Example 92 or the like, and 2-propanol (8 mL) were added, and the mixture was stirred overnight at reflux. The reaction solution was cooled to room temperature, and then was concentrated under reduced pressure. The resulting residue was purified by column chromatography ("COLUMN-B"; n-hexane:ethyl acetate=71:29→50:50), and thus the title compound (1.3571 g) was obtained.

$^1$H-NMR (300 MHz, CDCl$_3$); δ (ppm) 1.71 (9H, s), 2.55 (3H, s), 2.65 (1H, dd, J=10.2. 13.1), 2.91 (1H, dd, J=3.6, 13.1), 3.01-3.23 (2H, m), 3.86 (2H, dd, 13.1, 67.4), 4.10-4.20 (2H, m), 4.71 (1H, dd, J=3.2, 10.2), 6.94 (1H, dd, J=2.1, 8.4), 7.18-7.33 (6H, m), 7.51 (1H, d, J=8.4), 7.56 (1H, ddd, J=2.1, 4.0, 8.4), 7.62 (1H, s), 8.00 (1H, dd, J=2.1, 7.3)

LCMS: 565 [M+H]; Retention time: 1.87 minutes; LCMS condition: C

Reference Example 96

(R)-tert-butyl 6-(2-((2-(3-amino-4-fluorophenyl)-2-hydroxyethyl)(tert-butoxycarbonyl)amino)ethoxy)-3-methylindazole-1-carboxylate

[Chemical Formula 163]

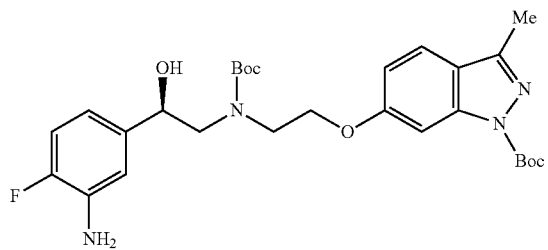

(R)-tert-butyl 6-(2-(benzyl(2-(4-fluoro-3-nitrophenyl)-2-hydroxyethyl)amino)ethoxy)-3-methylindazole-1-carboxylate (1.2046 g) that can be produced by the method described in Reference Example 95 or the like, and 10% palladium on carbon-PE-type-50% wet with water (0.2793 g; manufactured by N.E. Chemcat Corp.) were suspended in a 0.1 mol/L hydrochloric acid-ethanol solution (42.6 mL; manufactured by Kanto Chemical Co., Inc.). Subsequently, the reaction system was purged with hydrogen, and under a hydrogen atmosphere, the reaction solution was stirred for one hour at room temperature. The reaction system was purged with nitrogen, and then the reaction solution was filtered. Triethylamine (1.18 mL; manufactured by Kanto Chemical Co., Inc.) was added to the filtrate, and then the mixture was concentrated under reduced pressure. The resulting residue was dissolved in methanol (20 mL), and Boc$_2$O (458 μL; manufactured by Wako Pure Chemical Industries, Ltd.) was added thereto. The mixture was stirred for 5 days at room temperature. The reaction solution was concentrated under reduced pressure, and then the obtained residue was designated as "residue-A". Furthermore, (R)-tert-butyl 6-(2-(benzyl(2-(4-fluoro-3-nitrophenyl)-2-hydroxyethyl)amino)ethoxy)-3-methylindazole-1-carboxylate (119.8 mg) that can be produced by the method described in Reference Example 95 or the like, and 10% palladium on carbon-PE-type-50% wet with water (21.7 g; manufactured by N.E. Chemcat Corp.) were suspended in a 0.1 mol/L hydrochloric acid-ethanol solution (4 mL; manufactured by Kanto Chemical Co., Inc.). Subsequently, the reaction system was purged with hydrogen, and under a hydrogen atmosphere, the reaction solution was stirred for one hour at room temperature. The reaction system was purged with nitrogen, and then the reaction solution was filtered. Triethylamine (111 μL; manufactured by Kanto Chemical Co., Inc.) was added to the filtrate, and then the mixture was concentrated under reduced pressure. The resulting residue was dissolved in CH$_2$Cl$_2$ (4 mL) and methanol (2 mL), and Boc$_2$O (41 μL; manufactured by Wako Pure Chemical Industries, Ltd.) was added thereto. The mixture was stirred overnight at room temperature, and was left to stand for 12 days. The reaction solution was concentrated under reduced pressure, and then the resulting residue was designated as "residue-B". The "residue-A" and "residue-B" were combined and purified by column chromatography ("COLUMN-B"; n-hexane:ethyl acetate=64:36→43:57). Thus, the title compound (1.1753 g) was obtained.

LCMS: 545 [M+H]; Retention time: 1.85 minutes; LCMS Condition: C

Reference Example 97

(R)-tert-butyl 6-(2-((2-(3-amino-4-fluorophenyl)-2-(triethylsilyloxy)ethyl)(tert-butoxycarbonyl)amino)ethoxy)-3-methylindazole-1-carboxylate

[Chemical Formula 164]

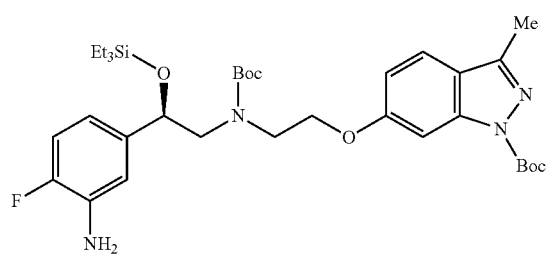

(R)-tert-butyl 6-(2-((2-(3-amino-4-fluorophenyl)-2-hydroxyethyl)(tert-butoxycarbonyl)amino)ethoxy)-3-methylindazole-1-carboxylate (1.1753 g) that can be produced by the method described in Reference Example 96, or the like, and imidazole (578.2 mg; manufactured by Tokyo Chemical Industry Co., Ltd.) were dissolved in dehydrated DMF (10 mL), and chlorotriethylsilane (1.40 mL; Shin-Etsu Chemical Co., Ltd.) as added to the solution. The mixture was stirred for 30 minutes at room temperature. The reaction solution was poured into a saturated solution of sodium hydrogen carbonate, and the mixture was extracted once with ethyl acetate. The organic layer was washed once with water and once with brine. The solvent was evaporated under reduced pressure. The resulting residue was purified by column chromatography ("COLUMN-B"; n-hexane:ethyl acetate=84:16→64:36), and thus the title compound (1.2861 g) was obtained.

$^1$H-NMR (300 MHz, CDCl$_3$); δ (ppm) 0.52 (6H, q, J=8.0), 0.88 (9H, t, J=8.0), 1.47 (9H, s), 1.70 (9H, s), 2.53 (3H, s), 3.13-3.76 (4H, m), 4.04-4.12 (2H, m), 4.77-4.96 (1H, m), 6.57-6.94 (4H, m), 7.46 (1H, d, J=8.7), 7.55 (1H, s)

LCMS: 659 [M+H]; Retention time: 1.87 minutes; LCMS condition: E

Reference Example 98

(R)-tert-butyl 6-(2-(benzyl(2-(4-chloro-3-nitrophenyl)-2-hydroxyethyl)amino)ethoxy)-3-methylindazole-1-carboxylate

[Chemical Formula 165]

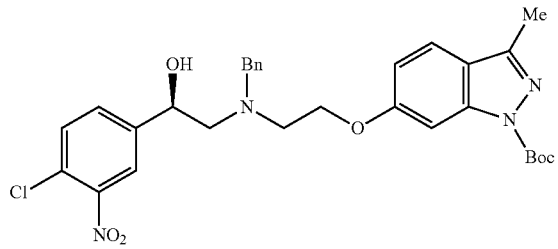

Tert-butyl 6-(2-(benzylamino)ethoxy)-3-methylindazole-1-carboxylate (3.0074 g) that can be produced by the method described in Reference Example 94, (R)-2-(4-chloro-3-nitrophenyl)oxirane (1.6147 g), and 2-propanol (8 mL) were added, and the mixture was stirred overnight at reflux. The reaction solution was cooled to room temperature, and then was concentrated under reduced pressure. The resulting residue was purified by column chromatography ("COLUMN-B"; n-hexane:ethyl acetate=71:29→50:50), and thus the title compound (3.307 g) was obtained.

$^1$H-NMR (300 MHz, CDCl$_3$); δ (ppm) 1.71 (9H, s), 2.55 (3H, s), 2.65 (1H, dd, J=10.2, 12.8), 2.91 (1H, dd, J=3.2, 12.8), 3.01-3.22 (2H, m), 3.85 (2H, dd, J=13.5, 66.3), 4.13-4.21 (3H, m), 4.70 (1H, dd, J=3.2, 9.8), 6.94 (1H, dd, J=2.1, 8.4), 7.27-7.35 (5H, m), 7.42-7.53 (2H, m), 7.52 (1H, d, J=8.4), 7.61 (1H, d, J=1.4), 7.83 (1H, d, J=1.4)

LCMS: 581 [M+H]; Retention time: 2.01 minutes; LCMS condition: C

Reference Example 99

(R)-tert-butyl 6-(2-((2-(3-amino-4-chlorophenyl)-2-hydroxyethyl)(benzyl)amino)ethoxy)-3-methylindazole-1-carboxylate

[Chemical Formula 166]

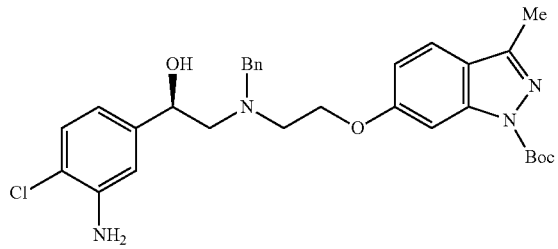

(R)-tert-butyl 6-(2-(benzyl(2-(4-chloro-3-nitrophenyl)-2-hydroxyethyl)amino)ethoxy)-3-methylindazole-1-carboxylate (3.2091 g) that can be produced by the method described in Reference Example 98 or the like, and CM-101 catalyst (6.6902 g; manufactured by N.E. Chemcat Corp.) were suspended in methanol (25 mL) and THF (25 mL). Subsequently, the reaction system was purged with hydrogen, and under a hydrogen atmosphere, the reaction solution was stirred for 4 days at room temperature. The reaction system was purged with nitrogen, and then the reaction solution was filtered. The filtrate was concentrated under reduced pressure, and then CH$_2$Cl$_2$ was added to the resulting residue. The organic layer was dried over anhydrous sodium sulfate, and the solvent was evaporated under reduced pressure. Thus, the title compound (2.2493 g) was obtained.

LCMS: 551 [M+H]; Retention time: 1.53 minutes; LCMS condition: C

Reference Example 100

(R)-tert-butyl 6-(2-((2-(3-amino-4-chlorophenyl)-2-hydroxyethyl)(tert-butoxycarbonyl)amino)ethoxy)-3-methylindazole-carboxylate

[Chemical Formula 167]

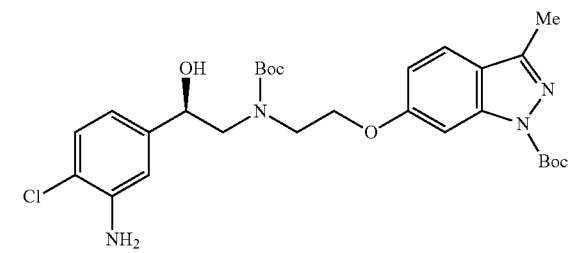

(R)-tert-butyl 6-(2-((2-(3-amino-4-chlorophenyl)-2-hydroxyethyl)(benzyl)amino)ethoxy)-3-methylindazole-1-carboxylate (2.1101 g) that can be produced by the method described in Reference Example 99 or the like, and 10% palladium on carbon-PE-type-50% wet with water (417.6 mg; manufactured by N.E. Chemcat Corp.) were suspended in a 0.1 mol/L hydrochloric acid-ethanol solution (76.6 mL; manufactured by Kanto Chemical Co., Inc.). Subsequently, the reaction system was purged with hydrogen, and under a hydrogen atmosphere, the reaction solution was stirred for 40 minutes at room temperature. The reaction system was purged with nitrogen, and then the reaction solution was filtered. Triethylamine (2.12 mL; manufactured by Kanto Chemical Co., Inc.) was added to the filtrate, and then the mixture was concentrated under reduced pressure. The resulting residue was dissolved in CH$_2$Cl$_2$ (20 mL), and Boc$_2$O (792 μL; manufactured by Wako Pure Chemical Industries, Ltd.) and triethylamine (0.5 mL; manufactured by Kanto Chemical Co., Inc.) were added thereto. The mixture was stirred overnight at room temperature. The reaction solution was concentrated under reduced pressure, and then the resulting residue was purified by column chromatography ("COLUMN-B"; n-hexane:ethyl acetate=63:37→42:58). Thus, the title compound (1.5424 g) was obtained.

$^1$H-NMR (300 MHz, CDCl$_3$); δ (ppm) 1.48 (9H, s), 1.70 (9H, s), 2.54 (3H, s), 3.22-3.78 (4H, m), 4.06-4.34 (5H, m), 4.91 (1H, brs), 6.68-6.91 (3H, m), 7.19 (1H, d, J=8.0), 7.48 (1H, d, J=8.7), 7.60 (1H, brs)

Reference Example 101

(R)-tert-butyl 6-(2-((2-(3-amino-4-chlorophenyl)-2-(triethylsilyloxy)ethyl)(tert-butoxycarbonyl)amino)ethoxy)-3-methylindazole-1-carboxylate

[Chemical Formula 168]

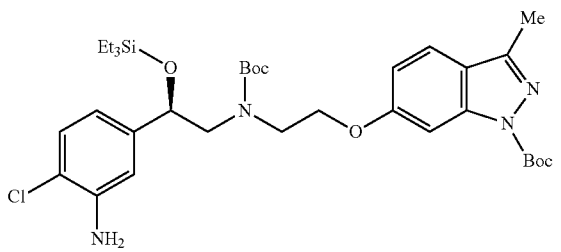

(R)-tert-butyl 6-(2-((2-(3-amino-4-chlorophenyl)-2-hydroxyethyl)(tert-butoxycarbonyl)amino)ethoxy)-3-methylindazole-1-carboxylate (1.5310 g) that can be produced by the method described in Reference Example 100 or the like; was dissolved in dehydrated DMF (12 mL), and imidazole (751 mg; manufactured by Tokyo Chemical Industry Co., Ltd.) and chlorotriethylsilane (1.84 mL; manufactured by Shin-Etsu Chemical Co., Ltd.) were added thereto. The mixture was stirred for 50 minutes at room temperature. The reaction solution was poured into a saturated solution of sodium hydrogen carbonate, and the mixture was extracted once with ethyl acetate. The organic layer was washed once with water and once with brine, and the solvent was evaporated under reduced pressure. The resulting residue was purified by column chromatography ("COLUMN-B"; n-hexane: ethyl acetate=88:12→67:33), and thus the title compound (1.6137 g) was obtained.

$^1$H-NMR (300 MHz, CDCl$_3$); δ (ppm) 0.53 (6H, q, J=7.6), 0.88 (9H, t, J=7.6), 1.46-1.47 (9H, m), 1.70 (9H, s), 2.53 (3H, s), 3.12-3.77 (4H, m), 4.03-4.12 (4H, m), 4.77-4.98 (1H, m), 6.59-6.89 (3H, m), 7.17 (1H, d, J=8.0), 7.46 (1H, d, J=8.7), 7.55 (1H, s)

Reference Example 102

Tert-butyl 6-(2-(dibenzylamino)ethoxy)-3-(trifluoromethyl)indazole-1-carboxylate

[Chemical Formula 169]

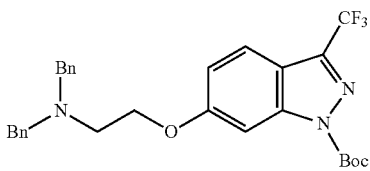

The title compound (9.6091 g) was obtained by the same method as that used in Reference Example 93, using tert-butyl 6-hydroxy-3-(trifluoromethyl)indazole-1-carboxylate (6.056 g) that can be produced by the method described in Reference Example 38 or the like, instead of tert-butyl 6-hydroxy-3-methylindazole-1-carboxylate.

$^1$H-NMR (300 MHz, CDCl$_3$); δ (ppm) 1.71 (9H, s), 2.96 (2H, t, J=5.8), 3.73 (4H, s), 4.14 (2H, t, J=5.8), 6.97 (1H, dd, J=2.1, 8.7), 7.20-7.41 (10H, m), 7.59 (1H, d, J=2.1), 7.65 (1H, d, J=8.7)

LCMS: 526 [M+H]; Retention time: 2.44 minutes; LCMS condition: C

Reference Example 103

Tert-butyl 6-(2-(benzylamino)ethoxy)-3-(trifluoromethyl)indazole-1-carboxylate

[Chemical Formula 170]

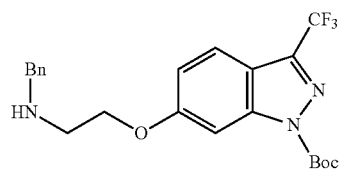

The title compound (6.6701 g) was obtained by the same method as that used in Reference Example 94, using tert-butyl 6-(2-(dibenzylamino)ethoxy)-3-(trifluoromethyl)indazole-1-carboxylate (8.3435 g) that can be produced by the method described in Reference Example 102 or the like, instead of tert-butyl 6-(2-(dibenzylamino)ethoxy)-3-methylindazole-1-carboxylate.

$^1$H-NMR (300 MHz, CDCl$_3$); δ (ppm) 1.72 (9H, s), 3.09 (2H, t, J=5.1), 3.89 (2H, s), 4.20 (2H, t, J=5.1), 7.03 (1H, dd, J=2.1, 9.1), 7.27-7.37 (5H, m), 7.66-7.68 (2H, m)

LCMS: 436 [M+H]; Retention time: 1.37 minutes; LCMS condition! C

Reference Example 104

(R)-tert-butyl 6-(2-(benzyl(2-(4-fluoro-3-nitrophenyl)-2-hydroxyethyl)amino)ethoxy)-3-(trifluoromethyl)indazole-1-carboxylate

[Chemical Formula 171]

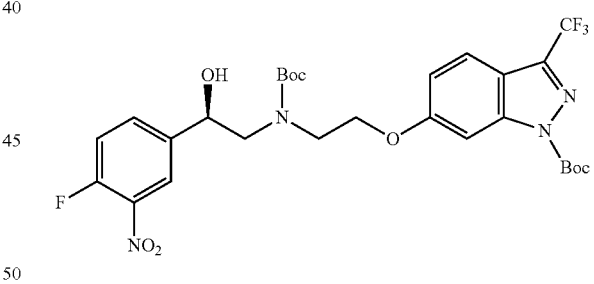

The title compound (828.1 mg) was obtained by the same method as that used in Reference Example 95, using tert-butyl 6-(2-(benzylamino)ethoxy)-3-(trifluoromethyl)indazole-1-carboxylate (1.7941 g) that can be produced by the method described in Reference Example 103 or the like, instead of tert-butyl 6-(2-(benzylamino)ethoxy)-3-methylindazole-1-carboxylate.

$^1$H-NMR (300 MHz, CDCl$_3$); δ (ppm) 1.72 (9H, s), 2.66 (1H, dd, J=10.2, 12.8), 2.92 (1H, dd, J=3.2, 12.8), 3.03-3.23 (2H, m), 3.86 (2H, dd, J=13.4, 69.2), 4.12-4.18 (2H, m), 4.71 (1H, dd, J=3.2, 10.2), 7.05 (1H, dd, J=2.1, 8.7), 7.23 (1H, d, J=8.7), 7.27-7.36 (5H, m), 7.57 (1H, ddd, J=2.1, 4.0, 8.7), 7.66 (1H, d, J=2.1), 7.69 (1H, d, J=8.7), 8.01 (1H, dd, J=2.1, 6.9)

LCMS: 619 [M+H]; Retention time: 2.23 minutes; LCMS condition: C

Reference Example 105

(R)-tert-butyl 6-(2-((2-(3-amino-4-fluorophenyl)-2-hydroxyethyl)(tert-butoxycarbonyl)amino)ethoxy)-3-(trifluoromethyl)indazole-1-carboxylate

[Chemical Formula 172]

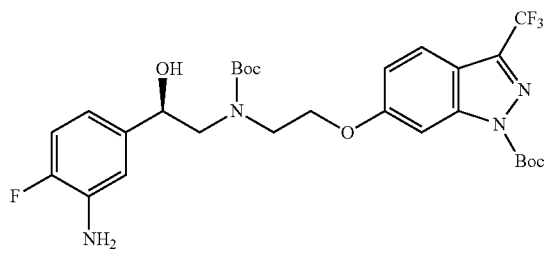

The title compound (681.5 mg) was obtained by the same method as that used in Reference Example 96, using (R)-tert-butyl 6-(2-(benzyl(2-(4-fluoro-3-nitrophenyl)-2-hydroxyethyl)amino)ethoxy)-3-(trifluoromethyl)indazole-1-carboxylate (1.4356 g) that can be produced by the method described in Reference Example 104 or the like, instead of (R)-tert-butyl 6-(2-(benzyl(2-(4-fluoro-3-nitrophenyl)-2-hydroxyethyl)amino)ethoxy)-3-methylindazole-1-carboxylate LCMS: 599 [M+H]; Retention time: 2.11 minutes; LCMS condition: C

Reference Example 106

(R)-tert-butyl 6-(2-((2-(3-amino-4-fluorophenyl)-2-(triethylsilyloxy)ethyl)(tert-butoxycarbonyl)amino)ethoxy)-3-(trifluoromethyl)indazole-1-carboxylate

[Chemical Formula 173]

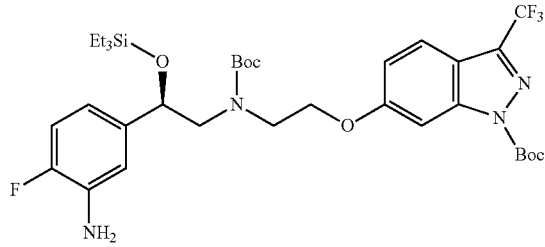

The title compound (709.9 mg) was obtained by the same method as that used in Reference Example 97, using (R)-tert-butyl 6-(2-((2-(3-amino-4-fluorophenyl)-2-hydroxyethyl)(tert-butoxycarbonyl)amino)ethoxy)-3-(trifluoromethyl)indazole-1-carboxylate (680.5 mg) that can be produced by the method described in Reference Example 105 or the like, instead of (R)-tert-butyl 6-(2-((2-(3-amino-4-fluorophenyl)-2-hydroxyethyl)(tert-butoxycarbonyl)amino)ethoxy)-3-methylindazole-1-carboxylate.

$^1$H-NMR (300 MHz, CDCl$_3$); δ (ppm) 0.52 (6H, q, J=7.6), 0.88 (9H, t, J=7.6), 1.47 (9H, s), 1.71 (9H, s), 3.12-3.77 (6H, m), 4.06-4.13 (2H, m), 4.77-4.97 (1H, m), 6.57-7.01 (4H, m), 7.61 (1H, s), 7.65 (1H, d, J=8.7)

Reference Example 107

Tert-butyl 6-(2-(dibenzylamino)ethoxy)-3-methoxyindazole-1-carboxylate

[Chemical Formula 174]

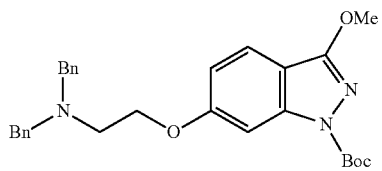

The title compound (9.456 g) was obtained by the same method as that used in Reference Example 93, using tert-butyl 6-hydroxy-3-methoxyindazole-1-carboxylate (5.3121 g) that can be produced by the method described in Reference Example 65 or the like, instead of tert-butyl 6-hydroxy-3-methylindazole-1-carboxylate.

$^1$H-NMR (300 MHz, CDCl$_3$); δ (ppm) 1.69 (9H, s), 2.94 (2H, t, J=5.8), 3.73 (4H, s), 4.10 (2H, t, J=5.8), 4.14 (3H, s), 6.81 (1H, dd, J=2.1, 8.4), 7.20-7.40 (11H, m), 7.47 (1H, d, J=8.4)

LCMS: 488 [M+H]; Retention time: 2.10 minutes; LCMS condition: C

Reference Example 108

Tert-butyl 6-(2-(benzylamino)ethoxy)-3-methoxyindazole-1-carboxylate

[Chemical Formula 175]

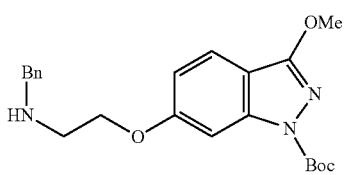

The title compound (7.8617 g) was obtained by the same method as that used in Reference Example 94, using tert-butyl 6-(2-(dibenzylamino)ethoxy)-3-methoxyindazole-1-carboxylate (9.45 g) that can be produced by the method described in Reference Example 107 or the like, instead of tert-butyl 6-(2-(dibenzylamino)ethoxy)-3-methylindazole-1-carboxylate.

$^1$H-NMR (300 MHz, CDCl$_3$); δ (ppm) 1.69 (9H, s), 3.06 (2H, t, J=5.1), 3.89 (2H, s), 4.14 (3H, s), 4.16 (2H, t, J=5.1), 6.86 (1H, dd, J=2.1, 8.7), 7.27-7.37 (5H, m), 7.47-7.50 (2H, m)

LCMS: 398 [M+H]; Retention time: 1.18 minutes; LCMS condition: C

Reference Example 109

(R)-tert-butyl 6-(2-(benzyl(2-(4-fluoro-3-nitrophenyl)-2-hydroxyethyl)amino)ethoxy)-3-methoxyindazole-1-carboxylate

[Chemical Formula 176]

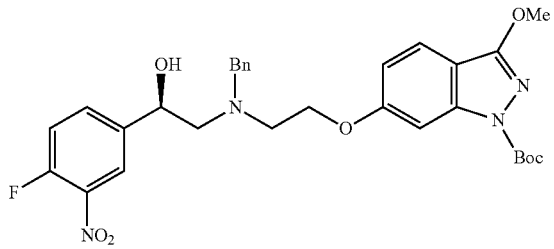

The title compound (1.5167 g) was obtained by the same method as that used in Reference Example 95, using tert-butyl 6-(2-(benzylamino)ethoxy)-3-methoxyindazole-1-carboxylate (1.6037 g) that can be produced by the method described in Reference Example 108 or the like, instead of tert-butyl 6-(2-(benzylamino)ethoxy)-3-methylindazole-1-carboxylate.

$^1$H-NMR (300 MHz, CDCl$_3$); δ (ppm) 1.69 (9H, s), 2.65 (1H, dd, J=10.2, 12.8), 2.91 (1H, dd, J=3.2, 12.8), 3.02-3.22 (2H, m), 3.86 (2H, dd, J=13.5, 66.7), 4.10-4.13 (2H, m), 4.15 (3H, s), 4.71 (1H, dd, J=3.2, 10.2), 6.88 (1H, dd, J=2.1, 8.7), 7.20 (1H, d, J=8.4), 7.27-7.33 (5H, m), 7.49 (1H, s), 7.52 (1H, d, J=8.7), 7.57 (1H, ddd, J=2.1, 4.0, 8.4), 8.00 (1H, dd, J=2.1, 6.9).

LCMS: 581 [M+H]; Retention time: 1.99 minutes; LCMS condition: C

Reference Example 110

(R)-tert-butyl 6-(2-((2-(3-amino-4-fluorophenyl)-2-hydroxyethyl)(tert-butoxycarbonyl)amino)ethoxy)-3-methoxyindazole-1-carboxylate

[Chemical Formula 177]

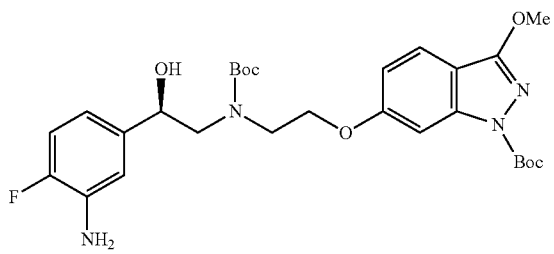

The title compound (1.0652 g) was obtained by the same method as that used in Reference Example 96, using (R)-tert-butyl 6-(2-(benzyl(2-(4-fluoro-3-nitrophenyl)-2-hydroxyethyl)amino)ethoxy)-3-methoxyindazole-1-carboxylate (1.5021 g) that can be produced by the method described in Reference Example 109 or the like, instead of (R)-tert-butyl 6-(2-(benzyl(2-(4-fluoro-3-nitrophenyl)-2-hydroxyethyl)amino)ethoxy)-3-methylindazole-1-carboxylate.

$^1$H-NMR (300 MHz, CDCl$_3$); δ (ppm) 1.48 (9H, s), 1.68 (9H, s), 3.17-3.89 (4H, m), 4.14-4.38 (5H, m), 4.89 (1H, brs), 6.67-6.97 (4H, m), 7.48-7.51 (2H, m)

LCMS: 561 [M+H]; Retention time: 1.93 minutes; LCMS condition: C

Reference Example 111

(R)-tert-butyl 6-(2-((2-(3-amino-4-fluorophenyl)-2-(triethylsilyloxy)ethyl)(tert-butoxycarbonyl)amino)ethoxy)-3-methoxyindazole-1-carboxylate

[Chemical Formula 178]

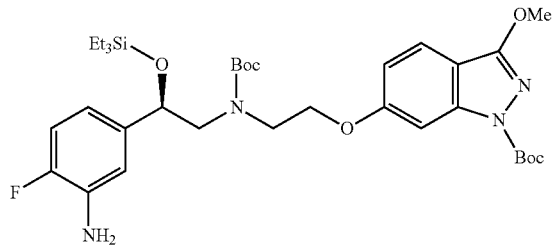

The title compound (1.0262 g) was obtained by the same method as that used in Reference Example 97, using (R)-tert-butyl 6-(2-((2-(3-amino-4-fluorophenyl)-2-hydroxyethyl)(tert-butoxycarbonyl)amino)ethoxy)-3-methoxyindazole-1-carboxylate (1.0634 g) that can be produced by the method described in Reference Example 110 or the like, instead of (R)-tert-butyl 6-(2-((2-(3-amino-4-fluorophenyl)-2-hydroxyethyl)(tert-butoxycarbonyl)amino)ethoxy)-3-methylindazole-1-carboxylate.

$^1$H-NMR (300 MHz, CDCl$_3$); δ (ppm) 0.51 (6H, q, J=8.0), 0.87 (9H, t, J=8.0), 1.46 (9H, s), 1.68 (9H, s), 3.12-3.75 (4H, m), 4.05-4.12 (2H, m), 4.13 (3H, s), 4.76-4.96 (1H, m), 6.57-6.94 (4H, m), 7.42 (1H, brs), 7.47 (1H, dd, J=2.1, 8.7)

LCMS: 675 [M+H]; Retention time: 2.03 minutes; LCMS condition: E

Reference Example 112

(R)-tert-butyl 6-(2-(benzyl(2-(4-chloro-3-nitrophenyl)-2-hydroxyethyl)amino)ethoxy)-3-methoxyindazole-1-carboxylate

[Chemical Formula 179]

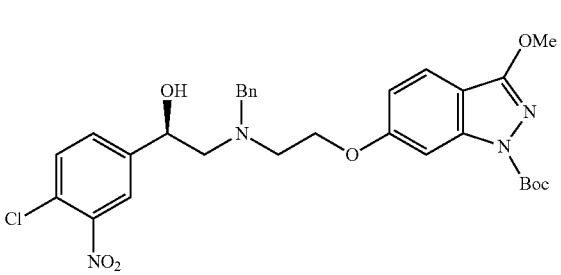

The title compound (3.6878 g) was obtained by the same method as that used in Reference Example 98, using tert-butyl 6-(2-(benzylamino)ethoxy)-3-methoxyindazole-1-carboxylate (3.1935 g) that can be produced by the method described in Reference Example 108, instead of tert-butyl 6-(2-(benzylamino)ethoxy)-3-methylindazole-1-carboxylate.

$^1$H-NMR (300 MHz, CDCl$_3$); δ (ppm) 1.69 (9H, s), 2.64 (1H, dd, J=10.2, 12.8), 2.92 (1H, dd, J=3.2, 12.8), 3.00-3.21 (2H, m), 3.85 (2H, dd, J=13.5, 64.5), 4.08-4.13 (2H, m), 4.14 (3H, s), 4.70 (1H, dd, J=3.2, 10.2), 6.88 (1H, dd, J=2.1, 8.4), 7.27-7.35 (5H, m), 7.44-7.48 (2H, m), 7.52 (1H, d, J=8.4), 7.83 (1H, d, J=1.4)

LCMS: 597 [M+H]; Retention time: 2.08 minutes; LCMS condition: C

Reference Example 113

(R)-tert-butyl 6-(2-((2-(3-amino-4-chlorophenyl)-2-hydroxyethyl)(benzyl)amino)ethoxy)-3-methoxy-indazole-1-carboxylate

[Chemical Formula 180]

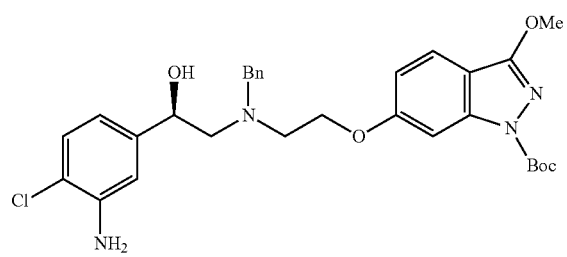

The title compound was obtained as a crude product (2.818 g) by the same method as that used in Reference Example 99, using (R)-tert-butyl 6-(2-(benzyl(2-(4-chloro-3-nitrophenyl)-2-hydroxyethyl)amino)ethoxy)-3-methylindazole-1-carboxylate (3.6514 g) that can be produced by the method described in Reference Example 112 or the like, instead of (R)-tert-butyl 6-(2-(benzyl(2-(4-chloro-3-nitrophenyl)-2-hydroxyethyl)amino)ethoxy)-3-methylindazole-1-carboxylate.

LCMS: 567 [M+H]; Retention time: 1.73 minutes; LCMS condition: C

Reference Example 114

(R)-tert-butyl 6-(2-((2-(3-amino-4-chlorophenyl)-2-hydroxyethyl)(tert-butoxycarbonyl)amino)ethoxy)-3-methoxyindazole-carboxylate

[Chemical Formula 181]

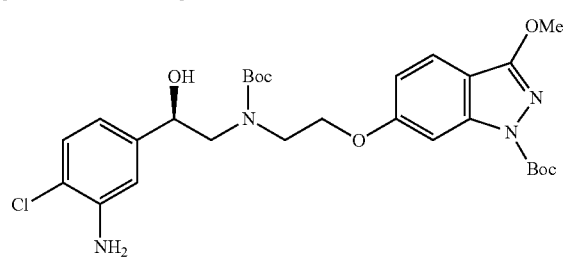

The title compound (1.9703 g) was obtained by the same method as that used in Reference Example 100, using (R)-tert-butyl 6-(2-((2-(3-amino-4-chlorophenyl)-2-hydroxyethyl)(benzyl)amino)ethoxy)-3-methoxyindazole-1-carboxylate (2.818 g) that can be produced by the method described in Reference Example 113 or the like, instead of (R)-tert-butyl 6-(2-((2-(3-amino-4-chlorophenyl)-2-hydroxyethyl)(benzyl)amino)ethoxy)-3-methylindazole-1-carboxylate.

$^1$H-NMR (300 MHz, CDCl$_3$); δ (ppm) 1.48 (9H, s), 1.68 (9H, s), 3.19-3.64 (4H, m), 4.05-4.29 (5H, m), 4.90 (1H, brs), 6.68-6.84 (3H, m), 7.20 (1H, d, J=8.4), 7.49-7.51 (2H, m)

LCMS: 577 [M+H]; Retention time: 2.03 minutes; LCMS condition: C

Reference Example 115

(R)-tert-butyl 6-(2-((2-(3-amino-4-chlorophenyl)-2-(triethylsilyloxy)ethyl)(tert-butoxycarbonyl)amino)ethoxy)-3-methoxyindazole-1-carboxylate

[Chemical Formula 182]

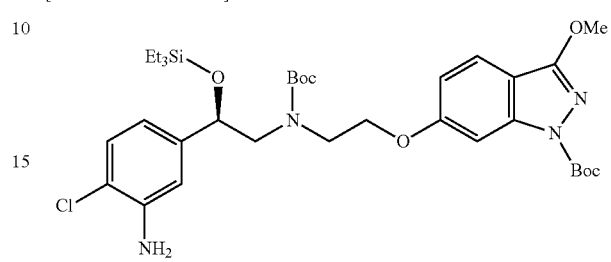

The title compound (2.1204 g) was obtained by the same method as that used in Reference Example 101, using (R)-tert-butyl 6-(2-((2-(3-amino-4-chlorophenyl)-2-hydroxyethyl)(tert-butoxycarbonyl)amino)ethoxy)-3-methoxyindazole-carboxylate (1.9428 g) that can be produced by the method described in Reference Example 114 or the like, instead of (R)-tert-butyl 6-(2-((2-(3-amino-4-chlorophenyl)-2-hydroxyethyl)(tert-butoxycarbonyl)amino)ethoxy)-3-methylindazole-carboxylate.

$^1$H-NMR (300 MHz, CDCl$_3$); δ (ppm) 0.52 (6H, q, J=7.6), 0.88 (9H, t, J=7.6), 1.46 (9H, s), 1.67 (9H, s), 3.12-3.76 (4H, m), 4.02-4.10 (2H, m), 4.13 (3H, s), 4.76-4.97 (1H, m), 6.58-6.83 (3H, m), 7.17 (1H, d, J=8.0), 7.42 (1H, brs), 7.47 (1H, dd, J=1.8, 8.4)

Reference Example 116

3-(6-(Benzyloxy)indazol-3-yl)-N,N-dimethylpropanamide

[Chemical Formula 183]

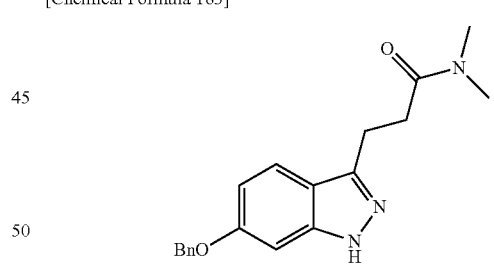

3-(6-Benzyloxy)-1-(tetrahydro-2H-pyran-2-yl)-indazol-3-yl)-N,N-dimethylpropanamide (7.4931 g) that can be produced by the method described in Reference Example 51 or the like, a 4 mol/L hydrochloric acid-1,4-dioxane solution (360 mL; manufactured by Kokusan Chemical Co., Ltd.), and dehydrated methanol (4 mL; manufactured by Kanto Chemical Co., Inc.) were added, and the mixture was stirred for 16 hours at 50° C. Precipitates in the reaction solution were filtered, and then the obtained solids were washed with MTBE and were introduced into an aqueous solution of sodium hydrogen carbonate. The aqueous layer was extracted once with ethyl acetate and once with chloroform. The organic layer was dehydrated over magnesium sulfate, and then was concentrated under reduced pressure. Thus, the title compound (5.5850 g) was obtained.

$^1$H-NMR (300 MHz, DMSO-d$_6$); δ (ppm) 2.73 (2H, t, J=8.0), 2.81 (3H, s), 2.94 (3H, s), 3.05 (2H, t, J=8.0), 5.15 (2H, s), 6.77 (1H, dd, J=2.1, 8.7), 6.91 (1H, d, J=2.1), 7.30-7.48 (5H, m), 7.59 (1H, d, J=8.7), 12.39 (1H, s)

LCMS: 324 [M+H]; Retention time: 1.37 minutes; LCMS condition: C

Reference Example 117

Tert-butyl 6-(benzyloxy)-3-(3-(dimethylamino)-3-oxopropyl)indazole-1-carboxylate

[Chemical Formula 184]

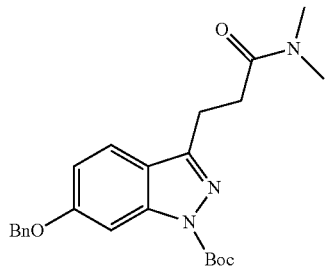

3-(6-(Benzyloxy)indazol-3-yl)-N,N-dimethylpropanamide (5.289 g) that can be produced by the method described in Reference Example 116 or the like, was dissolved in dehydrated THF, and Boc$_2$O (4.5 mL; manufactured by Wako Pure Chemical Industries, Ltd.), triethylamine (2.75 mL; manufactured by Kokusan Chemical Co., Ltd.), and 4-N,N-dimethylaminopyridine (203 mg) were added to the solution. The mixture was stirred overnight at room temperature. Ethyl acetate was added to the reaction solution, and the organic layer was washed twice with a 1 mol/L aqueous solution of hydrochloric acid, once with water and once with brine. The organic layer was dried over magnesium sulfate and then was concentrated under reduced pressure. Thus, the title compound (7.066 g) was obtained.

LCMS: 424 [M+H]; Retention time: 1.85 minutes; LCMS condition: C

Reference Example 118

Tert-butyl 3-(3-(dimethylamino)-3-oxopropyl)-6-hydroxyindazole-1-carboxylate

[Chemical Formula 185]

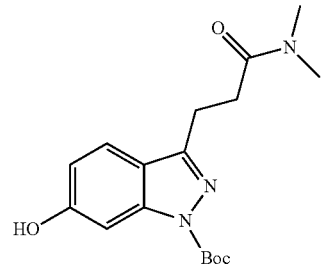

Tert-butyl 6-(benzyloxy)-3-(3-(dimethylamino)-3-oxopropyl)indazole-1-carboxylate (6.9915 g) that can be produced by the method described in Reference Example 117 or the like, and 5% palladium on carbon-STD-type-50% wet with water (3.5517 g; manufactured by N.E. Chemcat Corp.) were suspended in THF (81.5 mL). Subsequently, the reaction system was purged with hydrogen, and under a hydrogen atmosphere, the reaction solution was stirred overnight at room temperature. The reaction system was purged with nitrogen, and the reaction solution was filtered. The filtrate was concentrated under reduced pressure, and thus the title compound (5.7091 g) was obtained.

$^1$H-NMR (300 MHz, CDCl$_3$) δ (ppm) 1.62 (9H, s), 2.94 (2H, t, J=6.5), 2.97 (3H, s), 3.05 (3H, s), 3.24 (2H, t, J=6.5), 6.69 (1H, dd, J=1.8, 8.4), 7.26-7.29 (1H, m) 7.41 (1H, s), 8.65 (1H, s)

LCMS: 334 [M+H]; Retention time: 1.17 minutes; LCMS condition: C

Test Example 1-A

Measurement of Human β3 Adrenergic Receptor Agonist Activity

The measurement of human β3 adrenergic receptor agonist activity is carried out using CHO (Chinese Hamster Ovary) cells transfected with pcDNA3 (manufactured by Invitrogen, Inc.) to which human β3 gene has been inserted. In regard to human β3 gene, first, a human β3 cDNA fragment is obtained by PCR using human adipose tissue cDNA (manufactured by Clontech Laboratories, Inc.), with the primers for β3 gene (Krief et al., J. Clin. Invest., Vol. 91, pp. 344-349 (1993)). This human β3 cDNA fragment is used as a probe, and the full length human β3 gene is obtained from a human genomic library (manufactured by Clontech Laboratories, Inc.). The above cells are cultured in Ham's F-12 medium containing 10% fetal bovine serum and 400 μg/ml geneticin (manufactured by Invitrogen, Inc.). These cells are seeded on a 24-well plate to a concentration of 1×10$^5$ cells/well, and after being cultured for about 20 hours, the cells are left to stand in serum-free Ham's F-12 medium for 2 hours. A test compound is initially dissolved in DMSO, and then is diluted stepwise with Ham's F-12 containing 20 mmol/L HEPES, 1 mmol/L isobutylmethylxanthine, and 1 mmol/L ascorbic acid. The dilution is added to the cells. After the cells are cultured for 30 minutes, and then the medium is removed, followed by addition of 0.1 ml of 1 N NaOH to the cells. The cells are left to stand for 20 minutes, and then are added with 0.1 ml of 1 N acetic acid and are stirred. The resulting cell lysate is centrifuged, and then is subjected to quantification of cAMP with cAMP EIA kit (manufactured by Cayman Chemical Co.). Maximum response to isoproterenol as a positive control is taken as 100%, and the maximum response ratio of each test compound is calculated as the Intrinsic Activity [I.A. (%)]. The concentration of a drug solution that results in a response ratio of 50% (EC$_{50}$) is also determined.

Test Example 1-B

Measurement of Human β3 Adrenergic Receptor Agonist Activity

The measurement of human β3 adrenergic receptor agonist activity is carried out using CHO (Chinese Hamster Ovary) cells transfected with pcDNA3 (manufactured by Invitrogen, Inc.) to which human β3 gene has been inserted. In regard to human β3 gene, first, a human β3 cDNA fragment is obtained by PCR using human adipose tissue cDNA (manufactured by Clontech Laboratories, Inc.), with the primers for β3 gene (Krief et al., J. Clin. Invest., Vol. 91, pp. 344-349 (1993)). This human β3 cDNA fragment is used as a probe, and the full length human β3 gene is obtained from a human genomic library (manufactured by Clontech Laboratories, Inc.). The above cells are cultured in Ham's F-12 medium containing 10% fetal bovine serum and 400 µg/ml geneticin (manufactured by Invitrogen, Inc.). These cells are seeded on a 96-well plate to a concentration of $2 \times 10^4$ cells/well, and after being cultured for about 20 hours, the cells are left to stand in 80 µL of serum-free Ham's F-12 medium for 15 minutes. A test compound is initially dissolved in DMSO, and then is diluted stepwise with Ham's F-12 containing 100 mmol/L HEPES and 1 mmol/L isobutylmethylxanthine. 20 µL of the dilution is added to the cells. After the cells are cultured for 30 minutes, the medium is removed. 0.3. ml of the Assay/lysis Buffer included in cAMP-Screen kit (manufactured by Applied Biosystems, Inc.) is added to the cells, and the cells are incubated at 37° C. for 30 minutes. The resulting cell lysate is subjected to quantification of cAMP with the cAMP-Screen kit. Maximum response to isoproterenol as a positive control is taken as 100%, and the maximum response ratio of each test compound is calculated as the Intrinsic Activity [I.A. (%)]. The concentration of the drug solution that results in a response ratio of 50% ($EC_{50}$) is also determined.

Test Example 2-A

Measurement of Human β1 Adrenergic Receptor Agonist Activity

The measurement of human β1 adrenergic receptor agonist activity is carried out by the same method as the Measurement method of the Test Example 1-A, using CHO (Chinese Hamster Ovary) cells transfected with pcDNA3 (manufactured by Invitrogen, Inc.) to which human β1 gene has been inserted. Maximum response to isoproterenol as a positive control is taken as 100%, and the maximum response ratio of each test compound is calculated as the Intrinsic Activity [I.A. (%)]. The concentration of drug solution that results in a response ratio of 50% ($EC_{50}$) is also determined.

Test Example 2-B

Measurement of Human β1 Adrenergic Receptor Agonist Activity

The measurement of human β1 adrenergic receptor agonist activity is carried out by the same method as the measurement method of the Test Example 1-B, using CHO (Chinese Hamster Ovary) cells transfected with pcDNA3 (manufactured by Invitrogen, Inc.) to which human β1 gene has been inserted. Maximum response to isoproterenol as a positive control is taken as 100%, and the the maximum response ratio of each test compound is calculated as the Intrinsic Activity [I.A. (%)]. The concentration of a drug solution that results in a response ratio of 50% ($EC_{50}$) is also determined.

Test Example 3-A

Measurement of Human β2 Adrenergic Receptor Agonist Activity

The measurement of human β2 adrenergic receptor agonist activity is carried out by the same method as the measurement method of the Test Example 1-A, using CHO (Chinese Hamster Ovary) cells transfected with pcDNA3 (manufactured by Invitrogen, Inc.) to which human β2 gene has been inserted. Maximum response to isoproterenol as a positive control is taken as 100%, and the maximum response ratio of each test compound is calculated as the Intrinsic Activity [I.A. (%)]. The concentration of a drug solution that results in a response ratio of 50% ($EC_{50}$) is also determined.

Test Example 3-B

Measurement of Human β2 Adrenergic Receptor Agonist Activity

The measurement of human β2 adrenergic receptor agonist activity is carried out by the same method as the measurement method of the Test Example 1-B, using CHO (Chinese Hamster Ovary) cells transfected with pcDNA3 (manufactured by Invitrogen, Inc.) to which human β2 gene has been inserted. Maximum response to isoproterenol as a positive control is taken as 100%, and the maximum response ratio of each test compound is calculated as the Intrinsic Activity [I.A. (%)]. The concentration of a drug solution that results in a response ratio of 50% ($EC_{50}$) is also determined.

Test Example 4

Measurement of Human α1A Adrenergic Receptor Agonist Activity

The measurement of human α1A adrenergic receptor agonist activity is carried out using HEK293 cells transfected with pcDNA3.1(−) (manufactured by Invitrogen, Inc.) to which human α1A gene has been inserted. These cells are cultured in DMEM medium containing 10% fetal bovine serum, 400 µg/ml hygromycin B (manufactured by Gibco BRL), 100 U/ml penicillin and 100 µg/ml streptomycin. Subsequently, the cells are prepared to a solution at $5 \times 10^6$ cells/ml using Assay Buffer (20 mmol/L HEPES-KOH (pH 7.4), 115 mmol/L NaCl, 5.4 mmol/L KCl, 0.8 mmol/L $MgCl_2$, 1.8 mmol/L $CaCl_2$, 13.8 mmol/L D-glucose, and 0.1% bovine serum albumin) containing 0.2% Pluronic F-127 (manufactured by Invitrogen, Inc.) and 20 µmol/L Fura-2AM (manufactured by Wako Pure Chemical Industries, Ltd.). The cells are loaded in a $CO_2$ incubator for 30 minutes, and then are washed twice with the Assay Buffer to remove excess Fura-2AM. The cells are centrifuged, and then are prepared into a solution at $5 \times 10^6$ cells/ml with the Assay Buffer. Subsequently, the cells are dispensed on a 96-well plate (manufactured by Corning, Inc.) at a volume of 80 µl/well, and the plate is used as a cell plate. A sample plate provided by adding a test compound which has been diluted 10 times with the Assay Buffer from $10^{-5}$ to $10^{-12}$ M, as well as the cell plate are set up in FDSS4000 (manufactured by Hamamatsu Photonics K.K.) and are pre-incubated for 180 seconds. Subsequently, measurement of fluorescence intensity (excitation wavelength 340 nm and 380 nm, measurement wavelength 500 nm) is initiated at an interval of 2 seconds. After making measurements for about 30 seconds, 20 µl of the test sample from the sample plate is added to the cell plate, and measurements are further continued for 270 seconds. The Ca flux resulting from the test compound is calculated utilizing the difference between the maximum value of fluorescence intensity ratio at the wavelengths 340 nm and 380 nm after the addition of the test compound, and the fluorescence intensity ratio before the addition of the test compound, as the peak height. Maximum response to norepinephrine as a positive control is taken as 100%, and the maximum response ratio of each test compound is calculated as the Intrinsic Activity [I.A. (%)]. Furthermore, the concentration of a drug solution that results in a response ratio of 50% ($EC_{50}$) is also determined.

Test Example 5

Measurement of Human α1B Adrenergic Receptor Agonist Activity

The measurement of the human α1B adrenergic receptor agonist activity is carried out using HEK293 cells transiently co-transfected with pcDNA3.1 (manufactured by Invitrogen, Inc.) to which human α1B gene has been inserted and a luciferase gene-expressing vector, pSRE-Luc. plasmid (manufactured by Stratagene Corp.). These cells are seeded onto a 96-well plate at a concentration of 40,000 cells/well, and are cultured overnight in DMEM medium containing 2% fetal bovine serum, under the conditions of 37° C. and 5% $CO_2$. A test compound is dissolved in DMSO and then is diluted with the medium, and this dilution is added to the cells to react for several hours. The medium is removed by aspiration, and 30 μl/well of Pica Gene LT 2.0 (manufactured by Toyo Ink Manufacturing Co., Ltd.) is added to the cells. After 30 minutes, the luminescence value is measured. Maximum response to phenylephrine as a positive control is taken as 100%, and the maximum response ratio of each test compound is calculated as the Intrinsic Activity [I.A. (%)]. Furthermore, the concentration of a drug solution that results in a response ratio of 50% ($EC_{50}$) is also determined.

Test Example 6

Measurement of Human α1D Adrenergic Receptor Agonist Activity

The measurement of the human α1D adrenergic receptor agonist activity is carried out using HEK293 cells transiently co-transfected with pcDNA3.1 (manufactured by Invitrogen, Inc.) to which human α1D gene has been inserted, and with a luciferase gene-expressing vector, pSRE-Luc. plasmid (manufactured by Stratagene Corp.). These cells are seeded onto a 96-well plate at a concentration of 40,000 cells/well, and are cultured overnight in DMEM medium containing 2% fetal bovine serum, under the conditions of 37° C. and 5% $CO_2$. A test compound is dissolved in DMSO and then is diluted with the medium, and this dilution is added to the cells to react for several hours. The medium is removed by aspiration, and 30 μl/well of Pica Gene LT 2.0 (manufactured by Toyo Ink Manufacturing Co., Ltd.) is added to the cells. After 30 minutes, the luminescence value is measured. Maximum response to phenylephrine as a positive control is taken as 100%, and the maximum response ratio of each test compound is calculated as the Intrinsic Activity [I.A. (%)]. Furthermore, the concentration of a drug solution that results in a response ratio of 50% ($EC_{50}$) is also determined.

The results of Test Example 1-A, Test Example 2-A, Test Example 3-A and Test Example 4 were presented in Table 1.

The symbols in the Table 1 are defined as follows.

"β3 receptor" represents human β3 adrenergic receptor agonist activity; "β1 receptor" represents human β1 adrenergic receptor agonist activity; "β2 receptor" represents human β2 adrenergic receptor agonist activity; and "α1A receptor" represents human α1A adrenergic receptor agonist activity.

The terms "EC50" and "IA" have the same meanings as described in the Test Example 1-A, Test Example 2-A, Test Example 3-A, or Test Example 4.

Furthermore, N in the Table 1 represents the sample size. Specifically, the sample size means the following: A; n=3, triplicate, B; n=2, triplicate, C; n=1, duplicate, D; n=4, triplicate, E; n=3, duplicate, F; n=2, duplicate, and G; n=1, triplicate.

The term "compound" means the test compound. The term "ex" means Example, and for example, "ex1" represents Example 1. The term "z" means Comparative Example, and for example, "Z1" means Comparative Example 1. The Comparative Examples are compounds described in WO 03/035620, and specifically, Comparative Example 1 refers to the compound of Example 86 of the same International Patent Application, while Comparative Example 2 refers to the compound of Example 88, and Comparative Example 3 to the compound of Example 90.

From the results of Test Example 5, it was proved that Z1 did not have α1B agonist activity. It was also proved from the results of Test Example 6 that Z1 did not have α1D agonist activity, either.

TABLE 1

| compound | β3 receptor | | | β1 receptor | | | β2 receptor | | | α1A receptor | | |
|---|---|---|---|---|---|---|---|---|---|---|---|---|
| | N | EC50 [nM] | I.A. [%] | N | EC50 [nM] | I.A. [%] | N | EC50 [nM] | I.A. [%] | N | EC50 [nM] | I.A. [%] |
| Z1 | B | 26 | 64 | B | a) | 7.2 | B | 150 | 23 | C | 252 | 60 |
| Z2 | B | 4.7 | 52 | B | 140 | 22 | B | 18 | 15 | F | 39 | 59 |
| Z3 | B | 14 | 72 | B | 220 | 26 | B | 53 | 20 | F | 402 | 83 |
| ex2 | G | 29 | 77 | B | a) | 8.1 | B | a) | 3.0 | E | 855 | 24 |
| ex3 | G | 29 | 77 | | c) | | | c) | | C | b) | 0 |
| ex5 | B | 51 | 75 | B | a) | 3.3 | B | a) | 3.2 | C | 836 | 47 |
| ex6 | B | 7.4 | 82 | B | a) | 3.3 | B | a) | 7.6 | C | a) | 20 |
| Isoproterenol | A | 54 | 100 | A | 1.3 | 100 | A | 5.8 | 100 | | c) | |
| Norepinephrine | | c) | | | c) | | | c) | | A | 6.5 | 100 | a): much weaker activities
b): Not active
c): Not tested

The results of Test Example 1-B, Test Example 2-B, Test Example 3-B and Test Example 4 were presented in Table 2.

The symbols in the Table 2 are defined as follows.

"β3 receptor" represents human β3 adrenergic receptor agonist activity; "β1 receptor" represents human β1 adrenergic receptor agonist activity; "β2 receptor" represents human β2 adrenergic receptor agonist activity; and "α1A receptor" represents human α1A adrenergic receptor agonist activity.

The terms "EC50" and "IA" have the same meanings as described in the Test Example 1-B, Test Example 2-B, Test Example 3-B, or Test Example 4.

Furthermore, N in the Table 2 represents the sample size. Specifically, the sample size means the following: A; n=3, triplicate, B; n=2, triplicate, C; n=1, duplicate, D; triplicate, E; n=3, duplicate, F; n=2, duplicate, and G; n=1, triplicate.

The term "compound" means the test compound. The term "ex" means Example, and for example, "ex1" represents Example 1. The term "Z" means Comparative Example, and for example, "Z1" means Comparative Example 1. The Comparative Examples are compounds described in WO 03/035620, and specifically, Comparative Example 1 refers to the compound of Example 86 of the same International Patent Application, while Comparative Example 2 refers to the compound of Example 88, and Comparative Example 3 to the compound of Example 90.

From the results of Test Example 5, it was proved that Z1 did not have α1B agonist activity. It was also proved from the results of Test Example 6 that Z1 did not have α1D agonist activity, either.

TABLE 2

| compound | β3 receptor | | | β1 receptor | | | β2 receptor | | | α1A receptor | | |
|---|---|---|---|---|---|---|---|---|---|---|---|---|
| | N | EC50 [nM] | I.A. [%] | N | EC50 [nM] | I.A. [%] | N | EC50 [nM] | I.A. [%] | N | EC50 [nM] | I.A. [%] |
| Z1 | B | 40 | 67 | B | a) | 2.4 | | c) | | C | 252 | 60 |
| Z2 | | c) | | | c) | | | c) | | F | 39 | 59 |
| Z3 | | c) | | | c) | | | c) | | F | 402 | 83 |
| ex1 | A | 17 | 74 | B | a) | 12 | B | a) | 6.7 | E | a) | 8.0 |
| ex2 | A | 17 | 76 | B | a) | 5.8 | B | a) | 4.3 | E | 855 | 24 |
| ex3 | | c) | | B | a) | 1.0 | B | a) | 2.0 | C | b) | 0 |
| ex4 | A | 49 | 78 | G | a) | 6.3 | G | a) | 2.4 | E | 892 | 40 |
| ex5 | | c) | | | c) | | B | a) | 5.4 | C | 836 | 47 |
| ex7 | B | 13 | 65 | B | a) | 22 | B | a) | 8.0 | C | b) | 0 |
| ex8 | B | 17 | 61 | G | a) | 15 | G | a) | 11 | F | a) | 5.0 |
| ex9 | B | 29 | 58 | G | a) | 18 | G | a) | 8.0 | F | a) | 11 |
| ex10 | B | 41 | 53 | G | a) | 8.0 | G | a) | 3.0 | F | 1294 | 15 |
| ex11 | B | 15 | 65 | G | a) | 22 | G | a) | 5.0 | F | b) | 0 |
| ex12 | B | 84 | 84 | G | b) | −1.0 | G | a) | 2.0 | F | 1312 | 34 |
| ex13 | B | 47 | 80 | G | b) | −2.0 | G | b) | −3.0 | F | a) | 20 |
| ex14 | B | 10 | 90 | G | a) | 16 | G | b) | 0.0 | F | b) | 0 |
| ex15 | G | 13 | 80 | G | a) | 1.0 | G | b) | −3.0 | F | b) | 0 |
| ex16 | G | 17 | 75 | G | a) | 7.0 | G | a) | 3.0 | C | b) | 0 |
| ex20 | G | 11 | 80 | G | a) | 3.0 | G | a) | 5.0 | F | 488 | 26 |
| Isoproterenol | n = 34 triplicate | 119 | 100 | n = 14 triplicate | 1.5 | 100 | n = 22 triplicate | 12 | 22 | | a) | |
| Norepinephrine | | c) | | | c) | | | c) | | A | 6.5 | 100 | a): much weaker activities
b): Not active
c): Not tested

Test Example 7

Test for Relaxant Activity on Urinary Bladder Smooth Muscle Isolated From Common Marmoset The relaxant activity of a test compound on the urinary bladder smooth muscle isolated from the common marmoset can be verified by performing a test by making reference to the methods described in British Journal of Pharmacology, Vol. 122, 1720-1724 (1997). Common marmosets are (CLEA Japan, Inc.) exsanguinated to death, and then are subjected to laparotomy to isolate the urinary bladder therefrom. A smooth muscle strips are produced from the isolated bladder, and the strips are suspended in an organ bath filled with 10 mL of Krebs-Henseleit solution aerated with a gas mixture of 95% $O_2$ and 5% $CO_2$. The strips are applied a resting tension of 1 g, and are equilibrated for at least 30 minutes. After the resting tension of the strips have been equilibrated, KCl at a final concentration of 40 mmol/L is repeatedly added to the organ bath, and it is confirmed that contraction due to KCl becomes almost constant. After the tension is stabilized by contracting the specimen using KCl at a final concentration of 40 mmol/L, the test compound is cumulatively added (at an interval of 20 minutes) at a ratio of 10 times, and the relaxation response is observed. The final concentration is set at $10^{-9}$, $10^{-9}$, $10^{-7}$, $10^{-6}$, $10^{-5}$ and $10^{-4}$ mol/L. When the relaxation response at the maximum concentration of the test compound is completed, papaverine at a final concentration of $10^{-4}$ mol/L is added, and the maximum relaxation response of each strip is determined. With this relaxation response taken as 100%, the ratios of relaxation (%) at the test compound concentration of $10^{-5}$ mol/L and $10^{-4}$ mol/L are calculated.

The results of Test Example 7 were presented in Table 3.

The symbols in the Table 3 are defined as follows.

"n" means the number of strips. The term "relaxant activity (%)" means the ratio of relaxation (%). The terms "compound" and "ex" are as defined above.

TABLE 3

| | | relaxant activity (%) | |
|---|---|---|---|
| compound | n | $10^{-5}$ M | $10^{-4}$ M |
| ex1 | 3 | 49.9 | 68.6 |
| ex2 | 3 | 43.4 | 57.8 |
| ex4 | 3 | 40.8 | 73.5 |
| ex5 | 2 | 50.9 | 56.3 |
| ex6 | 2 | 35.3 | 42.6 |
| ex11 | 2 | 20.1 | 39.2 |
| isoproterenol | 7 | 58.0 | 62.8 |

Test Example 8

Test for Relaxant Activity on Human-Isolated Urinary Bladder Smooth Muscle

The relaxant activity of a test compound on the human-isolated urinary bladder smooth muscle can be verified by performing a test by making reference to the methods described in the Journal of Urology, Vol. 170, 649-653 (2003). That is, a smooth muscle strips obtained from a human-isolated urinary bladder are suspended in an organ bath filled with Krebs-Henseleit solution aerated with a gas mixture of 95% $O_2$ and 5% $CO_2$. The strips are applied a resting tension of 1 g, and are equilibrated for at least 30 minutes. After the resting tension of the strips have been equilibrated, carbachol at a final concentration of 0.1 μmol/L is repeatedly added to the organ bath, and it is confirmed that contraction due to carbachol becomes almost constant. After the developing tension is stabilized by contracting the strips using carbachol at a final concentration of 0.1 μmol/L, the test compounds are cumulatively added at an interval of 10 minutes at a ratio of 10 times, and the relaxation response is observed. The final concentration is set at $10^{-9}$, $10^{-9}$, $10^{-7}$, $10^{-6}$, $10^{-5}$ and $10^{-4}$ mol/L. When the relaxation response at the maximum concentration of the test compound is completed, papaverine at a final concentration of $10^{-4}$ mol/L is added, and the maximum relaxation response of each strips is determined. With this relaxation response taken as 100%, the ratio of relaxation is calculated.

Test Example 9

Effect on Blood Pressure and Heart Rate of Rat Under Pentobarbital Anesthesia

The effect of intravenous bolus administration of a test compound exerted on the blood pressure and heart rate can be investigated by measuring the blood pressure and heart rate of a rat under pentobarbital anesthesia. 50 mg/kg of pentobarbital sodium (manufactured by Tokyo Chemical Industry Co., Ltd.) is intraperitoneally administered to a male SD rat (supplied by Japan SLC, Inc.) to induce anesthesia, and then 25 mg/kg of pentobarbital sodium is subcutaneously administered to maintain anesthesia. The left femoral vein is exposed and detached, and then a polyethylene tube SP10 (connected to a three-way stopcock via a ¼ vein needle) filled with physiological saline is inserted and placed in the vein.

The inner side of the left femur is incised, and the femoral artery is exposed and detached. A polyethylene tube (SP31, connected to a three-way stopcock via a Terumo injection needle 22G) filled with heparized physiological saline is inserted in the artery, and is connected to a pressure transducer. The blood pressure is measured from the pressure transducer through a pressure amplifier (AP-641G, Nihon Koden Corp.). The heart rate is measured by the Heart Rate Counter (AT-601G, Nihon Koden Corp.), using the pulse wave of the blood pressure as the trigger. The blood pressure, mean blood pressure and heart rate are outputted to a recorder and recorded. Here, the mean blood pressure is recorded by a pressure amplifier (AP-641G) according to the formula: {diastolic blood pressure+(systolic blood pressure−diastolic blood pressure)/3}.

Measurement of the blood pressure and heart rate is initiated, and it is checked that the respective values are almost constant. 3 mg/kg of the test compound is administered through the left femoral vein for 30 seconds. Specifically, 3 mg/mL of the test compound is rapidly administered at a dose volume of 1 mL/kg. The relative values of the values of average blood pressure and heart rate at each time point with respect to the same values obtained before the initiation of administration, are determined for each individual, and the average value±standard error of the relative values (%) obtainable when each parameter changes the most, is determined.

The results of Test Example 9 were presented in Table 4.
The symbols in the Table 4 are defined as follows.
"n" means the number of animals. The terms "compound," "ex" and "Z" are as defined above. The term "MBP (mean blood pressure)" means the average blood pressure.

TABLE 4

| compound | n | increase in MBP (%) |
| --- | --- | --- |
| Z1 | 3 | 12.8 ± 4.4 |
| Z2 | 3 | 12.6 ± 4.1 |
| ex1 | 6 | 4.7 ± 2.1 |
| ex2 | 6 | 3.1 ± 0.5 |
| ex3 | 3 | 3.4 ± 3.7 |
| ex4 | 6 | 3.1 ± 2.1 |
| ex5 | 3 | 3.4 ± 2.2 |
| ex6 | 3 | 2.8 ± 1.1 |
| ex8 | 3 | 0.4 ± 0.5 |
| ex9 | 3 | 1.7 ± 2.7 |
| ex11 | 3 | 1.8 ± 1.4 |
| ex16 | 3 | 6.6 ± 3.2 |

Test Example 10

Saturation Solubility in Pure Water

A test compound is prepared in pure water to be in the saturated state. This solution is shaken for one hour at room temperature. After the shaking, the entire amount of the solution is transferred into a filter tube, and the solution is filtered by centrifugation. The filtrate is analyzed by HPLC, and the saturation solubility of the test compound is determined using a calibration curve, based on the peak area value.

A standard solution is prepared by precisely weighing each test compound, and preparing a solution that sufficiently dissolves in pure water. The calibration curve is produced by assigning the concentration of the standard solution to the horizontal axis, and assigning the HPLC area peak at the concentration to the vertical axis.

YMC-Pack C18 (4.6 mm×150 mm) (manufactured by YMC Co., Ltd.) is used as a separating column. The detection is performed with UV-254 nm. Elution is carried out at a flow rate of 1 ml/min, using solution A=water [containing 0.1% (v/v) acetic acid] and solution B=acetonitrile as the solvents, under the conditions in which a linear gradient of the solution B is run from 5 to 98% (v/v) from zero minute to 20 minute, subsequently solution B is eluted at 98% up to 25 minute, and the solution B is eluted at 5% from 25.01 minute to 35 minute.

As a result, the saturation solubility of the compound of Example 3. was 50 mg/mL; that of the compound of Example 2 was 204 mg/mL; that of the compound of Example 4 was 71 mg/mL; and that of the compound of Example 5 was 491 mg/mL.

Test Example 11

Test on Solubility in Hydrochloric Acid Buffer Solution at pH 1.2

A test compound is precisely weighed to 500 μg, and a hydrochloric acid buffer solution at pH 1.2 is added thereto to a concentration of 1 mg/mL. The solution is shaken at 37° C. for one hour. After the shaking, the entire amount of the solution is transferred into a filter tube, and the solution is filtered by centrifugation. The filtrate is analyzed by HPLC, and the solubility of the test compound is determined by dividing the peak area value of the filtrate by the peak area value of the standard solution.

The standard solution is prepared by precisely weighing 500 μg of the test compound, and dissolving the test compound in DMSO to a concentration of 1 mg/mL.

YMC-Pack C18 (4.6 mm×150 mm) (manufactured by YMC Co., Ltd.) is used as a separating column. The detection is performed with UV-254 nm. Elution is carried out at a flow rate of 1 ml/min, using solution A=water [containing 0.1% (v/v) acetic acid] and solution B=acetonitrile as the solvents, under the conditions in which a linear gradient of the solution B is run from 5 to 98% (v/v) from zero minute to 20 minute, subsequently solution B is eluted at 98% up to 25 minute, and the solution B is eluted at 5% from 25.01 minute to 15 minute.

As a result, the solubility of the compound of Example 1 was 1000 μg/mL or more (1005 μg/mL); that of the compound of Example 2 was 1000 μg/mL or more (1029 μg/mL); that of the compound of Example 4 was 963 μg/mL; that of the compound of Example 5 was 1000 μg/mL or more (1010 μg/mL); and that of the compound of Example 6 was 1000 μg/mL or more (1040 μg/mL).

Test Example 12

Test on Solubility in Physiological Saline

The solubility of a test compound is determined by performing the same test as that performed in Test Example 11, except that the hydrochloric acid buffer solution at pH 1.2 is changed to physiological saline.

As a result, the solubility of the compound of Example 1 was 1000 μg/mL or more (1012 μg/mL); that of the compound of Example 2 was 1000 μg/mL or more (1022 μg/mL); that of the compound of Example 4 was 932 μg/mL; that of the compound of Example 5 was 1000 μg/mL or more (1007 μg/mL); and that of the compound of Example 6 was 993 μg/mL.

Test Example 13

Test on Stability in Pure Water

A test compound is prepared in pure water to be in the saturated state. This solution is shaken for one hour at room temperature. After the shaking, the entire amount of the solution is transferred into a filter tube, and the solution is filtered by centrifugation. The filtrate is analyzed by HPLC immediately after filtration, 24 hours after filtration, and 48 hours after filtration. The stability of the test compound is determined using a calibration curve, based on the peak area value.

A standard solution is prepared by precisely weighing each test compound, and preparing a solution that sufficiently dissolves in pure water. The calibration curve is produced by assigning the concentration of the standard solution to the horizontal axis, and assigning the HPLC area peak at the concentration to the vertical axis.

YMC-Pack C18 (4.6 mm×150 mm) (manufactured by YMC Co., Ltd.) is used as a separating column. The detection is performed with UV-254 nm. The temperature in the column is set at 40° C. Elution is carried out at a flow rate of 1 ml/min, using solution A=water [containing 0.1% (v/v) acetic acid] and solution B=acetonitrile as the solvents, under the conditions in which a linear gradient of the solution B is run from 5 to 98% (v/v) from zero minute to 20 minute, subsequently solution B is eluted at 98% up to 25 minute, and the solution B is eluted at 5% from 25.01 minute to 35 minute.

As a result, the HPLC area percent of the compound of Example 1 was 100% immediately after filtration, 99.8% after 24 hours, and 99.8% after 48 hours. The HPLC area percent of the compound of Example 2 was 98.2% immediately after filtration, 98.2% after 24 hours, and 98.2% after 48 hours. The HPLC area percent of the compound of Example 4 was 98.7% immediately after filtration, 98.7% after 24 hours, and 98.6% after 48 hours.

Test Example 14

Test on Stability in Phosphate Buffer Solution at pH 6.8

The stability of a test compound is determined by performing the same test as that performed in Test Example 13, except that the pure water is changed to a phosphate buffer solution at pH 6.8.

As a result, the HPLC area percent of the compound of Example 1 was 99.8% immediately after filtration, 99.9% after 24 hours, and 100% after 48 hours. The HPLC area percent of the compound of Example 2 was 98.2% immediately after filtration, 98.2% after 24 hours, and 98.2% after 48 hours. The HPLC area percent of the compound of Example 4 was 99.6% immediately after filtration, 99.6% after 24 hours, and 99.6% after 48 hours.

The compound represented by formula (A-1) or formula (1) of the present invention, a possible stereoisomer or racemic form thereof, pharmaceutically acceptable salts of the compound, stereoisomer and racemic form, or hydrates and/or solvates of the compound, stereoisomer and racemic form, and crystals thereof have a β3 adrenergic receptor agonist activity. Therefore, these compounds are useful as therapeutic and prophylactic agents for diabetes mellitus, obesity, hyperlipidemia, depression, diseases caused by gallstones or hypermotility of the biliary tract, diseases caused by hyperactivity of the digestive tract, interstitial cystitis, overactive bladder or urinary incontinence, or as therapeutic and prophylactic agents for diseases concomitant with decreased tears, and the compounds find uses in the field of pharmaceutical industry.

The invention claimed is:

1. A compound selected from the group consisting of the following:
   (R)-N-(3-(2-(2-(3-ethylindazol-6-yloxy)ethylamino)-1-hydroxyethyl)phenyl)methanesulfonamide;
   (R)-N-(3-(2-(2-(3-n-propylindazol-6-yloxy)ethylamino)-1-hydroxyethyl)phenyl)methanesulfonamide;
   (R)-N-(3-(2-(2-(3-isopropylindazol-6-yloxy)ethylamino)-1-hydroxyethyl)phenyl)methanesulfonamide;
   (R)-N-(3-(2-(2-(3-trifluoromethylindazol-6-yloxy)ethylamino)-1-hydroxyethyl)phenyl)methanesulfonamide;
   (R)-N-(3-(2-(2-(3-methoxymethylindazol-6-yloxy)ethylamino)-1-hydroxyethyl)phenyl)methanesulfonamide;
   (R)-3-(6-(2-(2-hydroxy-2-(3-methylsulfonamido)phenyl)ethylamino)ethoxy)indazol-3-yl)-N,N-dimethylpropanamide;
   (R)-N-(2-chloro-5-(1-hydroxy-2-(2-(3-isopropylindazol-6-yloxy)ethylamino)ethyl)phenyl)methanesulfonamide;
   (R)-N-(5-(2-(2-(3-ethylindazol-6-yloxy)ethylamino)-1-hydroxyethyl)-2-fluorophenyl)methanesulfonamide;
   (R)-N-(2-chloro-5-(2-(2-(3-ethylindazol-6-yloxy)ethylamino)-1-hydroxyethyl)phenyl)methanesulfonamide;
   (R)-N-(2-fluoro-5-(1-hydroxy-2-(2-(3-(trifluoromethyl)indazol-6-yloxy)ethylamino)ethyl)phenyl)methanesulfonamide;
   (R)-N-(2-chloro-5-(1-hydroxy-2-(2-(3-(trifluoromethyl)indazol-6-yloxy)ethylamino)ethyl)phenyl)methanesulfonamide;
   (R)-N-(3-(1-hydroxy-2-(2-(3-methylindazol-6-yloxy)ethylamino)ethyl)phenyl)propane-2-sulfonamide;
   (R)-N-(3-(2-(2-(3-ethylindazol-6-yloxy)ethylamino)-1-hydroxyethyl)phenyl)propane-2-sulfonamide;
   (R)-N-(3-(1-hydroxy-2-(2-(3-methylindazol-6-yloxy)ethylamino)ethyl)phenyl)benzenesulfonamide;
   (R)-N-(3-(2-(2-(3-ethylindazol-6-yloxy)ethylamino)-1-hydroxyethyl)phenyl)benzenesulfonamide;
   (R)-N-(3-(1-hydroxy-2-(2-(3-methoxyindazol-6-yloxy)ethylamino)ethyl)phenyl)benzenesulfonamide; and
   (R)-N-(3-(2-(2-(3-ethylindazol-6-yloxy)ethylamino)-1-hydroxyethyl)phenyl)ethanesulfonamide,
   or a salt thereof.

2. A compound selected from the group consisting of the following:
   (R)-N-(3-(2-(2-(3-ethylindazol-6-yloxy)ethylamino)-1-hydroxyethyl)phenyl)methanesulfonamide;
   (R)-N-(3-(2-(2-(3-n-propylindazol-6-yloxy)ethylamino)-1-hydroxyethyl)phenyl)methanesulfonamide;
   (R)-N-(3-(2-(2-(3-isopropylindazol-6-yloxy)ethylamino)-1-hydroxyethyl)phenyl)methanesulfonamide;
   (R)-N-(3-(2-(2-(3-trifluoromethylindazol-6-yloxy)ethylamino)-1-hydroxyethyl)phenyl)methanesulfonamide;

(R)-N-(3-(2-(2-(3-methoxymethylindazol-6-yloxy)ethylamino)-1-hydroxyethyl)phenyl)methanesulfonamide;

(R)-3-(6-(2-(2-hydroxy-2-(3-(methylsulfonamido)phenyl)ethylamino)ethoxy)-indazol-3-yl)-N,N-dimethylpropanamide;

(R)-N-(5-(2-(2-(3-ethylindazol-6-yloxy)ethylamino)-1-hydroxyethyl)-2-fluorophenyl)methanesulfonamide;

(R)-N-(2-chloro-5-(2-(2-(3-ethylindazol-6-yloxy)ethylamino)-1-hydroxyethyl)phenyl)methanesulfonamide;

(R)-N-(2-chloro-5-(1-hydroxy-2-(2-(3-(trifluoromethyl)indazol-6-yloxy)ethylamino)ethyl)phenyl)methanesulfonamide; and (R)-N-(3-(1-hydroxy-2-(2-(3-methoxyindazol-6-yloxy)ethylamino)ethyl)phenyl)benzenesulfonamide, or a salt thereof.

3. A β3 adrenergic receptor agonist comprising the compound according to claim 1 or a salt thereof, as an active ingredient.

4. A medicine comprising the compound according to claim 1 or a salt thereof, as an active ingredient.

5. The medicine according to claim 4, which is a prophylactic and/or therapeutic agent for overactive bladder and urinary incontinence.

6. A method for activating a β3 adrenergic receptor in a body of a patient, the method comprising administering the compound according to claim 1 or a salt thereof, to a patient in need of treatment of overactive bladder and urinary incontinence.

7. A method for treatment of overactive bladder and urinary incontinence, the method comprising administering to a patient a therapeutically effective amount of the compound according to claim 1 or a salt thereof.

8. A method for treatment of urinary incontinence, the method comprising administering to a patient a therapeutically effective amount of the compound according to claim 1 or a salt thereof.

9. (R)-N-(3-(2-(2-(3-ethylindazol-6-yloxy)ethylamino)-1-hydroxyethyl)phenyl)methanesulfonamide or a salt thereof.

10. A β3 adrenergic receptor agonist comprising the compound according to claim 2 or a salt thereof as an active ingredient.

11. A medicine comprising the compound according to claim 2 or a salt thereof as an active ingredient.

12. The medicine according to claim 11, which is a prophylactic and/or therapeutic agent for overactive bladder and urinary incontinence.

13. A β3 adrenergic receptor agonist comprising the compound according to claim 9 or a salt thereof as an active ingredient.

14. A medicine comprising the compound according to claim 9 as an active ingredient.

15. The medicine according to claim 14, which is a prophylactic and/or therapeutic agent for overactive bladder and urinary incontinence.

* * * * *